(12) United States Patent
Brain et al.

(10) Patent No.: US 8,324,225 B2
(45) Date of Patent: Dec. 4, 2012

(54) PYRROLOPYRIMIDINE COMPOUNDS AND THEIR USES

(75) Inventors: Christopher Thomas Brain, Cambridge, MA (US); Moo Je Sung, Belmont, MA (US); Gebhard Thoma, Lörrach (DE)

(73) Assignees: Novartis AG, Basel (CH); Astex Therapeutics Limited, Cambridge (GB)

( * ) Notice: Subject to any disclaimer, the term of this patent is extended or adjusted under 35 U.S.C. 154(b) by 371 days.

(21) Appl. No.: 12/302,223

(22) PCT Filed: May 24, 2007

(86) PCT No.: PCT/US2007/069595
§ 371 (c)(1),
(2), (4) Date: Aug. 24, 2009

(87) PCT Pub. No.: WO2007/140222
PCT Pub. Date: Dec. 6, 2007

(65) Prior Publication Data
US 2009/0318441 A1 Dec. 24, 2009

Related U.S. Application Data

(60) Provisional application No. 60/808,605, filed on May 26, 2006.

(51) Int. Cl.
*A01N 43/90* (2006.01)
*A61K 31/519* (2006.01)
*C07D 487/00* (2006.01)

(52) U.S. Cl. ................. 514/265.1; 544/280

(58) Field of Classification Search .............. None
See application file for complete search history.

(56) References Cited

U.S. PATENT DOCUMENTS 7,319,102 B1 * 1/2008 Clark et al. ............... 514/265.1
2008/0139588 A1 6/2008 Clark

FOREIGN PATENT DOCUMENTS

| JP | 2006/241089 A1 | 9/2006 |
|---|---|---|
| WO | WO 03/074530 A1 | 9/2003 |
| WO | WO 2005/023761 A2 | 3/2005 |
| WO | WO 2005/023806 A2 | 3/2005 |
| WO | WO 2005/080393 A1 | 9/2005 |
| WO | WO 2005/085253 A1 | 9/2005 |
| WO | WO 2005/107760 A1 | 11/2005 |
| WO | WO 2006/042102 A2 | 4/2006 |
| WO | WO 2006/045828 A1 | 5/2006 |
| WO | WO 2006/074985 A1 | 7/2006 |
| WO | WO 2006/076595 A1 | 7/2006 |
| WO | WO 2006/091737 A1 | 8/2006 |
| WO | WO 2007/030438 A2 | 3/2007 |
| WO | WO 2007/039285 A1 | 4/2007 |
| WO | WO 2007/058990 A2 | 5/2007 |
| WO | WO 2007/071393 A2 | 6/2007 |
| WO | WO 2007/104053 A2 | 9/2007 |
| WO | WO 2007/125405 A2 | 11/2007 |
| WO | WO 2007/127382 A1 | 11/2007 |
| WO | WO 2009/098236 A1 | 8/2009 |

OTHER PUBLICATIONS

Dorwald F. A. Side Reactions in Organic Synthesis, 2005, Wiley: VCH, Weinheim p. IX of Preface.*
Choi et al., "Design and synthesis of 7H-pyrrolo[2,3-d]pyrimidines as focal adhesion kinase inhibitors. Part 1", Bioorganic & Medicinal Chemistry Letters, 2006 vol. 16 No. 8 pp. 2173-2176.
Gaulon et al., "A General and Facile Route to New Trisubstituted Purin-8-ones", Synthesis, 2005 vol. 13 pp. 2227-2233.
Moriarty et al., "The synthesis and SAR of 2-amino-pyrrolo[2,3-d]pyrimidines: A new class of Aurora-A kinase inhibitors", Bioorganic & Medicinal Chemistry Letters, 2006 vol. 16 No. 22 pp. 5778-5783.
Choi et al., "Design and synthesis of 7H-pyrrolo[2,3-d]pyrimidines as focal adhesion kinase inhibitors. Part 2", Bioorganic & Medicinal Chemistry Letters, 16:2689-2692 (2006).
Hong et al., "Identification and Characterization of Small-Molecule Inducers of Epidermal Keratinocyte Differentiation", ACS Chemical Biology, 2(3):171-175 (2007).
Koretskaya et al., "5-Substituted Pyrimidine Derivatives.: III. Synthesis of Pyrrolo(2,3-D) Pyrimidines (5,7-Diazaindoles)", Khimiko-Farmatsevticheskii Zhurnal, 6:5-12 (1968).
Siddiqi et al., "Search for New Purine- and Ribose-Modified Adenosine Analogues as Selective Agonists and Antagonists at Adenosine Receptors", J. Med. Chem., 38:1174-1188 (1995).

* cited by examiner

*Primary Examiner* — Jeffrey Murray
(74) *Attorney, Agent, or Firm* — Laura K. Madden

(57) ABSTRACT

The present application describes organic compounds that are useful for the treatment, prevention and/or amelioration of diseases, particularly pyrrolopyrimidine compounds and derivatives are described which inhibit protein kinases. The organic compounds are useful in treating proliferative disease.

9 Claims, No Drawings

PYRROLOPYRIMIDINE COMPOUNDS AND THEIR USES

This application is a U.S. National Phase filing of International Application Serial No. PCT/US2007/069595 filed 24 May 2007, and claims priority to U.S. Provisional Application Ser. No. 60/808,605 filed 26 May 2006, the contents of which are incorporated herein by reference in their entirety.

BACKGROUND

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (Hardie, G. and Hanks, S. The Protein Kinase Facts Book, I and II, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., FASEB J. 1995, 9, 576-596; Knighton et al., Science 1991, 253, 407-414; Hiles et al., Cell 1992, 70, 419-429; Kunz et al., Cell 1993, 73, 585-596; Garcia-Bustos et al., EMBO J. 1994, 13, 2352-2361).

In general, protein kinases mediate intracellular signaling by affecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor-$\alpha$ (TNF-$\alpha$)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. The pharmaceutical intervention in the JAK/STAT pathway has been reviewed [Frank Mol. Med. 5: 432-456 (1999) & Seidel, et al, Oncogene 19: 2645-2656 (2000)].

JAK1, JAK2, and TYK2 are ubiquitously expressed, while JAK3 is predominantly expressed in hematopoietic cells. JAK3 binds exclusively to the common cytokine receptor gamma chain ($\gamma_c$) and is activated by IL-2, IL-4, IL-7, IL-9, and IL-15. The proliferation and survival of murine mast cells induced by IL-4 and IL-9 have, in fact, been shown to be dependent on JAK3- and $65_c$-signaling [Suzuki et al, Blood 96: 2172-2180 (2000)].

Cross-linking of the high-affinity immunoglobulin (Ig) E receptors of sensitized mast cells leads to a release of proinflammatory mediators, including a number of vasoactive cytokines resulting in acute allergic, or immediate (type I) hypersensitivity reactions [Gordon et al, Nature 346: 274-276 (1990) & Galli, N. Engl. J. Med., 328: 257-265 (1993)]. A crucial role for JAK3 in IgE receptor-mediated mast cell responses in vitro and in vivo has been established [Malaviya, et al, Biochem. Biophys. Res. Commun. 257: 807-813 (1999)]. In addition, the prevention of type I hypersensitivity reactions, including anaphylaxis, mediated by mast cell-activation through inhibition of JAK3 has also been reported [Malaviya et al, J. Biol. Chem. 274:27028-27038 (1999)].

The JAK family of tyrosine kinases have also been shown to play a role in immunosuppression and allograft acceptance [Kirken, Transpl. Proc. 33: 3268-3270 (2001)], rheumatoid arthritis [Muller-Ladner, et al., J. Immunol. 164: 3894-3901 (2000)], Familial amyotrophic lateral sclerosis [Trieu, et al., Biochem. Biophys. Res. Commun. 267: 22-25 (2000)], and leukemia [Sudbeck, et al., Clin. Cancer Res. 5: 1569-1582 (1999)].

Initiation, progression, and completion of the mammalian cell cycle are regulated by various cyclin-dependent kinase (CDK) complexes, which are critical for cell growth. These complexes comprise at least a catalytic (the CDK itself) and a regulatory (cyclin) subunit. Some of the more important complexes for cell cycle regulation include cyclin A (CDK1—also known as cdc2, and CDK2), cyclin B1-B3 (CDK1) and cyclin D1-D3 (CDK2, CDK4, CDK5, CDK6), cyclin E (CDK2). Each of these complexes is involved in a particular phase of the cell cycle. Not all members of the CDK family are involved exclusively in cell cycle control, however. Thus CDKs 7, 8, and 9 are implicated in the regulation of transcription, and CDK5 plays a role in neuronal and secretory cell function.

The activity of CDKs is regulated post-translationally, by transitory associations with other proteins, and by alterations of their intracellular localization. Tumor development is closely associated with genetic alteration and deregulation of CDKs and their regulators, suggesting that inhibitors of CDKs may be useful anti-cancer therapeutics. Indeed, early results suggest that transformed and normal cells differ in their requirement for, e.g., cyclin A/CDK2 and that it may be possible to develop novel antineoplastic agents devoid of the general host toxicity observed with conventional cytotoxic and cytostatic drugs. While inhibition of cell cycle-related CDKs is clearly relevant in, e.g., oncology applications, this may not be the case for the inhibition of RNA polymerase-regulating CDKs. On the other hand, inhibition of CDK9/cyclin T function was recently linked to prevention of HIV replication and the discovery of new CDK biology thus continues to open up new therapeutic indications for CDK inhibitors (Sausville, E. A. Trends Molec. Med. 2002, 8, S32-S37).

The function of CDKs is to phosphorylate and thus activate or deactivate certain proteins, including e.g. retinoblastoma proteins, lamins, histone H1, and components of the mitotic spindle. The catalytic step mediated by CDKs involves a phospho-transfer reaction from ATP to the macromolecular enzyme substrate. Several groups of compounds (reviewed in e.g. Fischer, P. M. Curr. Opin. Drug Discovery Dev. 2001, 4, 623-634) have been found to possess anti-proliferative properties by virtue of CDK-specific ATP antagonism.

Thus, there is a continued need to find new therapeutic agents to treat human diseases. Accordingly, there is a great need to develop inhibitors of protein kinases, such as Jak1, Jak2 and Jak3, as well as CDK1, CDK2, CDK4, CDK5, CDK6, CDK7, CDK8 and CDK9.

SUMMARY OF THE INVENTION

There remains a need for new treatments and therapies for protein kinase-associated disorders. There is also a need for compounds useful in the treatment or prevention or amelioration of one or more symptoms of cancer, transplant rejections, and autoimmune diseases. Furthermore, there is a need for methods for modulating the activity of protein kinases, such as Jak1, Jak2 and Jak3, as well as CDK1, CDK2, CDK4, CDK5, CDK6, CDK7, CDK8 and CDK9, using the compounds provided herein. In one aspect, the invention provides a compound of Formula I:

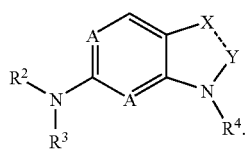

In one aspect of the invention, the protein kinase is a protein tyrosine kinase. In one embodiment, the protein kinase is selected from the group consisting of abl, ATK, ber-abl, Blk, Brk, Btk, c-fms, e-kit, c-met, c-src, CDK, cRafl, CSFIR, CSK, EGFR, ErbB2, ErbB3, ErbB4, ERK, Fak, fes, FGFR1, 25 FGFR2, FGFR3, FGFR4, FGFR5, Fgr, FLK-4, flt-1, Fps, Frk, Fyn, GSK, Gst-Flkl, Hck, Her-2, Her-4, IGF-1R, INS-R, Jak, JNK, KDR, Lck, Lyn, MEK, p38, PANHER, PDGFR, PLK, PKC, PYK2, Raf, Rho, ros, SRC, t'eII t'e2, TRK, TYK2, UL97, VEGFR, Yes, and Zap70. In another embodiment, the protein kinase is selected from the group consisting of CDK1, CDK2, CDK4, CDK5, CDK6, CDK7, CDK8 and CDK9. In yet another embodiment, the protein kinase is selected from the group consisting of Jak1, Jak2 and Jak3. In still another embodiment, the protein kinase is selected from the group consisting of Jak3 and CDK4.

In another aspect of the invention, the protein kinase is in a cell culture. In still another aspect, the protein kinase is in a mammal.

In another aspect, the invention provides a method of treating a protein kinase-associated disorder, wherein the method includes administering to a subject in need thereof a pharmaceutically acceptable amount of a compound of the Formula I, such that the protein kinase-associated disorder is treated. In one embodiment, the protein kinase is selected from the group consisting of CDK1, CDK2, CDK4, CDK5, CDK6, CDK7, CDK8, CDK9, Jak1, Jak2 and Jak3. In a particular embodiment, the protein kinase is selected from the group consisting of Jak3 and CDK4.

In another embodiment, the protein kinase-associated disorder is selected from the group consisting of blood vessel proliferative disorders, fibrotic disorders, mesangial cell proliferative disorders, metabolic disorders, allergies, asthma, thrombosis, nervous system diseases and cancer.

In another embodiment, the protein kinase-associated disorder is cancer. In yet another embodiment, the cancer is selected from the group consisting of breast, stomach, ovary, colon, lung, brain, larynx, lymphatic system, genitourinary tract (including bladder and prostate), ovarian, gastric, bone, and pancreatic cancer.

In another embodiment, the protein kinase-associated disorder is selected from the group consisting of organ transplant rejection, xeno transplantation, lupus, multiple sclerosis, rheumatoid arthritis, psoriasis, Type 1 diabetes and complications from diabetes, cancer, asthma, atopic dermatitis, autoimmune thyroid disorders, ulcerative colitis, Crohn's disease, Alzheimer's disease and leukemia.

In still another embodiment, the disease is selected from an immune response, an autoimmune disease, a neurodegenerative disease, or a solid or hematologic malignancy. In yet another embodiment, the disease is selected from an allergic or type I hypersensitivity reaction, asthma, graft versus host disease, rheumatoid arthritis, amyotrophic lateral sclerosis, multiple sclerosis, Familial amyotrophic lateral sclerosis, leukemia, or lymphoma In another aspect, the invention provides a method of treating an autoimmune disease, wherein the treatment includes administering to a subject in need thereof a pharmaceutically acceptable amount of a compound of the Formula I, such that the autoimmune disease is treated. In one embodiment, the autoimmune disease is selected from the group consisting of autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis, multiple sclerosis, neuritis, uveitis ophthalmia, polyendocrinopathies, purpura, Reiter's Disease, Stiff-Man Syndrome, autoimmune pulmonary inflammation, autism, Guillain-Barre Syndrome, insulin dependent diabetes mellitis, autoimmune inflammatory eye, autoimmune thyroiditis, hypothyroidism, systemic lupus erhythematosus, Goodpasture's syndrome, Pemphigus, Receptor autoimmunities, autoimmune hemolytic anemia, autoimmune thrombocytopenic purpura, rheumatoid arthritis, mixed connective tissue disease, polymyositis/dermatomyositis, pernicious anemia, idiopathic Addison's disease, infertility, glomerulonephritis, bullous pemphigoid, Sjogren's syndrome, diabetes millitus, adrenergic drug resistance, chronic active hepatitis, primary biliary cirrhosis, vitiligo, vasculitis, post-MI, cardiotomy syndrome, urticaria, atopic dermatitis, asthma, inflammatory myopathies, chronic active hepatitis, primary biliary cirrhosis and T-cell mediated hypersensitivity diseases.

In another aspect, the invention provides a method of treating transplant rejection, wherein the treatment includes administering to a subject in need thereof a pharmaceutically acceptable amount of a compound of the Formula I such that the transplant rejection is treated. In one embodiment, the transplant rejection is selected from the group consisting of graft versus host disease, rejection related to xeno transplantation, rejection related to organ transplant, rejection related to acute transplant, heterograft or homograft rejection and ischemic or reperfusion injury incurred during organ transplantation.

In another aspect, the invention provides a method of treating cancer, wherein the method includes administering to a subject in need thereof a pharmaceutically acceptable amount of a compound of the Formula I such that the cancer disease or disorder is treated. In one embodiment, the cancer is selected from the group consisting of bladder, head and neck, breast, stomach, ovary, colon, lung, brain, larynx, lymphatic system, genitourinary tract, gastrointestinal, ovarian, prostate, gastric, bone, small-cell lung, glioma, colorectal and pancreatic cancer.

In another aspect of the invention, the Formula I or salt thereof is administered, simultaneously or sequentially, with an antiinflammatory, antiproliferative, chemotherapeutic agent, immunosuppressant, anti-cancer, cytotoxic agent or kinase inhibitor other than a compound of the Formula I or salt thereof. In one embodiment, the compound of the Formula I or salt thereof is administered, simultaneously or sequentially, with one or more of a PTK inhibitor, cyclosporin A, CTLA4-Ig, antibodies selected from anti-ICAM-3, anti-IL-2 receptor, anti-CD45RB, anti-CD2, anti-CD3, anti-CD4, anti-CD80, anti-CD86, and monoclonal antibody OKT3, agents blocking the interaction between CD40 and gp39, fusion proteins constructed from CD40 and gp39, inhibitors of NF-kappa B function, non-steroidal antiinflammatory drugs, steroids, gold compounds, antiproliferative agents, FK506, mycophenolate mofetil, cytotoxic drugs, TNF-α inhibitors, anti-TNF antibodies or soluble TNF receptor, rapamycin, leflunimide, cyclooxygenase-2 inhibitors, paclitaxel, cisplatin, carboplatin, doxorubicin, caminomycin, daunorubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin, etoposide, etoposide phosphate, teniposide, melphalan, vinblastine, vincristine, leurosidine, epothilone, vindesine, leurosine, or derivatives thereof.

In another aspect, the invention provides a packaged protein kinase-associated disorder treatment, wherein the treatment includes a protein kinase-modulating compound of the Formula I, packaged with instructions for using an effective amount of the protein kinase-modulating compound to treat a protein kinase-associated disorder.

DETAILED DESCRIPTION OF THE INVENTION

This invention is directed to compounds, e.g., pyrrolopyrimidine compounds, and intermediates thereto, as well as pharmaceutical compositions containing the compounds for use in treatment of protein kinase-associated disorders. This invention is also directed to the compounds of the invention or compositions thereof as modulators of Jak1, Jak2 and Jak3, as well as CDK1, CDK2, CDK4, CDK5, CDK6, CDK7, CDK8 and CDK9. The present invention is also directed to methods of combination therapy for inhibiting protein kinase activity in cells, or for treating, preventing or ameliorating of one or more symptoms of cancer, transplant rejections, and autoimmune diseases in patients using the compounds of the invention or pharmaceutical compositions, or kits thereof.

In one aspect, the invention provides compounds of the Formula I:

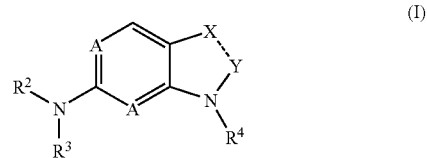

(I)

or a pharmaceutically acceptable salt or solvate thereof, wherein:
the dashed line indicates a single or double bond;
A is N or $CR^5$, wherein $R^5$ is hydrogen or $C_1$-$C_3$-alkyl;
$R^2$ and $R^3$ are each, independently, selected from the group consisting of hydrogen, hydroxyl, $C_1$-$C_3$-alkyl, $C_3$-$C_8$-cycloalkyl, heterocyclyl, aryl, heteroaryl, substituted $C_1$-$C_3$-alkyl, substituted $C_3$-$C_8$-cycloalkyl, substituted heterocyclyl, substituted aryl and substituted heteroaryl;
$R^4$ is selected from the group consisting of hydrogen, $C_1$-$C_8$-alkyl, substituted $C_1$-$C_8$-alkyl, $C_3$-$C_8$-cycloalkyl, substituted $C_3$-$C_8$-cycloalkyl, aryl, substituted aryl, heteroaryl and substituted heteroaryl;
when the bond between X and Y is a single bond, X is $CR^6R^7$, $NR^8$ or C=O, and Y is $CR^9R^{10}$ or C=O;
when the bond between X and Y is a double bond, X is N or $CR^{11}$, and Y is $CR^{12}$;
wherein $R^6$ and $R^7$ are each, independently selected from the group consisting of aryl, substituted aryl, heteroaryl, substituted heteroaryl, hydrogen, $C_1$-$C_3$-alkyl, $C_3$-$C_8$-cycloalkyl, heterocyclyl, substituted alkyl, substituted cycloalkyl, and substituted heterocyclyl;
$R^8$ is hydrogen, $C_1$-$C_3$-alkyl, and $C_3$-$C_8$-cycloalkyl;
$R^9$ and $R^{10}$ are each, independently, hydrogen, $C_1$-$C_3$-alkyl, or $C_3$-$C_8$-cycloalkyl;
$R^{11}$ and $R^{12}$ are each, independently, selected from the group consisting of halo, hydrogen, $C_1$-$C_3$-alkyl, $C_1$-$C_3$-alkoxy, CN, C=NOH, C=NOCH$_3$, C(O)H, C(O)C$_1$-$C_3$-alkyl, $C_3$-$C_8$-cycloalkyl, heterocyclyl, aryl, heteroaryl, substituted $C_1$-$C_3$-alkyl, substituted $C_3$-$C_8$-cycloalkyl, substituted heterocyclyl, substituted aryl, substituted heteroaryl, —BNR$^{13}$R$^{14}$, —BOR$^{13}$, —BC(O)R$^{13}$, —BC(O)OR$^{13}$, —BC(O)NR$^{13}$R$^{14}$; wherein B is a bond, $C_1$-$C_3$-alkyl or branched $C_1$-$C_3$-alkyl; wherein $R^{13}$ and $R^{14}$ are each, independently, selected from the group consisting of hydrogen, $C_1$-$C_3$-alkyl, $C_3$-$C_8$-cycloalkyl, heterocyclyl, aryl, heteroaryl, substituted alkyl, substituted cycloalkyl, substituted heterocyclyl, substituted aryl, and substituted heteroaryl.

In one embodiment, $R^4$ is branched or linear $C_1$-$C_5$-alkyl, wherein the branched $C_1$-$C_5$-alkyl group may be interrupted by one or more heteroatoms, and/or substituted with one or more heteroatoms, halogens, $C_3$-$C_8$ cycloalkyl groups, substituted $C_3$-$C_8$ cycloalkyl groups, $C_3$-$C_8$ heterocyclyl groups, aryl groups, heteroaryl groups, substituted aryl groups, or substituted heteroaryl groups.

In another embodiment, $R^{12}$ is not hydrogen, $R^4$ is selected from the group consisting of hydrogen, $C_1$-$C_8$-alkyl, $C_3$-$C_8$-cycloalkyl, $C_3$-$C_8$-substituted cycloalkyl, aryl, substituted aryl, heteroaryl, and substituted heteroaryl.

In still another embodiment, $R^{12}$ is not hydrogen, $R^4$ is branched or linear $C_1$-$C_5$-alkyl, wherein the branched $C_1$-$C_5$-alkyl group may be interrupted by one or more heteroatoms, and/or substituted with one or more heteroatoms, halogens, $C_3$-$C_8$ cycloalkyl groups, substituted $C_3$-$C_8$ cycloalkyl groups, $C_3$-$C_8$ heterocyclyl groups, aryl groups, heteroaryl groups, substituted aryl groups, or substituted heteroaryl groups.

In yet another embodiment, A is N.

In another embodiment, $R^4$ is selected from the group consisting of hydrogen, branched $C_1$-$C_5$-alkyl, branched $C_1$-$C_5$-alkyl substituted by phenyl and $C_3$-$C_6$-cycloalkyl.

In yet another embodiment, $R^4$ is $C(H)(CH_2CH_3)_2$, $C(H)(CH_2CH_3)Ph$, $CH_2CH_3$, cyclopropyl, cyclopentyl or cyclohexyl.

In still another embodiment, the dashed line is a single bond, X is $CH_2$, $C(C_1$-$C_3$-alkyl$)_2$ or $N(C_1$-$C_3$-alkyl), and Y is C=O. In another embodiment, X is $CH_2$ or $C(CH_3)_2$ and Y is C=O. In yet another embodiment, the dashed line is a double bond, X is CH, N, C—C(O)$C_1$-$C_3$-alkyl or C—($C_1$-$C_3$-alkyl), and Y is CH, C—CHO, C—$C_1$-$C_3$-alkyl, C—$C_1$-$C_3$-alkoxy, C—C(O)$C_1$-$C_3$-alkyl, C—C=NOH or C—C=NOCH$_3$.

In another embodiment, $R^2$ is H.

In yet another embodiment, $R^3$ is an aryl group, which is further independently substituted one or more times by halogen, $C_1$-$C_4$-alkoxy, $R^{15}$-amine, $R^{15}$-heterocycle, or $R^{15}$-heteroaryl, wherein $R^{15}$ is a bond, C(O), N(H)C(O), N(H)SO$_2$, OC(O) or $(CH_2)_{1-4}$, wherein the $(CH_2)_{1-4}$ group may be interrupted by O, N(CH$_3$) or N(H).

In still another embodiment, the aryl group is phenyl.

In another embodiment, the phenyl group is independently substituted one or more times with fluoro, methoxy, diethylamine, $R^{15}$-piperazinyl, $R^{15}$-morpholinyl, $R^{15}$-piperidinyl, $R^{15}$-triazolyl, $R^{15}$-phenyl, $R^{15}$-pyridinyl, $R^{15}$-piperazinyl, $R^{15}$-indazolyl, $R^{15}$-pyrrolidinyl or $R^{15}$-imidazolyl, wherein the piperazinyl, morpholinyl, piperidinyl, triazolyl, phenyl, pyridinyl, piperazinyl, indazolyl, pyrrolidinyl or imidazolyl groups may be further substituted with $C_1$-$C_4$-alkyl, C(O)$C_1$-$C_4$-alkyl, S(O)$_2C_1$-$C_4$-alkyl, OH, C(O)(CH$_2$)$_{1-3}$CN or N(H)C(O)$C_1$-$C_4$-alkyl.

In yet another embodiment, the phenyl group is substituted by N(H)C(O)aryl, C(O)N(H)$C_1$-$C_4$-alkyl, C(O)N($C_1$-$C_4$-alkyl)$_2$ or C(O)N(H)$C_3$-$C_6$-cycloalkyl.

Preferred embodiments of Formula I (including pharmaceutically acceptable salts thereof, as well as enantiomers, stereoisomers, rotamers, tautomers, diastereomers, atropisomers or racemates thereof) are shown below in Table A, Table B, Table C and Table D, and are also considered to be "compounds of the invention." The compounds of the invention are also referred to herein as "protein kinase inhibitors."

TABLE A

| | Jak-3/IC50 (nM) |
|---|---|
| 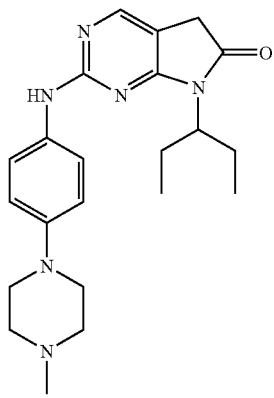 | * |
| 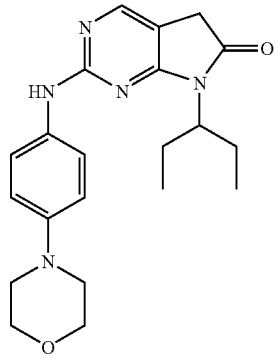 | * |
| 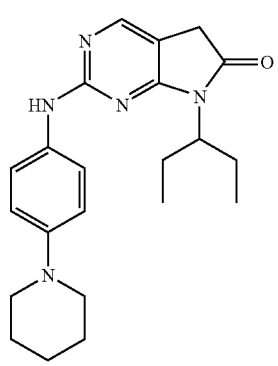 | ** |
| 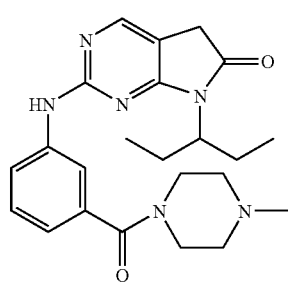 | ** |
| 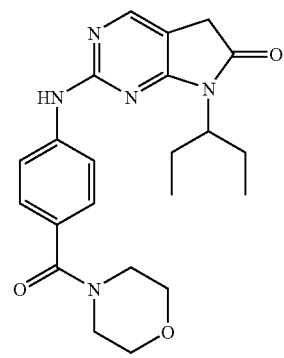 | ** |

TABLE A-continued
| | Jak-3/IC50 (nM) |
|---|---|
| 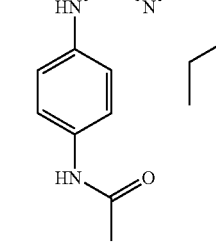 | ** |
| 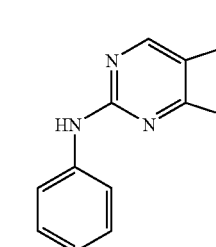 | ** |
| 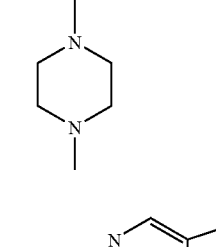 | * |
| 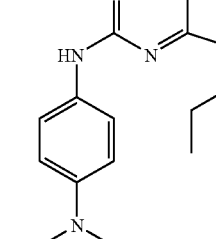 | ** |
TABLE A-continued
| | Jak-3/IC50 (nM) |
|---|---|
| 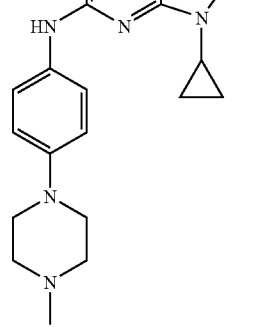 | ** |
| 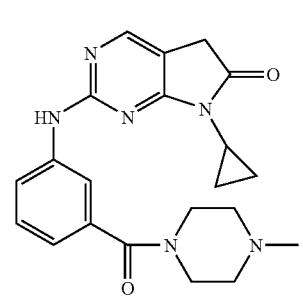 | ** |
| 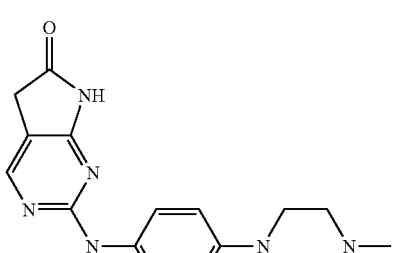 | ** |
| 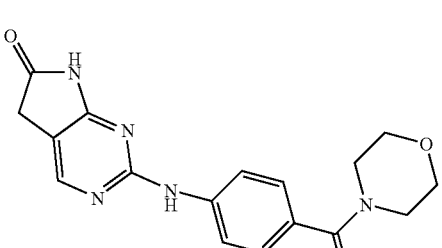 | ** |
| 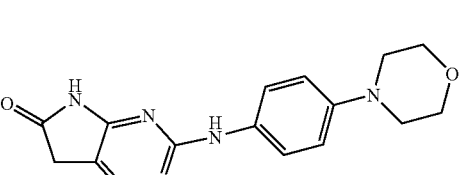 | ** |

TABLE A-continued
| | Jak-3/IC50 (nM) |
|---|---|
| 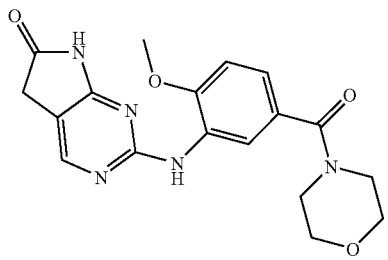 | ** |
| 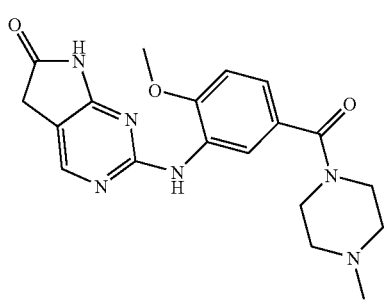 | ** |
| 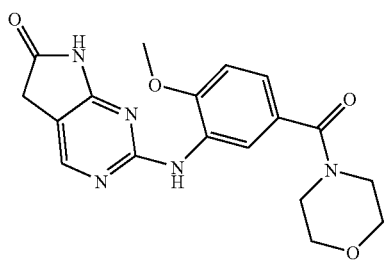 | ** |
| 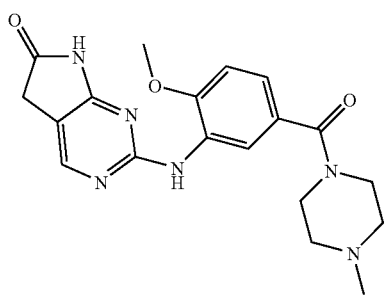 | ** |
| 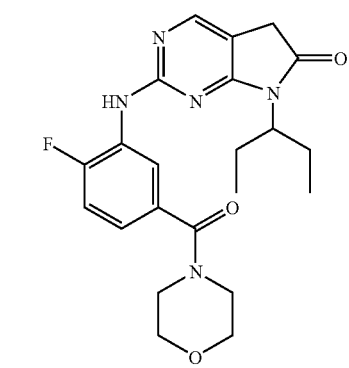 | ** |
TABLE A-continued
| | Jak-3/IC50 (nM) |
|---|---|
| 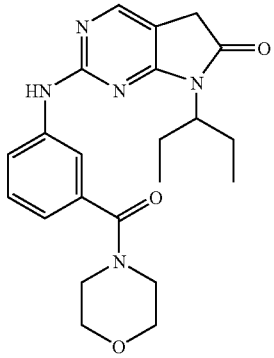 | ** |
| 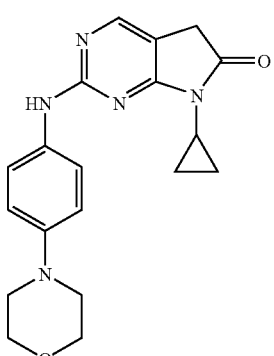 | ** |
| 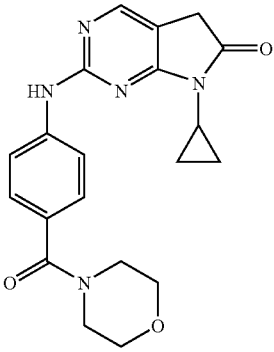 | ** |
| 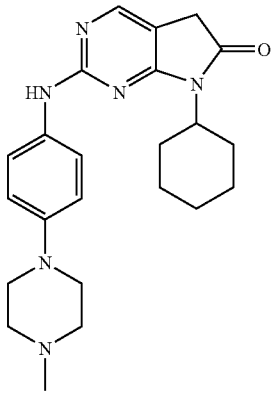 | * |

TABLE A-continued
| | Jak-3/IC50 (nM) |
|---|---|
| 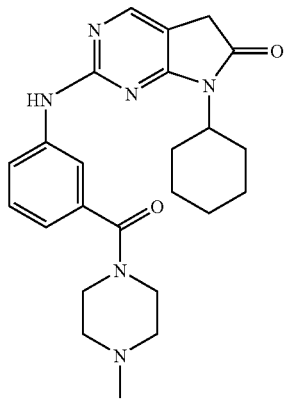 | ** |
| 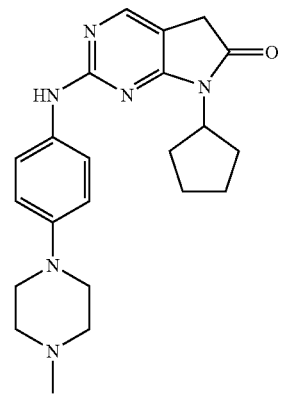 | ** |
| 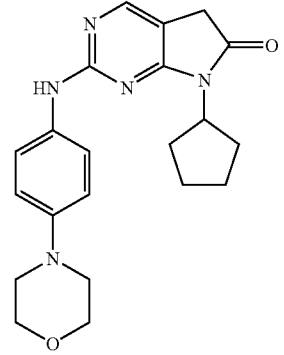 | ** |
| 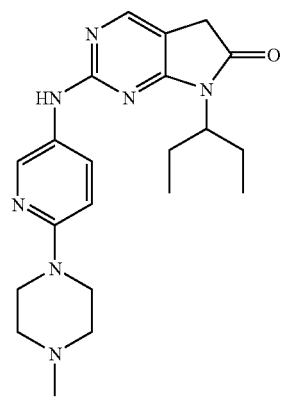 | ** |
TABLE A-continued
| | Jak-3/IC50 (nM) |
|---|---|
| 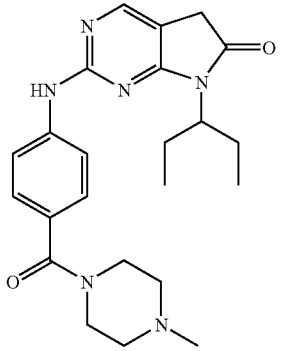 | ** |
| 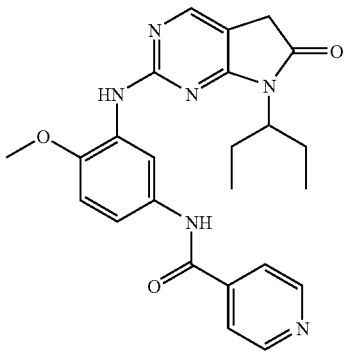 | ** |
| 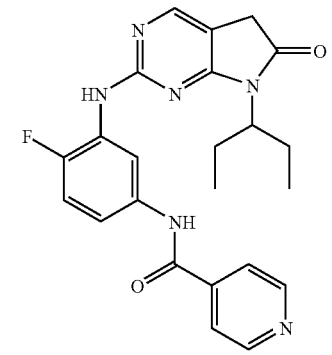 | ** |
| 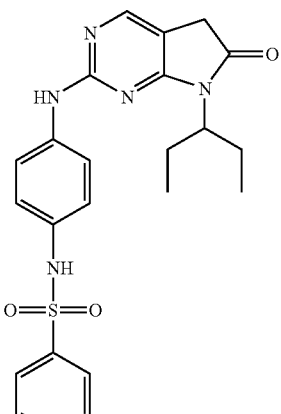 | ** |

TABLE A-continued
| | Jak-3/IC50 (nM) |
|---|---|
| 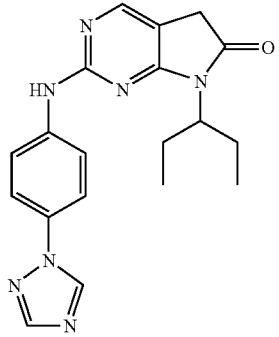 | ** |
| 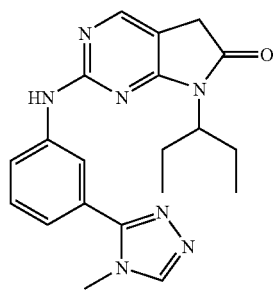 | ** |
| 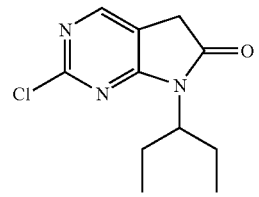 | ** |
| 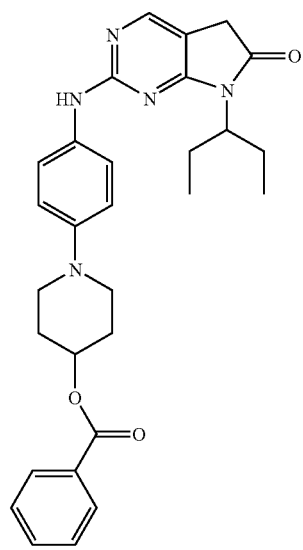 | ** |
TABLE A-continued
| | Jak-3/IC50 (nM) |
|---|---|
| 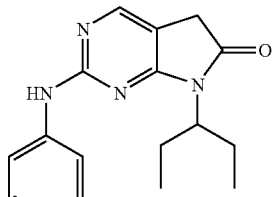 | * |
| 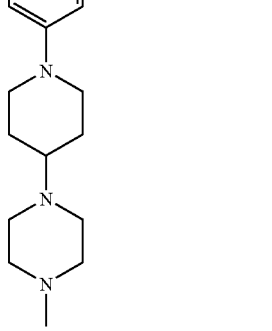 | * |
| 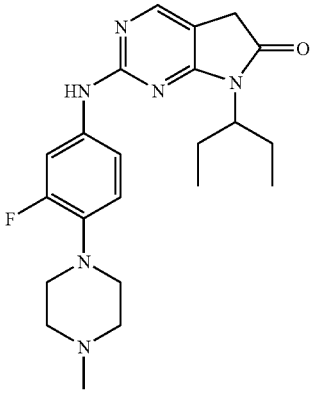 | ** |
| 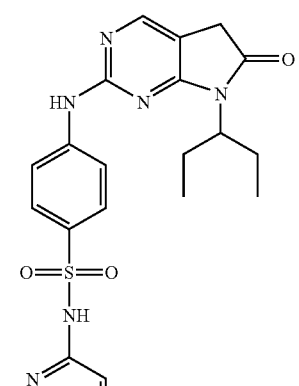 | ** |

TABLE A-continued

| Structure | Jak-3/IC50 (nM) |
|---|---|
| 2-(3-(isonicotinamido)phenylamino)-7-(pentan-3-yl)-5H-pyrrolo[2,3-d]pyrimidin-6(7H)-one | * |
| 2-(4-(4-hydroxypiperidin-1-yl)phenylamino)-7-(pentan-3-yl)-5H-pyrrolo[2,3-d]pyrimidin-6(7H)-one | * |
| 5-bromo-N2-(4-(4-acetylpiperazin-1-yl)phenyl)-N4-(pyridin-2-yl)pyrimidine-2,4-diamine | * |
| 2-(1H-indazol-5-ylamino)-7-(pentan-3-yl)-5H-pyrrolo[2,3-d]pyrimidin-6(7H)-one | ** |
| 7-(pentan-3-yl)-2-(4-(2-(pyrrolidin-1-yl)ethoxy)phenylamino)-5H-pyrrolo[2,3-d]pyrimidin-6(7H)-one | * |
| 2-(4-(4-methylpiperazin-1-ylsulfonyl)phenylamino)-7-(pentan-3-yl)-5H-pyrrolo[2,3-d]pyrimidin-6(7H)-one | ** |
| 7-(pentan-3-yl)-2-(3-(2-(pyrrolidin-1-yl)ethoxy)phenylamino)-5H-pyrrolo[2,3-d]pyrimidin-6(7H)-one | * |

TABLE A-continued
| | Jak-3/IC50 (nM) |
|---|---|
| 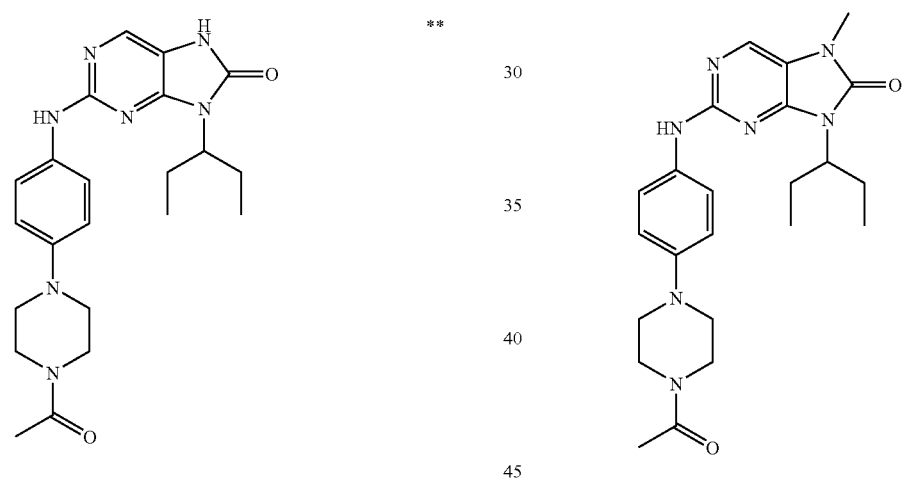 | *<br><br><br><br> |
| 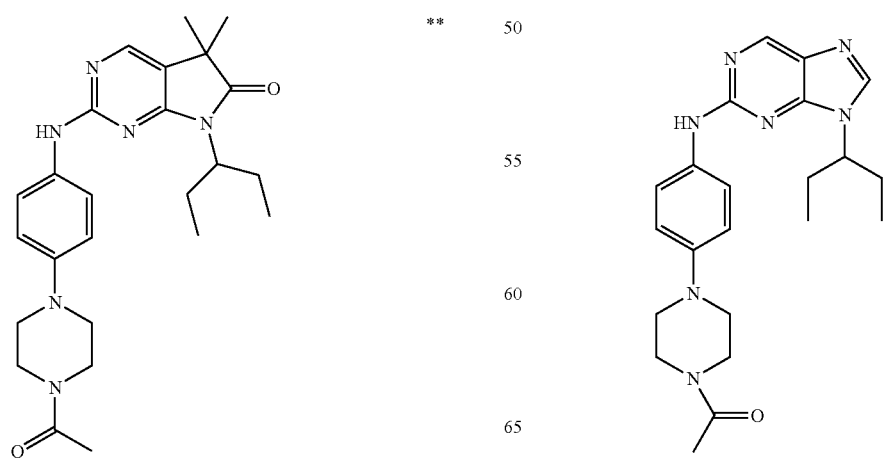 | *<br><br>*<br><br>** |

TABLE A-continued
| | Jak-3/IC50 (nM) |
|---|---|
| 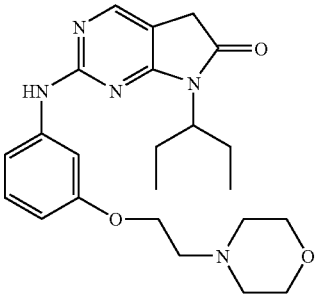 | ** |
| 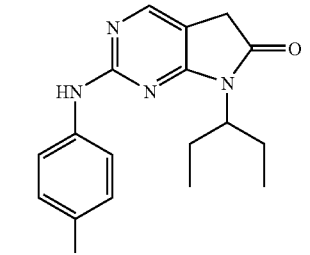 | ** |
| 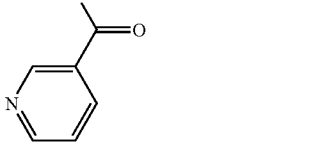 | * |
| 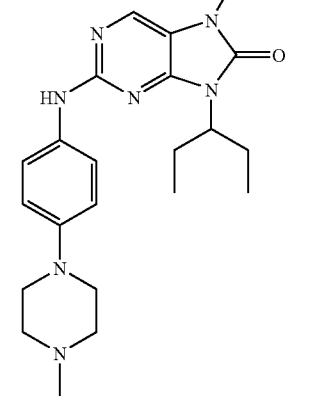 | ** |
TABLE A-continued
| | Jak-3/IC50 (nM) |
|---|---|
| 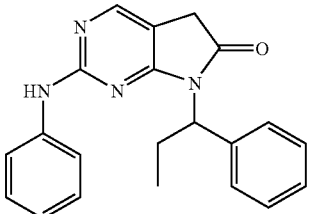 | ** |
| 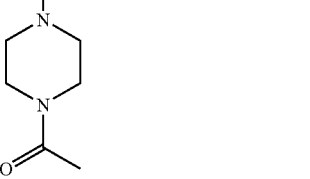 | ** |
| 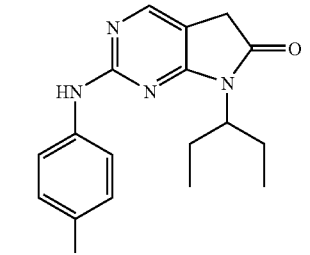 | ** |
| 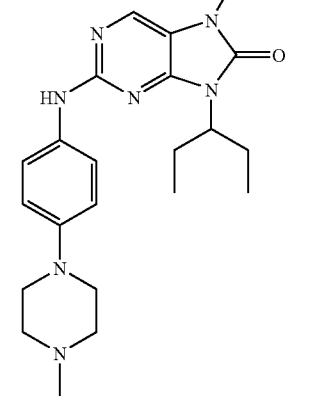 | ** |

TABLE A-continued
| | Jak-3/IC50 (nM) |
|---|---|
| 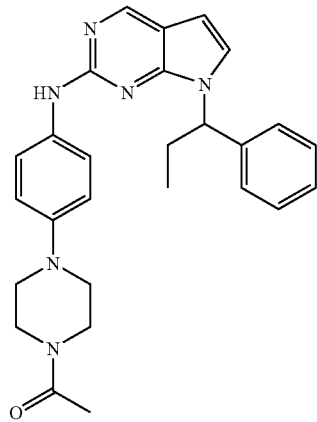 | * |
| 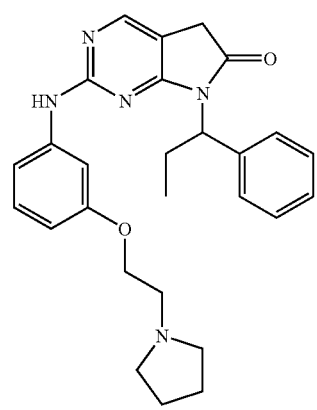 | ** |
| 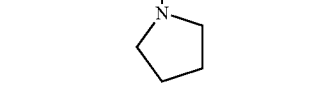 | ** |
TABLE A-continued
| | Jak-3/IC50 (nM) |
|---|---|
| 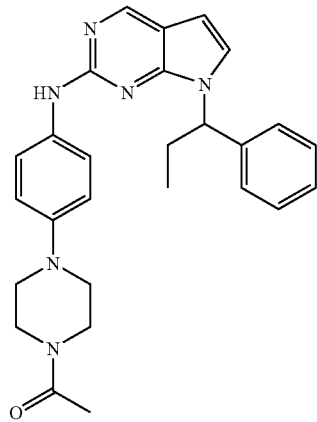 | * |
| 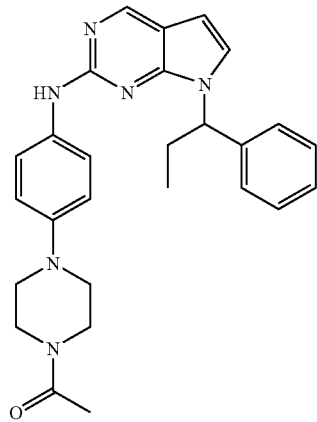 | * |
| 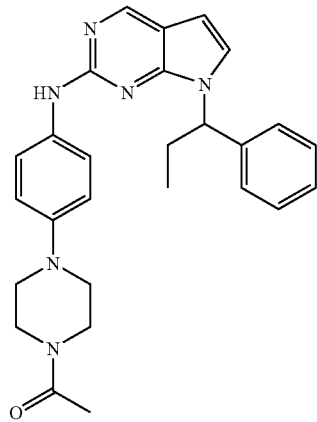 | * |
| 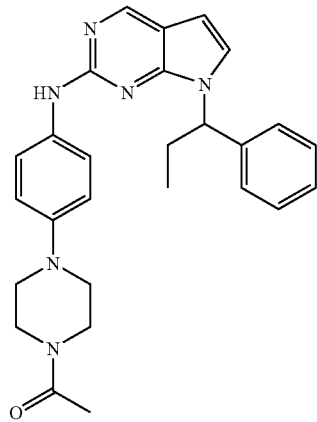 | ** |

TABLE A-continued

| Structure | Jak-3/IC50 (nM) |
|---|---|
| (pyrrolopyrimidinone with 4-(N-isopropylcarbamoyl)phenylamino and pentan-3-yl substituents) | ** |
| (pyrrolopyrimidinone with 4-(N-cyclopentylcarbamoyl)phenylamino and pentan-3-yl substituents) | * |
| (pyrrolopyrimidinone with 4-(N-ethylcarbamoyl)phenylamino and pentan-3-yl substituents) | * |
| (pyrrolopyrimidinone with 4-(N-tert-butylcarbamoyl)phenylamino and pentan-3-yl substituents) | ** |
| (pyrrolopyrimidine with 3-(2-pyrrolidin-1-ylethoxy)phenylamino and pentan-3-yl substituents) | * |
| (pyrrolopyrimidinone with 4-(N-methylcarbamoyl)phenylamino and pentan-3-yl substituents) | ** |
| (pyrrolopyrimidinone with 4-(N,N-dimethylcarbamoyl)phenylamino and pentan-3-yl substituents) | ** |
| (pyrrolopyrimidinone with 4-(N-(2-dimethylaminoethyl)carbamoyl)phenylamino and pentan-3-yl substituents) | ** |
| (pyrrolopyrimidinone with 4-(N-(2-piperidin-1-ylethyl)carbamoyl)phenylamino and pentan-3-yl substituents) | ** |
| (pyrrolopyrimidinone with 4-(N-(2-(4-methylpiperazin-1-yl)ethyl)carbamoyl)phenylamino and 2-ethylbutyl substituents) | ** |

TABLE A-continued
| | Jak-3/IC50 (nM) |
|---|---|
| 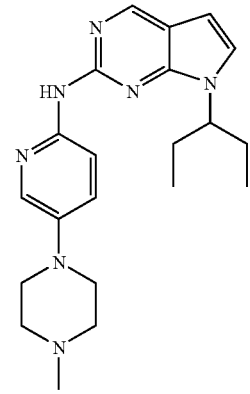 | ** |
| 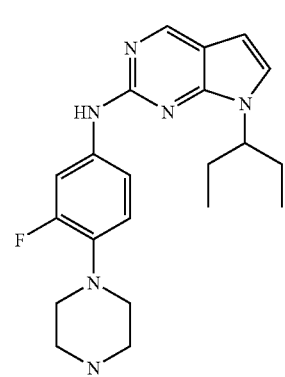 | * |
| 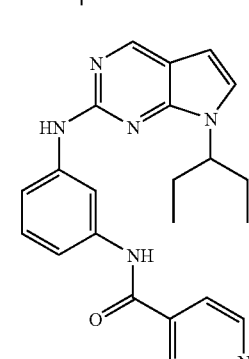 | ** |
TABLE A-continued
| | Jak-3/IC50 (nM) |
|---|---|
| 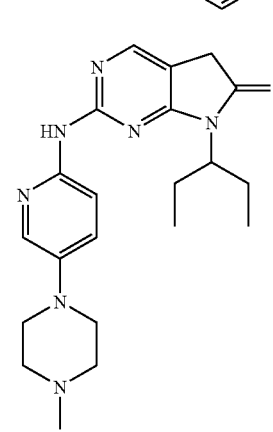 | ** |
| | * |
| | * |
| | ** |

TABLE A-continued
| | Jak-3/IC50 (nM) |
|---|---|
| 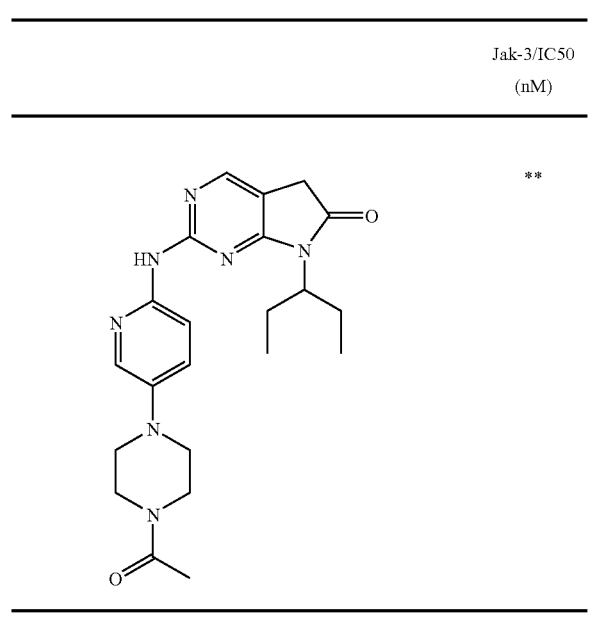 | ** |
Table A Key
* ≦ 100 nM
100 nM ≦ **
TABLE B
| | Jak-3 Lance/ IC50 [nmol l-1] |
|---|---|
| 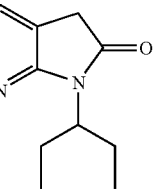 | |
| 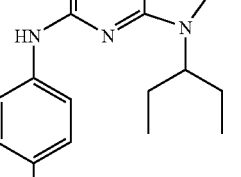 | |
TABLE B-continued
| | Jak-3 Lance/ IC50 [nmol l-1] |
|---|---|
| 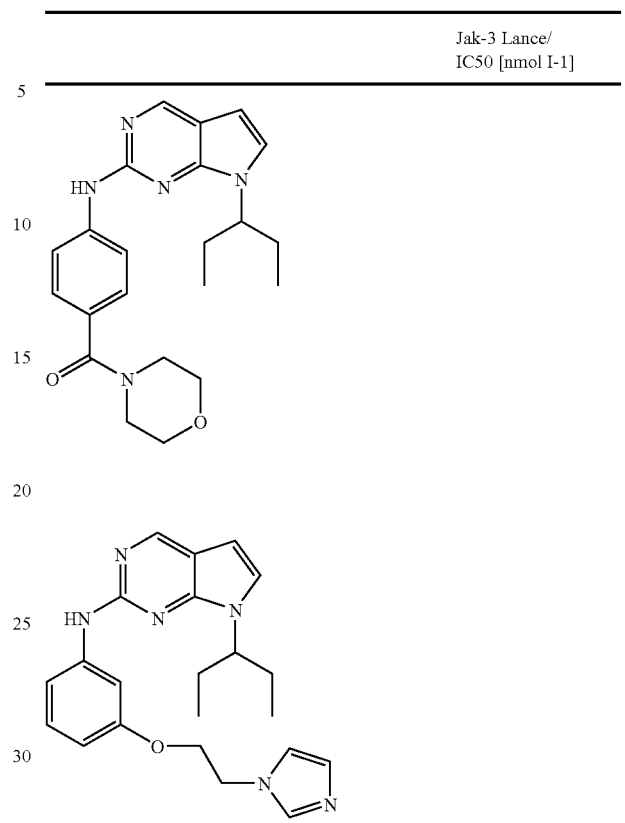 | |
|  | |
| 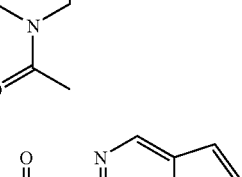 | |
| 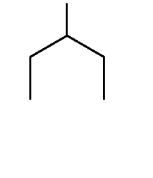 | |

TABLE B-continued
| | Jak-3 Lance/ IC50 [nmol l-1] |
|---|---|
| 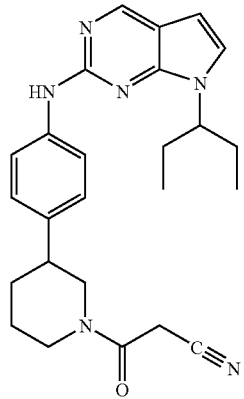 | |
| 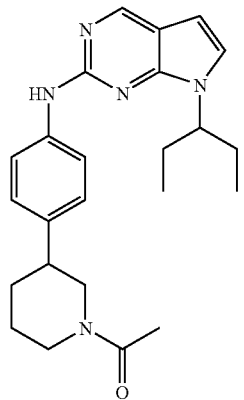 | |
| 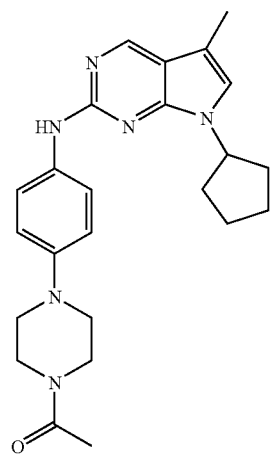 | |
TABLE B-continued
| | Jak-3 Lance/ IC50 [nmol l-1] |
|---|---|
| 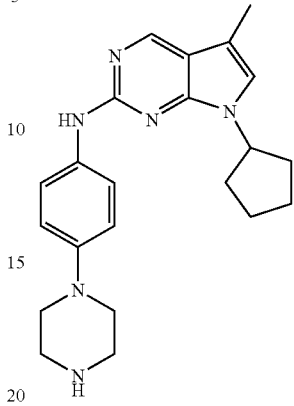 | |
| 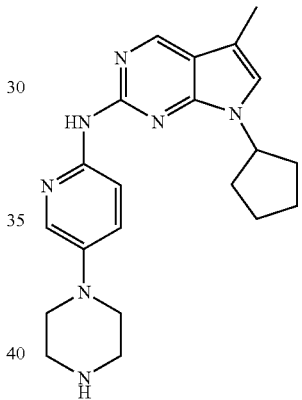 | ** |
| 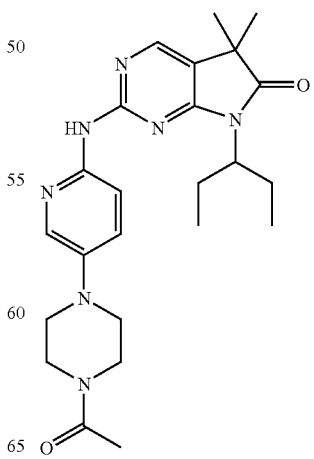 | |

TABLE B-continued

| | Jak-3 Lance/ IC50 [nmol l-1] |
|---|---|
| (structure: 2-(4-(cyclopentylcarbamoyl)phenylamino)-7-(pentan-3-yl)-7H-pyrrolo[2,3-d]pyrimidine) | * |
| (structure: N-cyclopropyl-7-(pentan-3-yl)-7H-pyrrolo[2,3-d]pyrimidin-2-amine) | ** |
| (structure: 2-(4-(4-acetylpiperazin-1-yl)phenylamino)-5-methyl-7-(pentan-3-yl)-7H-pyrrolo[2,3-d]pyrimidine) | ** |
| (structure: 5-methyl-2-(4-(4-methylpiperazin-1-yl)phenylamino)-7-cyclopentyl-7H-pyrrolo[2,3-d]pyrimidine) | ** |

TABLE B-continued

| | Jak-3 Lance/ IC50 [nmol l-1] |
|---|---|
| (structure: 5-methyl-2-(4-(4-methylpiperazin-1-yl)phenylamino)-7-(pentan-3-yl)-7H-pyrrolo[2,3-d]pyrimidine) | ** |
| (structure: 5,5-dimethyl-2-(5-(piperazin-1-yl)pyridin-2-ylamino)-7-(pentan-3-yl)-5,7-dihydro-6H-pyrrolo[2,3-d]pyrimidin-6-one) | ** |
| (structure: 5,5-dimethyl-2-(4-(4-methylpiperazin-1-yl)phenylamino)-7-(pentan-3-yl)-5,7-dihydro-6H-pyrrolo[2,3-d]pyrimidin-6-one) | ** |

TABLE B-continued
| | Jak-3 Lance/ IC50 [nmol l-1] |
|---|---|
| 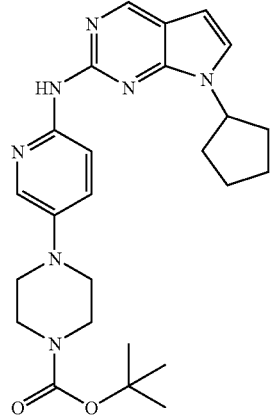 | |
| 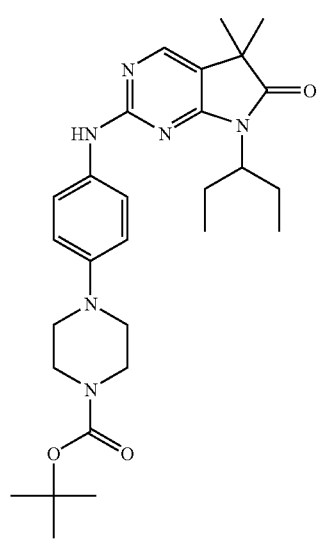 | |
| 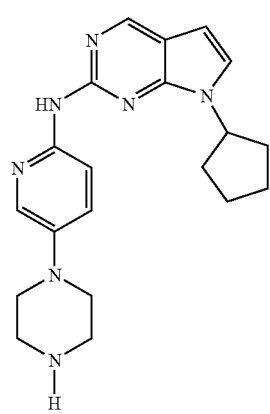 | |
TABLE B-continued
| | Jak-3 Lance/ IC50 [nmol l-1] |
|---|---|
| 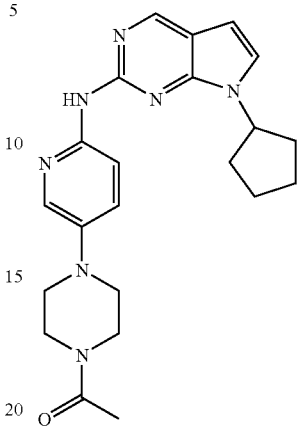 | |
| | |
| 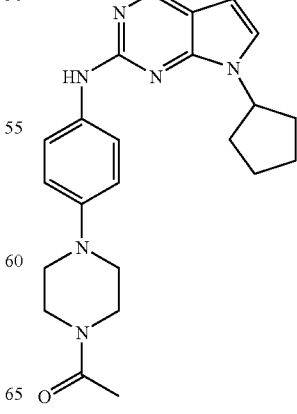 | ** |

TABLE B-continued
| | Jak-3 Lance/ IC50 [nmol l-1] |
|---|---|
| 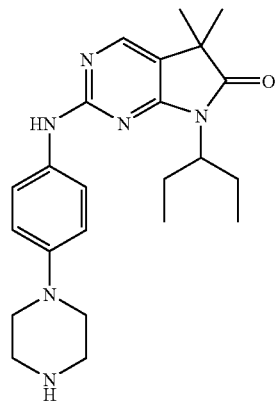 | ** |
| 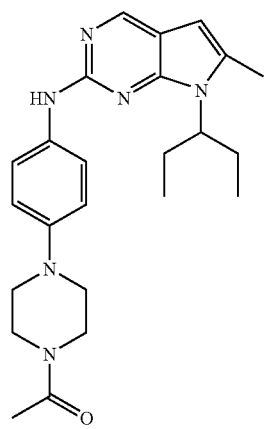 | |
| 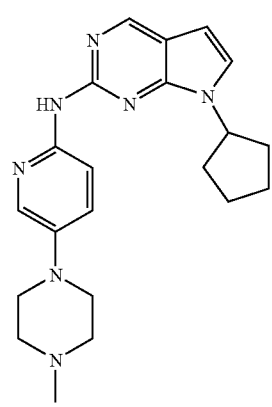 | |
TABLE B-continued
| | Jak-3 Lance/ IC50 [nmol l-1] |
|---|---|
| 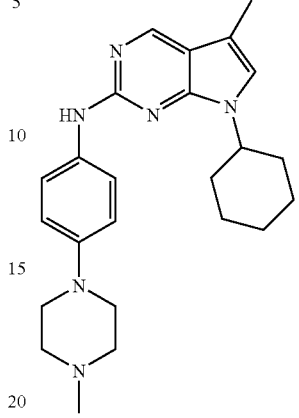 | ** |
| | ** |
| 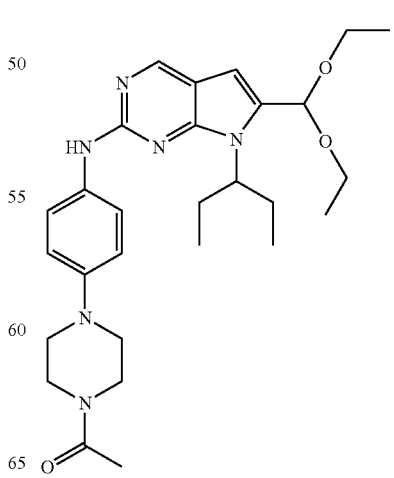 | ** |

TABLE B-continued

| | Jak-3 Lance/ IC50 [nmol l-1] |
|---|---|
| (structure) | * |
| (structure) | * |
| (structure) | ** |
| (structure) | ** |
| (structure) | ** |
| (structure) | ** |
| (structure) | ** |

TABLE B-continued
| | Jak-3 Lance/ IC50 [nmol l-1] |
|---|---|
| 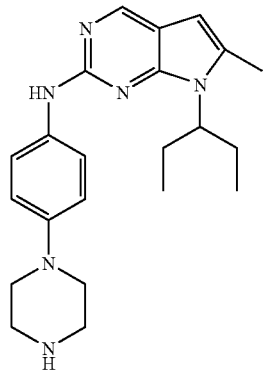 | * |
| 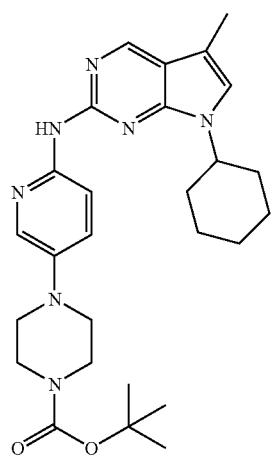 | |
| 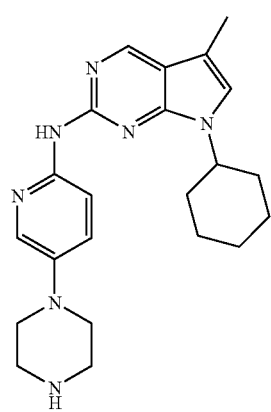 | ** |
TABLE B-continued
| | Jak-3 Lance/ IC50 [nmol l-1] |
|---|---|
| 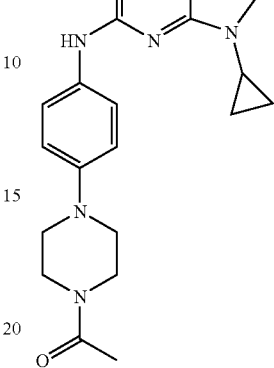 | |
| 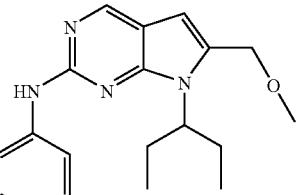 | |
| 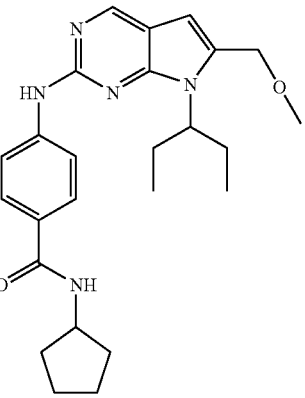 | |

TABLE B-continued
| | Jak-3 Lance/ IC50 [nmol l-1] |
|---|---|
| 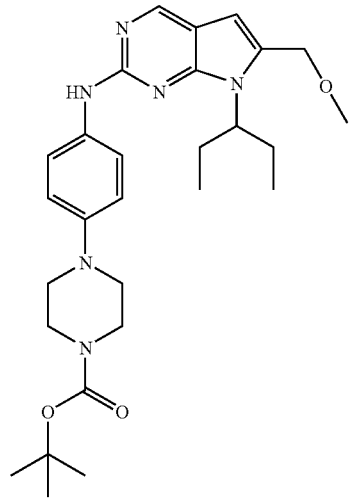 | |
| 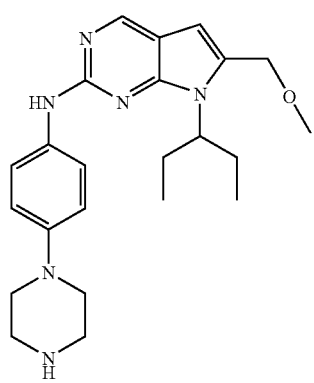 | |
| 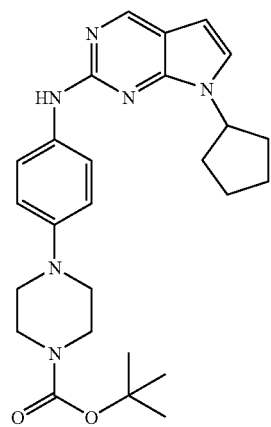 | |
TABLE B-continued
| | Jak-3 Lance/ IC50 [nmol l-1] |
|---|---|
| 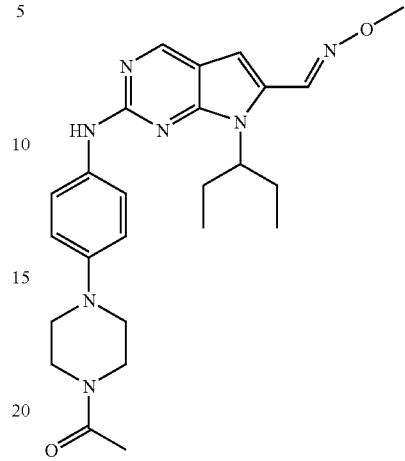 | |
| 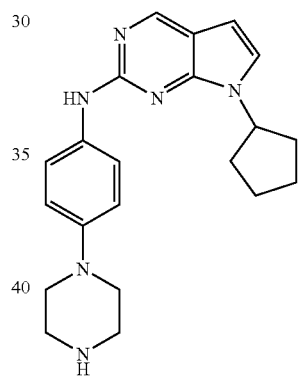 | |
| 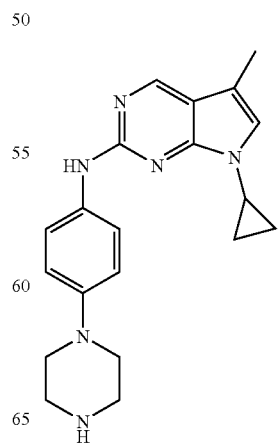 | |

TABLE B-continued
| | Jak-3 Lance/ IC50 [nmol l-1] |
|---|---|
| 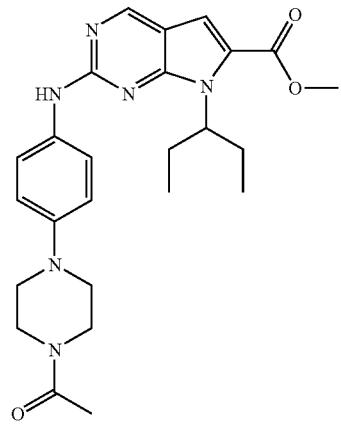 | |
| 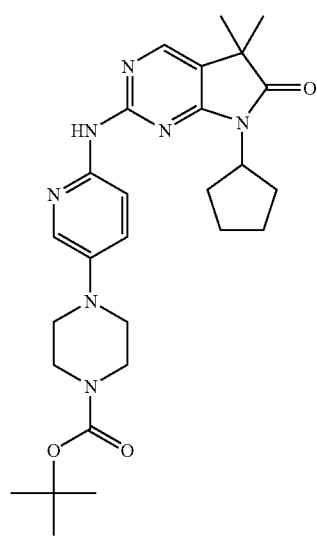 | |
| 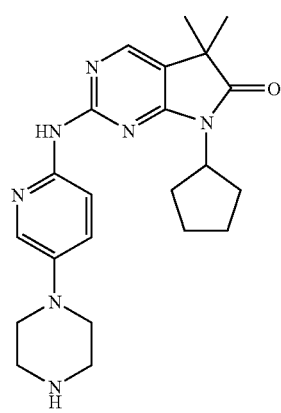 | |
TABLE B-continued
| | Jak-3 Lance/ IC50 [nmol l-1] |
|---|---|
| 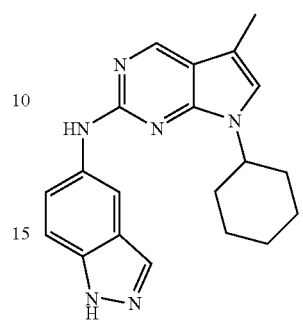 | |
| 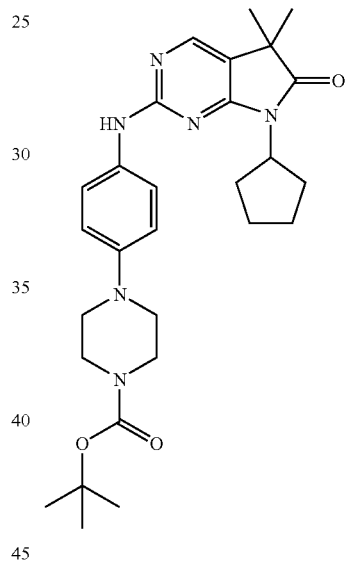 | |
| 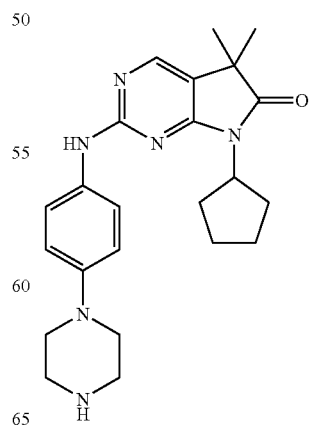 | |

TABLE B-continued
Jak-3 Lance/ IC50 [nmol I-1]
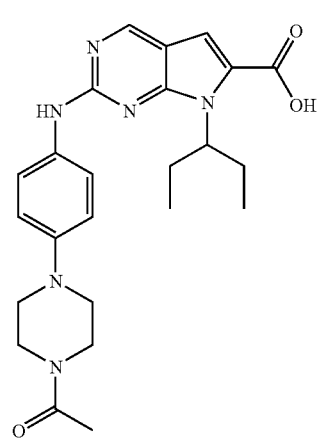
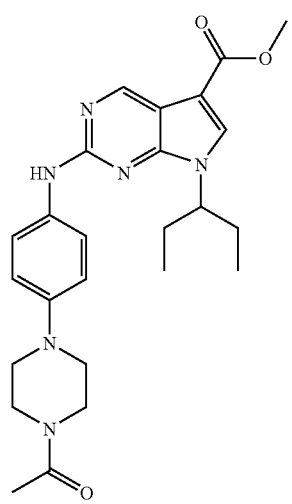
TABLE B-continued
Jak-3 Lance/ IC50 [nmol I-1]
Table B Key
* ≦ 100 nmol⁻¹
100 nmol⁻¹ ≦ **
TABLE C
| | CDK4 IC50, μM | CDK2 IC50, μM |
|---|---|---|
| | ** | * |
| | * | |
| | * | * |

TABLE C-continued

| | CDK4 IC50, μM | CDK2 IC50, μM |
|---|---|---|
| (structure: 7-cyclopentyl-5-methyl-2-[(4-piperazin-1-yl-phenyl)amino]-7H-pyrrolo[2,3-d]pyrimidine) | * | * |
| (structure: 7-cyclopentyl-5-methyl-2-[(5-piperazin-1-yl-pyridin-2-yl)amino]-7H-pyrrolo[2,3-d]pyrimidine) | * | ** |
| (structure: 7-(pentan-3-yl)-5,5-dimethyl-2-[(5-piperazin-1-yl-pyridin-2-yl)amino]-5,7-dihydro-6H-pyrrolo[2,3-d]pyrimidin-6-one, with N-acetyl piperazine) | ** | ** |

TABLE C-continued

| | CDK4 IC50, μM | CDK2 IC50, μM |
|---|---|---|
| (structure: 7-cyclopentyl-5-methyl-2-{[4-(4-methylpiperazin-1-yl)phenyl]amino}-7H-pyrrolo[2,3-d]pyrimidine) | * | ** |
| (structure: 7-(pentan-3-yl)-5,5-dimethyl-2-[(5-piperazin-1-yl-pyridin-2-yl)amino]-5,7-dihydro-6H-pyrrolo[2,3-d]pyrimidin-6-one) | * | ** |
| (structure: 7-(pentan-3-yl)-5,5-dimethyl-2-{[4-(4-methylpiperazin-1-yl)phenyl]amino}-5,7-dihydro-6H-pyrrolo[2,3-d]pyrimidin-6-one) | * | * |

TABLE C-continued

| | CDK4 IC50, μM | CDK2 IC50, μM |
|---|---|---|
| (structure) | ** | |
| (structure) | ** | |
| (structure) | ** | |
| (structure) | ** | |
| (structure) | * | |
| (structure) | ** | |

TABLE C-continued

| | CDK4 IC50, μM | CDK2 IC50, μM |
|---|---|---|
| [structure] | * | |
| [structure] | | |
| [structure] | | |
| [structure] | * | |
| [structure] | * | |
| [structure] | * | |
| [structure] | * | |
| [structure] | * | |

TABLE C-continued

| | CDK4 IC50, μM | CDK2 IC50, μM |
|---|---|---|
| [structure: 5-methyl-7-cyclopropyl-pyrrolopyrimidine with 2-NH-(5-piperazinyl-pyridin-2-yl)] | * | |

Table C Key

* ≦ 10 μM

10 μM ≦ **

TABLE D

[structure: 5-methyl-7-cyclopropyl-pyrrolopyrimidine-2-ylamino-phenyl-(4-acetyl-piperazin-1-yl)]

[structure: 5-methyl-7-cyclohexyl-pyrrolopyrimidine-2-ylamino-phenyl-(4-acetyl-piperazin-1-yl)]

TABLE D-continued

[structure: 5,5-dimethyl-6-oxo-7-cyclopentyl-pyrrolopyrimidine-2-ylamino-phenyl-(4-Boc-piperazin-1-yl)]

[structure: 5-methyl-7-cyclohexyl-pyrrolopyrimidine-2-ylamino-phenyl-piperazin-1-yl]

[structure: 5-methyl-7-cyclopropyl-pyrrolopyrimidine-2-ylamino-phenyl-(4-methyl-piperazin-1-yl)]

TABLE D-continued

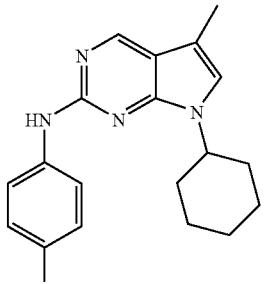

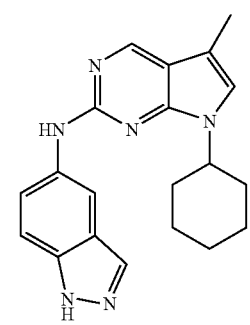

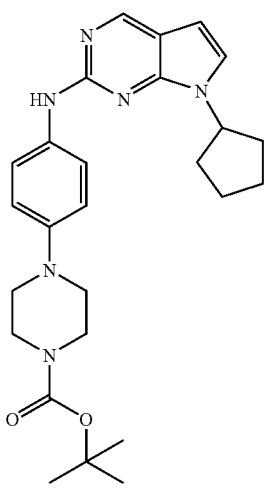

TABLE D-continued

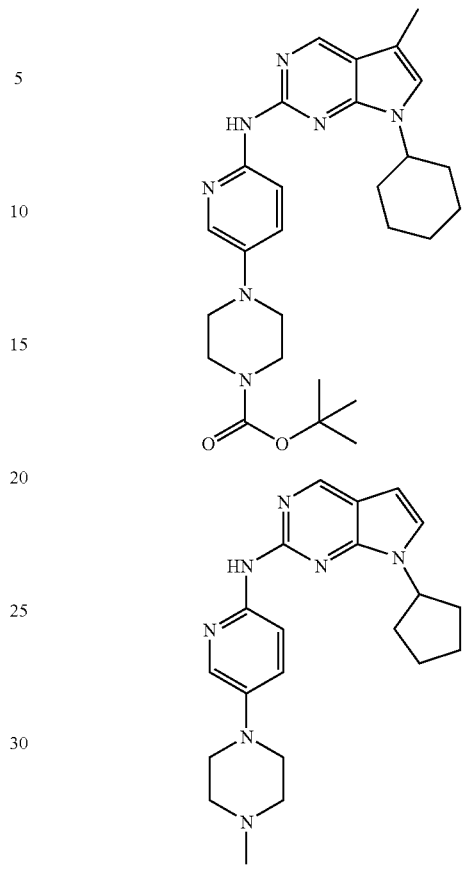

In certain embodiments, the compound of the present invention is further characterized as a modulator of a protein kinase, including, but not limited to, protein kinases selected from the group consisting of abl, ATK, ber-abl, Blk, Brk, Btk, c-fms, e-kit, c-met, c-src, CDK, cRafl, CSFIR, CSK, EGFR, ErbB2, ErbB3, ErbB4, ERK, Fak, fes, FGFRI, 25 FGFR2, FGFR3, FGFR4, FGFR5, Fgr, FLK-4, flt-1, Fps, Frk, Fyn, GSK, Gst-Flkl, Hck, Her-2, Her-4, IGF-1R, INS-R, Jak, JNK, KDR, Lck, Lyn, MEK, p38, PANHER, PDGFR, PLK, PKC, PYK2, Raf, Rho, ros, SRC, t'eII t'e2, TRK, TYK2, UL97, VEGFR, Yes, and Zap70.

In a preferred embodiment, the protein kinase is selected from the group consisting of CDK1, CDK2, CDK4, CDK5, CDK6, CDK7, CDK8 and CDK9. In another preferred embodiment, the protein kinase is selected from the group consisting of Jak1, Jak2 and Jak3. In a particularly preferred embodiment, the protein kinase is selected from the group consisting of Jak3 and CDK4.

In other embodiments, the compounds of the present invention are used for the treatment of protein kinase-associated disorders. As used herein, the term "protein kinase-associated disorder" includes disorders and states (e.g., a disease state) that are associated with the activity of a protein kinase, e.g., CDK4 and Jak3. Non-limiting examples of a protein kinase-associated disorder include blood vessel proliferative disorders, fibrotic disorders, mesangial cell proliferative disorders, metabolic disorders, allergies, asthma, thrombosis, nervous system diseases, organ transplant rejection, autoimmune diseases, and cancer. In another embodiment, the compound of the present invention is further characterized as a modulator of a combination of protein kinases, e.g., Jak3 and CDK4.

In certain embodiments, a compound of the present invention is used for protein kinase-associated diseases, and use of the compound of the present invention as an inhibitor of any one or more protein kinases. It is envisioned that a use can be a treatment of inhibiting one or more isoforms of protein kinases.

The compounds of the invention are inhibitors of cyclin-dependent kinase enzymes (CDKs). Without being bound by theory, inhibition of the CDK4/cyclin D1 complex blocks phosphorylation of the Rb/inactive E2F complex, thereby preventing release of activated E2F and ultimately blocking E2F-dependent DNA transcription. This has the effect of inducing $G_1$ cell cycle arrest. In particular, the CDK4 pathway has been shown to have tumor-specific deregulation and cytotoxic effects.

Furthermore, the compounds of this invention have the potential to block the expansion of auto- or alloreactive T cells, and thus have beneficial effects on autoimmune diseases, as well as transplant rejections.

The present invention includes treatment of one or more symptoms of cancer, transplant rejections, and autoimmune diseases, as well as protein kinase-associated disorders, as described above, but the invention is not intended to be limited to the manner by which the compound performs its intended function of treatment of a disease. The present invention includes treatment of diseases described herein in any manner that allows treatment to occur, e.g., cancer, transplant rejections, and autoimmune diseases.

In certain embodiments, the invention provides a pharmaceutical composition of any of the compounds of the present invention. In a related embodiment, the invention provides a pharmaceutical composition of any of the compounds of the present invention and a pharmaceutically acceptable carrier or excipient of any of these compounds. In certain embodiments, the invention includes the compounds as novel chemical entities.

In one embodiment, the invention includes a packaged protein kinase-associated disorder treatment. The packaged treatment includes a compound of the invention packaged with instructions for using an effective amount of the compound of the invention for an intended use.

The compounds of the present invention are suitable as active agents in pharmaceutical compositions that are efficacious particularly for treating protein kinase-associated disorders, e.g., cancer, transplant rejections, and autoimmune diseases. The pharmaceutical composition in various embodiments has a pharmaceutically effective amount of the present active agent along with other pharmaceutically acceptable excipients, carriers, fillers, diluents and the like. The phrase, "pharmaceutically effective amount" as used herein indicates an amount necessary to administer to a host, or to a cell, issue, or organ of a host, to achieve a therapeutic result, especially the regulating, modulating, or inhibiting protein kinase activity, e.g., inhibition of the activity of a protein kinase, or treatment of cancer, transplant rejections, or autoimmune diseases.

In other embodiments, the present invention provides a method for inhibiting the activity of a protein kinase. The method includes contacting a cell with any of the compounds of the present invention. In a related embodiment, the method further provides that the compound is present in an amount effective to selectively inhibit the activity of a protein kinase.

In other embodiments, the present invention provides a use of any of the compounds of the invention for manufacture of a medicament to treat cancer, transplant rejections, or autoimmune diseases in a subject.

In other embodiments, the invention provides a method of manufacture of a medicament, including formulating any of the compounds of the present invention for treatment of a subject.

DEFINITIONS

The term "treat," "treated," "treating" or "treatment" includes the diminishment or alleviation of at least one symptom associated or caused by the state, disorder or disease being treated. In certain embodiments, the treatment comprises the induction of a protein kinase-associated disorder, followed by the activation of the compound of the invention, which would in turn diminish or alleviate at least one symptom associated or caused by the protein kinase-associated disorder being treated. For example, treatment can be diminishment of one or several symptoms of a disorder or complete eradication of a disorder.

The term "subject" is intended to include organisms, e.g., prokaryotes and eukaryotes, which are capable of suffering from or afflicted with a disease, disorder or condition associated with the activity of a protein kinase. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancer, transplant rejections, and autoimmune diseases, and for other diseases or conditions described herein. In another embodiment, the subject is a cell.

The language "protein kinase-modulating compound," "modulator of protein kinase" or "protein kinase inhibitor" refers to compounds that modulate, e.g., inhibit, or otherwise alter, the activity of a protein kinase. Examples of protein kinase-modulating compounds include compounds of Formula I, as well as Table A, Table B, Table C, Table D, Table E, and other examples as described herein (including pharmaceutically acceptable salts thereof, as well as enantiomers, stereoisomers, rotamers, tautomers, diastereomers, atropisomers or racemates thereof).

Additionally, a method of the invention includes administering to a subject an effective amount of a protein kinase-modulating compound of the invention, e.g., protein kinase-modulating compounds of Formula I, as well as Table A, Table B, Table C, Table D, Table E, and other examples as described herein (including pharmaceutically acceptable salts thereof, as well as enantiomers, stereoisomers, rotamers, tautomers, diastereomers, atropisomers or racemates thereof).

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term "alkyl" also includes alkenyl groups and alkynyl groups. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl. Moreover, the term $C_{3-6}$-cycloalkyl includes, but is not limited to, cyclopropyl, cyclopentyl, and cyclohexyl. As discussed below, these alkyl groups, as well as cycloalkyl groups, may be further substituted.

The term "halo" as used herein means halogen, and includes fluorine, chlorine, bromine, or iodine, especially fluorine and chlorine.

The term alkyl further includes alkyl groups which can further include oxygen, nitrogen, sulfur or phosphorous atoms replacing one or more carbons of the hydrocarbon backbone. In an embodiment, a straight chain or branched chain alkyl has 10 or fewer carbon atoms in its backbone (e.g., $C_1$-$C_{10}$ for straight chain, $C_3$-$C_{10}$ for branched chain), and more preferably 6 or fewer carbons. Likewise, preferred cycloalkyls have from 4-7 carbon atoms in their ring structure, and more preferably have 5 or 6 carbons in the ring structure.

Moreover, alkyl (e.g., methyl, ethyl, propyl, butyl, pentyl, hexyl, etc.) include both "unsubstituted alkyl" and "substituted alkyl", the latter of which refers to alkyl moieties having substituents replacing a hydrogen on one or more carbons of the hydrocarbon backbone, which allow the molecule to perform its intended function.

The term "substituted" is intended to describe moieties having substituents replacing a hydrogen on one or more atoms, e.g. C, O or N, of a molecule. Such substituents can include, for example, oxo, alkyl, alkoxy, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, morpholino, phenol, benzyl, phenyl, piperizine, cyclopentane, cyclohexane, pyridine, 5H-tetrazole, triazole, piperidine, or an aromatic or heteroaromatic moiety, and any combination thereof.

Further examples of substituents of the invention, which are not intended to be limiting, include moieties selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., —$NH_2$), $(CR'R'')_{0-3}CN$ (e.g., —CN), —$NO_2$, halogen (e.g., —F, —Cl, —Br, or —I), $(CR'R'')_{0-3}C(halogen)_3$ (e.g., —$CF_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., —$SO_3H$, —$OSO_3H$), $(CR'R'')_{0-3}O(CR'R'')_{0-3}H$ (e.g., —$CH_2OCH_3$ and —$OCH_3$), $(CR'R'')_{0-3}S(CR'R'')_{0-3}H$ (e.g., —SH and —$SCH_3$), $(CR'R'')_{0-3}OH$ (e.g., —OH), $(CR'R'')_{0-3}COR'$, $(CR'R'')_{0-3}$ (substituted or unsubstituted phenyl), $(CR'R'')_{0-3}(C_3$-$C_8$ cycloalkyl), $(CR'R'')_{0-3}CO_2R'$ (e.g., —$CO_2H$), or $(CR'R'')_{0-3}OR'$ group, or the side chain of any naturally occurring amino acid; wherein R' and R" are each independently hydrogen, a $C_1$-$C_5$ alkyl, $C_2$-$C_5$ alkenyl, $C_2$-$C_5$ alkynyl, or aryl group. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, oxime, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety, and any combination thereof. In certain embodiments, a carbonyl moiety (C=O) may be further derivatized with an oxime moiety, e.g., an aldehyde moiety may be derivatized as its oxime (—C=N—OH) analog. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (i.e., benzyl)).

The term "alkenyl" includes unsaturated aliphatic groups analogous in length and possible substitution to the alkyls described above, but which contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups that include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "amine" or "amino" should be understood as being broadly applied to both a molecule, or a moiety or functional group, as generally understood in the art, and may be primary, secondary, or tertiary. The term "amine" or "amino" includes compounds where a nitrogen atom is covalently bonded to at least one carbon, hydrogen or heteroatom. The terms include, for example, but are not limited to, "alkylamino," "arylamino," "diarylamino," "alkylarylamino," "alkylaminoaryl," "arylaminoalkyl," "alkaminoalkyl," "amide," "amido," and "aminocarbonyl." The term "alkyl amino" comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "aryl" includes groups, including 5- and 6-membered single-ring aromatic groups that may include from zero to four heteroatoms, for example, phenyl, pyrrole, furan, thiophene, thiazole, isothiaozole, imidazole, triazole, tetrazole, pyrazole, oxazole, isoxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, anthryl, phenanthryl, naphthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics." The aromatic ring can be substituted at one or more ring positions with such substituents as described above, as for example, alkyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrahydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

Attachment of a heterocyclyl substituent can occur via a carbon atom or via a heteroatom.

The term "acyl" includes compounds and moieties which contain the acyl radical ($CH_3CO—$) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups and may include cyclic groups such as cyclopentoxy. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "carbonyl" or "carboxy" includes compounds and moieties which contain a carbon connected with a double bond to an oxygen atom, and tautomeric forms thereof. Examples of moieties that contain a carbonyl include aldehydes, ketones, carboxylic acids, amides, esters, anhydrides, etc. The term "carboxy moiety" or "carbonyl moiety" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl moiety. For example, the term includes moieties such as, for example, aminocarbonyl moieties, (wherein a nitrogen atom is bound to the carbon of the carbonyl group, e.g., an amide), aminocarbonyloxy moieties, wherein an oxygen and a nitrogen atom are both bond to the carbon of the carbonyl group (e.g., also referred to as a "carbamate"). Furthermore, aminocarbonylamino groups (e.g., ureas) are also include as well as other combinations of carbonyl groups bound to heteroatoms (e.g., nitrogen, oxygen, sulfur, etc. as well as carbon atoms). Furthermore, the heteroatom can be further substituted with one or more alkyl, alkenyl, alkynyl, aryl, aralkyl, acyl, etc. moieties.

The term "thiocarbonyl" or "thiocarboxy" includes compounds and moieties which contain a carbon connected with a double bond to a sulfur atom. The term "thiocarbonyl moiety" includes moieties that are analogous to carbonyl moieties. For example, "thiocarbonyl" moieties include aminothiocarbonyl, wherein an amino group is bound to the carbon atom of the thiocarbonyl group, furthermore other thiocarbonyl moieties include, oxythiocarbonyls (oxygen bound to the carbon atom), aminothiocarbonylamino groups, etc.

The term "ether" includes compounds or moieties that contain an oxygen bonded to two different carbon atoms or heteroatoms. For example, the term includes "alkoxyalkyl" which refers to an alkyl, alkenyl, or alkynyl group covalently bonded to an oxygen atom that is covalently bonded to another alkyl group.

The term "ester" includes compounds and moieties that contain a carbon or a heteroatom bound to an oxygen atom that is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom that is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" include moieties with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

Additionally, the phrase "any combination thereof" implies that any number of the listed functional groups and molecules may be combined to create a larger molecular architecture. For example, the terms "phenyl," "carbonyl" (or "=O"), "—O—," "—OH," and $C_{1-6}$ (i.e., —CH$_3$ and —CH$_2$CH$_2$CH$_2$—) can be combined to form a 3-methoxy-4-propoxybenzoic acid substituent. It is to be understood that when combining functional groups and molecules to create a larger molecular architecture, hydrogens can be removed or added, as required to satisfy the valence of each atom.

It is to be understood that all of the compounds of the invention described above will further include bonds between adjacent atoms and/or hydrogens as required to satisfy the valence of each atom. That is, bonds and/or hydrogen atoms are added to provide the following number of total bonds to each of the following types of atoms: carbon: four bonds; nitrogen: three bonds; oxygen: two bonds; and sulfur: two-six bonds.

It will be noted that the structures of some of the compounds of this invention include asymmetric carbon atoms. It is to be understood accordingly that the isomers arising from such asymmetry (e.g., all enantiomers, stereoisomers, rotamers, tautomers, diastereomers, or racemates) are included within the scope of this invention. Such isomers can be obtained in substantially pure form by classical separation techniques and by stereochemically controlled synthesis. Furthermore, the structures and other compounds and moieties discussed in this application also include all tautomers thereof. Compounds described herein may be obtained through art recognized synthesis strategies.

It will also be noted that the substituents of some of the compounds of this invention include isomeric cyclic structures. It is to be understood accordingly that constitutional isomers of particular substituents are included within the scope of this invention, unless indicated otherwise. For example, the term "tetrazole" includes tetrazole, 2H-tetrazole, 3H-tetrazole, 4H-tetrazole and 5H-tetrazole.

Use in Cancer, Transplant Rejections, and Autoimmune Diseases

The compounds of the present invention have valuable pharmacological properties and are useful in the treatment of diseases. In certain embodiments, compounds of the invention are useful in the treatment of a proliferative disease, or cancer.

A proliferative disease is mainly a tumor disease (or cancer) (and/or any metastases). The inventive compounds are particularly useful for treating a tumor which is a breast cancer, genitourinary cancer, lung cancer, gastrointestinal cancer, epidermoid cancer, melanoma, ovarian cancer, pancreas cancer, neuroblastoma, head and/or neck cancer or bladder cancer, or in a broader sense renal, brain or gastric cancer; in particular (i) a breast tumor; an epidermoid tumor, such as an epidermoid head and/or neck tumor or a mouth tumor; a lung tumor, for example a small cell or non-small cell lung tumor; a gastrointestinal tumor, for example, a colorectal tumor; or a genitourinary tumor, for example, a prostate tumor (especially a hormone-refractory prostate tumor); or (ii) a proliferative disease that is refractory to the treatment with other chemotherapeutics; or (iii) a tumor that is refractory to treatment with other chemotherapeutics due to multidrug resistance.

In a broader sense of the invention, a proliferative disease may furthermore be a hyperproliferative condition such as leukemias, hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty.

Where a tumor, a tumor disease, a carcinoma or a cancer are mentioned, also metastasis in the original organ or tissue and/or in any other location are implied alternatively or in addition, whatever the location of the tumor and/or metastasis.

The inventive compound is selectively toxic or more toxic to rapidly proliferating cells than to normal cells, particularly in human cancer cells, e.g., cancerous tumors, the compound has significant antiproliferative effects and promotes differentiation, e.g., cell cycle arrest and apoptosis.

In other certain embodiments, compounds of the invention are useful in the treatment of transplant rejections. Examples of transplant rejections that may be treated by the compounds of the invention include, but are not limited to, graft versus host disease, rejection related to xeno transplantation, rejection related to organ transplant, rejection related to acute transplant, heterograft or homograft rejection and ischemic or reperfusion injury incurred during organ transplantation.

In still other certain embodiments, compounds of the invention are useful in the treatment of autoimmune diseases. Examples of autoimmune diseases to be treated by the compounds of the invention include, but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis, multiple sclerosis, neuritis, uveitis ophthalmia, polyendocrinopathies, purpura, Reiter's Disease, Stiff-Man Syndrome, autoimmune pulmonary inflammation, autism, Guillain-Barre Syndrome, insulin dependent diabetes mellitis, autoimmune inflammatory eye, autoimmune thyroiditis, hypothyroidism, systemic lupus erhythematosus, Goodpasture's syndrome, Pemphigus, Receptor autoimmunities, autoimmune hemolytic anemia, autoimmune thrombocytopenic purpura, rheumatoid arthritis, mixed connective tissue disease, polymyositis/dermatomyositis, pernicious anemia, idiopathic Addison's disease, infertility, glomerulonephritis, bullous pemphigoid, Sjogren's syndrome, diabetes millitus, adrenergic drug resistance, chronic active hepatitis, primary biliary cirrhosis, vitiligo, vasculitis, post-MI, cardiotomy syndrome, urticaria, atopic dermatitis, asthma, inflammatory myopathies, chronic active hepatitis, primary biliary cirrhosis and T-cell mediated hypersensitivity diseases.

The term "use" includes any one or more of the following embodiments of the invention, respectively: the use in the treatment of protein kinase-associated disorders; the use for the manufacture of pharmaceutical compositions for use in the treatment of these diseases, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise. In particular, diseases to be treated and are thus preferred for use of a compound of the present invention are selected from cancer, transplant rejections, or autoimmune diseases, as well as those diseases that depend on the activity of protein kinases. The term "use" further includes embodiments of compositions herein which bind to a protein kinase sufficiently to serve as tracers or labels, so that when coupled to a fluor or tag, or made radioactive, can be used as a research reagent or as a diagnostic or an imaging agent.

Assays

The inhibition of protein kinase activity by the compounds of the invention may be measured using a number of assays available in the art. Examples of such assays are described in the Exemplification section below.

Pharmaceutical Compositions

The language "effective amount" of the compound is that amount necessary or sufficient to treat or prevent a protein kinase-associated disorder, e.g. prevent the various morphological and somatic symptoms of a protein kinase-associated disorder, and/or a disease or condition described herein. In an example, an effective amount of the compound of the invention is the amount sufficient to treat a protein kinase-associated disorder in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of a protein kinase-associated disorder. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

Compounds of the invention may be used in the treatment of states, disorders or diseases as described herein, or for the manufacture of pharmaceutical compositions for use in the treatment of these diseases. Methods of use of compounds of the present invention in the treatment of these diseases, or pharmaceutical preparations having compounds of the present invention for the treatment of these diseases.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin;

absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures, of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories. Oral and/or IV administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats a protein kinase-associated disorder.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

Synthetic Procedure

Compounds of the present invention are prepared from commonly available compounds using procedures known to those skilled in the art, including any one or more of the following conditions without limitation:

Within the scope of this text, only a readily removable group that is not a constituent of the particular desired end product of the compounds of the present invention is designated a "protecting group," unless the context indicates otherwise. The protection of functional groups by such protecting groups, the protecting groups themselves, and their cleavage reactions are described for example in standard reference works, such as e.g. Science of Synthesis: Houben-Weyl Methods of Molecular Transformation. Georg Thieme Verlag, Stuttgart, Germany. 2005. 41627 pp. (URL: http://www.science-of-synthesis.com (Electronic Version, 48 Volumes)); J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide und Derivate" (*Chemistry of Carbohydrates: Monosaccharides and Derivatives*), Georg Thieme Verlag, Stuttgart 1974. A characteristic of protecting groups is that they can be removed readily (i.e., without the occurrence of undesired secondary reactions) for example by solvolysis, reduction, photolysis or alternatively under physiological conditions (e.g., by enzymatic cleavage).

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g., the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g., by treating the compounds with an acid or a suitable anion exchange reagent. Internal salts of compounds of the present invention containing acid and basic salt-forming groups, e.g., a free carboxy group and a free amino group, may be formed, e.g., by the neutralisation of salts, such as acid addition salts, to the isoelectric point, e.g., with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g., using chromatographic methods, distribution methods, (re-) crystallization, and the like.

General Process Conditions

The following applies in general to all processes mentioned throughout this disclosure.

The process steps to synthesize the compounds of the invention can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g., in the H$^+$ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described in Science of Synthesis: Houben-Weyl Methods of Molecular Transformation. Georg Thieme Verlag, Stuttgart, Germany. 2005.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

Prodrugs

This invention also encompasses pharmaceutical compositions containing, and methods of treating protein kinase-associated disorders through administering, pharmaceutically acceptable prodrugs of compounds of the compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

Any reference to a compound of the present invention is therefore to be understood as referring also to the corresponding pro-drugs of the compound of the present invention, as appropriate and expedient.

Combinations

A compound of the present invention may also be used in combination with other agents, e.g., an additional protein kinase inhibitor that is or is not a compound of the invention, for treatment of a protein kinase-associated disorder in a subject.

By the term "combination" is meant either a fixed combination in one dosage unit form, or a kit of parts for the combined administration where a compound of the present invention and a combination partner may be administered independently at the same time or separately within time intervals that especially allow that the combination partners show a cooperative, e.g., synergistic, effect, or any combination thereof.

The compounds of the invention may be administered, simultaneously or sequentially, with an antiinflammatory, antiproliferative, chemotherapeutic agent, immunosuppressant, anti-cancer, cytotoxic agent or kinase inhibitor other than a compound of the Formula I or salt thereof. Further examples of agents that may be administered in combination with the compounds of the invention include, but are not limited to, a PTK inhibitor, cyclosporin A, CTLA4-Ig, antibodies selected from anti-ICAM-3, anti-IL-2 receptor, anti-CD45RB, anti-CD2, anti-CD3, anti-CD4, anti-CD80, anti-CD86, and monoclonal antibody OKT3, agents blocking the interaction between CD40 and gp39, fusion proteins constructed from CD40 and gp39, inhibitors of NF-kappa B function, non-steroidal antiinflammatory drugs, steroids, gold compounds, antiproliferative agents, FK506, mycophenolate mofetil, cytotoxic drugs, TNF-α inhibitors, anti-TNF antibodies or soluble TNF receptor, rapamycin, leflunimide, cyclooxygenase-2 inhibitors, paclitaxel, cisplatin, carboplatin, doxorubicin, caminomycin, daunorubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin, etoposide, etoposide phosphate, teniposide, melphalan, vinblastine, vincristine, leurosidine, epothilone, vindesine, leurosine, or derivatives thereof.

The compound of the invention and any additional agent may be formulated in separate dosage forms. Alternatively, to decrease the number of dosage forms administered to a patient, the compound of the invention and any additional agent may be formulated together in any combination. For example, the compound of the invention inhibitor may be formulated in one dosage form and the additional agent may be formulated together in another dosage form. Any separate dosage forms may be administered at the same time or different times.

Alternatively, a composition of this invention comprises an additional agent as described herein. Each component may be present in individual compositions, combination compositions, or in a single composition.

EXEMPLIFICATION OF THE INVENTION

The invention is further illustrated by the following examples, which should not be construed as further limiting. The practice of the present invention will employ, unless otherwise indicated, conventional techniques of cell biology, cell culture, molecular biology, transgenic biology, microbiology and immunology, which are within the skill of the art.

General Synthesis Methods

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

LIST OF ABBREVIATIONS

BINAP (±)-(1,1'-binaphthalene-2-2'diyl)bis(diphenylphosphine)
DIEA Diethylamine
DIPEA Diisoproylethylamine
DMF Dimethylformamide
HPLC High pressure liquid chromatography
HRMS High resolution mass spectrometry
HBTU O-Benzotriazol-1-yl-N,N,N',N'-tetramethyluronium hexafluorophosphate
HOBt 1-Hydroxy-1H-benzotriazol
LC/MS Liquid chromatography/mass spectrometry
NMM N-methylmorpholine
NMP N-methylpyrrolidine
RT room temperature
THF Tetrahydrofuran
Et Ethyl
NBS N-Bromosuccinimide
DIAD Diisopropyl azo dicarboxylate
Ts Tosyl
TBAF Tetra-n-butylammonium fluoride

EXAMPLE 1

(5-Bromo-2-chloro-pyrimidin-4-yl)-(1-ethyl-propyl)-amine

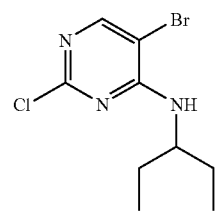

To a solution of 5-Bromo-2,4-dichloropyrimidine (4.56 g, 20 mmol) in Ethanol (9 mL) is added 1-Ethylpropylamine (2.6 mL, 22 mmol) and DIEA (7 mL, 40 mmol) at ambient temperature. The reaction mixture is stirred at ambient temperature for 16 hrs, then is concentrated in vacuo and the residue is purified by flash chromatography (silica gel, ethyl acetate:hexane=3:97 to 30:70) to give (5-Bromo-2-chloro-pyrimidin-4-yl)-(1-ethyl-propyl)-amine. MS (ESI) m/z 280 (M+H)$^+$. $^1$H NMR (CDCl$_3$, 400 MHz) δ 8.1 (s, 1H), 5.24 (d, 1H), 4.1 (m, 1H), 1.58 (m, 4H), 0.93 (t, 6H).

EXAMPLE 2

Tributyl-((Z)-2-ethoxy-vinyl)-stannane

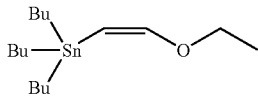

To a solution of Ethyl ethynyl ether (2.26 mL, 50% in hexane, 15 mmol) in toluene (40 mL) is added Tri-n-butyl hydride (2.7 mL, 10 mmol) and AIBN (81 mg, 0.5 mmol) at ambient temperature. The reaction mixture is heated at 100° C. for 16 hrs. After cooling down, the mixture is concentrated in vacuo to give tributyl-((Z)-2-ethoxy-vinyl)-stannane. The crude product is used as is.

EXAMPLE 3

[2-Chloro-5-((Z)-2-ethoxy-vinyl)-pyrimidin-4-yl]-(1-ethyl-propyl)-amine

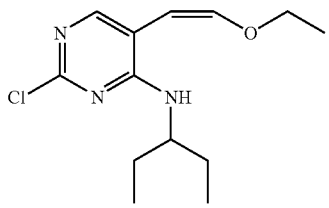

To a solution of crude compound from example 2 (4.25 g, ~75%, 8.8 mmol) in CH$_3$CN (10 mL) is added (5-Bromo-2-chloro-pyrimidin-4-yl)-(1-ethyl-propyl)-amine (2.25 g, 8 mmol), Et$_4$NCl (1.33 g, 8 mmol) and Pd(PPh$_3$)$_2$Cl$_2$ (280 mg, 0.4 mmol) at ambient temperature. The reaction mixture is purged with N$_2$, sealed in a microwave reactor and heated at 100° C. for 17 mins. After cooling down the mixture is concentrated in vacuo and the residue is purified by flash chromatography (silica gel, ethyl acetate:hexane=5:95 to 40:60) to give [2-Chloro-5-((Z)-2-ethoxy-vinyl)-pyrimidin-4-yl]-(1-ethyl-propyl)-amine. MS (ESI) m/z 270 (M+H)$^+$. $^1$H NMR (CDCl$_3$, 400 MHz). δ 8.02 (s, 1H), 6.26 (d, 1H), 5.46 (d, 1H), 4.91 (d, 1H), 4.16 (m, 1H), 3.99 (q, 2H), 1.60-1.69 (m, 2H), 1.43-1.52 (m, 2H), 1.32 (t, 3H), 0.92 (t, 6H).

EXAMPLE 7

2-Chloro-7-(1-ethyl-propyl)-7H-pyrrolo[2,3-d]pyrimidine

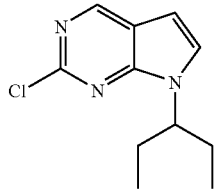

To a solution of [2-Chloro-5-((Z)-2-ethoxy-vinyl)-pyrimidin-4-yl]-(1-ethylpropyl)-amine (1.1 g, 4.07 mmol) in EtOH (8 mL) is added concentrated HCl (0.1 mL) at ambient temperature. The reaction mixture is sealed in a microwave reactor and heated at 100° C. for 10 mins. After cooling down the mixture is concentrated in vacuo to provide 2-Chloro-7-(1-ethyl-propyl)-7H-pyrrolo[2,3-d]pyrimidine. The crude product is used as it is. The material can be purified by flash chromatography (SiO$_2$, EtOAc:Hexane=1:5).

MS (ESI) m/z 224 (M+H)$^+$. $^1$H NMR (CDCl$_3$, 400 MHz). δ 8.87 (s, 1H), 7.30 (d, 1H), 6.69 (d, 1H), 4.69 (m, 1H), 1.77-1.99 (m, 4H), 0.77 (t, 6H).

EXAMPLE 8

5,5-Dibromo-2-chloro-7-(1-ethyl-propyl)-5,7-dihydro-pyrrolo[2,3-d]pyrimidin-6-one

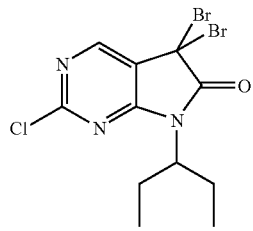

To a mixture of 2-Chloro-7-(1-ethyl-propyl)-7H-pyrrolo[2,3-d]pyrimidine (crude, ~4.07 mmol) in t-BuOH (7 mL) is added 2 mL of H$_2$O at ambient temperature, then NBS (2.28 g, 12.8 mmol) is added to the orange color solution. The mixture is stirred at 28-30° C. for 2.5 hrs, then is concentrated and taken up in ethyl acetate, washed with NaHCO$_3$ aqueous solution, and brine. The organics are dried with Na$_2$SO$_4$, filtered and concentrated to provide 5,5-Dibromo-2-chloro-7-(1-ethyl-propyl)-5,7-dihydro-pyrrolo[2,3-d]pyrimidin-6-one. The crude product is used as it is.

MS (ESI) m/z 398 (M+H)$^+$.

EXAMPLE 9

2-Chloro-7-(1-ethyl-propyl)-5,7-dihydro-pyrrolo[2,3-d]pyrimidin-6-one

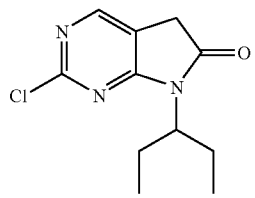

To a solution of 5,5-Dibromo-2-chloro-7-(1-ethyl-propyl)-5,7-dihydro-pyrrolo[2,3-d]pyrimidin-6-one (crude, ~5.3 mmol) in acetic acid (6 mL) and THF (4 mL) is added Zn dust (1.37 g, 21 mmol) at 0° C. The mixture is stirred at 0° C. for 2 mins then heated to room temperature, stirring for 30 mins. The mixture is filtered through celite, rinsed with ethyl acetate. The filtrate is concentrated in vacuo and the residue is purified by flash chromatography (ethyl acetate:hexane=5:95 to 40:60) to give 2-Chloro-7-(1-ethyl-propyl)-5,7-dihydro-pyrrolo[2,3-d]pyrimidin-6-one.

MS (ESI) m/z 240 (M+H)$^+$. $^1$H NMR (CDCl$_3$, 400 MHz). δ 8.17 (s, 1H), 4.20 (m, 1H), 3.58 (s, 2H), 2.10 (m, 2H), 1.84 (m, 2H), 0.84 (t, 6H).

EXAMPLES 10-13

By repeating the procedures described in example 6-9, using appropriate starting materials, the following compounds are obtained.

| Structure | MS (m/z) (M + 1) |
|---|---|
| (2-chloro, N-cyclopropyl pyrrolopyrimidinone) | 210 |
| (2-chloro, N-cyclohexyl pyrrolopyrimidinone) | 252 |
| (2-chloro, N-cyclopentyl pyrrolopyrimidinone) | 238 |
| (2-chloro, N-(1-phenylpropyl) pyrrolopyrimidinone) | 288 |

EXAMPLE 14

(3-Amino-phenyl)-(4-methyl-piperazin-1-yl)-methanone

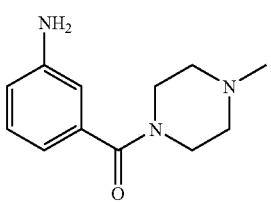

A solution of 3-aminobenzoic acid (1.51 g, 11 mmol), 1-methylpiperazine (1.1 mL, 10 mmol), EDCI.HCl (2.87 g, 15 mmol) and Et$_3$N (2.8 mL, 20 mmol) in CH$_2$Cl$_2$ (10 mL) is stirred at room temperature for 20 hours. Then saturated NaHCO$_3$ aqueous solution is added. The aqueous layer was extracted with CH$_2$Cl$_2$, and the organic extracts were dried over Na$_2$SO$_4$, filtered and concentrated under reduced pressure. The crude product is purified by column chromatography (SiO$_2$, MeOH:CH$_2$Cl$_2$=0.7:99.3 to 6:93) to give 1.75 g of the title compound as a yellow solid.

MS (ESI) m/z 220 (M+H)$^+$

EXAMPLES 15-20

By repeating the procedures described in example 14, using appropriate starting materials, the following compounds are obtained.

| Structure | MS (m/z) (M + 1) |
|---|---|
| (3-amino-4-methoxyphenyl morpholinyl methanone) | 237 |

-continued

| Structure | MS (m/z) (M + 1) |
|---|---|
| 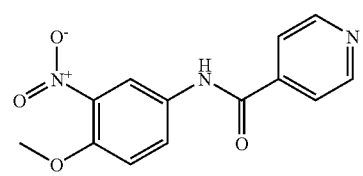 | 250 |
| 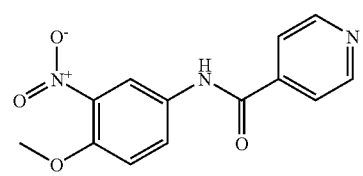 | 225 |
| 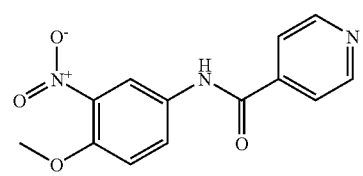 | 238 |
| 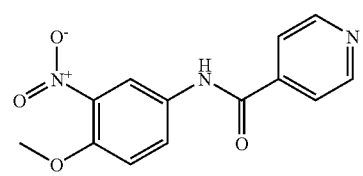 | 207 |
| 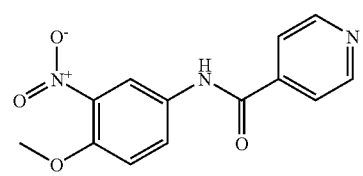 | 220 |

EXAMPLE 21

N-(4-Methoxy-3-nitro-phenyl)-isonicotinamide

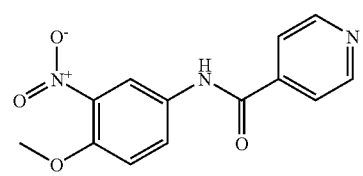

A mixture of 4-methoxy-3-nitroaniline (168 mg, 1 mmol) and Isonicotinoyl chloride hydrogen chloride (267 mg, 0.2 M in 1.5 mmol) in pyridine (1 mL) is sealed in a microwave reactor and heated at 100° C. under microwave radiation for 5 mins. Then 1N NaOH aqueous solution is added to the reaction mixture. After stirring at room temperature for several minutes, the mixture is filtered. The solid is washed with $H_2O$ and air dried to give 263 mg of the title compound as a yellow solid.

MS (ESI) m/z 274 (M+H)$^+$

EXAMPLE 22

N-(4-Fluoro-3-nitro-phenyl)-isonicotinamide

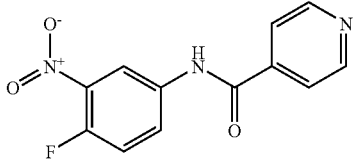

The same procedure is repeated as described in example 21 to give the title compound as a pink solid.

MS (ESI) m/z 262 (M+H)$^+$.

EXAMPLE 23

N-(3-Amino-4-fluoro-phenyl)-isonicotinamide

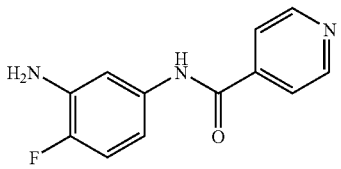

A mixture of 4-fluoro-3-nitroaniline (100 mg, 0.38 mmol) and Tin chloride (180 mg, 0.95 mmol) in EtOH (1 mL) with 4 drops of concentrated HCl is heated at 80° C. for 4 hour. Then saturated $NaHCO_3$ aqueous solution is added. The aqueous layer was extracted with EtOAc, and the organic extracts are washed with brine, dried over $Na_2SO_4$, filtered and concentrated under reduced pressure. The crude product is purified by column chromatography (SiO2, MeOH:$CH_2Cl_2$=1:99 to 10:90) to give 55.5 mg of the title compound as yellow solid.

MS (ESI) m/z 232 (M+H)$^+$

EXAMPLE 24

N-(3-Amino-4-methoxy-phenyl)-isonicotinamide

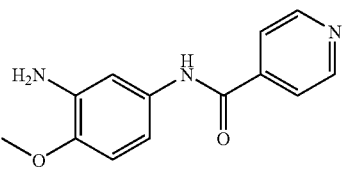

The same procedure can be repeated as described in example 23 to give the title compound as a pink solid.

MS (ESI) m/z 244 (M+H)$^+$.

EXAMPLE 25

1-(4-Nitro-phenyl)-piperidin-4-one

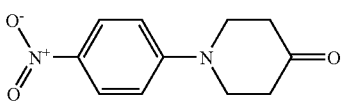

To a solution of 1-(4-Nitro-phenyl)-piperidin-4-ol (100 mg, 0.45 mmol) in $CH_2Cl_2$ (2 mL) is added Dess-Martin periodinane (286 mg, 0.675 mmol) at for 2.5 hours. The reaction is quenched with 1N NaOH aqueous solution. The aqueous layer is extracted with $CH_2Cl_2$, and the organic extracts are dried over $Na_2SO_4$, filtered and concentrated under reduced pressure. The crude product is purified by column chromatography (SiO2, EtOAc:Hexane=12:88 to 100:0) to give 84 mg of the title compound as a white solid.

MS (ESI) m/z 221 (M+H)$^+$

EXAMPLE 26

1-Methyl-4-[1-(4-nitro-phenyl)-piperidin-4-yl]piperazine

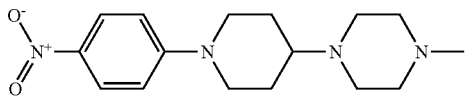

A mixture of 1-(4-Nitro-phenyl)-piperidin-4-one (84 mg, 0.38 mmol) and 1-methylpiperazine (0.085 mL, 0.76 mmol) in MeOH (2 mL) is stirred at room temperature for 5 hours. Then to the reaction mixture is added 0.2 mL of HOAc, followed by $NaCNBH_3$ (72 mg, 1.14 mmol). The mixture is stirred at room temperature for 0.5 hour, then concentrated. The residue is taken up in EtOAc, washed with saturated $NaHCO_3$ aqueous solution and brine, dried over $Na_2SO_4$, filtered and concentrated under reduced pressure. The crude product is purified by column chromatography (SiO2, 2N $NH_3$ in MeOH:$CH_2Cl_2$=1:99 to 10:90) to give 46 mg of the title compound as a yellow solid.

MS (ESI) m/z 305 (M+H)$^+$

EXAMPLE 27

4-[4-(4-Methyl-piperazin-1-yl)-piperidin-1-yl]-phenylamine

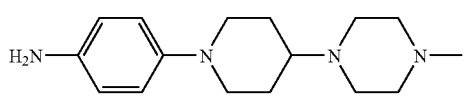

A suspension of 1-Methyl-4-[1-(4-nitro-phenyl)-piperidin-4-yl]-piperazine-(46 mg, 0.15 mmol) and Pd/C (10%, 8 mg) in MeOH (2 mL) is stirred at room temperature under $H_2$ (balloon pressure) for 16 hours, then filtered through celite, washed with EtOAc, concentrated under reduced pressure to give 42 mg of the title compound as a light grey solid.

MS (ESI) m/z 275 (M+H)$^+$

EXAMPLE 28

Benzoic acid 1-(4-amino-phenyl)-piperidin-4-yl ester

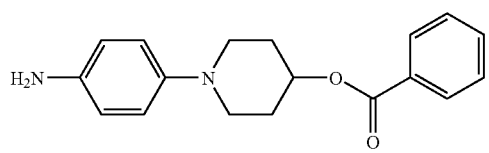

The same procedure is repeated as described in example 23 to give the title compound as a pink solid.

MS (ESI) m/z 297 (M+H)$^+$.

EXAMPLE 29

3-(2-Pyrrolidin-1-yl-ethoxy)-phenylamine

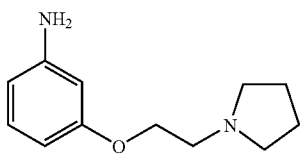

To a mixture of $PPh_3$ (866 mg, 3.3 mmol) in THF (6 mL) is added DIAD (0.65 mL, 3.3 mmol) at 0° C. The suspension was stirred for 10 minutes, then heated to room temperature. To the mixture, 4-nitrophenol (460 mg, 3.3 mmol) and 1-(2-hydroxyethyl)-pyrrolidine (0.26 mL, 2.2 mmol) is added, and the mixture is stirred at room temperature for 16 hours, then concentrated. The residue is taken up in EtOAc, washed with 1N NaOH aqueous solution and brine, dried over $Na_2SO_4$, filtered and concentrated under reduced pressure. The crude product is purified by column chromatography (SiO2, MeOH:$CH_2Cl_2$=1:99 to 10:90) to give 277 mg of 1-[2-(4-Nitro-phenoxy)-ethyl]-pyrrolidine as a white solid.

MS (ESI) m/z 237 (M+H)$^+$

The same procedure is repeated as described in example 27 by using 1-[2-(4-Nitro-phenoxy)-ethyl]-pyrrolidine as a starting material to give the title compound as a yellow oil.

MS (ESI) m/z 207 (M+H)$^+$.

EXAMPLE 30-33

By repeating the procedures described in example 29, using appropriate starting materials, the following compounds are obtained.

| Structure | MS (m/z) (M + 1) |
|---|---|
| 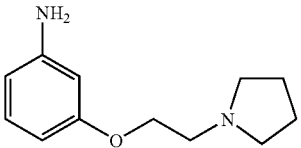 | 207 |
| 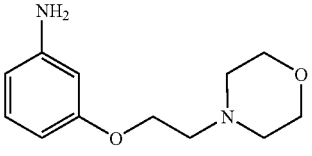 | 223 |
| 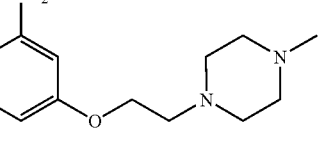 | 236 |
| 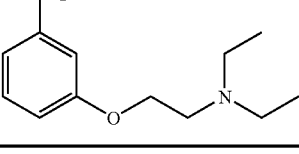 | 209 |

EXAMPLE 34

(3-Nitro-phenyl)-(2-pyrrolidin-1-yl-ethyl)-amine

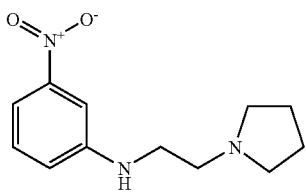

The mixture of 1-fluoro-3-nitrobenzene (420 mg, 3 mmol) in DMF (1.5 mL), N-(2-aminoethyl)-pyrrolidine (514 mg, 4.5 mmol) and Cs$_2$CO$_3$ (977 mg, 3 mmol) is heated at 100° C. under microwave radiation for 2.5 hours, then concentrated. The mixture is diluted with EtOAc, washed with saturated NaHCO$_3$ aqueous solution and brine, dried over Na$_2$SO$_4$, filtered and concentrated under reduced pressure. The crude product is purified by column chromatography (SiO2, MeOH:CH$_2$Cl$_2$=1:99 to 10:90) to give 130 mg of the title compound as a light brown oil.

MS (ESI) m/z 236 (M+H)$^+$

EXAMPLE 35

[2-(4-Methyl-piperazin-1-yl)-ethyl]-(3-nitro-phenyl)-amine

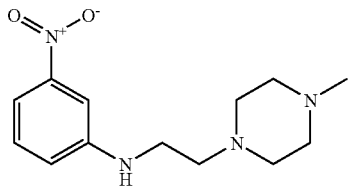

The same procedure is repeated as described in example 34 to give the title compound as a yellow oil.

MS (ESI) m/z 265 (M+H)$^+$.

EXAMPLE 36

N-(2-Pyrrolidin-1-yl-ethyl)-benzene-1,3-diamine

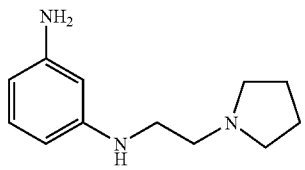

The same procedure is repeated as described in example 27 to give the title compound as a light brown oil.

MS (ESI) m/z 206 (M+H)$^+$.

EXAMPLE 37

N-[2-(4-Methyl-piperazin-1-yl)-ethyl]-benzene-1,3-diamine

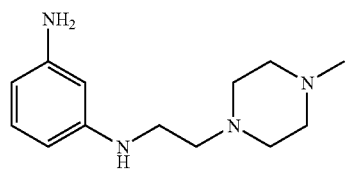

The same procedure is repeated as described in example 27 to give the title compound as a light brown oil.

MS (ESI) m/z 235 (M+H)$^+$.

EXAMPLE 38

1-Methyl-4-(6-nitro-pyridin-3-yl)-piperazine

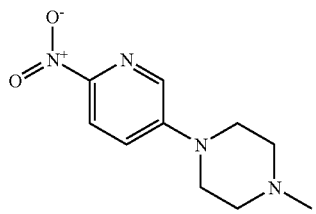

A mixture of 5-bromo-2-nitropyridine (500 mg, 2.46 mmol) and 1-methylpiperazine (1 mL) is heated at 80° C. for 2 hour. Then water is added. The aqueous layer is extracted with EtOAc, and the organic extracts were washed with brine, dried over $Na_2SO_4$, filtered and concentrated under reduced pressure. The crude product is purified by column chromatography (SiO2, MeOH:$CH_2Cl_2$=0.7:99.3 to 6:93) to give 520 mg of the title compound as yellow solid.

MS (ESI) m/z 223 (M+H)$^+$

EXAMPLE 39

1-[4-(6-Nitro-pyridin-3-yl)-piperazin-1-yl]-ethanone

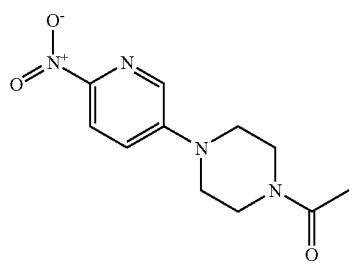

To a mixture of 5-bromo-2-nitropyridine (406 mg, 2 mmol) and 1-acetylpiperazine (256 mg, 2 mmol) in toluene (5 mL) is added $Cs_2CO_3$, then Pd2(dba)3 (74 mg, 0.08 mmol) and BINAP (100 mg, 0.16 mmol) are added. The mixture is degassed, and heated at 100° C. for 16 hours. Then the mixture is cooled down to room temperature, diluted with EtOAc, and filtered through celite. The filtrate is concentrated under reduced pressure. The crude product is purified by column chromatography (SiO2, MeOH:$CH_2Cl_2$=0.7:99.3 to 6:93) to give 270 mg of the title compound as yellow solid.

MS (ESI) m/z 251 (M+H)$^+$

EXAMPLE 40

5-(4-Methyl-piperazin-1-yl)-pyridin-2-ylamine

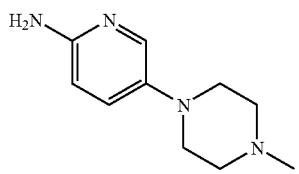

The same procedure is repeated as described in example 27 to give the title compound as a light brown solid.

MS (ESI) m/z 193 (M+H)$^+$.

EXAMPLE 41

1-[4-(6-Amino-pyridin-3-yl)-piperazin-1-yl]-ethanone

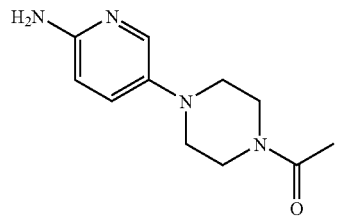

The same procedure is repeated as described in example 27 to give the title compound as a brown solid.

MS (ESI) m/z 221 (M+H)$^+$.

EXAMPLE 42

1-[4-(4-Nitro-phenyl)-piperidin-1-yl]-ethanone

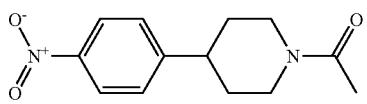

To a solution of 4-(4-Nitro-phenyl)-piperidin (206 mg, 1 mmol) in $CH_2Cl_2$ (3 mL) is added AcCl (0.106 mL, 1.5 mmol) at 0° C. Then $Et_3N$ (0.253 mL, 1.8 mmol) is added slowly. The mixture is stirred at 0° C. for 10 minutes. Then saturated $NaHCO_3$ aqueous solution is added. The aqueous layer is extracted with $CH_2Cl_2$, and the organic extracts are dried over $Na_2SO_4$, filtered and concentrated under reduced pressure. The crude product is purified by column chromatography (SiO$_2$, MeOH:$CH_2Cl_2$=0.7:99.3 to 6:93) to give 273 mg of the title compound as yellow solid.

MS (ESI) m/z 249 (M+H)$^+$

EXAMPLE 43

1-[4-(4-Amino-phenyl)-piperidin-1-yl]-ethanone

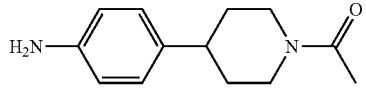

The same procedure is repeated as described in example 27 to give the title compound as a yellow solid.

MS (ESI) m/z 219 (M+H)$^+$.

EXAMPLE 44

7-(1-Ethyl-propyl)-2-[3-fluoro-4-(4-methyl-piperazin-1-yl)-phenylamino]-5,7-dihydro-pyrrolo[2,3-d]pyrimidin-6-one

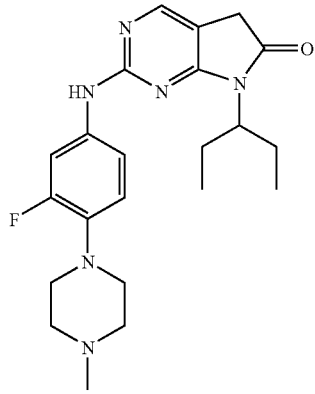

To a mixture of 2-Chloro-7-(1-ethyl-propyl)-5,7-dihydro-pyrrolo[2,3-d]pyrimidin-6-one (18 mg, 0.075 mmol) and TsOH (1.12 ml, 0.2 M in 1,4 dioxane) is added 3-Fluoro-4-(4-methylpiperazin)aniline (23.5 mg, 0.1125 mmol), and DMF (0.25 mL) at ambient temperature. The reaction mixture is sealed in a microwave reactor and heated at 140° C. for 30 mins. The mixture is diluted with EtOAc, washed with NaHCO$_3$ aqueous solution and brine, dried (Na$_2$SO4), filtered and concentrated. The crude product is purified by prep-HPLC to give 27 mg of the title compound as a brown solid.

MS (ESI) m/z 413 (M+H)$^+$.

$^1$H NMR (DMSO, 400 MHz). δ 9.48 (s, 1H), 8.09 (s, 1H), 7.72 (d, 1H), 7.34 (d, 1H), 6.96 (t, 1H), 4.08 (m, 1H), 3.60 (s, 2H), 2.96 (s, 4H), 2.51 (s, 2H), 2.10 (m, 2H), 1.78 (m, 2H), 0.79 (t, 6H).

EXAMPLES 45-90

By repeating the procedures described in example 44, using appropriate starting materials, the following compounds are obtained.

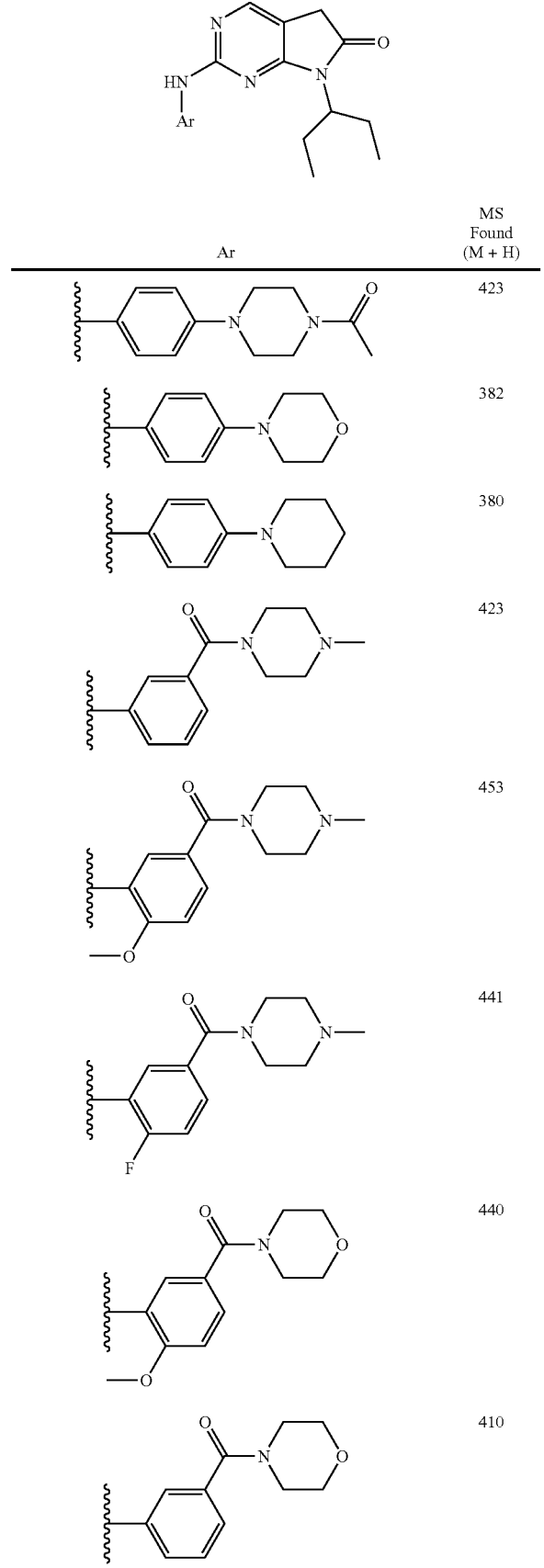

| Ar | MS Found (M + H) |
|---|---|
| 3-(morpholine-4-carbonyl)-4-fluorophenyl | 428 |
| 4-(morpholine-4-carbonyl)phenyl | 410 |
| 4-(4-methylpiperazine-1-carbonyl)phenyl | 423 |
| 6-(4-methylpiperazin-1-yl)pyridin-3-yl | 396 |
| 4-acetamidophenyl | 354 |
| N-(isonicotinoyl)-3-amino-4-methoxyphenyl | 447 |
| N-(isonicotinoyl)-3-amino-4-fluorophenyl | 435 |

| Ar | MS Found (M + H) |
|---|---|
| 3-(isonicotinamido)phenyl | 417 |
| 4-(4-methylphenylsulfonamido)phenyl | 466 |
| 4-(4-methylpiperazin-1-ylsulfonyl)phenyl | 459 |
| 4-(4-(methylsulfonyl)piperazin-1-yl)phenyl | 459 |
| 4-(N-(pyridin-2-yl)sulfamoyl)phenyl | 382 |
| 4-(1H-1,2,4-triazol-1-yl)phenyl | 364 |
| 3-(4-methyl-4H-1,2,4-triazol-3-yl)phenyl | 378 |
| 1H-indazol-6-yl | 337 |
| 4-(4-(benzoyloxy)piperidin-1-yl)phenyl | 500 |

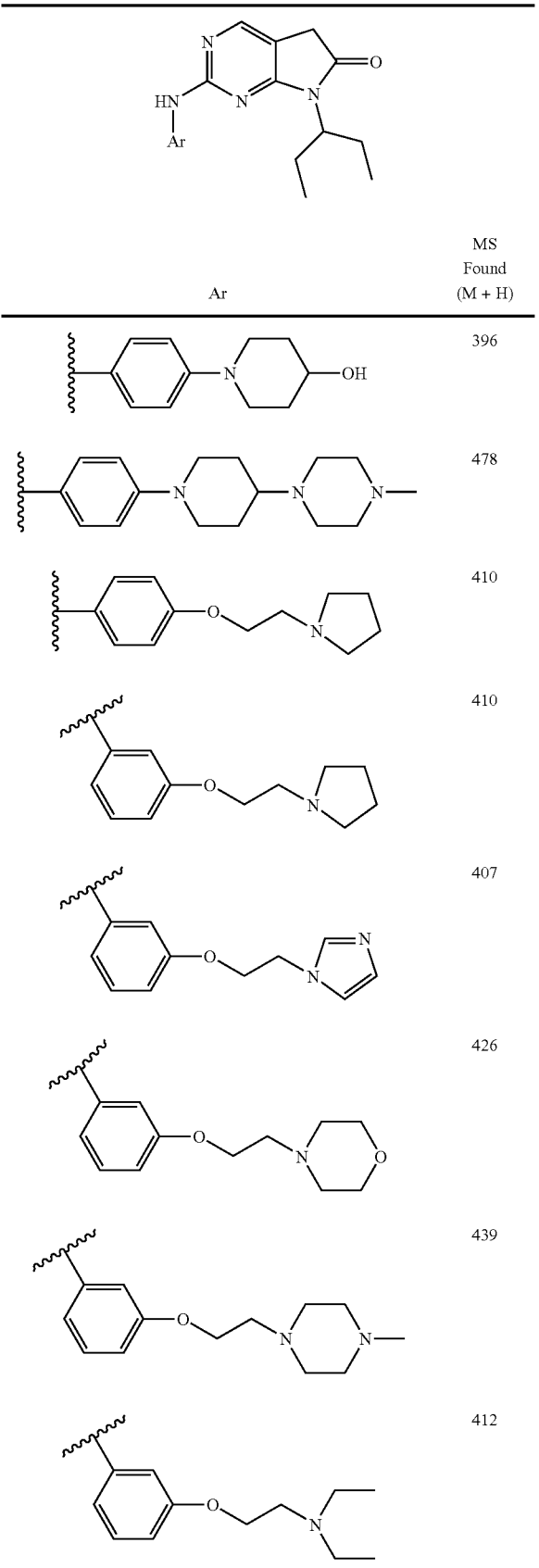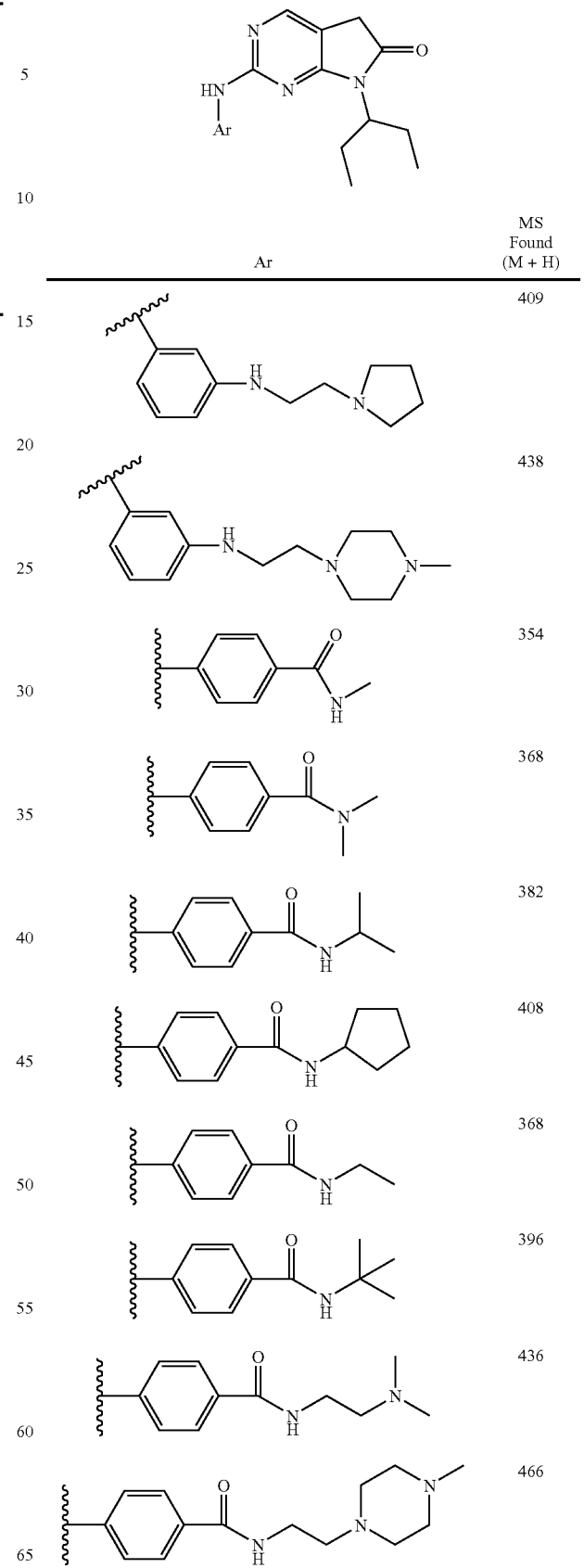

97
-continued

| Ar | MS Found (M + H) |
|---|---|
| 4-(piperidinylethylaminocarbonyl)phenyl | 451 |
| 6-(4-methylpiperazin-1-yl)pyridin-3-yl | 396 |
| 6-(4-acetylpiperazin-1-yl)pyridin-3-yl | 424 |

EXAMPLES 91-93

By repeating the procedures described in example 44, using appropriate starting materials, the following compounds are obtained.

| Ar | MS Found (M + H) |
|---|---|
| 4-(4-acetylpiperazin-1-yl)phenyl | 455 |
| 3-(2-pyrrolidin-1-ylethoxy)phenyl | 458 |

98
-continued

| Ar | MS Found (M + H) |
|---|---|
| 3-(2-imidazol-1-ylethoxy)phenyl | 407 |

EXAMPLES 94-97

By repeating the procedures described in example 44, using appropriate starting materials, the following compounds are obtained.

| Ar | MS Found (M + H) |
|---|---|
| 4-(morpholin-4-ylcarbonyl)phenyl | 380 |
| 4-morpholin-4-ylphenyl | 352 |
| 4-(4-methylpiperazin-1-yl)phenyl | 365 |
| 3-(4-methylpiperazin-1-ylcarbonyl)phenyl | 393 |

EXAMPLE 98-99

By repeating the procedures described in example 44, using appropriate starting materials, the following compounds are obtained.

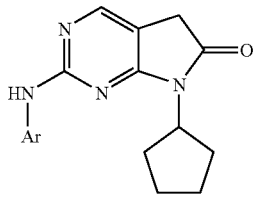

| Ar | MS Found (M + H) |
|---|---|
| 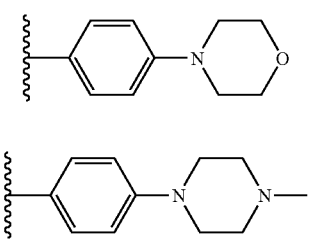 (top: morpholine-phenyl) | 380 |
| (bottom: 4-methylpiperazine-phenyl) | 393 |

EXAMPLES 100-101

By repeating the procedures described in example 44, using appropriate starting materials, the following compounds are obtained.

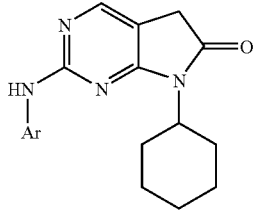

| Ar | MS Found (M + H) |
|---|---|
| 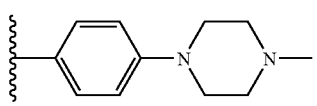 | 407 |
| 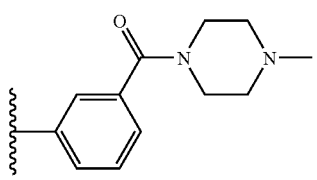 | 435 |

EXAMPLE 102

1-(1-{4-[7-(1-Ethyl-propyl)-7H-pyrrolo[2,3-d]pyrimidin-2-ylamino]-phenyl}-piperidin-4-yl)-ethanone

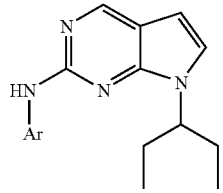

To a mixture of 1-[4-(4-Amino-phenyl)-piperazin-1-yl]-ethanone (70.5 mg, 0.32 mmol) and NaOtBu (38.4 mg, 0.4 mmol) in 1,4-dioxane (0.3 mL) is added a solution of 2-Chloro-7-(1-ethyl-propyl)-7H-pyrrolo[2,3-d]pyrimidine (60 mg, 0.26 mmol) in 1,4-dioxane (0.6 mL) and a suspension of $Pd_2(dba)_3$ (12.2 mg, 0.013 mmol) and BINAP (16.6 mg, 0.026 mmol). The mixture is degassed, and heated at 100° C. for 3 hours. Then the mixture is cooled down to room temperature, diluted with EtOAc, and filtered through celite. The filtrate is concentrated under reduced pressure. The crude product is purified prep-HPLC to give 84.9 mg of the title compound as pale white solid.

MS (ESI) m/z 407 (M+H)$^+$

EXAMPLE 103-117

By repeating the procedures described in example 102, using appropriate starting materials, the following compounds are obtained.

| Ar | MS Found (M + H) |
|---|---|
| 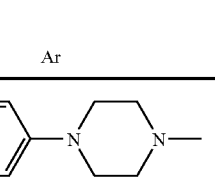 | 395 |

101
-continued
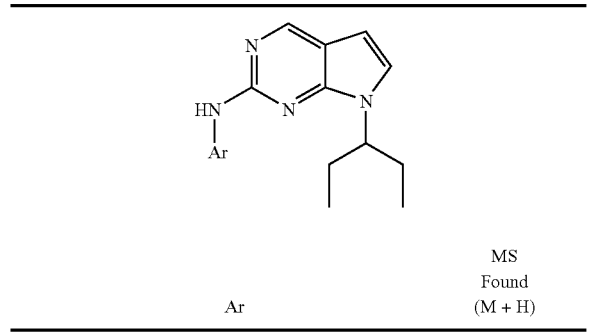
| Ar | MS Found (M + H) |
|---|---|
| 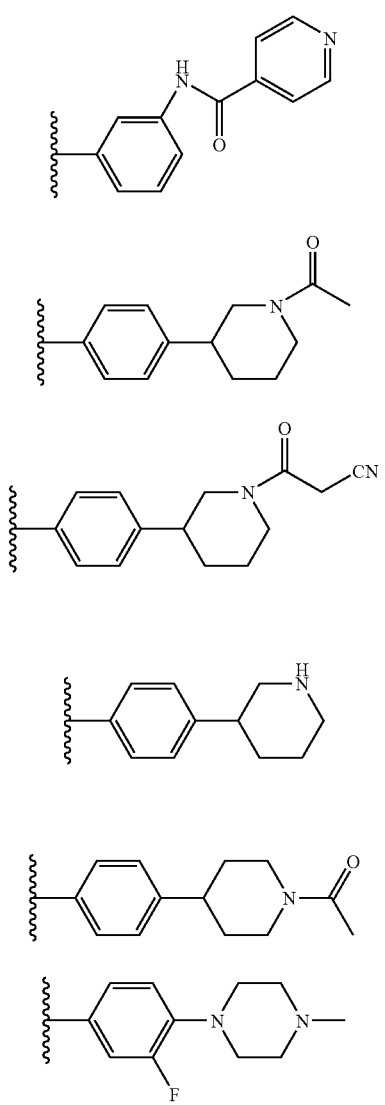 | 417 |
| | 406 |
| | 431 |
| | 364 |
| | 406 |
| | 397 |
| | 380 |
| | 408 |
102
-continued
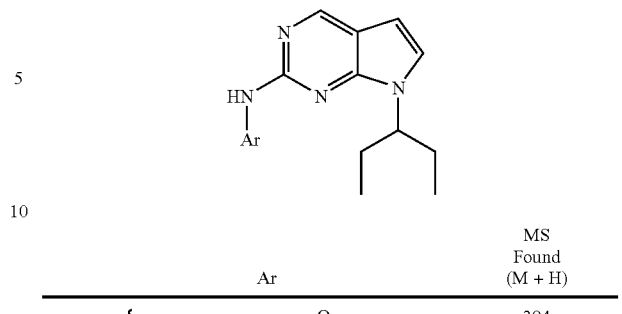
| Ar | MS Found (M + H) |
|---|---|
| 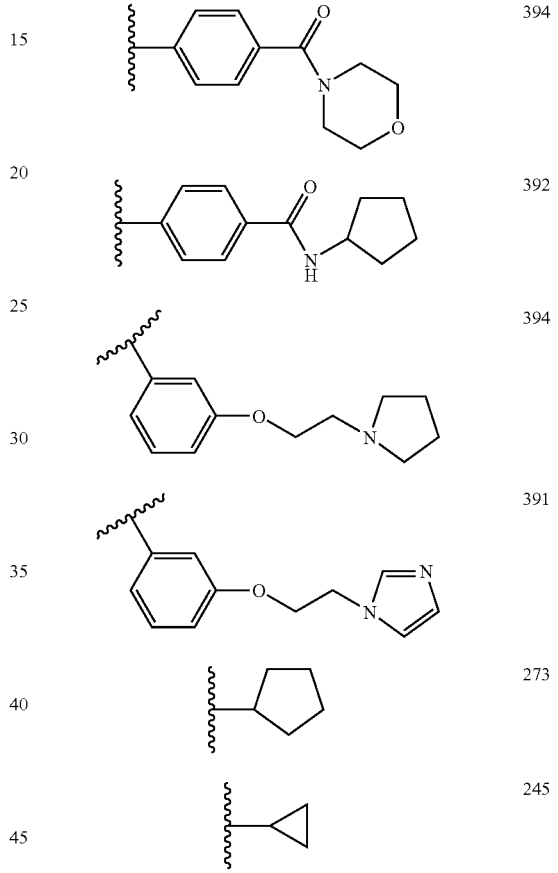 | 394 |
| | 392 |
| | 394 |
| | 391 |
| | 273 |
| | 245 |
EXAMPLE 118
(2-Chloro-5-nitro-pyrimidin-4-yl)-(1-ethyl-propyl)-amine
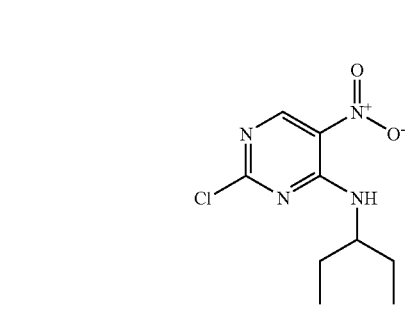

To a solution of 2,4-dichloro-5-nitro-pyrimidine (2 g, 10.31 mmol) in anhydrous EtOH (20 ml) is added 1-ethyl-propylamine (1.322 ml, 11.341 mmol) at 0 C (ice bath) under inert atmosphere. To this is added neat DIPEA (2.694 ml, 15.465 mmol). The reaction is stirred at r.t. for 8 hrs. The reaction mixture was concentrated in vacuo and the residue is dissolved with EtOAc. The organic layer is washed with sat. NaHCO$_3$ and brine, dried over Na$_2$SO$_4$, and concentrated in vacuo. Purification with column chromatography (SiO2, 1:3 EtOAC/Hexane) gives the desired product.

MS (ESI) m/z 245.1

EXAMPLE 119

(2-Chloro-5-amino-pyrimidin-4-yl)-(1-ethyl-propyl)-amine

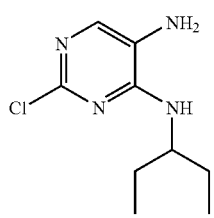

To a solution of (2-Chloro-5-nitro-pyrimidin-4-yl)-(1-ethyl-propyl)-amine (1 g, 4.087 mmol) in anhydrous EtOH (50 ml) is added Tin(II) chloride (2.324 g, 12.2607 mmol) and concentrated HCl (1 ml) at ambient temperature. The reaction is heated to 80° C. for 1 h and quenched with 1N NaOH at 0° C. The mixture is extracted with EtOAc, washed with brine, dried over Na2SO4, and concentrated in vacuo to give the crude product. The crude is used as is.

MS (ESI) m/z 215.2

EXAMPLE 120

2-Chloro-9-(1-ethyl-propyl)-7,9-dihydro-purin-8-one

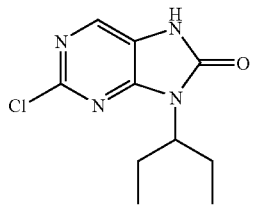

To a microwave vial is added the crude (2-Chloro-5-amino-pyrimidin-4-yl)-(1-ethyl-propyl)-amine (0.5 g, 2.329 mmol) and anhydrous DMF (15 ml) followed by 1,1'-carbonyldiimidazole (1.133 g, 6.987 mmol). Sealed vial and microwave heated at 100° C. for 10 min. The reaction mixture is diluted with EtOAc, washed with water, dried over Na$_2$SO4, and concentrated in vacuo. Purification with column chromatography (SiO2, 1:1 EtOAC/Hexane) gives the desired product.

MS (ESI) m/z 241.1

EXAMPLE 121

2-[4-(4-Acetyl-piperazin-1-yl)-phenylamino]-9-(1-ethyl-propyl)-7,9-dihydro-purin-8-one

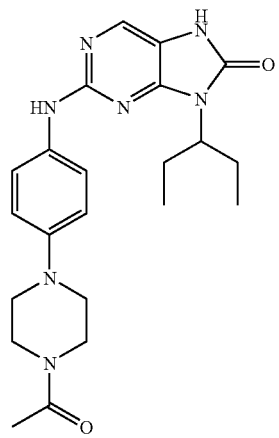

By repeating the procedures described in example 44, using 2-Chloro-9-(1-ethyl-propyl)-7,9-dihydro-purin-8-one as a starting material, the desired product is obtained.

MS (ESI) 424.2.

EXAMPLE 122

2-Chloro-9-(1-ethyl-propyl)-7-methyl-7,9-dihydro-purin-8-one

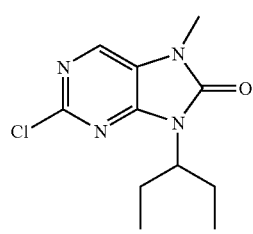

To a solution of 2-Chloro-9-(1-ethyl-propyl)-7,9-dihydro-purin-8-one (100 mg, 0.41 mmol) in anhydrous DMF (2 ml) is added methyl iodide (21 ul, 0.41 mmol) followed by NaH (50%, 22 mg, 0.4571 mmol). The reaction is stirred under nitrogen for 1.5 h. The reaction mixture is quenched with ice water and extracted with EtOAc. The extracts are dried over Na$_2$SO$_4$ and concentrated in vacuo to give the crude 2-Chloro-9-(1-ethyl-propyl)-7-methyl-7,9-dihydro-purin-8-one. The crude product is used as is.

MS (ESI) m/z 255.1

EXAMPLE 123

2-[4-(4-Acetyl-piperazin-1-yl)-phenylamino]-9-(1-ethyl-propyl)-7-methyl-7,9-dihydro-purin-8-one

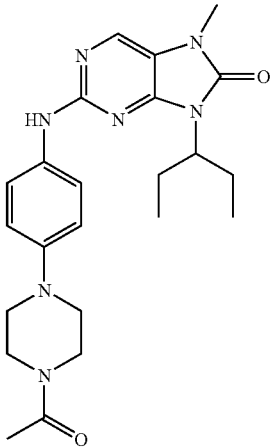

By repeating the procedures described in example 44, using 2-Chloro-9-(1-ethyl-propyl)-7-methyl-7,9-dihydro-purin-8-one as a starting material, the desired product is obtained.
MS (ESI) m/z 438.2

EXAMPLE 124

Allyl-(1-ethyl-propyl)-amine

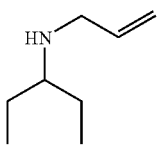

To a solution of 3-pentanone (1 g, 11.61 mmol) in anhydrous 1,2-dichloroethane (45 ml) is added allylamine (0.872 ml, 11.61 mmol) followed by NaBH(OAc)3 (3.44 g, 16.254 mmol) at ambient temperature and under nitrogen. The reaction is stirred at room temperature overnight. The reaction mixture is quenched with 1N NaOH and extracted with dichloromethane. The extract is dried over Na$_2$SO$_4$ and concentrated in vacuo to allyl-(1-ethyl-propyl)-amine

EXAMPLE 125

Allyl-(5-bromo-2-chloro-pyrimidin-4-yl)-(1-ethyl-propyl)-amine

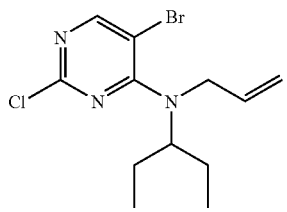

To a solution of allyl-(1-ethyl-propyl)-amine (10 mmol) is added anhydrous isopropanol (50 ml) and 5-bromo-2,4-dichloropyrimidine (2.979 g, 5 mmol) followed by diisopropylethylamine (2.61 ml, 15 mmol) at ambient temperature. The reaction is stirred overnight and concentrated in vacuo. The residue is purified with column chromatography (SiO2, 1:5 EtOAC/Hexane) to give the desired product.
MS (ESI) m/z 320.0.

EXAMPLE 126

2-Chloro-7-(1-ethyl-propyl)-5-methyl-7H-pyrrolo[2,3-d]pyrimidine

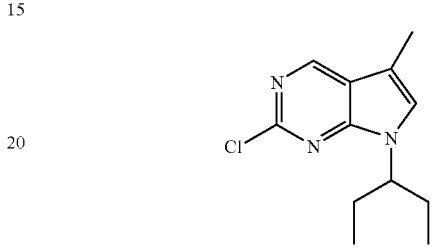

To a solution of allyl-(5-bromo-2-chloro-pyrimidin-4-yl)-(1-ethyl-propyl)-amine (2.76 g, 8.7 mmol) in anhydrous DMF (15 ml) was added 8 mol % of Pd(OAc)$_2$ (156 mg, 0.69 mmol) and 8 mol % of PPh3 (182 mg, 0.69 mmol) and triethylamine (2.4 ml, 17.3 mmol) a The reaction is stirred at 100° C. overnight. The reaction mixture is diluted with EtOAc, washed with water, dried over Na2SO4, and concentrated in vacuo. Purification with column chromatography (SiO2, 1:2 EtOAC/Hexane) gives the desired product.
MS (ESI) m/z 238.2

EXAMPLE 127

1-(4-{4-[7-(1-Ethyl-propyl)-5-methyl-7H-pyrrolo[2,3-d]pyrimidin-2-ylamino]-phenyl}-piperazin-1-yl)-ethanone

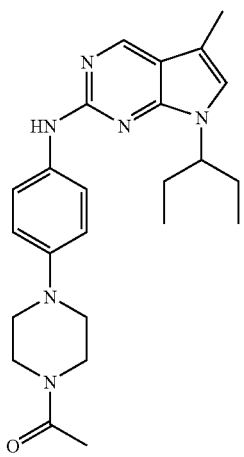

By repeating the procedures described in example 102, using 2-Chloro-7-(1-ethyl-propyl)-5-methyl-7H-pyrrolo[2,3-d]pyrimidine as a starting material, the desired product is obtained.
MS (ESI) m/z 421.2

EXAMPLE 128

(2-Chloro-5-prop-1-ynyl-pyrimidin-4-yl)-(1-ethyl-propyl)-amine

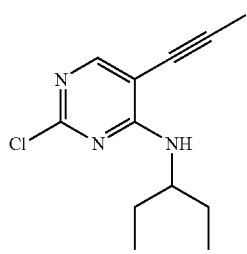

To a microwave vial is added a solution of (5-Bromo-2-chloro-pyrimidin-4-yl)-(1-ethyl-propyl)-amine (0.5 g, 1.80 mmol) in anhydrous toluene (10 ml), tributyl(1-propynyl)-tin (1.1 ml, 3.6 mmol) and 2 mol % of Pd(PPh3)4 (41.5 mg, 0.036 mmol). The reaction is heated at 120° C. for 1 hr by employing microwave. The reaction mixture is diluted with EtOAc, washed with sat. NaHCO$_3$ aqueous solution and water, dried over Na$_2$SO$_4$, and concentrated in vacuo. Purification with column chromatography (SiO2, 1:5 EtOAC/Hexane) gives 0.32 g of the desired product.

MS (ESI) m/z 238.2

EXAMPLE 129

2-Chloro-7-(1-ethyl-propyl)-6-methyl-7H-pyrrolo[2,3-d]pyrimidine

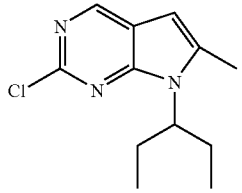

In a microwave vial is added (2-Chloro-5-prop-1-ynyl-pyrimidin-4-yl)-(1-ethyl-propyl)-amine (0.22 g, 0.92 mmol), anhydrous DMF (3 ml), and CuI (53 mg, 0.27 mmol). The reaction is heated at 160° C. for 1 hr by employing microwave. The reaction mixture is diluted with EtOAc, washed with sat. NaHCO3 aqueous solution and water, dried over Na$_2$SO$_4$, and concentrated in vacuo. Purification with column chromatography (SiO$_2$, 1:4 EtOAC/Hexane) gives 43 mg of the desired product.

MS (ESI) m/z 238.2.

EXAMPLE 130

1-(4-{4-[7-(1-Ethyl-propyl)-6-methyl-7H-pyrrolo[2,3-d]pyrimidin-2-ylamino]-phenyl}-piperazin-1-yl)-ethanone

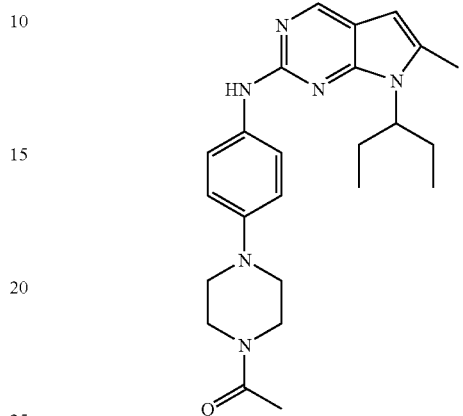

By repeating the procedures described in example 102, using 2-Chloro-7-(1-ethyl-propyl)-6-methyl-7H-pyrrolo[2,3-d]pyrimidine as a starting material, the desired product is obtained.

MS (ESI) m/z 421.4

EXAMPLE 131

[7-(1-Ethyl-propyl)-6-methyl-7H-pyrrolo[2,3-d]pyrimidin-2-yl]-(4-piperazin-1-yl-phenyl)-amine

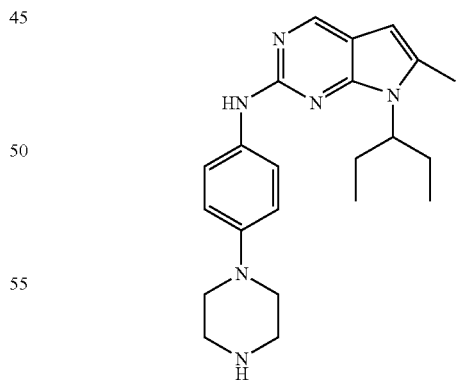

By repeating the procedures described in example 102, using 2-Chloro-7-(1-ethyl-propyl)-6-methyl-7H-pyrrolo[2,3-d]pyrimidine as a starting material, the desired product is obtained.

MS (ESI) m/z 379.1

EXAMPLE 132

[2-Chloro-5-(3,3-diethoxy-prop-1-ynyl)-pyrimidin-4-yl]-(1-ethyl-propyl)-amine

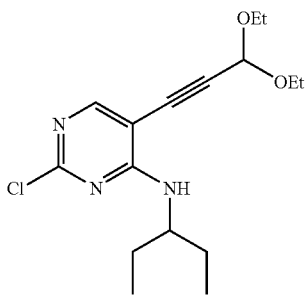

To a mixture of (5-Bromo-2-chloro-pyrimidin-4-yl)-(1-ethyl-propyl)-amine (420 mg, 1.5 mmol) and propiolaldehyde diethyl acetal (0.32 mL, 2.25 mmol) in DMF (6 mL) is added PdCl$_2$(PPh$_3$)$_2$ (105 mg, 0.15 mmol) and CuI (28 mg, 0.15 mmol), followed by Et$_3$N (0.42 mL, 3 mmol). The mixture is degassed and heated at 55° C. for 16 h. Then the mixture is cooled down to room temperature, diluted with EtOAc, washed with water and brine. The organic layer is dried (Na$_2$SO$_4$), filtered and concentrated under reduced pressure. The crude product is purified by column chromatography (SiO2, EtOAc:Heptane=5:95 to 40:60) to give 182 mg of the title compound as a light brown oil.

MS (ESI) m/z 326 (M+H)$^+$

EXAMPLE 133

2-Chloro-6-diethoxymethyl-7-(1-ethyl-propyl)-7H-pyrrolo[2,3-d]pyrimidine

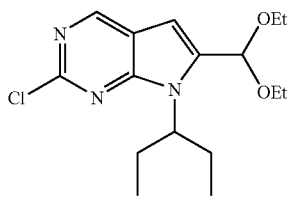

To a solution of [2-Chloro-5-(3,3-diethoxy-prop-1-ynyl)-pyrimidin-4-yl]-(1-ethyl-propyl)-amine (326 mg, 1 mmol) in THF (2 mL) is added a solution of 1M TBAF in THF (5 mL, 5 mmol) at ambient temperature. The reaction mixture is heated at 68° C. for 2 hours. After cooling down, the mixture is concentrated in vacuo. The crude product is purified by column chromatography (SiO2, EtOAc:Heptane=5:95 to 40:60) to give 307 mg of the title compound as a colorless oil.

MS (ESI) m/z 326 (M+H)$^+$.

EXAMPLE 134

1-(4-{4-[6-Diethoxymethyl-7-(1-ethyl-propyl)-7H-pyrrolo[2,3-d]pyrimidin-2-ylamino]-phenyl}-piperazin-1-yl)-ethanone

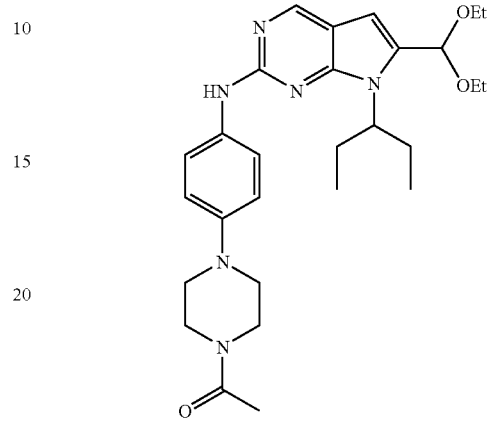

By repeating the procedures described in example 102, using -Chloro-6-diethoxymethyl-7-(1-ethyl-propyl)-7H-pyrrolo[2,3-d]pyrimidine as a starting material, the desired product is obtained.

MS (ESI) m/z 509 (M+H)$^+$

EXAMPLE 135

2-[4-(4-Acetyl-piperazin-1-yl)-phenylamino]-7-(1-ethyl-propyl)-7H-pyrrolo[2,3-d]pyrimidine-6-carbaldehyde

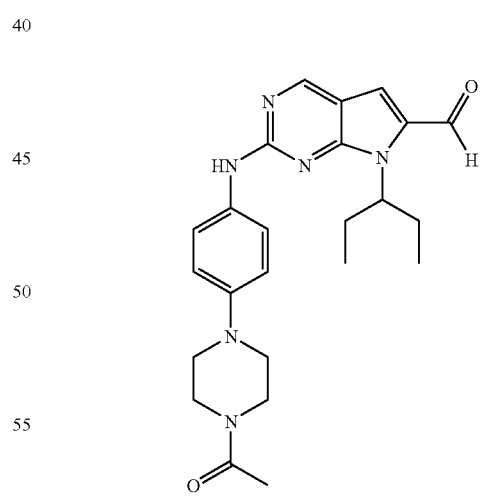

To a solution 1-(4-{4-[6-Diethoxymethyl-7-(1-ethyl-propyl)-7H-pyrrolo[2,3-d]pyrimidin-2-ylamino]-phenyl}-piperazin-1-yl)-ethanone (178 mg, 0.35 mmol) in 1,4 dioxane (2.8 mL) is added 0.8 mL of concentrated HCl at ambient temperature. The reaction mixture is stirred at ambient temperature for 30 mins. The mixture is neutralized with 1 N NaOH aqueous solution and saturated NaHCO$_3$ aqueous solution, extracted with EtOAc. The organic layer is washed with brine, dried Na$_2$SO$_4$, and concentrated under reduced pressure to give 160 mg of the title compound as a yellow solid.

MS (ESI) m/z 435 (M+H)$^+$.

EXAMPLE 136

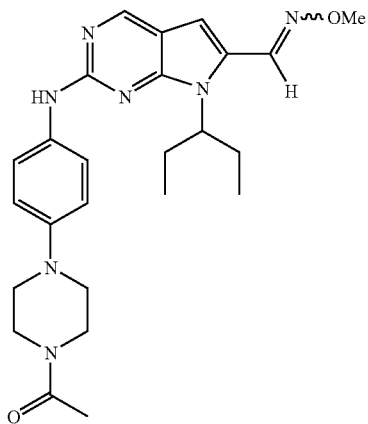

A mixture of 2-[4-(4-Acetyl-piperazin-1-yl)-phenylamino]-7-(1-ethyl-propyl)-7H-pyrrolo[2,3-d]pyrimidine-6-carbaldehyde (25 mg, 0.057 mmol), methoxylamine hydrochloride (20 mg, 0.22 mmol) and 6N HCl (0.03 mL) in EtOH (1 mL) is stirred at ambient temperature for 6 h. The mixture is quenched with saturated NaHCO$_3$ aqueous solution, extracted with CH$_2$Cl$_2$. The organic layer is washed with brine, dried over Na$_2$SO$_4$, and concentrated under reduced pressure to give the crude product. The crude product is purified by prep-HPLC to give 12 mg of the title compound as a bright yellow solid.

MS (ESI) m/z 464 (M+H)$^+$.

EXAMPLE 137

7-(1-Ethyl-propyl)-2-[3-fluoro-4-(4-methyl-piperazin-1-yl)-phenylamino]-5,7-dihydro-pyrrolo[2,3-d]pyrimidin-6-one

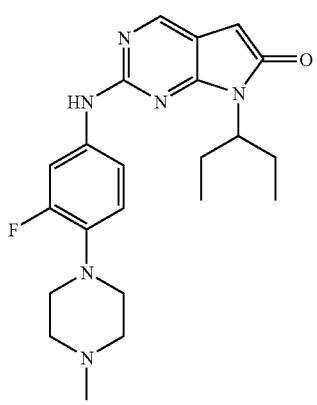

To a solution of 5-bromo-2,4-dichloropyrimidine (4.56 g, 20 mmol) in ethanol (9 mL) is added 1-ethylpropylamine (2.6 mL, 22 mmol) and N,N-diisopropylethylamine (7 mL, 40 mmol) at ambient temperature. The reaction mixture is stirred at ambient temperature for 16 h and concentrated in vacuo. The residue is purified by flash chromatography (SiO$_2$, EtOAc/hexane 3:97 to 30:70) to give (5-bromo-2-chloro-pyrimidin-4-yl)-(1-ethyl-propyl)-amine. LCMS: 280 (M+H)$^+$ $^1$H NMR (CDCl$_3$, 400 MHz) δ 8.1 (s, 1H), 5.24 (d, 1H), 4.1 (m, 1H), 1.58 (m, 4H), 0.93 (t, 6H).

To a solution of tributyl-((Z)-2-ethoxy-vinyl)-stannane (4.25 g, 8.8 mmol) in CH$_3$CN (10 mL) is added (5-bromo-2-chloro-pyrimidin-4-yl)-(1-ethyl-propyl)-amine (2.25 g, 8 mmol), Et$_4$NCl (1.33 g, 8 mmol) and Pd(PPh$_3$)$_2$Cl$_2$ (280 mg, 0.4 mmol) at ambient temperature. The reaction mixture is purged with N$_2$, sealed in a microwave reactor and heated at 100° C. for 20 min. After cooling to room temperature, the mixture is concentrated in vacuo and the residue is purified by flash chromatography (SiO$_2$, EtOAc/hexane 5:95 to 40:60) to give [2-Chloro-5-((Z)-2-ethoxy-vinyl)-pyrimidin-4-yl]-(1-ethyl-propyl)-amine.

LCMS: 270 (M+H)$^+$ $^1$H NMR (CDCl$_3$, 400 MHz). δ 8.02 (s, 1H), 6.26 (d, 1H), 5.46 (d, 1H), 4.91 (d, 1H), 4.16 (m, 1H), 3.99 (q, 2H), 1.60-1.69 (m, 2H), 1.43-1.52 (m, 2H), 1.32 (t, 3H), 0.92 (t, 6H).

To a solution of [2-chloro-5-((Z)-2-ethoxy-vinyl)-pyrimidin-4-yl]-(1-ethylpropyl)-amine (1.1 g, 4.07 mmol) in EtOH (8 mL) is added concentrated HCl (0.1 mL) at ambient temperature. The reaction mixture is sealed in a microwave reactor and heated at 100° C. for 10 min. After cooling to room temperature, the mixture is concentrated in vacuo to provide 2-chloro-7-(1-ethyl-propyl)-7H-pyrrolo[2,3-d]pyrimidine. The crude product is used as it is. The crude product can be purified by flash chromatography (SiO$_2$, EtOAc/Hexane 1:5).

LCMS: 224 (M+H)$^+$ $^1$H NMR (CDCl$_3$, 400 MHz). δ 8.87 (s, 1H), 7.30 (d, 1H), 6.69 (d, 1H), 4.69 (m, 1H), 1.77-1.99 (m, 4H), 0.77 (t, 6H).

To a mixture of 2-chloro-7-(1-ethyl-propyl)-7H-pyrrolo[2,3-d]pyrimidine (crude, 4.07 mmol) in t-BuOH (7 mL) was added 2 mL of H$_2$O at ambient temperature, then NBS (2.28 g, 12.8 mmol) was added to the orange color solution. The mixture is stirred at 30° C. for 2.5 h, then is concentrated and taken up in ethyl acetate, washed with NaHCO$_3$ aqueous solution, and brine. The organic portion is dried with Na$_2$SO$_4$, filtered and concentrated to provide 5,5-dibromo-2-chloro-7-(1-ethyl-propyl)-5,7-dihydro-pyrrolo[2,3-d]pyrimidin-6-one. The crude product is used as it is.

LCMS: 398 (M+H)$^+$.

To a solution of 5,5-dibromo-2-chloro-7-(1-ethyl-propyl)-5,7-dihydro-pyrrolo[2,3-d]pyrimidin-6-one (crude, ~5.3 mmol) in acetic acid (6 mL) and THF (4 mL) is added Zn dust (1.37 g, 21 mmol) at 0° C. The mixture is stirred at 0° C. for 2 min then warmed up to room temperature, stirred for 30 min. The mixture is filtered through a pad of Celite, rinsed with ethyl acetate. The filtrate is concentrated in vacuo and the residue is purified by flash chromatography (SiO$_2$, EtOAc/hexane 5:95 to 40:60) to give 2-chloro-7-(1-ethyl-propyl)-5,7-dihydro-pyrrolo[2,3-d]pyrimidin-6-one.

LCMS: 240 (M+H)$^+$ $^1$H NMR (CDCl$_3$, 400 MHz). δ 8.17 (s, 1H), 4.20 (m, 1H), 3.58 (s, 2H), 2.10 (m, 2H), 1.84 (m, 2H), 0.84 (t, 6H).

To a mixture of 2-chloro-7-(1-ethyl-propyl)-5,7-dihydro-pyrrolo[2,3-d]pyrimidin-6-one (18 mg, 0.075 mmol) and TsOH (1.12 ml, 0.2 M in 1,4 dioxane) is added 3-fluoro-4-(4-methylpiperazine)aniline (23.5 mg, 0.1125 mmol), and DMF (0.25 mL) at ambient temperature. The reaction mixture is sealed in a microwave reactor and heated at 140° C. for 30 min. The mixture is diluted with EtOAc, washed with NaHCO$_3$ aqueous solution and brine. The organics is dried over Na$_2$SO$_4$, filtered and concentrated. The crude product is purified by preparative HPLC to give 27 mg of 7-(1-ethyl-propyl)-2-[3-fluoro-4-(4-methyl-piperazin-1-yl)-phenylamino]-5,7-dihydro-pyrrolo[2,3-d]pyrimidin-6-one as a brown solid.

LCMS: 413 (M+H)+.

$^1$H NMR (DMSO, 400 MHz). δ 9.48 (s, 1H), 8.09 (s, 1H), 7.73 (d, 1H), 7.36 (d, 1H), 6.96 (t, 1H), 4.08 (m, 1H), 3.60 (s, 2H), 3.32 (m, 4H), 2.96 (m, 4H), 2.25 (s, 3H), 2.11 (m, 2H), 1.78 (m, 2H), 0.79 (t, 6H).

EXAMPLES 138-199

By repeating the procedures described in example 137, using appropriate starting materials, the following compounds are obtained.

| Example | Structure | MS found (M + 1) |
| --- | --- | --- |
| 138 | | 395 |
| 139 | | 382 |
| 140 | | 380 |
| 141 | 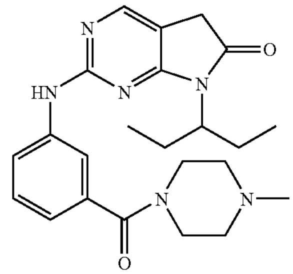 | 423 |
| 142 | 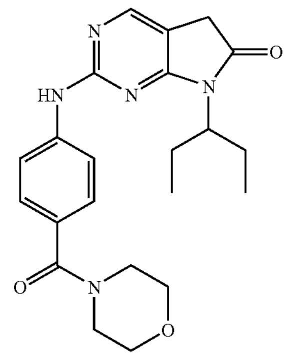 | 410 |
| 143 | 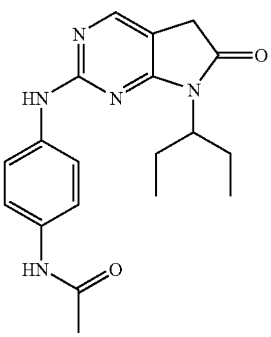 | 354 |
| 144 | 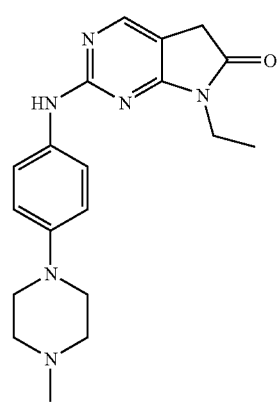 | 353 |

-continued

| Example | Structure | MS found (M + 1) |
|---|---|---|
| 145 | 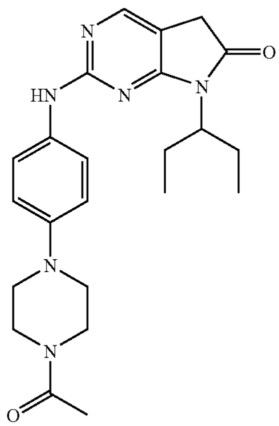 | 423 |
| 146 | 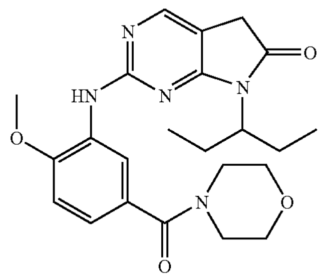 | 440 |
| 147 | 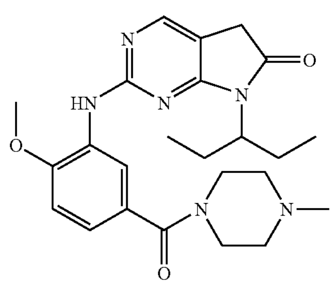 | 453 |
| 148 | 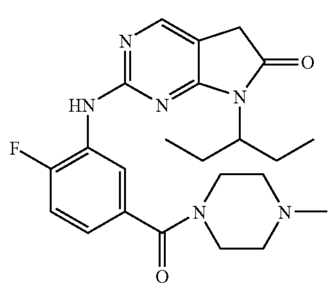 | 441 |

-continued

| Example | Structure | MS found (M + 1) |
|---|---|---|
| 149 | | 365 |
| 150 | | 393 |
| 151 | | 428 |
| 152 | | 410 |

-continued
| Example | Structure | MS found (M + 1) |
|---|---|---|
| 153 | 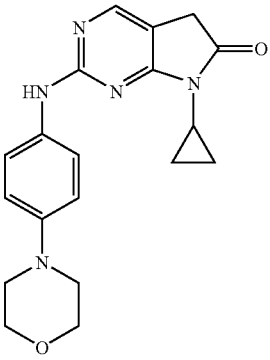 | 352 |
| 154 | 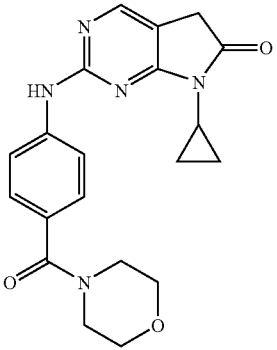 | 380 |
| 155 | 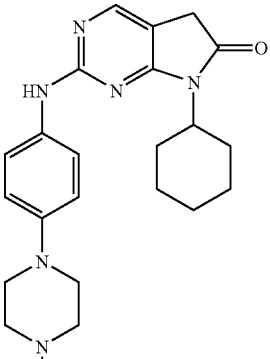 | 407 |
| 156 | 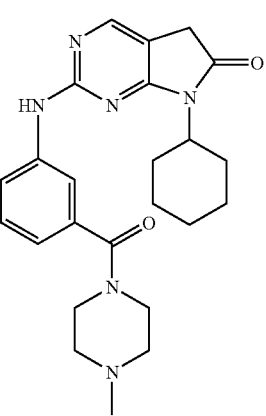 | 435 |
-continued
| Example | Structure | MS found (M + 1) |
|---|---|---|
| 157 | 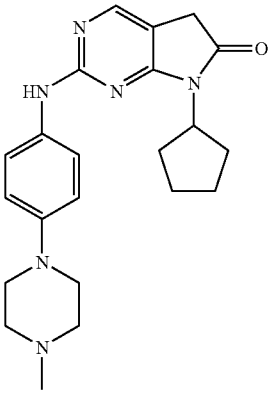 | 393 |
| 158 | 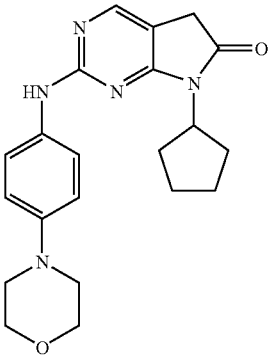 | 380 |
| 159 | 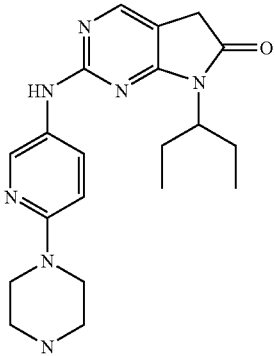 | 396 |
| 160 | 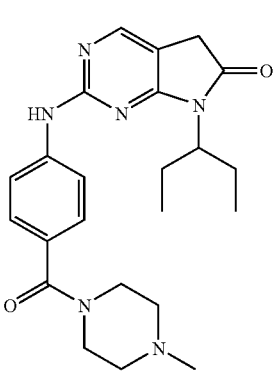 | 423 |

-continued
| Example | Structure | MS found (M + 1) |
|---|---|---|
| 161 | 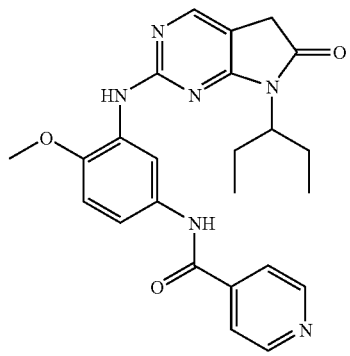 | 447 |
| 162 | 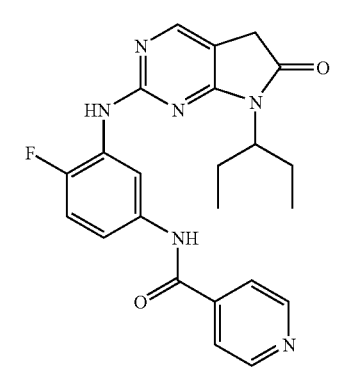 | 435 |
| 163 | 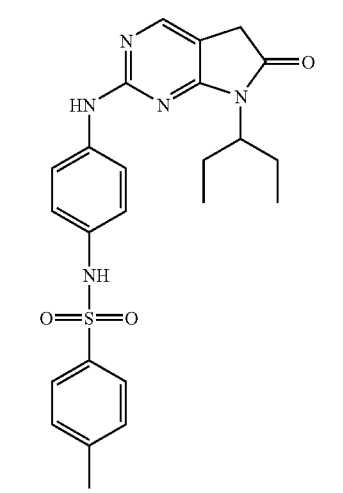 | 466 |
| 164 | 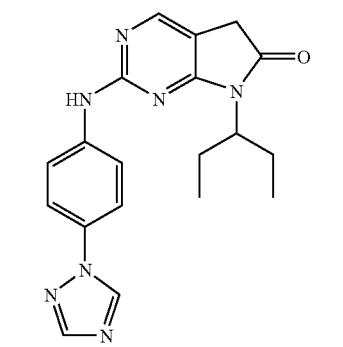 | 364 |
-continued
| Example | Structure | MS found (M + 1) |
|---|---|---|
| 165 | 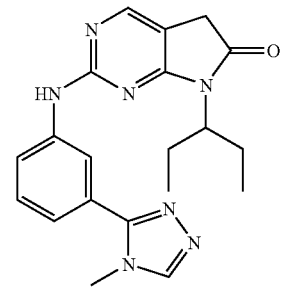 | 378 |
| 166 | 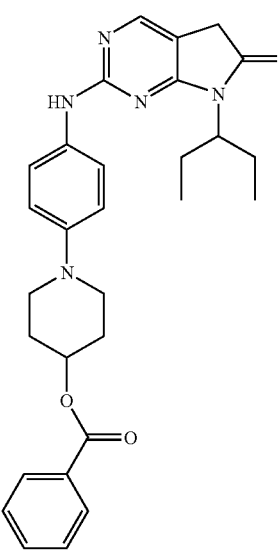 | 500 |
| 167 | 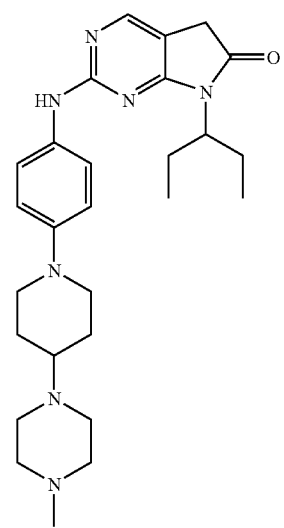 | 478 |

-continued

| Example | Structure | MS found (M + 1) |
|---------|-----------|------------------|
| 168 | 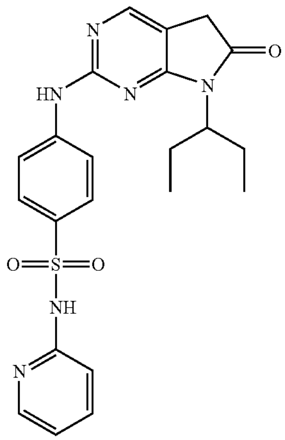 | 382 |
| 169 | 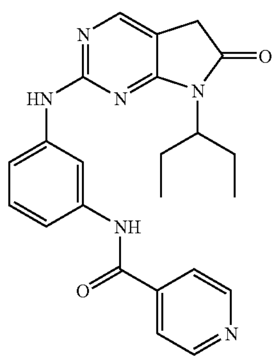 | 417 |
| 170 | 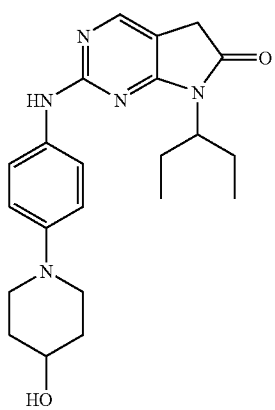 | 396 |
| 171 | 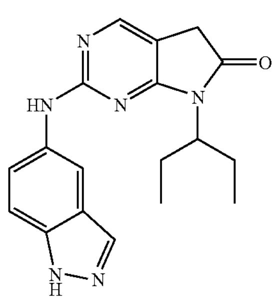 | 337 |
| 172 | 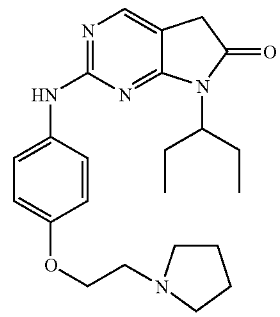 | 410 |
| 173 | 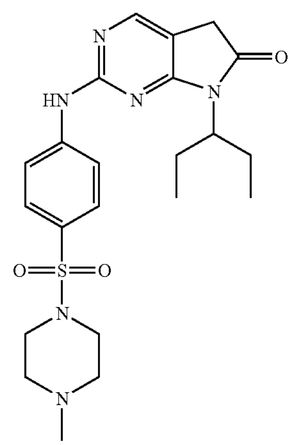 | 459 |
| 174 | 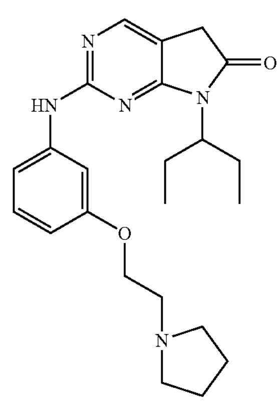 | 410 |

-continued

| Example | Structure | MS found (M + 1) |
|---|---|---|
| 175 | 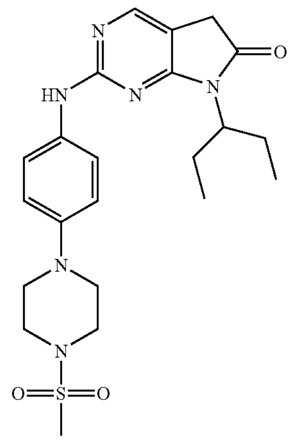 | 459 |
| 176 | 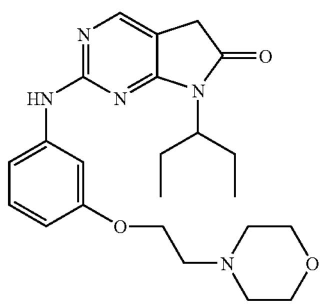 | 426 |
| 177 | 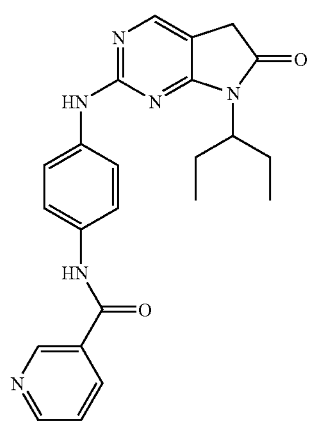 | 417 |

-continued

| Example | Structure | MS found (M + 1) |
|---|---|---|
| 178 | 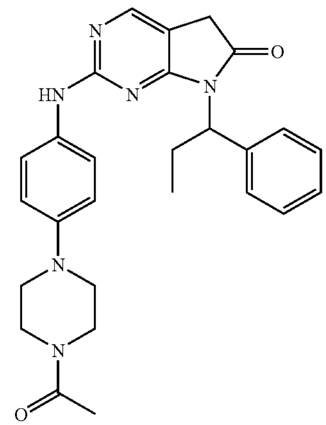 | 455 |
| 179 | 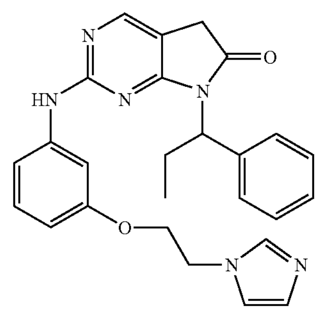 | 407 |
| 180 | 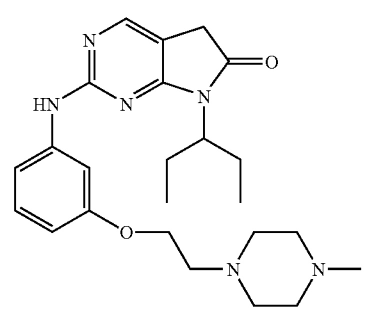 | 439 |
| 181 | 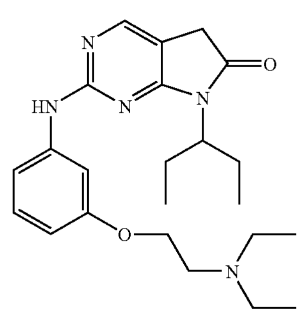 | 412 |

TABLE-continued

| Example | Structure | MS found (M + 1) |
|---|---|---|
| 182 | 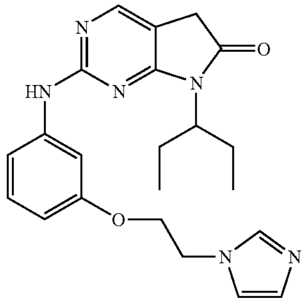 | 407 |
| 183 | 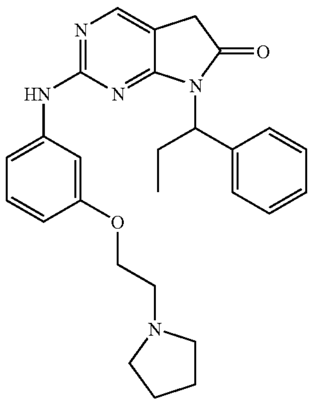 | 458 |
| 184 | 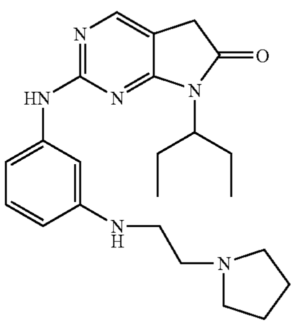 | 409 |
| 185 | 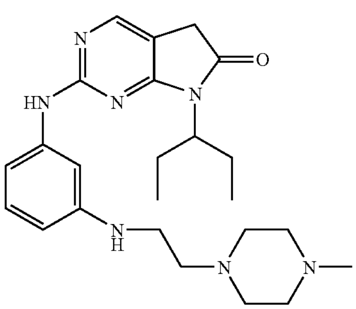 | 438 |
| 186 | | 417 |
| 187 | | 382 |
| 188 | | 408 |
| 189 | | 368 |

-continued

| Example | Structure | MS found (M + 1) |
|---------|-----------|------------------|
| 190 | 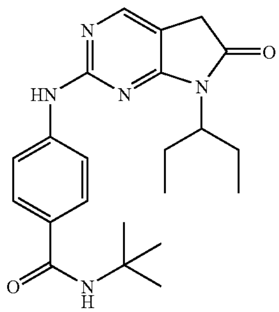 | 396 |
| 191 | 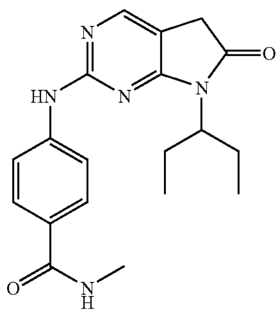 | 354 |
| 192 | 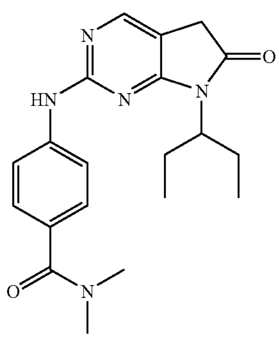 | 368 |
| 193 | 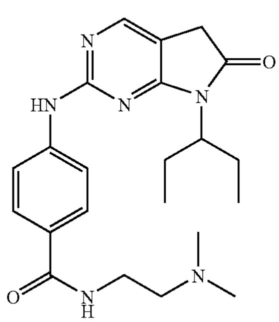 | 436 |

-continued

| Example | Structure | MS found (M + 1) |
|---------|-----------|------------------|
| 194 | 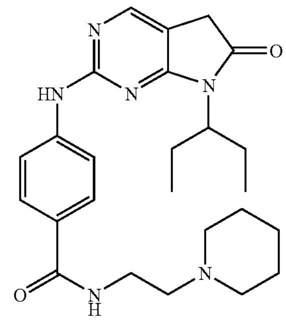 | 451 |
| 195 | 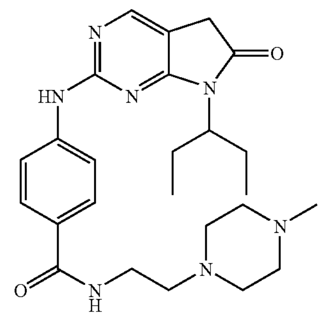 | 466 |
| 196 | 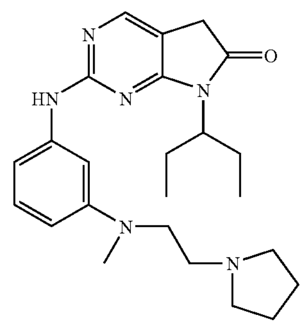 | 423 |
| 197 | 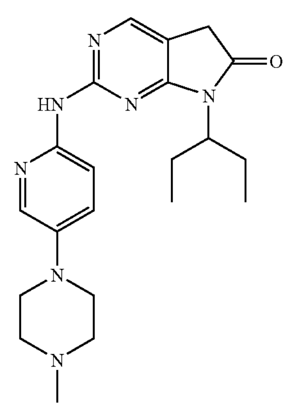 | 396 |

-continued

| Example | Structure | MS found (M + 1) |
|---|---|---|
| 198 | 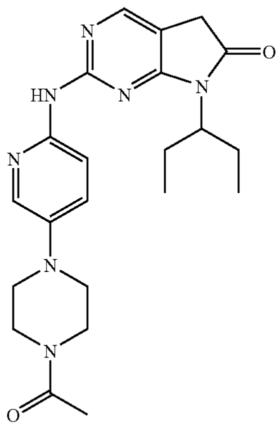 | 424 |
| 199 | 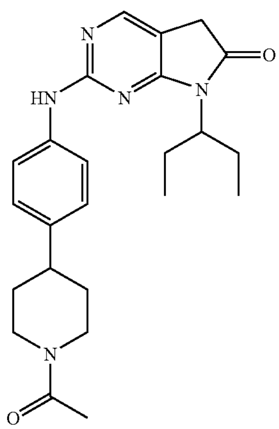 | 422 |

EXAMPLE 200

2-[4-(4-Acetyl-piperazin-1-yl)-phenylamino]-7-(1-ethyl-propyl)-5,5-dimethyl-5,7-dihydro-pyrrolo[2,3-d]pyrimidin-6-one

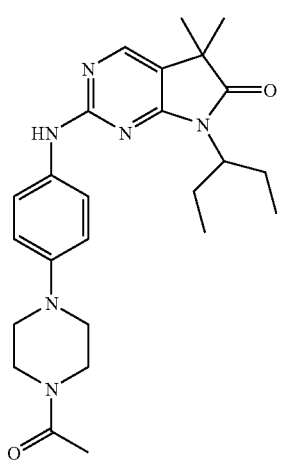

To a solution of 2-chloro-7-(1-ethyl-propyl)-5,7-dihydro-pyrrolo[2,3-d]pyrimidin-6-one (40 mg, 0.17 mmol) in THF (1.5 mL) is added NaH (60% dispersion in mineral oil, 20 mg, 0.42 mmol) at 0° C. The reaction mixture is stirred for 30 min and then cooled to 0° C. After the addition of iodomethane (0.023 mL, 0.37 mmol) at 0° C., the mixture is stirred for 3 hr. The reaction mixture is quenched with aqueous ammonium chloride solution and extracted with ethyl acetate. The organics is washed with aqueous sodium carbonate solution and brine, dried over anhydrous sodium sulfate, evaporated in vacuo. The residue is purified by flash chromatography ($SiO_2$, EtOAc/Hexane 1:10) to give 20 mg of 2-chloro-7-(1-ethyl-propyl)-5,5-dimethyl-5,7-dihydro-pyrrolo[2,3-d]pyrimidin-6-one.

$^1$H NMR ($CDCl_3$, 400 MHz). δ 8.11 (s, 1H), 4.18 (m, 1H), 2.14 (m, 2H), 1.80 (m, 2H), 1.42 (s, 6H), 0.82 (t, 6H).

To a solution of 2-chloro-7-(1-ethyl-propyl)-5,5-dimethyl-5,7-dihydro-pyrrolo[2,3-d]pyrimidin-6-one (20 mg, 0.075 mmol) in 1,4-dioxane (1 mL) and DMF (0.2 mL) are added 1-[4-(4-amino-phenyl)-piperazin-1-yl]-ethanone (24.5 mg, 0.11 mmol) and p-toluenesulfonic acid (17 mg, 0.089 mmol). The reaction mixture is sealed in a microwave reactor and heated at 140° C. for 30 min. The mixture is diluted with EtOAc and washed with 1N NaOH solution. The organics is dried over $Na_2SO_4$, filtered, and concentrated. The residue is purified by prep-HPLC to give 30 mg of 2-[4-(4-acetyl-piperazin-1-yl)-phenylamino]-7-(1-ethyl-propyl)-5,5-dimethyl-5,7-dihydro-pyrrolo[2,3-d]pyrimidin-6-one as a pale yellow solid.

LCMS: 451 (M+H)$^+$.

$^1$H NMR ($CDCl_3$, 400 MHz). δ 7.95 (s, 1H), 7.49 (d, 2H), 6.93 (d, 2H), 6.91 (br s, 1H), 4.15 (m, 1H), 3.78 (t, 2H), 3.63 (t, 2H), 3.13 (m, 4H), 2.19 (m, 2H), 2.14 (s, 3H), 1.77 (m, 2H), 1.38 (s, 6H), 0.83 (t, 3H).

EXAMPLE 201

1-(1-{4-[7-(1-Ethyl-propyl)-7H-pyrrolo[2,3-d]pyrimidin-2-ylamino]-phenyl}-piperidin-4-yl)-ethanone

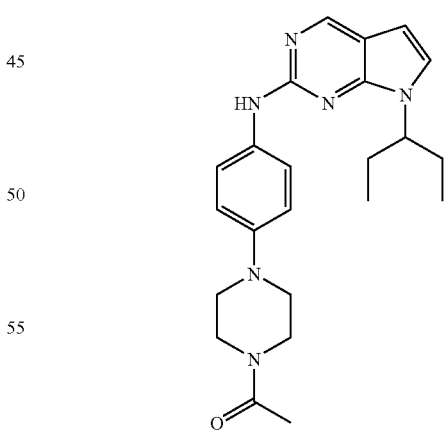

To a mixture of 1-[4-(4-amino-phenyl)-piperazin-1-yl]-ethanone (70.5 mg, 0.32 mmol) and sodium tert-butoxide (38.4 mg, 0.4 mmol) in 1,4-dioxane (0.3 mL) are added a solution of 2-chloro-7-(1-ethyl-propyl)-7H-pyrrolo[2,3-d]pyrimidine (60 mg, 0.26 mmol) in 1,4-dioxane (0.6 mL), $Pd_2(dba)_3$ (12.2 mg, 0.013 mmol) and BINAP (16.6 mg, 0.026 mmol). The mixture is degassed, and heated at 100° C.

for 3 h. The mixture is cooled to room temperature, diluted with EtOAc, and filtered through a pad of Celite. The filtrate is concentrated under reduced pressure. The crude product is purified by preparative HPLC to give 84.9 mg of 1-(1-{4-[7-(1-ethyl-propyl)-7H-pyrrolo[2,3-d]pyrimidin-2-ylamino]-phenyl}-piperidin-4-yl)-ethanone as a pale white solid.

LCMS: 407.3 (M+H)⁺

$^1$H NMR (CDCl$_3$, 400 MHz). δ 8.59 (s, 1H), 7.66 (d, 2H), 7.25 (br s, 1H), 6.97 (d, 2H), 6.96 (d, 1H), 6.44 (d, 1H), 4.50 (m, 1H), 3.81 (t, 2H), 3.65 (t, 2H), 3.14 (m, 4H), 2.17 (s, 3H), 1.90 (m, 4H), 0.82 (t, 6H).

EXAMPLE 202

[7-(1-Ethyl-propyl)-7H-pyrrolo[2,3-d]pyrimidin-2-yl]-(4-piperazin-1-yl-phenyl)-amine

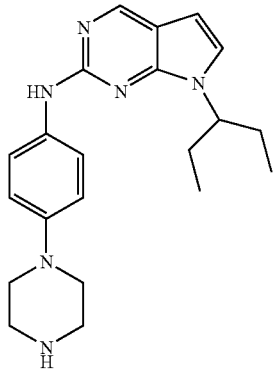

To a mixture of 4-(4-amino-phenyl)-piperazine-1-carboxylic acid tert-butyl ester (133 mg, 0.48 mmol) and sodium tert-butoxide (57.6 mg, 0.6 mmol) in 1,4-dioxane (0.5 mL) is added a solution of 2-chloro-7-(1-ethyl-propyl)-7H-pyrrolo[2,3-d]pyrimidine (90 mg, 0.4 mmol) in 1,4-dioxane (1.0 mL), Pd$_2$(dba)$_3$ (18.3 mg, 0.02 mmol) and BINAP (25 mg, 0.04 mmol). The mixture is degassed, and heated at 100° C. for 3 h. The mixture is cooled to room temperature, diluted with EtOAc, and filtered through celite. The filtrate is concentrated under reduced pressure. The residue is purified by flash chromatography (SiO$_2$, EtOAc:Hexane=1:1) to give 167 mg of 4-{4-[7-(1-ethyl-propyl)-7H-pyrrolo[2,3-d]pyrimidin-2-ylamino]-phenyl}-piperazine-1-carboxylic acid tert-butyl ester as a pale yellow solid.

LCMS: 465.5 (M+H)⁺

To a solution of 4-{4-[7-(1-ethyl-propyl)-7H-pyrrolo[2,3-d]pyrimidin-2-ylamino]-phenyl}-piperazine-1-carboxylic acid tert-butyl ester (167 mg, 0.36 mmol) in dichloromethane (3 mL) is added trifluoroacetic acid (1 mL). The reaction mixture is stirred for 1 h and concentrated in vacuo. The residue is diluted with dichloromethane, washed with NaHCO$_3$ solution, dried over Na$_2$SO$_4$, and concentrated in vacuo. Purification by preparative HPLC afforded 130 mg of [7-(1-ethyl-propyl)-7H-pyrrolo[2,3-d]pyrimidin-2-yl]-(4-piperazin-1-yl-phenyl)-amine as a yellowish solid.

LCMS: 365.2 (M+H)⁺

EXAMPLES 203-262

By repeating the procedures described in example 201 and 202, using appropriate starting materials, the following compounds are obtained.

| Example | Structure | MS found (M + 1) |
|---|---|---|
| 203 | 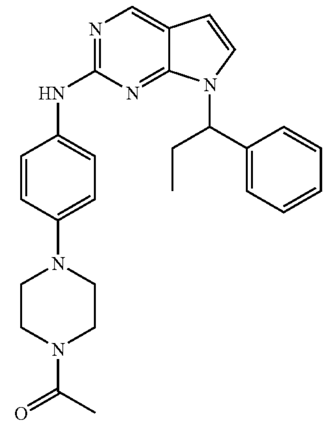 | 455.2 |
| 204 | 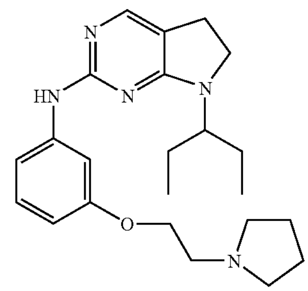 | 394 |
| 205 | 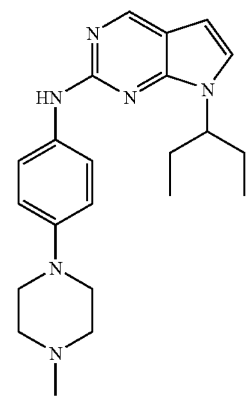 | 395 |
| 206 | 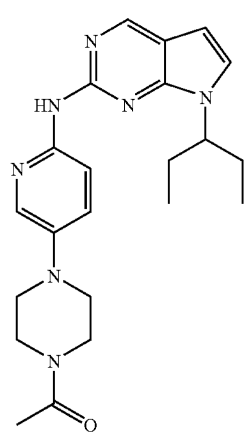 | 408 |

-continued

| Example | Structure | MS found (M + 1) |
|---|---|---|
| 207 | 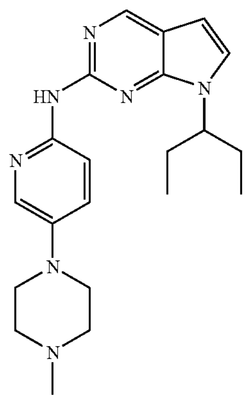 | 380 |
| 208 | 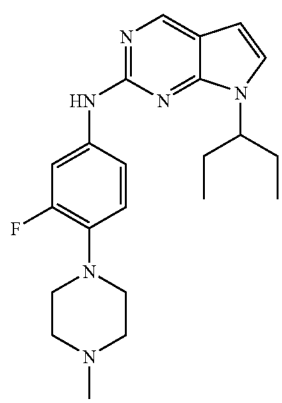 | 397 |
| 209 | 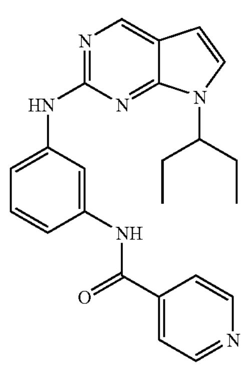 | 417 |
| 210 | 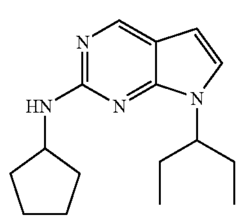 | 273 |

-continued

| Example | Structure | MS found (M + 1) |
|---|---|---|
| 211 | 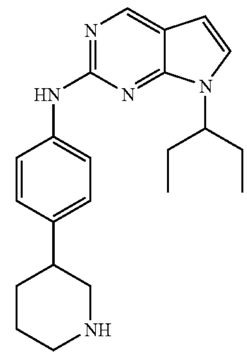 | 364 |
| 212 | 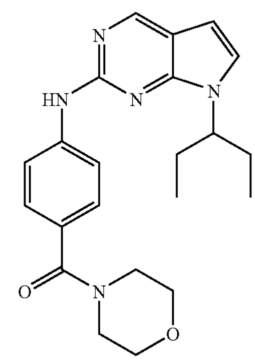 | 394 |
| 213 | 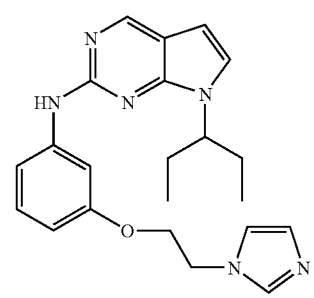 | 391 |
| 214 | 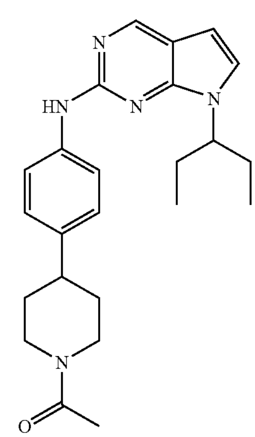 | 406 |

-continued

| Example | Structure | MS found (M + 1) |
|---|---|---|
| 215 | 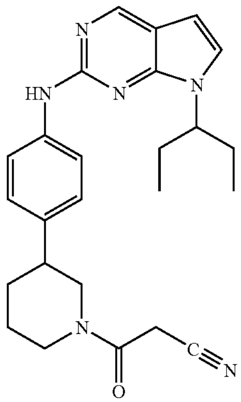 | 431 |
| 216 | 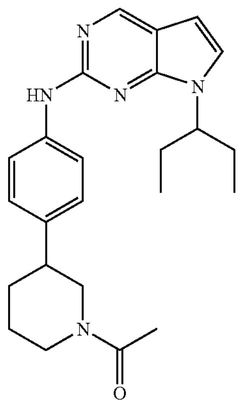 | 406 |
| 217 | 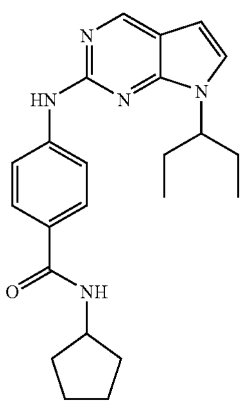 | 392 |
| 218 | 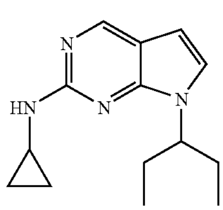 | 245 |

-continued

| Example | Structure | MS found (M + 1) |
|---|---|---|
| 219 | 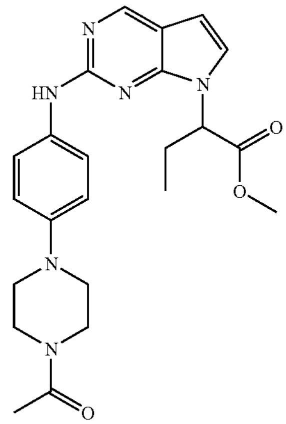 | 437.4 |
| 220 | 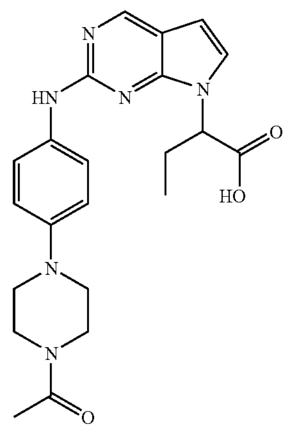 | 423.4 |
| 221 | 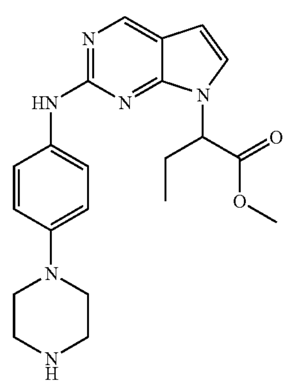 | 395.3 |

TABLE-continued
| Example | Structure | MS found (M + 1) |
|---|---|---|
| 222 | 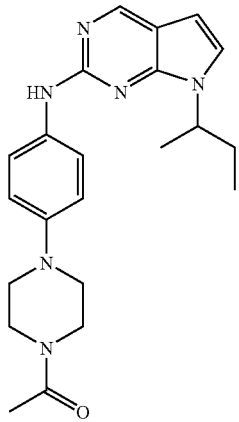 | 393.2 |
| 223 | 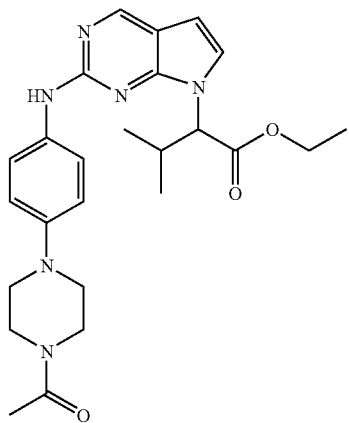 | 465.3 |
| 224 | 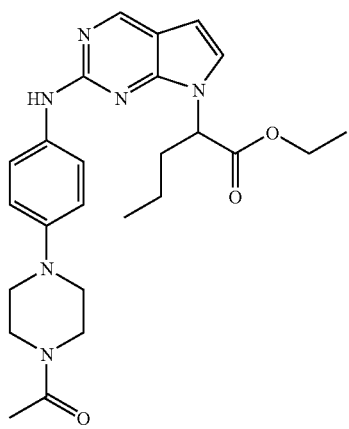 | 465.4 |
TABLE-continued
| Example | Structure | MS found (M + 1) |
|---|---|---|
| 225 | 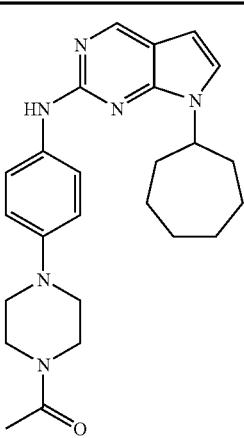 | 433.3 |
| 226 | 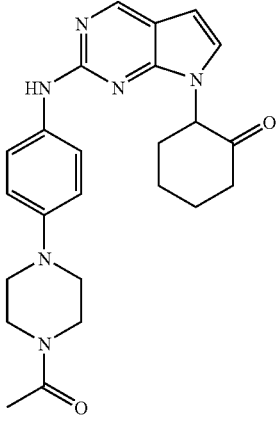 | 433.2 |
| 227 | 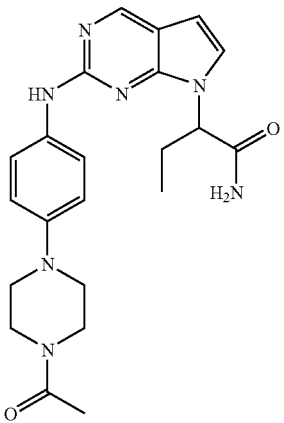 | 422.4 |

-continued

| Example | Structure | MS found (M + 1) |
|---|---|---|
| 228 | 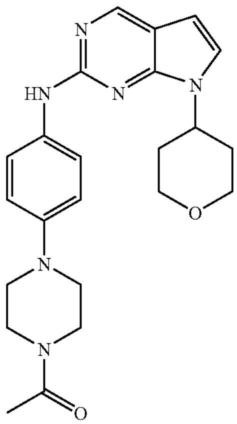 | 421.4 |
| 229 | 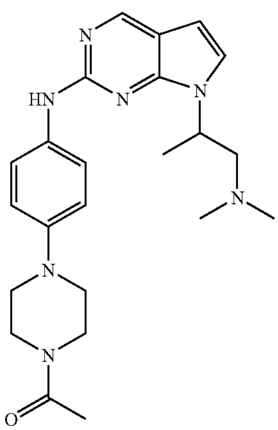 | 422.4 |
| 230 | 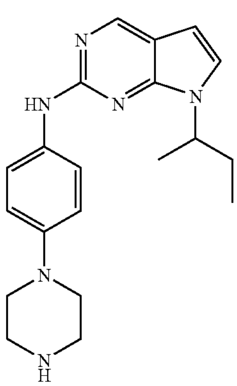 | 351.2 |
| 231 | 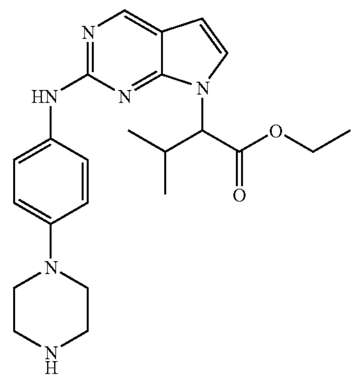 | 423.2 |
| 232 | 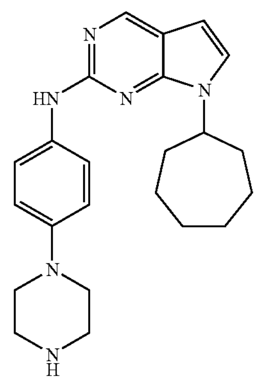 | 391.2 |
| 233 | 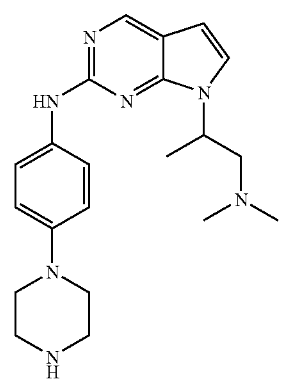 | 380.3 |
| 234 | 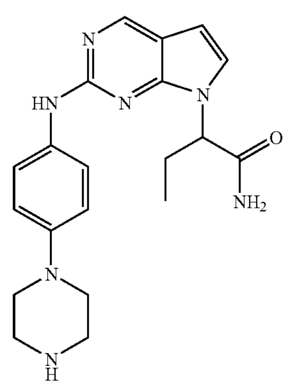 | 380.3 |

-continued

| Example | Structure | MS found (M + 1) |
|---|---|---|
| 235 | 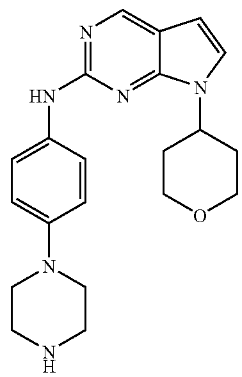 | 379.2 |
| 236 | 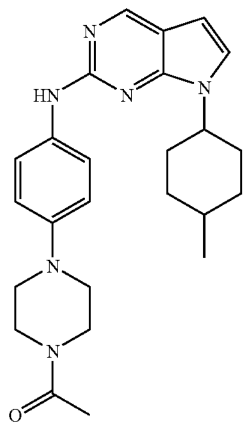 | 433.3 |
| 237 | 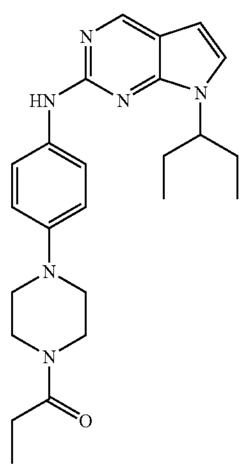 | 421.3 |

-continued

| Example | Structure | MS found (M + 1) |
|---|---|---|
| 238 | 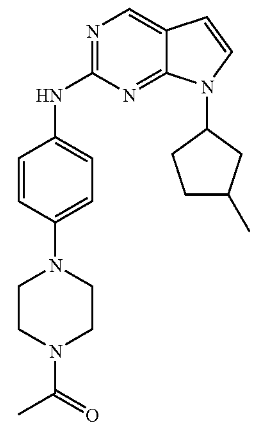 | 419.4 |
| 239 | 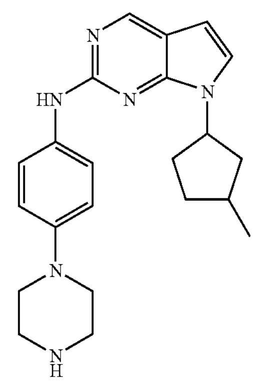 | 377.4 |
| 240 | 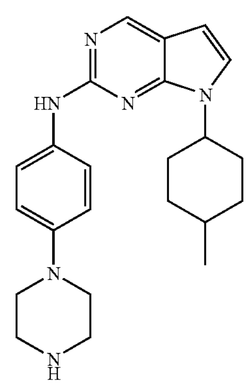 | 391.3 |

-continued

| Example | Structure | MS found (M + 1) |
|---|---|---|
| 241 | 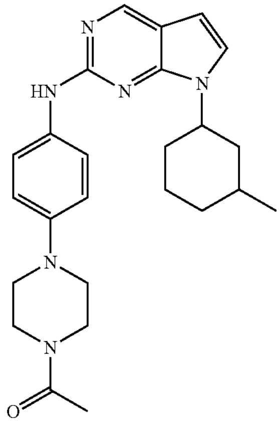 | 433.4 |
| 242 | 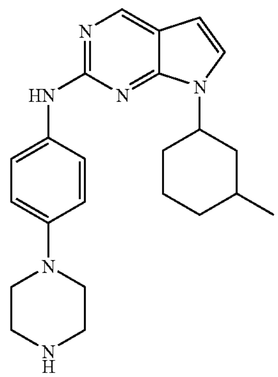 | 391.3 |
| 243 | 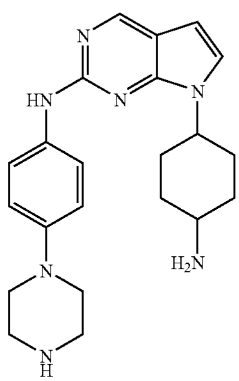 | 392.3 |
| 244 | 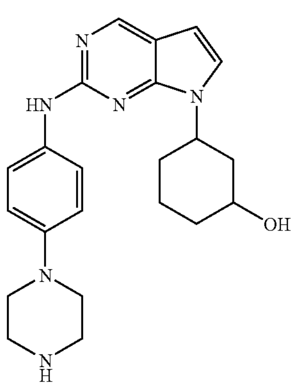 | 393.3 |

-continued

| Example | Structure | MS found (M + 1) |
|---|---|---|
| 245 | 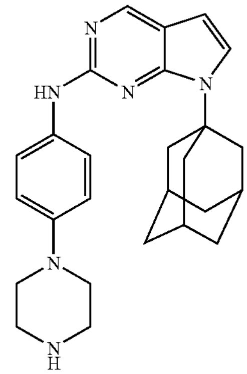 | 429.2 |
| 246 | 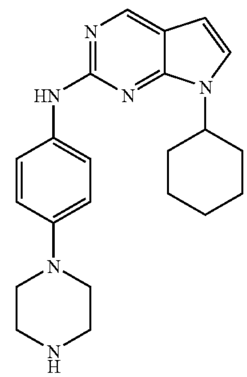 | 377.2 |
| 247 | 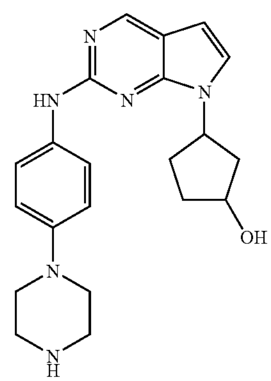 | 379.3 |
| 248 | 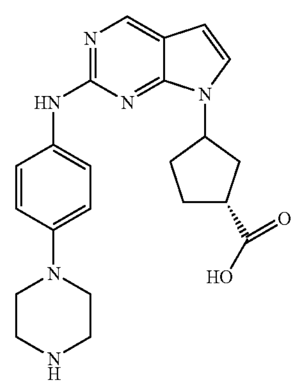 | 407.3 |

145
-continued
| Example | Structure | MS found (M + 1) |
|---|---|---|
| 249 | 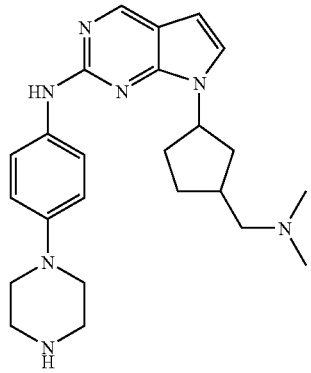 | 420.5 |
| 250 | 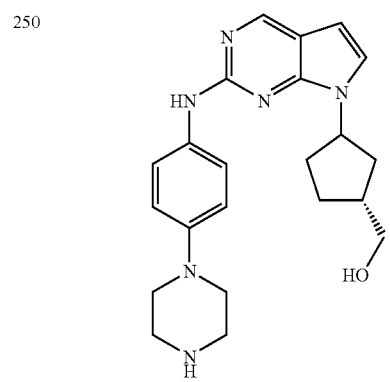 | 393.2 |
| 251 | 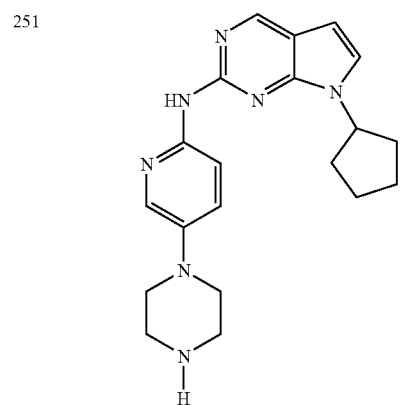 | 364 |
146
-continued
| Example | Structure | MS found (M + 1) |
|---|---|---|
| 252 | 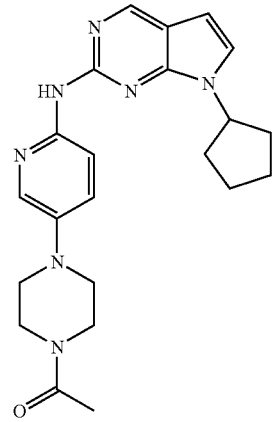 | 406 |
| 253 | 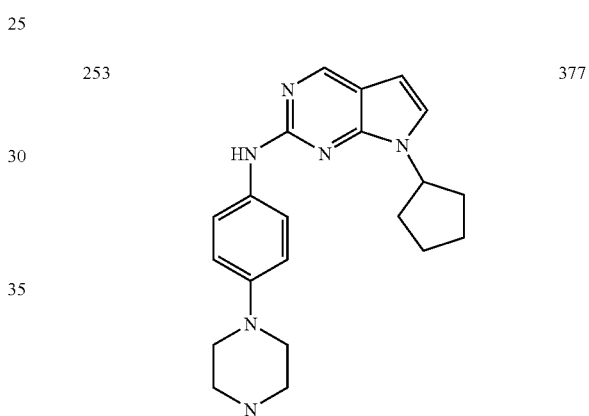 | 377 |
| 254 | 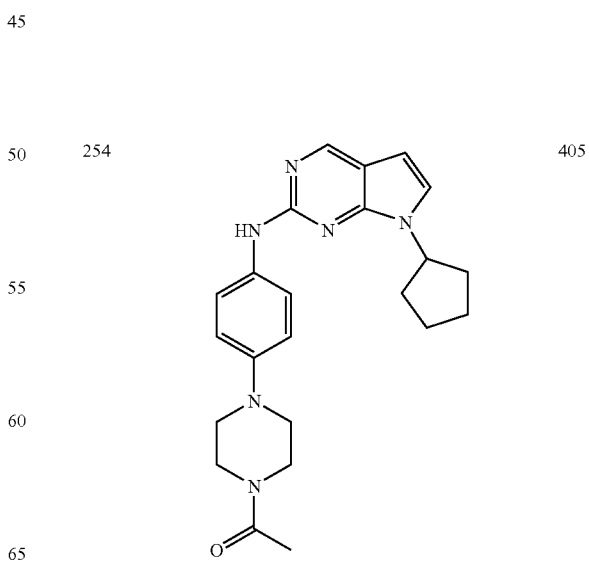 | 405 |

-continued
| Example | Structure | MS found (M + 1) |
|---------|-----------|------------------|
| 255 | 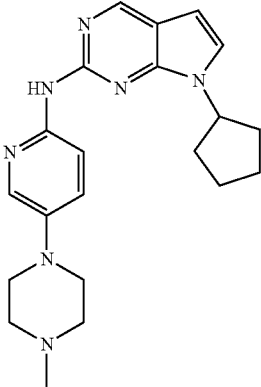 | 378 |
| 256 | 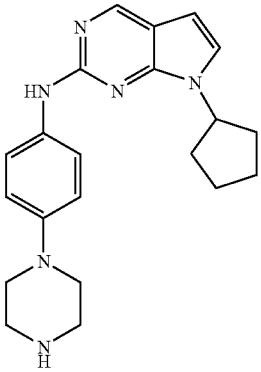 | 363.23 |
| 257 | 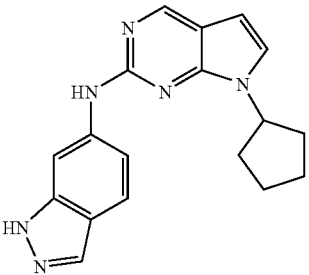 | 319.16 |
| 258 | 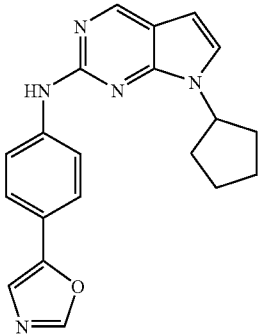 | 346.17 |
-continued
| Example | Structure | MS found (M + 1) |
|---------|-----------|------------------|
| 259 | 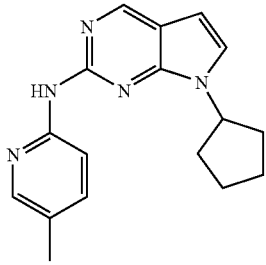 | 294.17 |
| 260 | 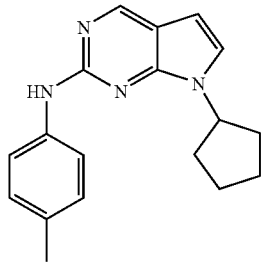 | 203.17 |
| 261 | 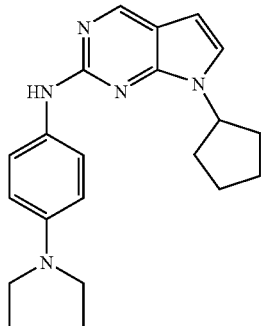 | 350.23 |
| 262 | 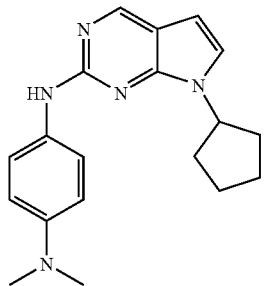 | 322.20 |

EXAMPLE 263

1-(4-{4-[7-(1-Ethyl-propyl)-5-methyl-7H-pyrrolo[2,3-d]pyrimidin-2-ylamino]-phenyl}-piperazin-1-yl)-ethanone

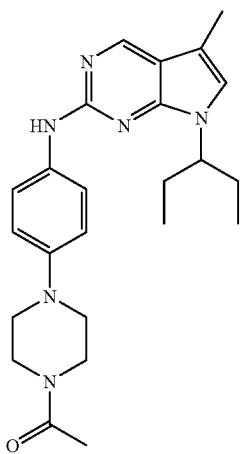

To a solution of 3-pentanone (1 g, 11.6 mmol) in anhydrous 1,2-dichloroethane (45 mL) is added allylamine (0.872 mL, 11.6 mmol) followed by NaBH(OAc)$_3$ (3.44 g, 16.3 mmol) at ambient temperature. The reaction mixture is stirred at room temperature overnight. The reaction mixture is quenched with 1N NaOH and extracted with dichloromethane. The extract is dried over Na$_2$SO$_4$ and concentrated in vacuo to give 1.27 g of allyl-(1-ethyl-propyl)-amine. The crude product is used as it is.

To a solution of allyl-(1-ethyl-propyl)-amine (1.27 g, 10 mmol) is added anhydrous isopropanol (50 mL) and 5-bromo-2,4-dichloropyrimidine (3.0 g, 5 mmol) and diisopropylethylamine (2.61 mL, 15 mmol) at ambient temperature. The reaction mixture is stirred overnight and concentrated in vacuo. The residue is purified with column chromatography (SiO$_2$, EtOAC/hexane 1:5) to give 2.76 g of allyl-(5-bromo-2-chloro-pyrimidin-4-yl)-(1-ethyl-propyl)-amine.

LCMS: 320.0 (M+H)$^+$

To a solution of allyl-(5-bromo-2-chloro-pyrimidin-4-yl)-(1-ethyl-propyl)-amine (2.76 g, 8.7 mmol) in anhydrous DMF (15 mL) is added Pd(OAc)$_2$ (156 mg, 0.69 mmol) and PPh$_3$ (182 mg, 0.69 mmol) and triethylamine (2.4 mL, 17.3 mmol). The reaction mixture is, stirred at 100° C. overnight. The reaction mixture is diluted with EtOAc, washed with water, dried over Na$_2$SO$_4$, and concentrated in vacuo. Purification with column chromatography (SiO$_2$, EtOAC/hexane 1:2) gives 0.95 g of 2-chloro-7-(1-ethyl-propyl)-5-methyl-7H-pyrrolo[2,3-d]pyrimidine.

LCMS: 238.2 (M+H)$^+$

By repeating the procedures described in example 65, using 2-chloro-7-(1-ethyl-propyl)-5-methyl-7H-pyrrolo[2,3-d]pyrimidine as a starting material, 1-(4-{4-[7-(1-ethyl-propyl)-5-methyl-7H-pyrrolo[2,3-d]pyrimidin-2-ylamino]-phenyl}-piperazin-1-yl)-ethanone is obtained.

LCMS: 421.2 (M+H)$^+$

EXAMPLES 264-319

By repeating the procedures described in example 115, using appropriate starting materials, the following compounds are obtained.

| Example | Structure | MS found (M + 1) |
|---|---|---|
| 264 | 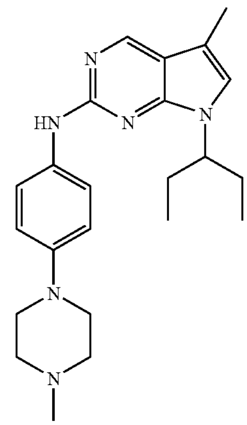 | 393.3 |
| 265 | 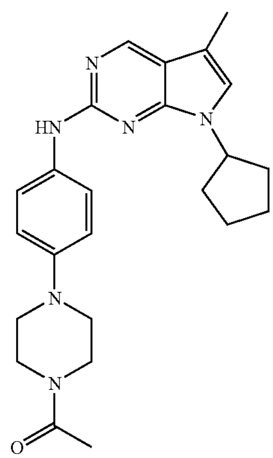 | 419.26 |
| 266 | 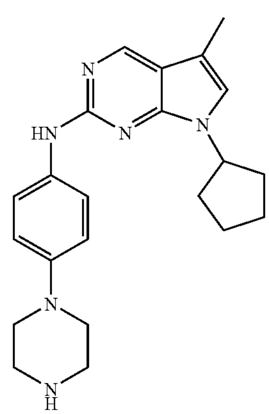 | 377.24 |

TABLE-continued
| Example | Structure | MS found (M + 1) |
|---|---|---|
| 267 | 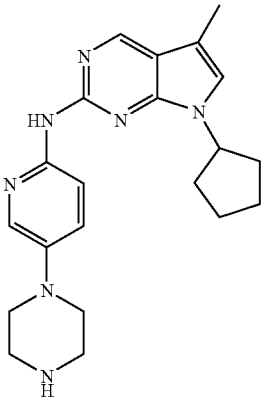 | 377.24 |
| 268 | 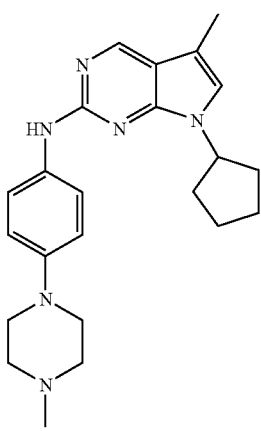 | 391.26 |
| 269 | 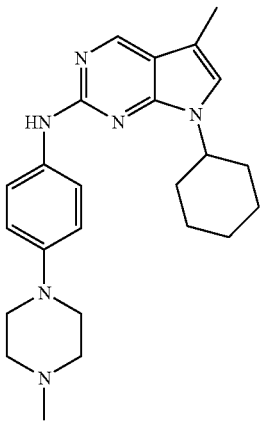 | 405.28 |
TABLE-continued
| Example | Structure | MS found (M + 1) |
|---|---|---|
| 270 | 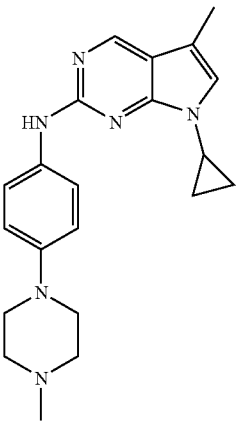 | 363.23 |
| 271 | 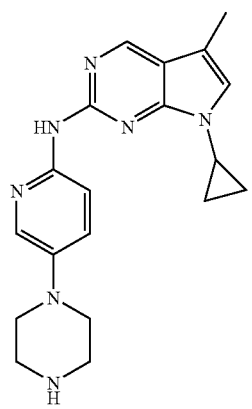 | 350.21 |
| 272 | 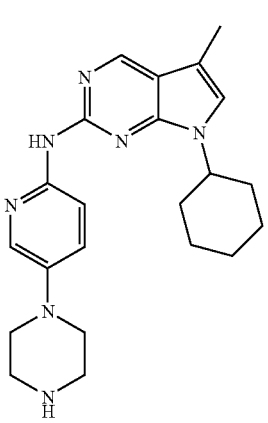 | 392.26 |

-continued
| Example | Structure | MS found (M + 1) |
|---|---|---|
| 273 | 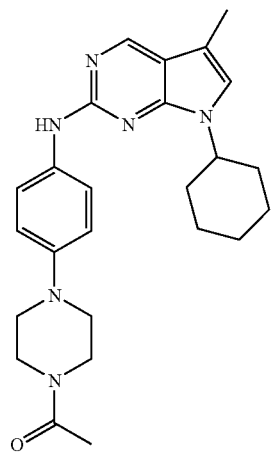 | 385 |
| 274 | 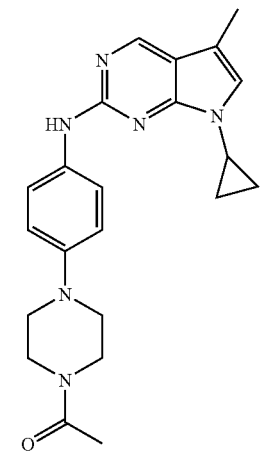 | 433.28 |
| 275 | 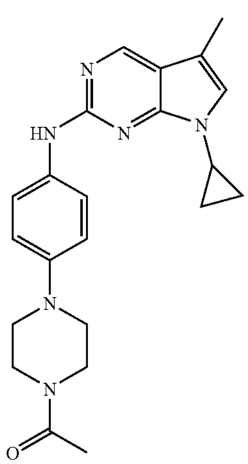 | 391.22 |
-continued
| Example | Structure | MS found (M + 1) |
|---|---|---|
| 276 | 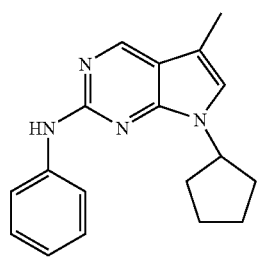 | 349.21 |
| 277 | 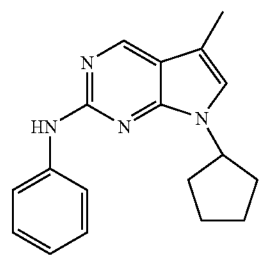 | 293.2 |
| 278 | 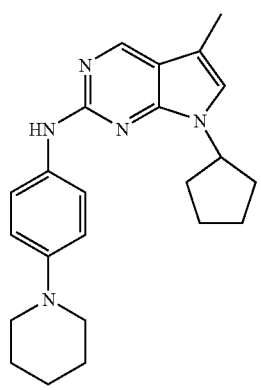 | 376.6 |
| 279 | 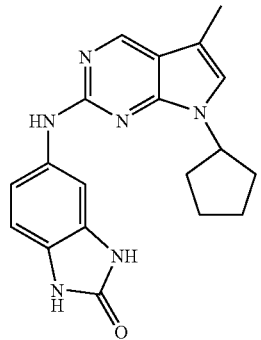 | 349.2 |

-continued
| Example | Structure | MS found (M + 1) |
|---|---|---|
| 280 | 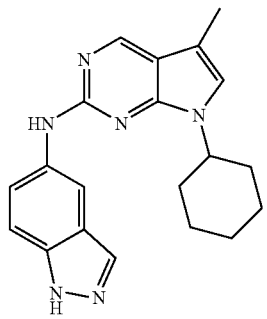 | 347.20 |
| 281 | 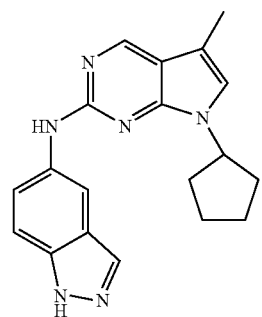 | 333.2 |
| 282 | 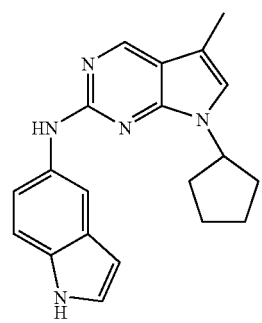 | 332.2 |
| 283 | 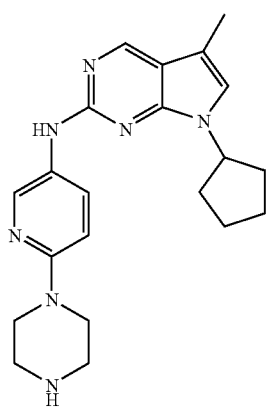 | 378.24 |
-continued
| Example | Structure | MS found (M + 1) |
|---|---|---|
| 284 | 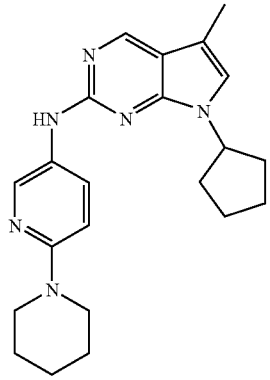 | 377.24 |
| 285 | 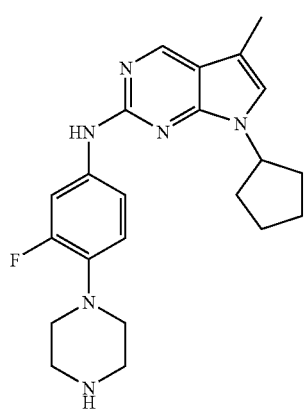 | 395 |
| 286 | 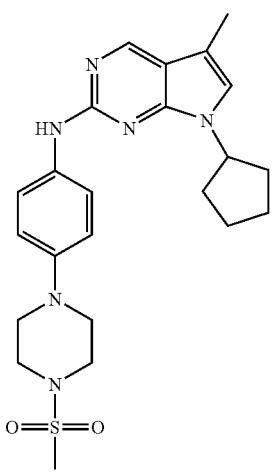 | 455.17 |

-continued

| Example | Structure | MS found (M + 1) |
|---|---|---|
| 287 | 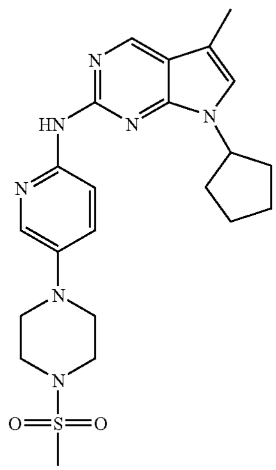 | 456.1 |
| 288 | 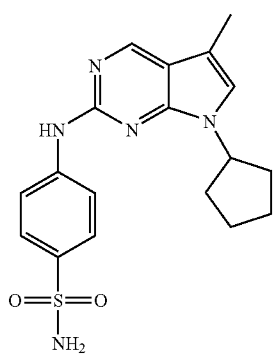 | 372.07 |
| 289 | 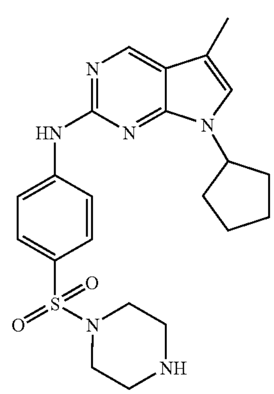 | 441.21 |

-continued

| Example | Structure | MS found (M + 1) |
|---|---|---|
| 290 | 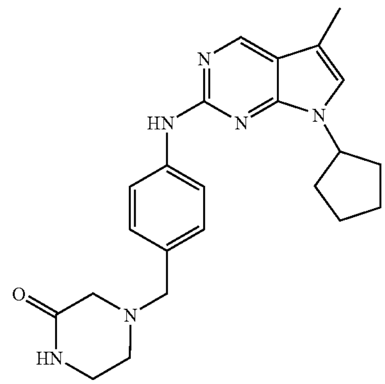 | 405.24 |
| 291 | 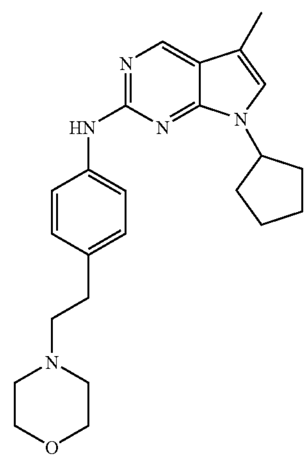 | 406.26 |
| 292 | 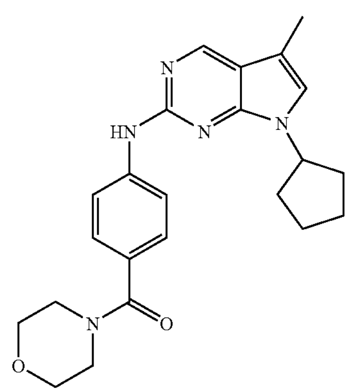 | 406.22 |
| 293 | 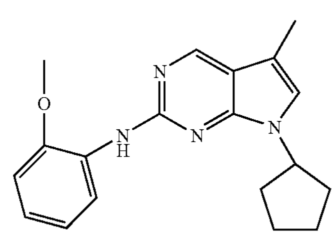 | 323.2 |

| Example | Structure | MS found (M+1) |
|---|---|---|
| 294 | 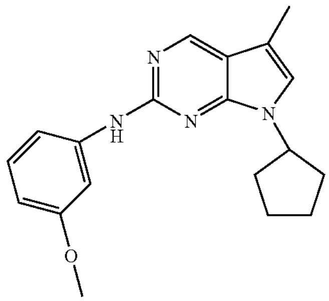 | 323.2 |
| 295 | 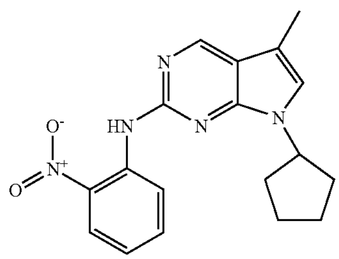 | 338.1 |
| 296 | 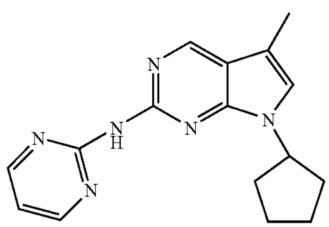 | 295.2 |
| 297 | 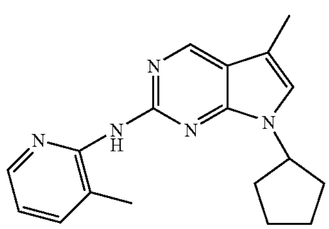 | 308.2 |
| 298 | 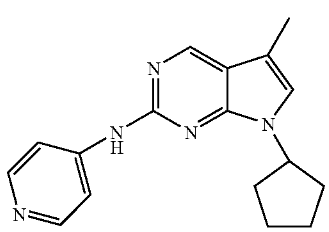 | 294.2 |
| 299 | 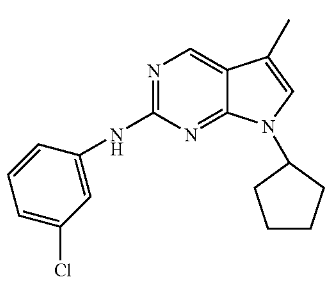 | 327.1 |
| 300 | | 294.2 |
| 301 | | 318.2 |
| 302 | | 379.22 |
| 303 | | 344.2 |
| 304 | | 295.2 |

-continued
| Example | Structure | MS found (M + 1) |
|---|---|---|
| 305 | 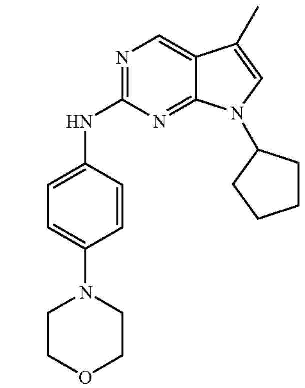 | 378.2 |
| 306 | 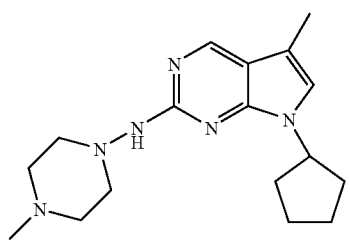 | 315.2 |
| 307 | 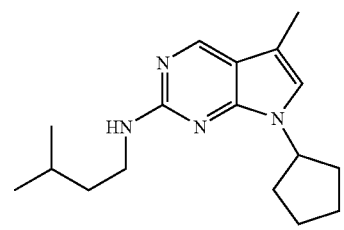 | 288.28 |
| 308 | 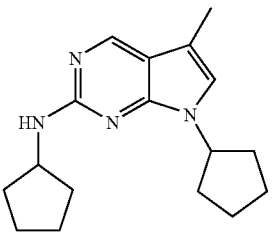 | 286.31 |
| 309 | 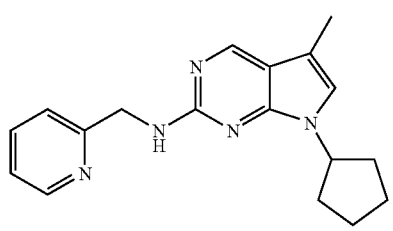 | 308.03 |
| 310 | 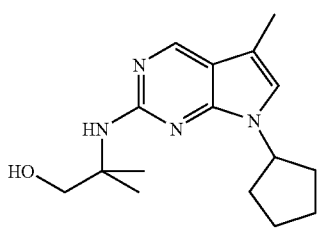 | 364.2 |
-continued
| Example | Structure | MS found (M + 1) |
|---|---|---|
| 311 | 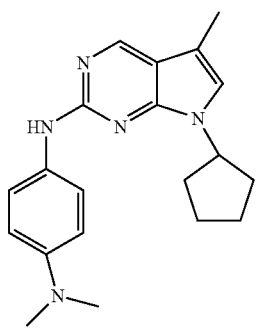 | 336.2 |
| 312 | 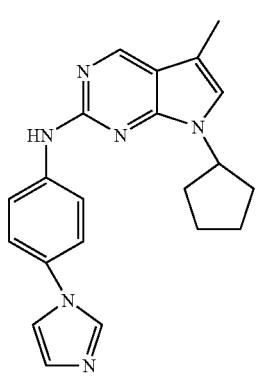 | 359.2 |
| 313 | 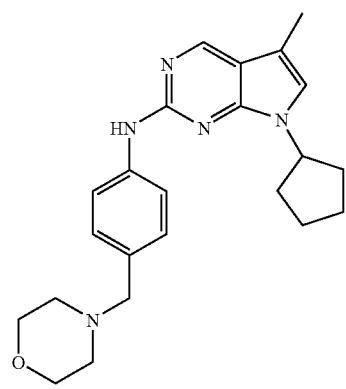 | 392.25 |
| 314 | 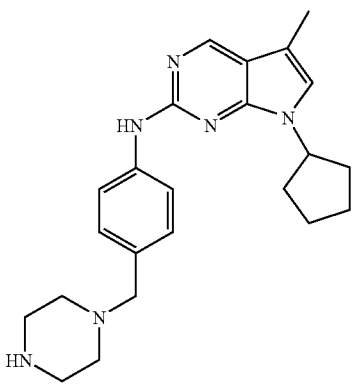 | 391.26 |

163
-continued

| Example | Structure | MS found (M + 1) |
|---|---|---|
| 315 | 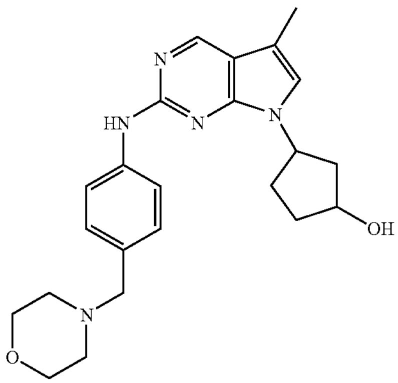 | 408.24 |
| 316 | 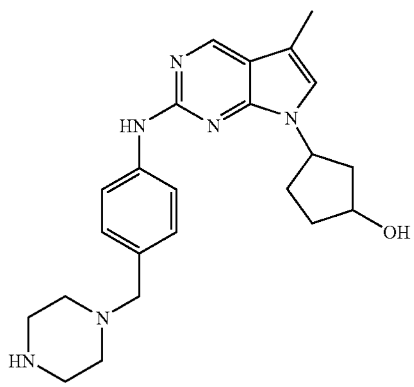 | 407.26 |
| 317 | 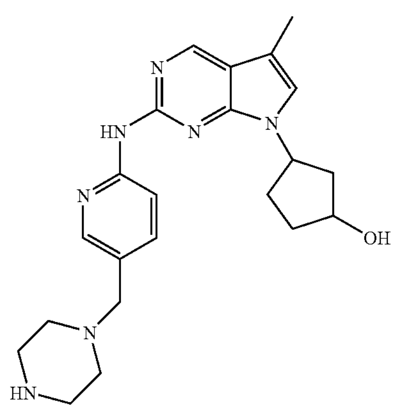 | 408.25 |
| 318 | 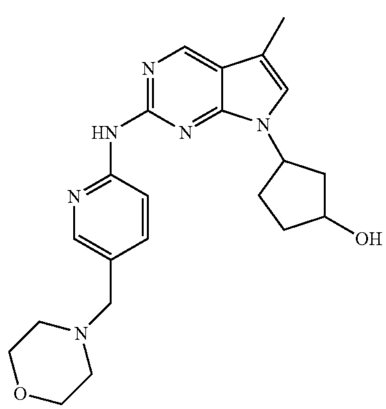 | 409.23 |

164
-continued

| Example | Structure | MS found (M + 1) |
|---|---|---|
| 319 | | 406.3 |

EXAMPLE 320

(5-Methyl-7-pyridin-2-yl-7H-pyrrolo[2,3-d]pyrimidin-2-yl)-(5-piperazin-1-yl-pyridin-2-yl)-amine A solution of 5-bromo-2,4-dichloropyrimidine (5.0 g, 22 mmol), allylamine (1.98 mL, 26.4 mmol), and diisopropylethylamine (5.6 mL, 33.0 mmol) are stirred in ethanol (100 mL) at 50° C. overnight. The solvent is removed in vacuo and the residue is partitioned between ethyl acetate and saturated aqueous ammonium chloride solution. The organic layer is washed with brine, dried over anhydrous sodium sulfate and evaporated to provide Allyl-(5-bromo-2-chloro-pyrimidin-4-yl)-amine as a white crystalline solid (89%), which is used without further purification.

A mixture of Allyl-(5-bromo-2-chloro-pyrimidin-4-yl)-amine (1 g, 4 mmol), palladium(II) acetate, (90 mg, 0.40 mmol), triphenylphosphine (211 mg, 0.80 mmol) and triethylamine (1.1 mL, 8.0 mmol) in DMF (10 mL) is heated at 100° C. overnight. After cooling to room temperature the reaction mixture is diluted with ethyl acetate and washed with brine. The organic phase is dried (anhydrous $Na_2SO_4$) and the solvent is evaporated. The crude product is purified by flash chromatography (gradient elution EtOAC:Heptanes 0:0 to 1:1) on silicagel to afford 2-Chloro-5-methyl-7H-pyrrolo[2,3-d]pyrimidine as a white solid (40%).

A mixture of 2-Chloro-5-methyl-7H-pyrrolo[2,3-d]pyrimidine (80 mg, 0.48 mmol), 2-bromopyridine (113 mg, 0.72 mmol), copper(I) iodide (9.1 mg, 0.48 mmol), K₃PO₄ (2.02 g, 23.84 mmol), and trans-1,2-diaminocyclohexane (5.44 mg, 0.48 mmol) in 1,4-dioxane (7 mL) is stirred at 90° C. for 1.5 hrs. After cooling to room temperature the reaction mixture is diluted with ethyl acetate and washed with brine. The organic phase is dried (anhydrous Na₂SO₄) and the solvent is evaporated. The crude product is purified by flash chromatography (gradient elution ethyl acetate:heptanes 0:1 to 1:4) on silica-gel to afford 2-Chloro-5-methyl-7-pyridin-2-yl-7H-pyrrolo[2,3-d]pyrimidine as a white solid (55%).

A mixture of 2-Chloro-5-methyl-7-pyridin-2-yl-7H-pyrrolo[2,3-d]pyrimidine (15 mg, 0.06 mmol), 4-(6-Amino-pyridin-3-yl)-piperazine-1-carboxylic acid tert-butyl ester (20.5 mg, 0.075 mmol), Pd₂(dba)₃ (2.8 mg, 0.0031 mmol), BINAP (3.82 mg, 0.0061 mmol), sodium tert-butoxide (8.84 mg, 0.092 mmol), and 1,4-dioxane (4 mL) under nitrogen is heated in a sealed tube apparatus at 100° C. for 2.5 h. After cooling to room temperature the reaction mixture is diluted with ethyl acetate and washed with brine. The organic phase is dried (anhydrous Na₂SO₄) and the solvent is evaporated. The crude product is dissolved in DCM (2 mL) and TFA (0.5 ml was added). The solution is stirred at room temperature. The reaction mixture is diluted with ethyl acetate and washed with brine. The organic phase is dried (anhydrous Na₂SO₄) and the solvent is evaporated. The crude product is purified by hplc to afford (5-Methyl-7-pyridin-2-yl-7H-pyrrolo[2,3-d]pyrimidin-2-yl)-(5-piperazin-1-yl-pyridin-2-yl)-amine as a pale yellow solid (27%, two steps). ¹H NMR (400 MHz, DMSO-d6) 8.80-8.81 (m, 2H), 8.51 (s, 1H), 8.12 (d, J=5.0 Hz, 1H), 8.0-8.11 (m, 1H), 8.0 (d, J=2.9 Hz, 1H), 7.90 (s, 1H), 7.49 (d, J=2.4 Hz, 1H), 7.32 (d, J=2.4 Hz, 1H), 3.04-3.06 (m, 4H), (2.86-2.89 (m, 4H), 2.32 (s, 3H). MS (ESI) m/z 387.09 [M+H]⁺.

EXAMPLES 321-325

By repeating the procedure described in example 320, using 2-Chloro-5-methyl-7H-pyrrolo[2,3-d]pyrimidine and appropriate starting materials, the following compounds are prepared.

| Example | Structure | MS found (M + 1) |
|---|---|---|
| 321 | | 393.16 |
| 322 | 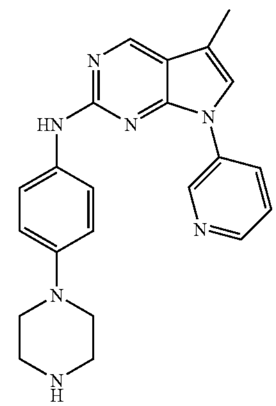 | 386.11 |
| 323 | 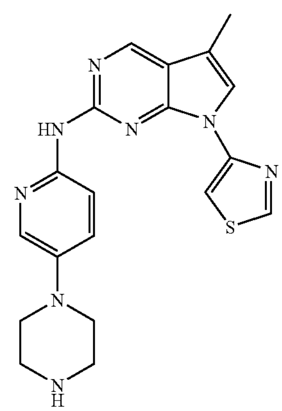 | 393.03 |
| 324 | 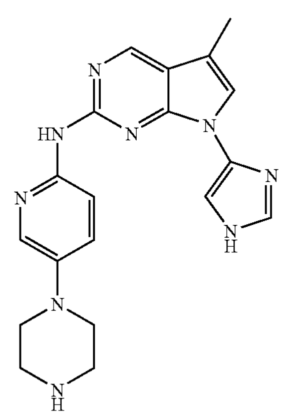 | 376.04 |

| Example | Structure | MS found (M + 1) |
|---|---|---|
| 325 | 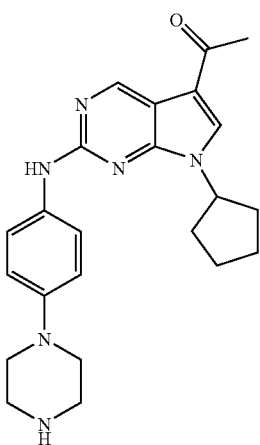 | 366 |

EXAMPLE 326

1-[7-cyclopentyl-2-(4-piperazin-1-yl-phenylamino)-7H-pyrrolo[2,3-d]pyrimidin-5-yl]-ethanone 2-chloro-7-(cyclopentyl)-7H-pyrrolo[2,3-d]pyrimidine is prepared from cyclopentyl amine and 5-bromo-2,4-dichloropyrimidine using a method similar to that for the preparation of 2-chloro-7-(1-ethyl-propyl)-7H-pyrrolo[2,3-d]pyrimidine given in example 1.

To a solution of aluminium chloride (400 mg, 2.99 mmol) and acetyl chloride (711 uL, 10 mmol) in dichloromethane (2 mL) is added 2-chloro-7-(cyclopentyl)-7H-pyrrolo[2,3-d]pyrimidine (221 mg, 1.0 mmol) in dichloromethane (5 mL), dropwise. After 20 minutes saturated aqueous sodium bicarbonate is added to pH 9-10 and the solution is extracted with dichloromethane. The organic phase is dried, anhydrous $Na_2SO_4$ and concentrated to obtain 1-(2-Chloro-7-cyclopentyl-7H-pyrrolo[2,3-d]pyrimidin-5-yl)-ethanone (255 mg, 97%) as an off-white amorphous solid (97%). $^1$H-NMR and LCMS.

1-[7-cyclopentyl-2-(4-piperazin-1-yl-phenylamino)-7H-pyrrolo[2,3-d]pyrimidin-5-yl]-ethanone is prepared from 1-(2-Chloro-7-cyclopentyl-7H-pyrrolo[2,3-d]pyrimidin-5-yl)-ethanone and 4-(4-Aminophenyl)-piperazine-1-carboxylic acid tert-butyl ester using a method similar to that for the preparation of Example 202. [M+H$^+$] 405.2.

EXAMPLE 327

(7-Cyclopentyl-5-isopropyl-7H-pyrrolo[2,3-d]pyrimidin-2-yl)-(5-piperazin-1-yl-pyridin-2-yl)-amine

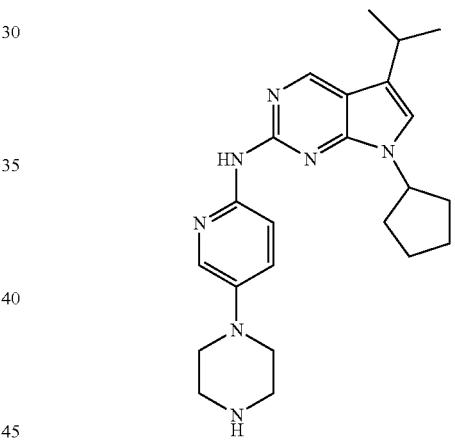

2-Chloro-7-cyclopentyl-5-isopropyl-7H-pyrrolo[2,3-d]pyrimidine is prepared from 2-chloro-7-(cyclopentyl)-7H-pyrrolo[2,3-d]pyrimidine and 2-chloropropane using a method similar to that for the preparation of 1-(2-Chloro-7-cyclopentyl-7H-pyrrolo[2,3-d]pyrimidin-5-yl)-ethanone given in Example 325.

(7-Cyclopentyl-5-isopropyl-7H-pyrrolo[2,3-d]pyrimidin-2-yl)-(5-piperazin-1-yl-pyridin-2-yl)-amine is prepared from 2-Chloro-7-cyclopentyl-5-isopropyl-7H-pyrrolo[2,3-d]pyrimidine and 4-(6-Amino-pyridin-3-yl)-piperazine-1-carboxylic acid tert-butyl ester using a method similar to that for the preparation of Example 202. [MH+] 406.21

| Example | Structure | MS found (M + 1) |
|---|---|---|
| 328 | 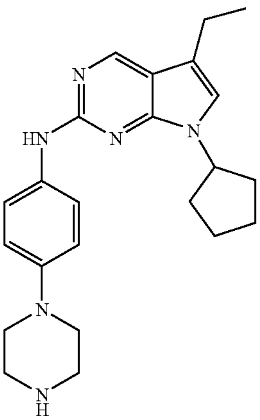 | 391.26 |

EXAMPLE 329

[7-(1-Ethyl-propyl)-6-methyl-7H-pyrrolo[2,3-d]pyrimidin-2-yl]-(4-piperazin-1-yl-phenyl)-amine

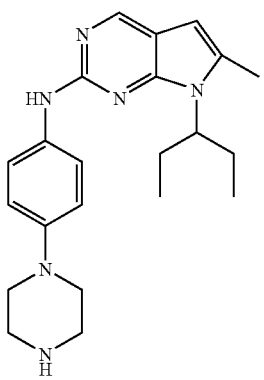

To a microwave vial is added a solution of (5-bromo-2-chloro-pyrimidin-4-yl)-(1-ethyl-propyl)-amine (0.5 g, 1.80 mmol) in anhydrous toluene (10 mL), tributyl(1-propynyl)-tin (1.1 mL, 3.6 mmol) and Pd(PPh$_3$)$_4$ (41.5 mg, 0.036 mmol). The reaction mixture is heated at 120° C. for 1 h by employing microwave. The reaction mixture is diluted with EtOAc, washed with NaHCO$_3$ aqueous solution and water, dried over Na$_2$SO$_4$, and concentrated in vacuo. Purification with column chromatography (SiO$_2$, EtOAC/hexane 1:5) gave 0.32 g of (2-chloro-5-prop-1-ynyl-pyrimidin-4-yl)-(1-ethyl-propyl)-amine

LCMS: 238.2 (M+H)$^+$

To a microwave vial are added (2-chloro-5-prop-1-ynyl-pyrimidin-4-yl)-(1-ethyl-propyl)-amine (0.22 g, 0.92 mmol), anhydrous DMF (3 mL), and CuI (53 mg, 0.27 mmol). The reaction is heated at 160° C. for 1 h by employing microwave. The reaction mixture is diluted with EtOAc, washed with NaHCO$_3$ aqueous solution and water, dried over Na$_2$SO$_4$, and concentrated in vacuo. Purification with column chromatography (SiO$_2$, EtOAC/hexane 1:4) gives 43 mg of 2-chloro-7-(1-ethyl-propyl)-6-methyl-7H-pyrrolo[2,3-d]pyrimidine.

LCMS: 238.2 (M+H)$^+$

By repeating the procedures described in example 202, using 2-chloro-7-(1-ethyl-propyl)-6-methyl-7H-pyrrolo[2,3-d]pyrimidine as a starting material, [7-(1-ethyl-propyl)-6-methyl-7H-pyrrolo[2,3-d]pyrimidin-2-yl]-(4-piperazin-1-yl-phenyl)-amine is obtained.

LCMS: 379.1 (M+H)$^+$

EXAMPLES 330-332

By repeating the procedures described in example 329, using appropriate starting materials, the following compounds are obtained.

| Example | Structure | MS found (M + 1) |
|---|---|---|
| 330 | 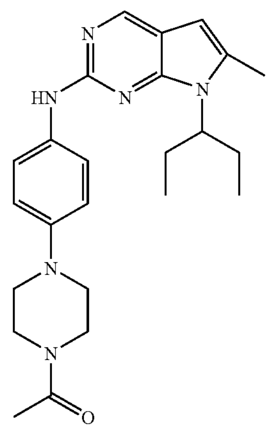 | 421.4 |
| 331 | 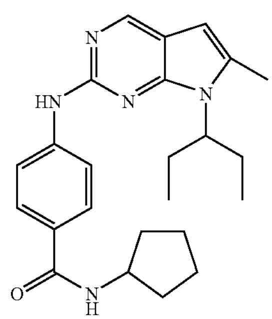 | 406.3 |
| 332 | 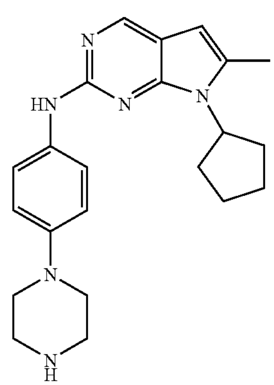 | 377.1 |

EXAMPLE 333

1-[7-Cyclopentyl-6-methyl-2-(4-piperazin-1-yl-phenylamino)-7H-pyrrolo[2,3-d]pyrimidin-5-yl]-ethanone

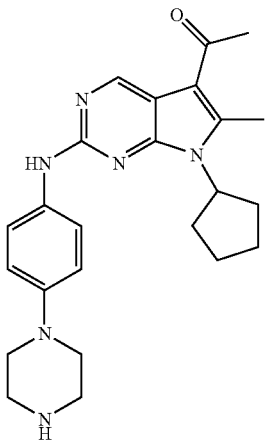

2-Chloro-7-cyclopentyl-6-methyl-7H-pyrrolo[2,3-d]pyrimidine is prepared from cyclopentyl amine and 5-bromo-2,4-dichloropyrimidine using a method similar to that for the preparation of 2-chloro-7-(1-ethyl-propyl)-6-methyl-7H-pyrrolo[2,3-d]pyrimidine.
given in example 328.

1-(2-Chloro-7-cyclopentyl-6-methyl-7H-pyrrolo[2,3-d]pyrimidin-5-yl)-ethanone is prepared from 2-Chloro-7-cyclopentyl-6-methyl-7H-pyrrolo[2,3-d]pyrimidine and acetyl chloride using a method similar to that for the preparation of 1-(2-Chloro-7-cyclopentyl-7H-pyrrolo[2,3-d]pyrimidin-5-yl)-ethanone given in Example 325.

1-[7-Cyclopentyl-6-methyl-2-(4-piperazin-1-yl-phenylamino)-7H-pyrrolo[2,3-d]pyrimidin-5-yl]-ethanone is prepared from 1-(2-Chloro-7-cyclopentyl-7H-pyrrolo[2,3-d]pyrimidin-5-yl)-ethanone and 4-(4-aminophenyl)piperazine-1-carboxylic acid tert-butyl ester using a method similar to that given for the preparation of Example 202. (MH+) 419.2

EXAMPLE 334

(5-chloro-7-cyclopentyl-6-methyl-7H-pyrrolo[2,3-d]pyrimidin-2-yl)-(4-piperazin-1-yl-phenyl)-amine

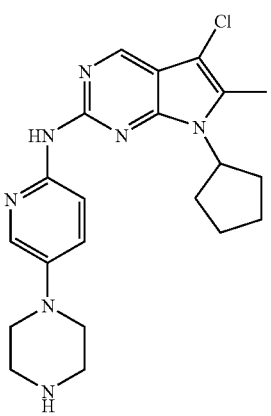

To a solution of 2-Chloro-7-cyclopentyl-6-methyl-7H-pyrrolo[2,3-d]pyrimidine (164 mg, 0.70 mmol) in dichloromethane (3 mL) is added N-chlorosuccinimide (0.4M in DCM, 1.1 eq) over 1 h. The reaction mixture is allowed to stir for 3 days at room temperature. The reaction mixture is diluted with dichloromethane and washed with saturated aqueous sodium bicarbonate followed by brine. The organic phase is concentrated and the crude product is purified by normal phase chromatography ($SiO_2$, EtOAc/heptane) to obtain 2,5-Dichloro-7-cyclopentyl-6-methyl-7H-pyrrolo[2,3-d]pyrimidine (158 mg, 84%).

(5-chloro-7-cyclopentyl-6-methyl-7H-pyrrolo[2,3-d]pyrimidin-2-yl)-(4-piperazin 1-yl-phenyl)-amine is prepared from 2,5-Dichloro-7-cyclopentyl-6-methyl-7H-pyrrolo[2,3-d] and 4-(6-Amino-pyridin-3-yl)-piperazine-1-carboxylic acid tert-butyl ester using a method similar to that for the preparation of Example 202. (MH+) 412.2

EXAMPLE 335

7-(1-ethyl-propyl)-2-(4-piperazin-1-yl-phenylamino)-7H-pyrrolo[2,3-d]pyrimidine-6-carboxylic acid dimethyl amide

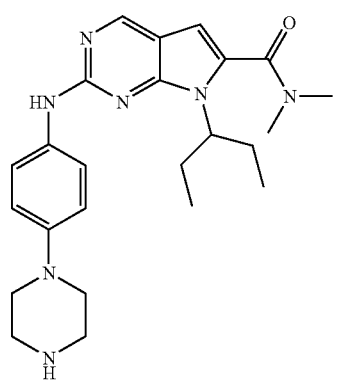

To a mixture of (5-bromo-2-chloro-pyrimidin-4-yl)-(1-ethyl-propyl)-amine (420 mg, 1.5 mmol) and propargylaldehyde diethyl acetal (0.32 mL, 2.25 mmol) in DMF (6 mL) is added $PdCl_2(PPh_3)_2$ (105 mg, 0.15 mmol) and CuI (28 mg, 0.15 mmol), followed by $Et_3N$ (0.42 mL, 3 mmol). The mixture is degassed, and heated at 55° C. for 16 h. After cooling to room temperature, the reaction mixture is diluted with EtOAc, washed with water and brine. The organic layer is dried over $Na_2SO_4$, filtered and concentrated under reduced pressure. The crude product is purified by column chromatography ($SiO_2$, EtOAc/heptane 5:95 to 40:60) to give 182 mg of [2-chloro-5-(3,3-diethoxy-prop-1-ynyl)-pyrimidin-4-yl]-(1-ethyl-propyl)-amine as a light brown oil.
LCMS: 326 (M+H)+

To a solution of [2-chloro-5-(3,3-diethoxy-prop-1-ynyl)-pyrimidin-4-yl]-(1-ethyl-propyl)-amine (326 mg, 1 mmol) in THF (2 mL) is added 1N TBAF in THF (5 mL, 5 mmol) at ambient temperature. The reaction mixture is heated at 70° C. for 2 h. After cooling down, the mixture is concentrated in vacuo and purified by BIOTAGE column (EtOAc/heptane 5:5 to 40:60) to give 307 mg of 2-chloro-6-diethoxymethyl-7-(1-ethyl-propyl)-7H-pyrrolo[2,3-d]pyrimidine as a light yellow oil.
LCMS: 326 (M+H)+.

To a solution of 2-chloro-6-diethoxymethyl-7-(1-ethyl-propyl)-7H-pyrrolo[2,3-d]pyrimidine (67 mg, 0.2 mmol) in 1,4-dioxane (0.7 mL) is added conc. HCl (0.2 mL) at ambient temperature. The reaction mixture is stirred for 30 min, then neutralized with 2N NaOH aqueous solution and saturated NaHCO₃ aqueous solution. The mixture is extracted with EtOAc. The extracts are washed with brine, dried over Na₂SO₄, filtered and concentrated in vacuo to give 54 mg of 2-chloro-7-(1-ethyl-propyl)-7H-pyrrolo[2,3-d]pyrimidine-6-carbaldehyde as a yellow solid. The crude product is used as it is.

LCMS: 252 (M+H)⁺.

To a mixture of 2-chloro-7-(1-ethyl-propyl)-7H-pyrrolo[2,3-d]pyrimidine-6-carbaldehyde (283 mg, 1.11 mmol) in DMF (3 mL) is added oxone (820 mg, 1.33 mmol) at room temperature. The mixture is stirred at room temperature for 5 h and is quenched with 20% Na₂S₂O₃ aqueous solution. After stirring for 10 min, the reaction mixture is acidified with 1N HCl aqueous solution (pH=5). The mixture is extracted with dichloromethane, dried over Na₂SO₄ and concentrated in vacuo. The solid is filtered, washed with acetonitrile, and dried under vacuum to give 130 mg of 2-chloro-7-(1-ethyl-propyl)-7H-pyrrolo[2,3-d]pyrimidine-6-carboxylic acid as a pale brown solid.

LCMS: 268 (M+H)⁺.

To a solution of 2-chloro-7-(1-ethyl-propyl)-7H-pyrrolo[2,3-d]pyrimidine-6-carboxylic acid (80 mg, 0.30 mmol), BOP (159 mg, 0.36 mmol) and N,N-diisopropylethylamine (0.078 mL, 0.45 mmol) in DMF (3 mL) is added 0.164 mL of 2 N dimethylamine in THF solution at room temperature. The mixture is stirred at room temperature for 3 h, quenched with 1N NaOH aqueous solution, and extracted with EtOAc. The organic extracts are washed with brine, dried over Na₂SO₄, filtered, and concentrated under reduced pressure. The crude product is purified by column chromatography (SiO₂, 5% MeOH in CH₂Cl₂) to give 64 mg of 2-chloro-7-(1-ethyl-propyl)-7H-pyrrolo[2,3-d]pyrimidine-6-carboxylic acid dimethylamide.

LCMS: 295.1 (M+H)⁺.

By repeating the procedures described in example 202, using 2-chloro-7-(1-ethyl-propyl)-7H-pyrrolo[2,3-d]pyrimidine-6-carboxylic acid dimethylamide as a starting material, 7-(1-ethyl-propyl)-2-(4-piperazin-1-yl-phenylamino)-7H-pyrrolo[2,3-d]pyrimidine-6-carboxylic acid dimethyl amide is obtained.

LCMS: 436.3 (M+H)⁺.

EXAMPLES 336-359

By repeating the procedures described in example 335, using appropriate starting materials, the following compounds are obtained.

| Example | Structure | MS found (M + 1) |
|---|---|---|
| 336 | 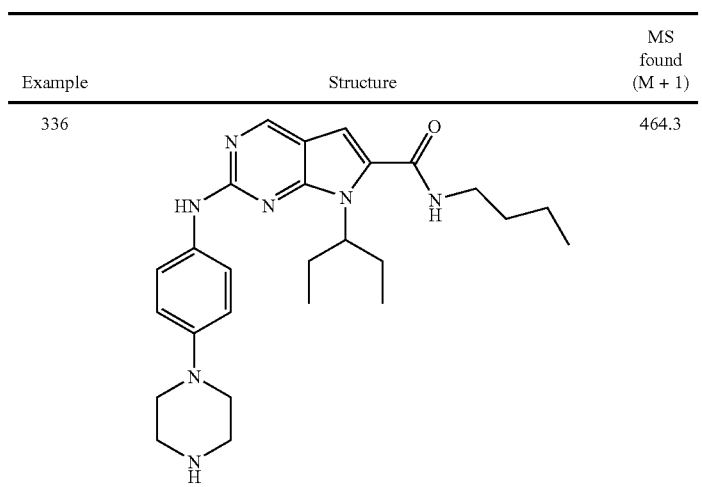 | 464.3 |
| 337 | 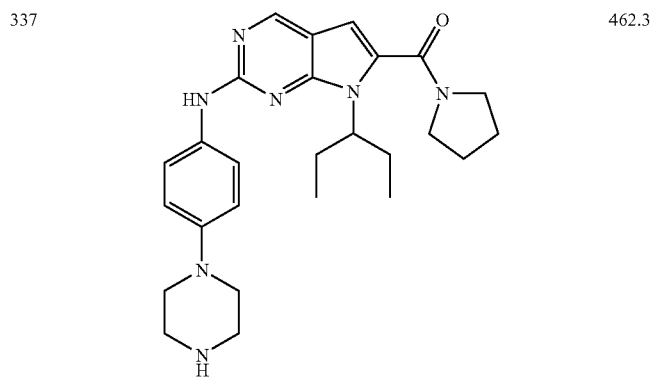 | 462.3 |

| Example | Structure | MS found (M + 1) |
|---------|-----------|------------------|
| 338 | 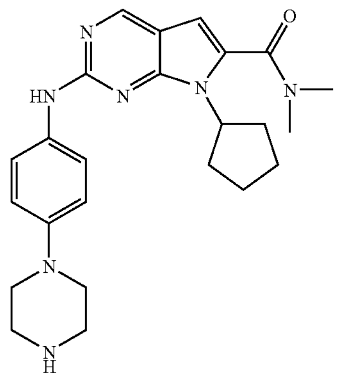 | 434.27 |
| 339 | 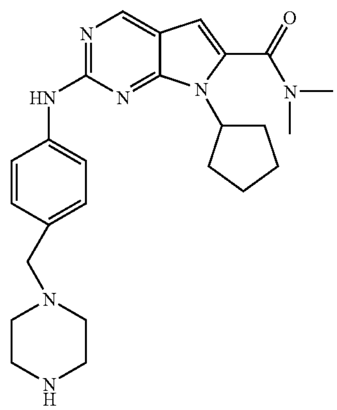 | 448.28 |
| 340 | 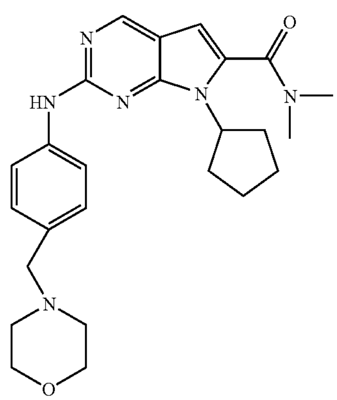 | 449.26 |
| 341 | 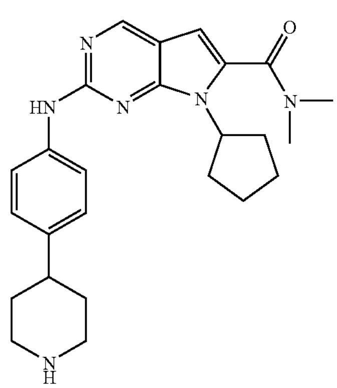 | 433.27 |

-continued

| Example | Structure | MS found (M + 1) |
|---------|-----------|------------------|
| 342 | 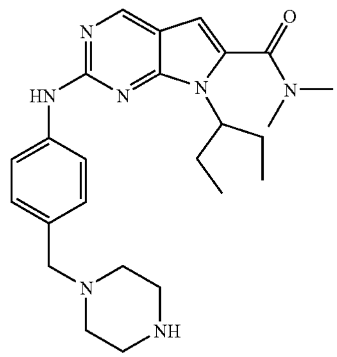 | 450.30 |
| 343 | 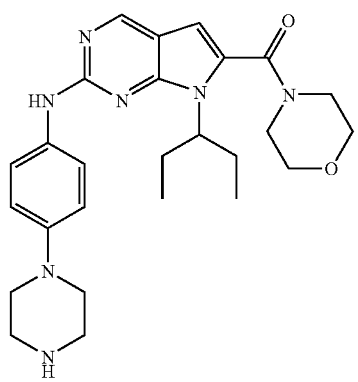 | 478.3 |
| 344 | 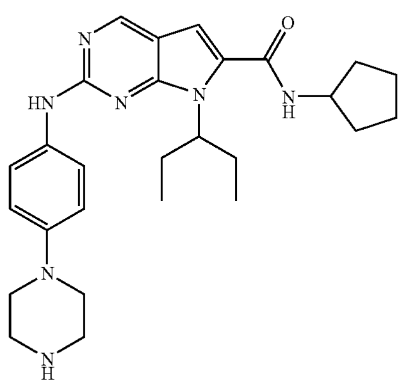 | 476.3 |
| 345 | 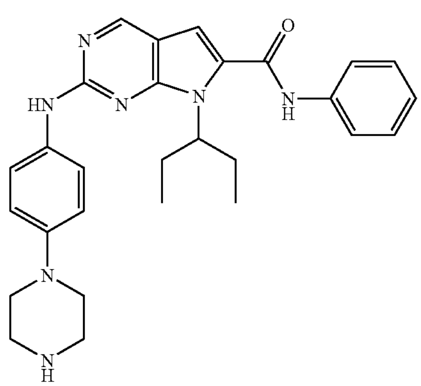 | 484.3 |

-continued

| Example | Structure | MS found (M + 1) |
|---|---|---|
| 346 | 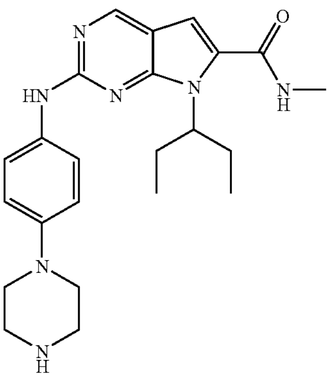 | 422.2 |
| 347 | 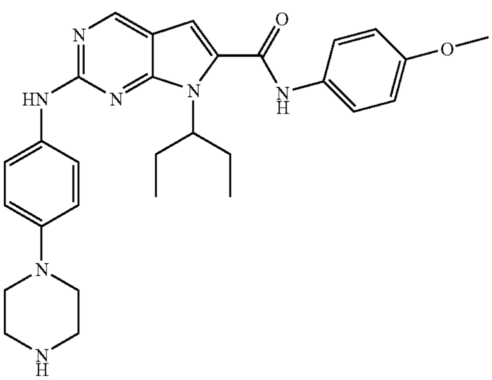 | 514.3 |
| 348 | 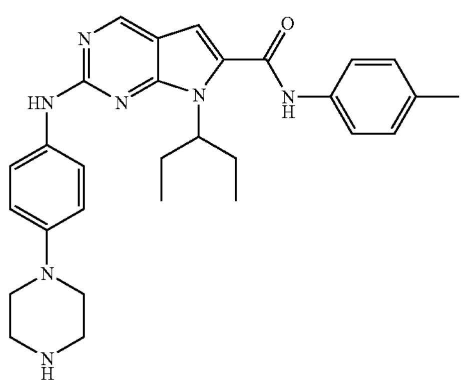 | 498.3 |
| 349 | 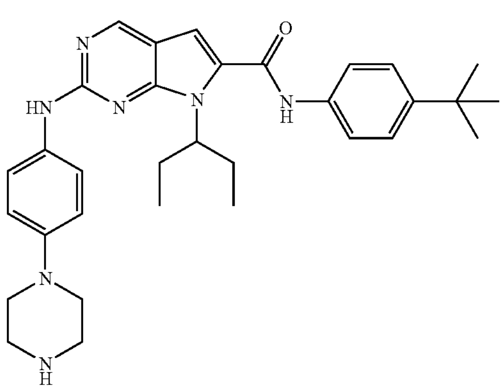 | 540.3 |

-continued

| Example | Structure | MS found (M + 1) |
|---|---|---|
| 350 | 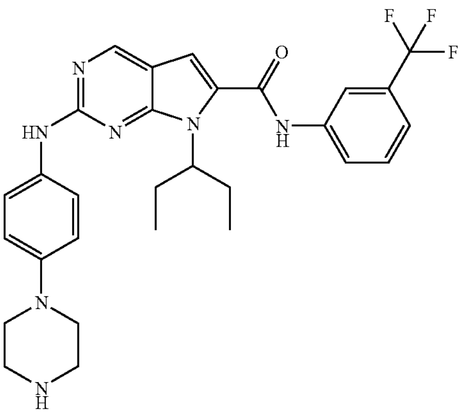 | 552.3 |
| 351 | 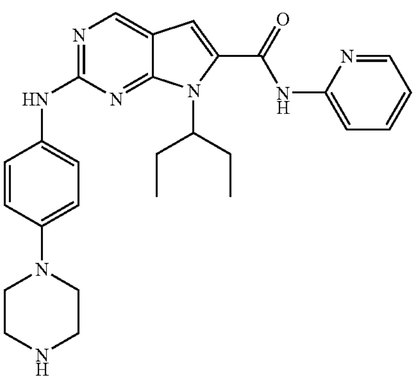 | 485.3 |
| 352 | 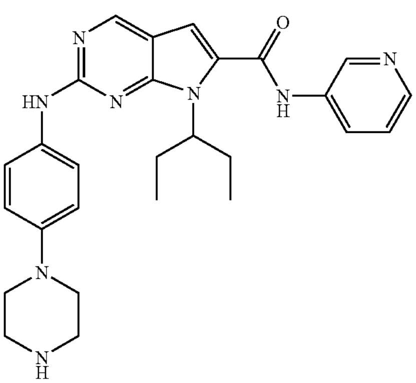 | 485.3 |
| 353 | 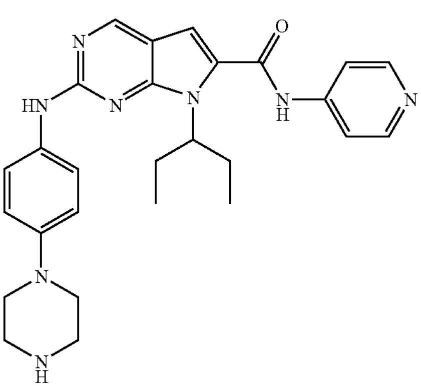 | 485.3 |

-continued

| Example | Structure | MS found (M + 1) |
|---|---|---|
| 354 | 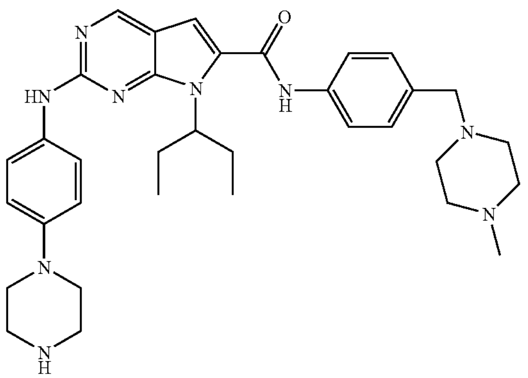 | 596.4 |
| 355 | 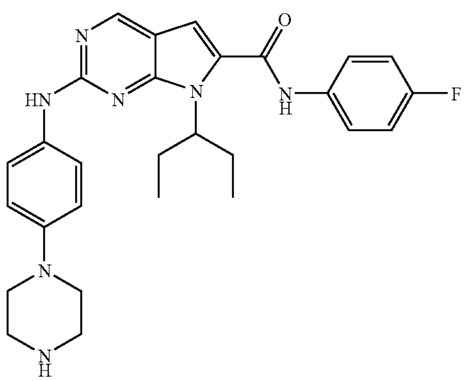 | 502.4 |
| 356 | 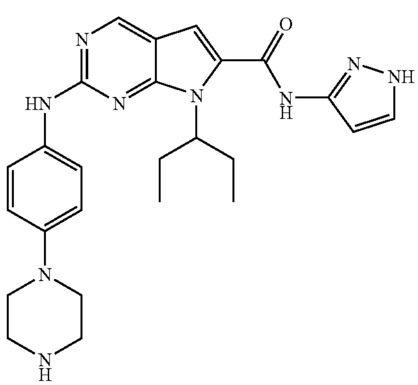 | 474.2 |
| 357 | 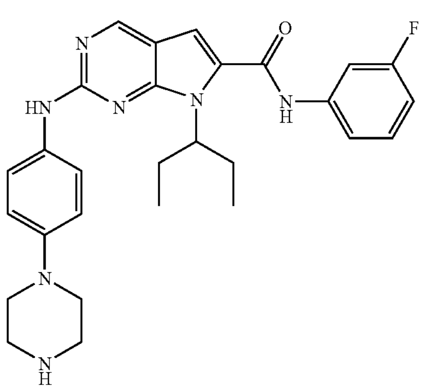 | 502.3 |

-continued

| Example | Structure | MS found (M + 1) |
|---|---|---|
| 358 | 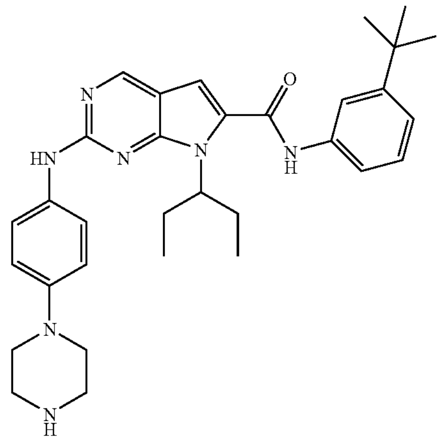 | 540.3 |
| 359 | 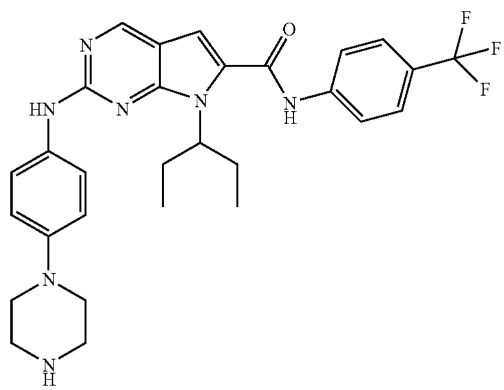 | 552.3 |

EXAMPLE 360

1-(4-{4-[6-Diethoxymethyl-7-(1-ethyl-propyl)-7H-pyrrolo[2,3-d]pyrimidin-2-ylamino]-phenyl}-piperazin-1-yl)-ethanone

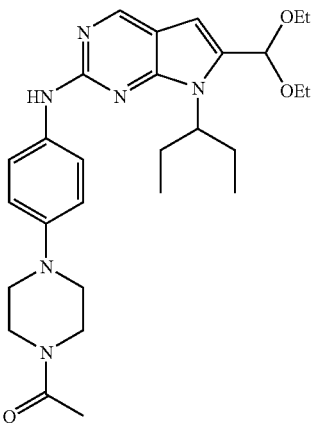

By repeating the procedures described in example 201, using 2-chloro-6-diethoxymethyl-7-(1-ethyl-propyl)-7H-pyrrolo[2,3-d]pyrimidine as a starting material, 1-(4-{4-[6-diethoxymethyl-7-(1-ethyl-propyl)-7H-pyrrolo[2,3-d]pyrimidin-2-ylamino]-phenyl}-piperazin-1-yl)-ethanone is obtained.

LCMS: 509 (M+H)$^+$

EXAMPLE 361

2-[4-(4-Acetyl-piperazin-1-yl)-phenylamino]-7-(1-ethyl-propyl)-7H-pyrrolo[2,3-d]pyrimidine-6-carbaldehyde

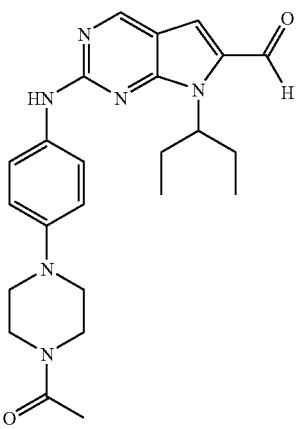

To a solution 1-(4-{4-[6-diethoxymethyl-7-(1-ethyl-propyl)-7H-pyrrolo[2,3-d]pyrimidin-2-ylamino]-phenyl}-piperazin-1-yl)-ethanone (0.178 g, 0.35 mmol) in 1,4 dioxane (2.8 mL) is added 0.8 mL of concentrated HCl at ambient temperature. The reaction mixture is stirred at ambient temperature for 30 min. The mixture is neutralized with 1 N NaOH aqueous solution and saturated NaHCO$_3$ aqueous solution, extracted with CH$_2$Cl$_2$. The extracts are washed with brine, dried over Na$_2$SO$_4$, and concentrated under reduced pressure to give 160 mg of 2-[4-(4-acetyl-piperazin-1-yl)-phenylamino]-7-(1-ethyl-propyl)-7H-pyrrolo[2,3-d]pyrimidine-6-carbaldehyde as a yellow solid.
LCMS: 435 (M+H)$^+$.

EXAMPLE 362

1-(4-{4-[7-(1-Ethyl-propyl)-6-hydroxymethyl-7H-pyrrolo[2,3-d]pyrimidin-2-ylamino]-phenyl}-piperazin-1-yl)-ethanone

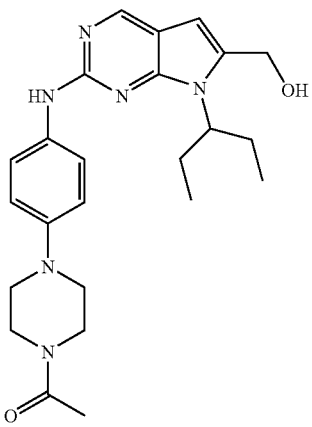

To a solution of 2-[4-(4-acetyl-piperazin-1-yl)-phenylamino]-7-(1-ethyl-propyl)-7H-pyrrolo[2,3-d]pyrimidine-6-carbaldehyde (20 mg, 0.046 mmol) in MeOH (1 mL) is added NaBH$_4$ (3.5 mg, 0.092 mmol). The reaction mixture is stirred for 1 h and concentrated in vacuo. The residue is purified by preparative HPLC to give 15 mg of 1-(4-{4-[7-(1-ethyl-propyl)-6-hydroxymethyl-7H-pyrrolo[2,3-d]pyrimidin-2-ylamino]-phenyl}-piperazin-1-yl)-ethanone.
LCMS: 437.3 (M+H)$^+$.

EXAMPLE 363

1-(4-{4-[7-(1-Ethyl-propyl)-6-oxazol-5-yl-7H-pyrrolo[2,3-d]pyrimidin-2-ylamino]-phenyl}-piperazin-1-yl)-ethanone

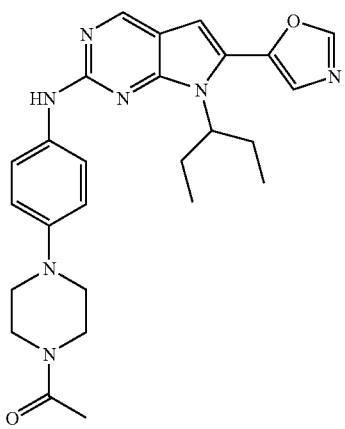

To a solution of 2-[4-(4-acetyl-piperazin-1-yl)-phenylamino]-7-(1-ethyl-propyl)-7H-pyrrolo[2,3-d]pyrimidine-6-carbaldehyde (30 mg, 0.07 mmol) in MeOH (1 mL) are added p-toluenesulfonyl isocyanide (16 mg, 0.08 mmol) and K$_2$CO$_3$ (29 mg, 0.21 mmol). The reaction mixture is heated at reflux for 1.5 h and concentrated in vacuo. The residue is purified by preparative HPLC to give 21 mg of 1-(4-{4-[7-(1-ethyl-propyl)-6-oxazol-5-yl-7H-pyrrolo[2,3-d]pyrimidin-2-ylamino]-phenyl}-piperazin-1-yl)-ethanone as a pale brown solid.
LCMS: 474.2 (M+H)$^+$.

EXAMPLE 364

1-{4-[4-(7-(1-Ethyl-propyl)-6-{1-methoxyimino-ethyl}-7H-pyrrolo[2,3-d]pyrimidin-2-ylamino)-phenyl]-piperazin-1-yl}-ethanone

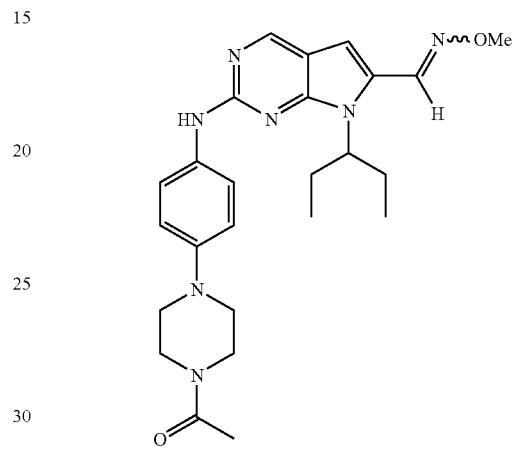

A mixture of 2-[4-(4-acetyl-piperazin-1-yl)-phenylamino]-7-(1-ethyl-propyl)-7H-pyrrolo[2,3-d]pyrimidine-6-carbaldehyde (25 mg, 0.057 mmol), methoxylamine hydrochloride (20 mg, 0.22 mmol) and 6N HCl (0.03 mL) in EtOH (1 mL) is stirred at ambient temperature for 6 h. The mixture was quenched with saturated NaHCO$_3$ aqueous solution, extracted with CH$_2$Cl$_2$. The extracts were washed with brine, dried over Na$_2$SO$_4$, and concentrated under reduced pressure to give the crude product. The crude product is purified by preparative HPLC to give 12 mg of 1-{4-[4-(7-(1-ethyl-propyl)-6-{1-methoxyimino-ethyl}-7H-pyrrolo[2,3-d]pyrimidin-2-ylamino)-phenyl]-piperazin-1-yl}-ethanone as a bright yellow solid.
LCMS: 464 (M+H)$^+$.

EXAMPLE 365

1-{4-[4-(7-(1-Ethyl-propyl)-6-{[(furan-2-ylmethyl)-amino]-methyl}-7H-pyrrolo[2,3-d]pyrimidin-2-ylamino)-phenyl]-piperazin-1-yl}-ethanone

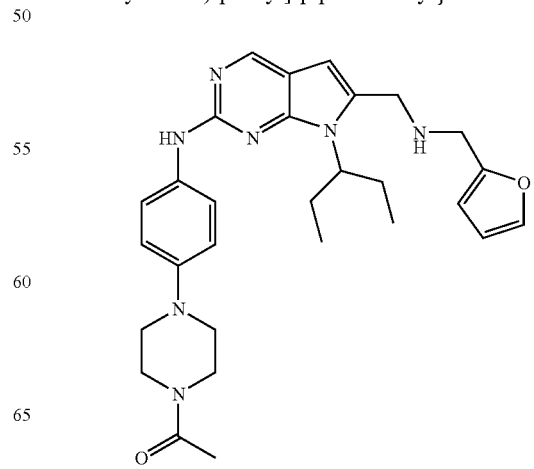

To a solution of 2-[4-(4-acetyl-piperazin-1-yl)-phenylamino]-7-(1-ethyl-propyl)-7H-pyrrolo[2,3-d]pyrimidine-6-carbaldehyde (30 mg, 0.07 mmol) in THF (1 mL) is added furfurylamine (0.03 mL, 0.35 mmol), NaBH(OAc)$_3$ (45 mg, 0.21 mmol), and acetic acid (1 mL). The reaction mixture is stirred for 16 h and concentrated in vacuo. The residue is purified by preparative HPLC to give 20 mg of 1-{4-[4-(7-(1-ethyl-propyl)-6-{[(furan-2-ylmethyl)-amino]-methyl}-7H-pyrrolo[2,3-d]pyrimidin-2-ylamino)-phenyl]-piperazin-1-yl}-ethanone as a pale yellow solid.

LCMS: 516.3 (M+H)$^+$.

EXAMPLES 366-372

By repeating the procedures described in example 365, using appropriate starting materials, the following compounds are obtained.

| Example | Structure | MS found (M + 1) |
|---------|-----------|------------------|
| 366 | 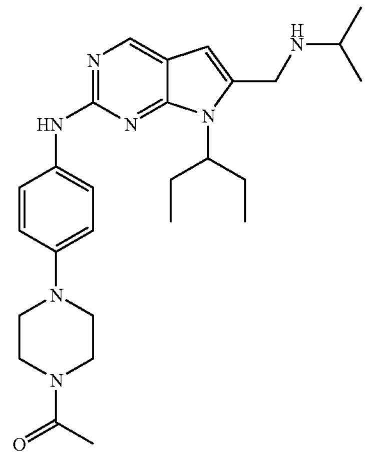 | 478.6 |
| 367 | 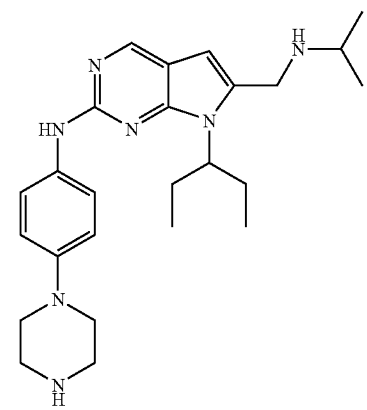 | 436.4 |
| 368 | 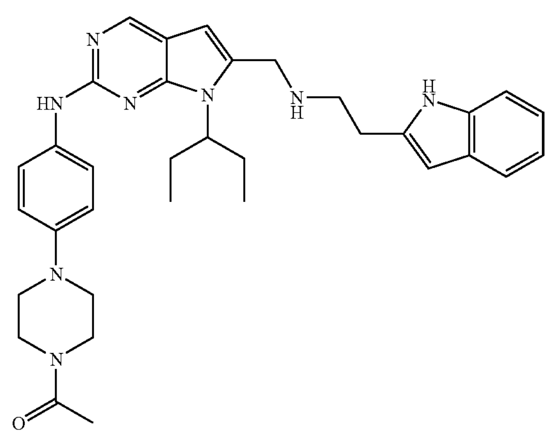 | 579.4 |

-continued

| Example | Structure | MS found (M + 1) |
|---|---|---|
| 369 | 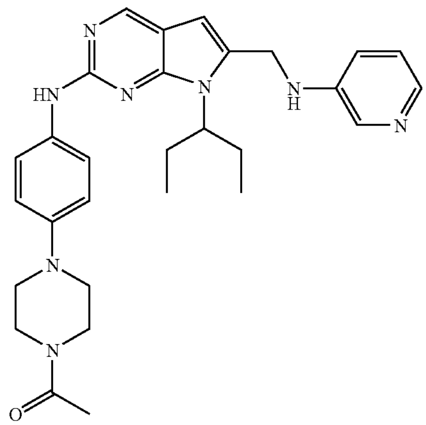 | 513.3 |
| 370 | 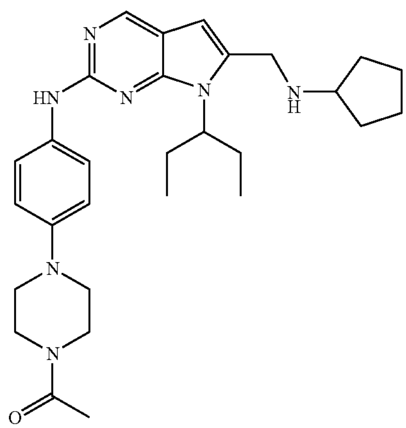 | 504.3 |
| 371 | 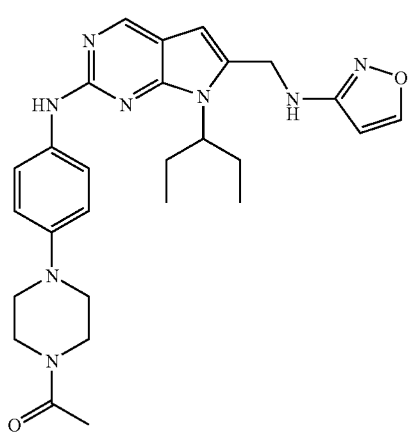 | 503.3 |

| Example | Structure | MS found (M + 1) |
|---|---|---|
| 372 | 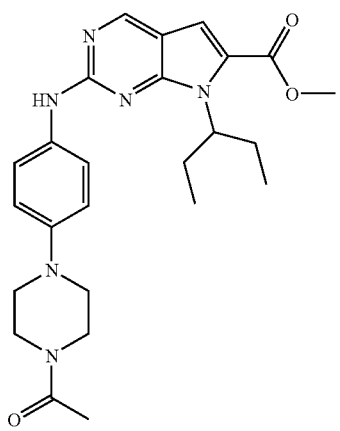 | 516.6 |

EXAMPLE 373

2-[4-(4-Acetyl-piperazin-1-yl)-phenylamino]-7-(1-ethyl-propyl)-7H-pyrrolo[2,3-d]pyrimidine-6-carboxylic acid methyl ester

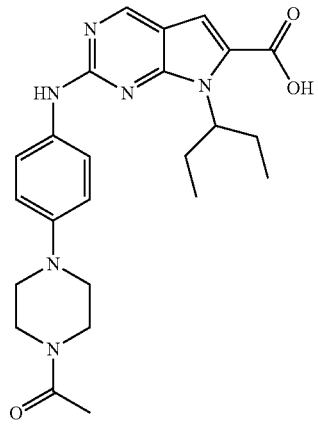

To a solution of 2-chloro-7-(1-ethyl-propyl)-7H-pyrrolo[2,3-d]pyrimidine-6-carboxylic acid (13 mg, 0.049 mmol) in MeOH (0.5 mL) is added (trimethylsilyl)diazomethane (0.07 mL of a 2.0 M in hexanes). The reaction mixture is stirred for 2 h and concentrated in vacuo to give 13 mg of 2-chloro-7-(1-ethyl-propyl)-7H-pyrrolo[2,3-d]pyrimidine-6-carboxylic acid methyl ester. The crude product is used as it is.

LCMS: 282.2 (M+H)$^+$.

To a solution of 1-[4-(4-amino-phenyl)-piperazin-1-yl]-ethanone (12.1 mg, 0.055 mmol) in 1,4-dioxane (0.5 mL) is added a solution of 2-chloro-7-(1-ethyl-propyl)-7H-pyrrolo[2,3-d]pyrimidine-6-carboxylic acid methyl ester (13 mg, 0.046 mmol) in 1,4-dioxane (0.6 mL), Pd$_2$(dba)$_3$ (2.2 mg, 0.0023 mmol), Xantphos (2.7 mg, 0.046 mmol) and Cs$_2$CO$_3$ (22.5 mg, 0.069 mmol). The mixture is degassed, and heated at 100° C. for 3 h. The mixture is cooled to room temperature, diluted with EtOAc, and filtered through a pad of Celite. The filtrate is concentrated under reduced pressure. The crude product is purified by preparative HPLC to give 8.6 mg of 2-[4-(4-acetyl-piperazin-1-yl)-phenylamino]-7-(1-ethyl-propyl)-7H-pyrrolo[2,3-d]pyrimidine-6-carboxylic acid methyl ester as a pale white solid.

LCMS: 465.4 (M+H)$^+$.

EXAMPLE 374

2-[4-(4-Acetyl-piperazin-1-yl)-phenylamino]-7-(1-ethyl-propyl)-7H-pyrrolo[2,3-d]pyrimidine-6-carboxylic acid To a solution of 2-[4-(4-acetyl-piperazin-1-yl)-phenylamino]-7-(1-ethyl-propyl)-7H-pyrrolo[2,3-d]pyrimidine-6-carboxylic acid methyl ester (19 mg, 0.041 mmol) in MeOH (1.5 mL) is added 2 N LiOH aqueous solution (0.5 mL). The reaction mixture is stirred overnight and concentrated in vacuo. The residue is purified by preparative HPLC to give 13.6 mg of 2-[4-(4-Acetyl-piperazin-1-yl)-phenylamino]-7-(1-ethyl-propyl)-7H-pyrrolo[2,3-d]pyrimidine-6-carboxylic acid.

LCMS: 451.4 (M+H)$^+$.

EXAMPLE 375

7-(1-Ethyl-propyl)-2-(4-piperazin-1-yl-phenylamino)-7H-pyrrolo[2,3-d]pyrimidine-6-carboxylic acid

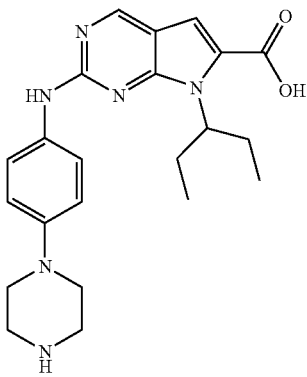

To a solution of 2-[4-(4-acetyl-piperazin-1-yl)-phenylamino]-7-(1-ethyl-propyl)-7H-pyrrolo[2,3-d]pyrimidine-6-carboxylic acid methyl ester (16 mg, 0.034 mmol) in THF (1.5 mL) is added 2 N LiOH aqueous solution (1 mL). The reaction mixture is stirred for 36 h and concentrated in vacuo. The residue is purified by preparative HPLC to give 9.4 mg of 7-(1-ethyl-propyl)-2-(4-piperazin-1-yl-phenylamino)-7H-pyrrolo[2,3-d]pyrimidine-6-carboxylic acid.

LCMS: 409.4 (M+H)$^+$.

EXAMPLE 376

1-(4-{4-[7-(1-Ethyl-propyl)-6-(1-hydroxy-ethyl)-7H-pyrrolo[2,3-d]pyrimidin-2-ylamino]-phenyl}-piperazin-1-yl)-ethanone

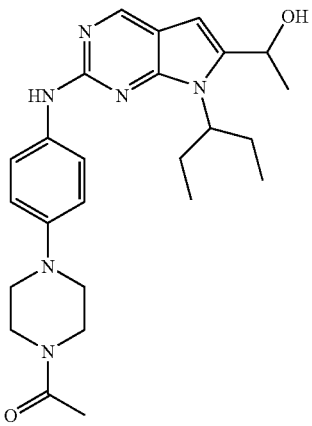

To a mixture of (5-bromo-2-chloro-pyrimidin-4-yl)-(1-ethyl-propyl)-amine (0.44 g, 1.58 mmol), Pd(Ph$_3$P)$_2$Cl$_2$ (0.11 g, 0.16 mmol), and CuI (0.03 g, 0.16 mmol) in DMF (14 mL) is added 3-butyn-2-ol (0.19 mL, 2.37 mmol) and triethylamine (0.44 mL, 3.16 mmol). The reaction mixture is stirred at 55° C. for 16 h, diluted with CH$_2$Cl$_2$, filtered through a pad of Celite, and concentrated in vacuo. Purification by flash chromatography (SiO$_2$, EtOAc/Hexane 1:3) gave 0.23 g of 4-[2-chloro-4-(1-ethyl-propylamino)-pyrimidin-5-yl]-but-3-yn-2-ol as yellowish oil.

LCMS: 268 (M+H)$^+$.

To a solution of 4-[2-chloro-4-(1-ethyl-propylamino)-pyrimidin-5-yl]-but-3-yn-2-ol (0.23 g, 0.85 mmol) in THF (0.5 mL) is added 1M TBAF (4.3 mL). The reaction mixture is heated at reflux for 16 h, diluted with water, extracted with EtOAc. The extracts are dried over Na$_2$SO$_4$ and concentrated in vacuo. The residue is purified by flash chromatography (SiO$_2$, EtOAc/Hexane 1:3) to provide 0.12 g of 1-[2-chloro-7-(1-ethyl-propyl)-7H-pyrrolo[2,3-d]pyrimidin-6-yl]-ethanol.

LCMS: 268 (M+H)$^+$.

By repeating the procedures described in example 65, using 1-[2-chloro-7-(1-ethyl-propyl)-7H-pyrrolo[2,3-d]pyrimidin-6-yl]-ethanol as a starting material, 1-(4-{4-[7-(1-ethyl-propyl)-6-(1-hydroxy-ethyl)-7H-pyrrolo[2,3-d]pyrimidin-2-ylamino]-phenyl}-piperazin-1-yl)-ethanone is obtained.

LCMS: 451.4 (M+H)$^+$.

EXAMPLE 377

1-[2-[4-(4-Acetyl-piperazin-1-yl)-phenylamino]-7-(1-ethyl-propyl)-7H-pyrrolo[2,3-d]pyrimidin-6-yl]-ethanone

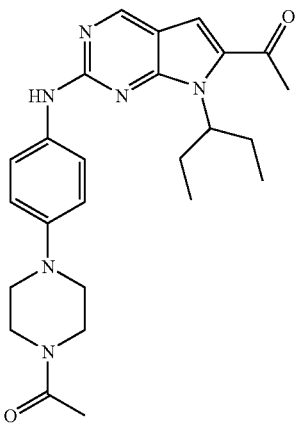

To a solution of 1-[2-chloro-7-(1-ethyl-propyl)-7H-pyrrolo[2,3-d]pyrimidin-6-yl]-ethanol (61 mg, 0.2 mmol) in CH$_2$Cl$_2$ (2 mL) is added Dess-Martin periodinane (242 mg, 0.5 mmol). The reaction mixture is stirred for 1 h, quenched with 10% NaS$_2$O$_3$:saturated NaHCO$_3$ (1:1) aqueous solution, and extracted with CH$_2$Cl$_2$. The extracts are washed with water and brine, dried over Na$_2$SO$_4$, and concentrated in vacuo. The residue is purified by flash chromatography (SiO$_2$, EtOAc/Hexane 1:3) to afford 58 mg of 1-[2-chloro-7-(1-ethyl-propyl)-7H-pyrrolo[2,3-d]pyrimidin-6-yl]-ethanone.

LCMS: 266 (M+H)$^+$.

By repeating the procedures described in example 201, using 1-[2-chloro-7-(1-ethyl-propyl)-7H-pyrrolo[2,3-d]pyrimidin-6-yl]-ethanone as a starting material, 1-[2-[4-(4-acetyl-piperazin-1-yl)-phenylamino]-7-(1-ethyl-propyl)-7H-pyrrolo[2,3-d]pyrimidin-6-yl]-ethanone is obtained.

LCMS: 449.4 (M+H)$^+$.

EXAMPLE 378

[7-(1-Ethyl-propyl)-6-(1-methoxy-ethyl)-7H-pyrrolo[2,3-d]pyrimidin-2-yl]-(4-piperazin-1-yl-phenyl)-amine

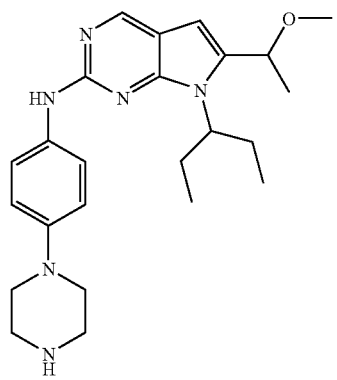

To a solution of 1-(4-{4-[7-(1-ethyl-propyl)-6-(1-hydroxy-ethyl)-7H-pyrrolo[2,3-d]pyrimidin-2-ylamino]-phenyl}-piperazin-1-yl)-ethanone (19 mg, 0.042 mmol) in MeOH (1 mL) is added 4N HCl in dioxane (1 mL). The reaction mixture is stirred at 60° C. for 2 h. The mixture is loaded on Solid Phase Extraction column (Sorbent: benzenesulfonic acid), washed with MeOH, eluted with EtOAc:MeOH:Et3N (1:1:0.05), concentrated in vacuo. The residue is purified by preparative HPLC to give 10 mg of [7-(1-ethyl-propyl)-6-(1-methoxy-ethyl)-7H-pyrrolo[2,3-d]pyrimidin-2-yl]-(4-piperazin-1-yl-phenyl)-amine.

LCMS: 423.4 (M+H)+.

EXAMPLES 379-382

By repeating the procedures described in example 378, using appropriate starting materials, the following compounds are obtained.

| Example | Structure | MS found (M + 1) |
|---|---|---|
| 379 | 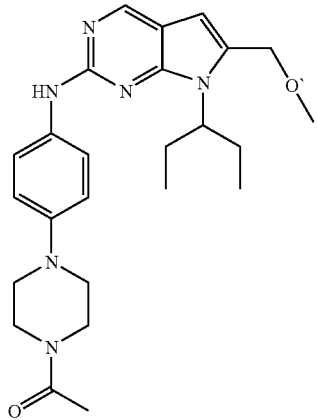 | 451.3 |
| 380 | 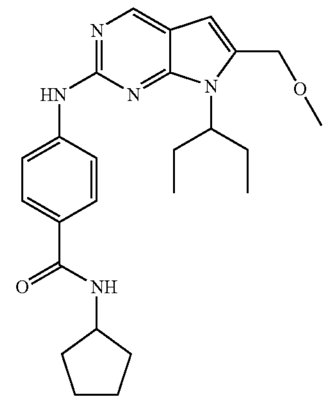 | 436.3 |
| 381 | 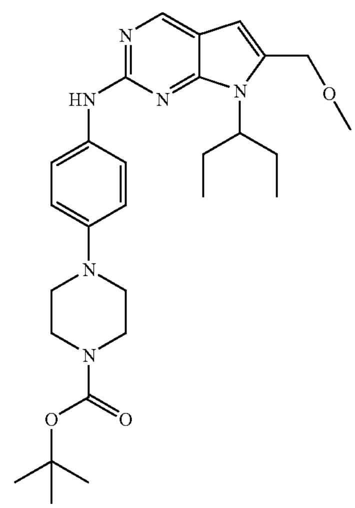 | 509.4 |
| 382 | 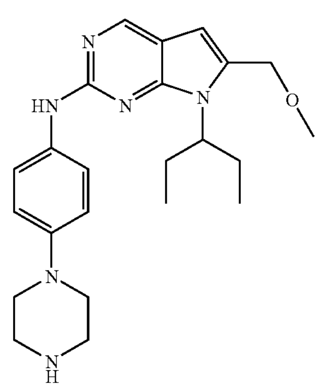 | 409.3 |

EXAMPLE 383

(7-Cyclopentyl-6-isopropenyl-5-methyl-7H-pyrrolo[2,3-d]pyrimidin-2-yl)-(4-piperazin-1-yl-phenyl)-amine

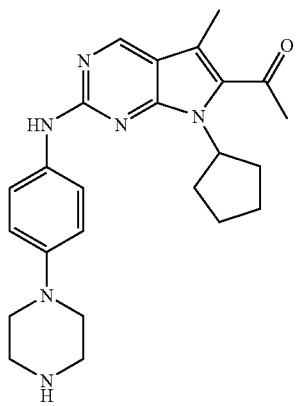

(5-Bromo-2-chloro-pyrimidin-4-yl)cyclopentylamine is prepared from cyclopentyl amine and 5-bromo-2,4-dichloropyrimidine using a method similar to that for the preparation of (5-Bromo-2-chloro-pyrimidin-4-yl)-(1-ethylpropyl)amine given in Example 137.

To a solution of (5-Bromo-2-chloro-pyrimidin-4-yl)cyclopentylamine (1 g, 3.616 mmol) is added lithium chloride (153.7 mg, 3.616 mmol) and potassium acetate (887.12 mg, 9.03 mmol) in DMF (50 mL). The solution is degassed and back-filled with $N_2$. Palladium(II) acetate (40.6 mg, 0.18 mmol) is added and the solution is degassed and back-filled with nitrogen three times. 3-pentyn-2-ol (1.0 mL, 10.8 mmol) is added and the reaction solution is heated at 120° C. for 5 hours. LC-MS analysis indicated the absence of starting material and the formation of a pair of regio-isomeric products. After cooling to room temperature, the mixture is filtered through Celite, diluted with water, and extracted with ethyl acetate EtOAc three times. The organic layers are combined, washed with brine and dried over anhydrous sodium sulfate. The solvent is evaporated and the crude material is purified using silica gel chromatography (30% ethyl acetate/70% hexanes to give 1-(2-Chloro-7-cyclopentyl-5-methyl-7H-pyrrolo[2,3-d]pyrimidin-6-yl)-ethanol as a pale powder (150 mg, 14.8%). $[M+H]^+=280.07$.

1-(2-Chloro-7-cyclopentyl-5-methyl-7H-pyrrolo[2,3-d]pyrimidin-6-yl)-ethanone is prepared by Dess-Martin periodinane oxidation of 1-(2-Chloro-7-cyclopentyl-5-methyl-7H-pyrrolo[2,3-d]pyrimidin-6-yl)-ethanol using a procedure similar to that described for 1-[2-chloro-7-(1-ethyl-propyl)-7H-pyrrolo[2,3-d]pyrimidin-6-yl]-ethanone in the synthesis of Example 376. $[M+H]^+=278.03$.

A solution of 1-(2-Chloro-7-cyclopentyl-5-methyl-7H-pyrrolo[2,3-d]pyrimidin-6-yl)-ethanone (40 mg, 0.144 mmol), 1-[4-(4-Amino-phenyl)-piperazin-1-yl]-ethanone (37.9 mg, 0.172 mmol), $Pd_2(dba)_3$ (6.7 mg, 0.007 mmol), BINAP (9.15 mg, 0.014 mmol) and NaOtBu (20.7 mg, 0.216 mmol) in 1,4-dioxane (4 mL) is degassed and back-filled with nitrogen three times. The reaction mixture is heated to 80° C. for 2 hours. After cooling to room temperature water is added and the reaction mixture is extracted with ethyl acetate three times. The organic layers are combined, washed with brine and dried over anhydrous sodium sulfate. The solvent is evaporated and the crude material is purified by preparative HPLC to provide 1-{2-[4-(4-Acetyl-piperazin-1-yl)-phenylamino]-7-cyclopentyl-5methyl-7H-pyrrolo[2,3-d]pyrimidin-6-yl}-ethanone (16 mg, 24%). $[M+H]^+=461.13$.

To a solution of 1-{2-[4-(4-Acetyl-piperazin-1-yl)-phenylamino]-7-cyclopentyl-5methyl-7H-pyrrolo[2,3-d]pyrimidin-6-yl}-ethanone (12 mg, 0.026 mmol) in methanol (3 mL) is added HCl (2 mL, 2M in dioxane), dropwise. The solution is heated to reflux for 2 h. The solvent is evaporated and the crude product is purified on HPLC to give a TFA salt of (7-Cyclopentyl-6-isopropenyl-5-methyl-7H-pyrrolo[2,3-d]pyrimidin-2-yl)-(4-piperazin-1-yl-phenyl)-amine as a yellow solid (7 mg, 42%). $[M+H]^+=419.17$.

EXAMPLE 384

7-Cyclopentyl-5-methyl-2-(5-piperazin-1-yl-pyridin-2-ylamino)-7H-pyrrolo[2,3-d]pyrimidine-6-carboxylic acid methyl ester

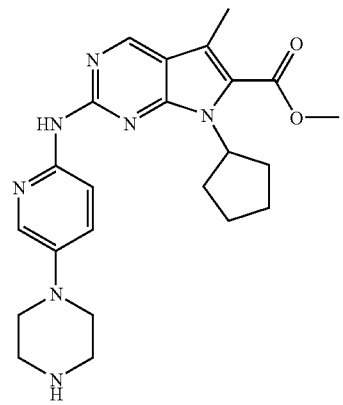

A solution of (5-Bromo-2-chloro-pyrimidin-4-yl)cyclopentylamine (8 g, 28.93 mmol), lithium chloride (1.23 g, 28.9 mmol), potassium carbonate (10 g, 72 mmol) and palladium acetate (324.68 mg, 1.45 mmol) in DMF (300 mL) is degassed and back-filled with nitrogen three times. Methyl-2-butynoate (8.5 mL, 87 mmol) is added and the reaction solution is heated at 120° C. for 5 h. LC-MS indicated the formation of two regioisomers and no starting material remaining. After cooling to room temperature the solution is filtered through Celite, diluted with water and extracted with ethyl acetate three times. The organic layers are combined, washed with brine and dried over anhydrous sodium sulfate. The solvent is evaporated and the crude product is purified using silica gel chromatography (~20% ethyl acetate/80% hexane) to give 2-chloro-7-cyclopentyl-5-methyl-7H-pyrrolo[2,3-d]pyrimidine-6-carboxylic acid methyl ester as a yellow solid (2.11 g, 25%). $[M+H]^+=294.04$.

A mixture of 2-chloro-7-cyclopentyl-5-methyl-7H-pyrrolo[2,3-d]pyrimidine-6-carboxylic acid methyl ester (110 mg, 0.374 mmol), 4-(6-Amino-pyridin-3-yl)-piperazine-1-carboxylic acid tert-butyl ester (114.66 mg, 0.412 mmol), $Pd_2(dba)_3$ (17.144 mg, 0.02 mmol), Xantphos (21.67 mg, 0.037 mmol) and cesium carbonate (183 mg, 0.562 mmol) in dioxane (5 mL) is degassed and back-filled with nitrogen three times. The reaction mixture is heated to 100° C. for 4 h. Water is added and the solution is extracted with ethyl acetate three times. The organic layers are combined, washed with brine and dried over anhydrous sodium sulfate. The solvent is evaporated and the crude product is dissolved in a small amount of ethyl acetate. White solid precipitates out and filters to give 2-[5-(4-tert-Butoxycarbonyl-piperazin-1-yl)-pyridin-2-ylamino]-7-cyclopentyl-5-methyl-7H-pyrrolo[2,3-d]pyrimidine-6-carboxylic acid methyl ester as a white solid (35 mg, 17%) which was carried onto the next step without further purification. [M+H]⁺=536.35.

To a solution of 2-[5-(4-tert-Butoxycarbonyl-piperazin-1-yl)-pyridin-2-ylamino]-7-cyclopentyl-5-methyl-7H-pyrrolo[2,3-d]pyrimidine-6-carboxylic acid methyl ester (35 mg, 0.065 mmol) in DCM (8 mL) is added TFA (2 mL) dropwise. The solution is stirred at room temperature for 2 hours. Solvent is evaporated and the crude material is purified by preparative HPLC to give the TFA salt of 7-Cyclopentyl-5-methyl-2-(5-piperazin-1-yl-pyridin-2-ylamino)-7H-pyrrolo[2,3-d]pyrimidine-6-carboxylic acid methyl ester as yellow solid (32 mg, 74%). [M+H]⁺=436.2458.

EXAMPLE 385

7-Cyclopentyl-6-methyl-2-(5-piperazin-1-yl-pyridin-2-ylamino)-7H-pyrrolo[2,3-d]pyrimidine-5-carboxylic acid methyl ester

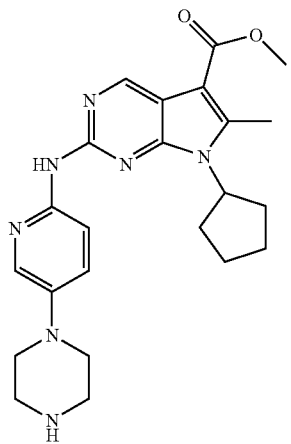

2-chloro-7-cyclopentyl-6-methyl-7H-pyrrolo[2,3-d]pyrimidine-5-carboxylic acid methyl ester is prepared using the procedure shown for the preparation of its regio-isomer 2-chloro-7-cyclopentyl-5-methyl-7H-pyrrolo[2,3-d]pyrimidine-6-carboxylic acid methyl ester given in the procedure for the synthesis of Example 384.

7-Cyclopentyl-6-methyl-2-(5-piperazin-1-yl-pyridin-2-ylamino)-7H-pyrrolo[2,3-d]pyrimidine-5-carboxylic acid methyl ester is prepared from 2-chloro-7-cyclopentyl-5-methyl-7H-pyrrolo[2,3-d]pyrimidine-6-carboxylic acid methyl ester using a procedure similar to that given for the preparation of 7-Cyclopentyl-5-methyl-2-(5-piperazin-1-yl-pyridin-2-ylamino)-7H-pyrrolo[2,3-d]pyrimidine-6-carboxylic acid methyl ester, Example 384.

[M+H]⁺=436.25.

EXAMPLE 386

[7-Cyclopentyl-5-methyl-6-(5-methyl-[1,3,4]oxadiazol-2-yl)-7H-pyrrolo[2,3d]pyrimidin-2-yl]-(5-piperazin-1-yl-pyridin-2-yl)-amine

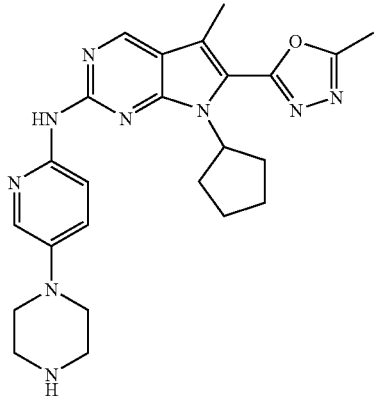

To a suspension of 2-[5-(4-tert-Butoxycarbonyl-piperazin-1-yl)-pyridin-2-ylamino]-7-cyclopentyl-5-methyl-7H-pyrrolo[2,3-d]pyrimidine-6-carboxylic acid methyl ester (250 mg, 0.467 mmol) (prepared as described in the procedure for the synthesis of Example 384), in MeOH/H₂O/DCM (70 mL) is added a solution of lithium hydroxide (39.2 mg, 0.93 mmol) in water (15 mL). The reaction mixture is heated to reflux for 4 hours. The reaction mixture is allowed to cool to room temperature and concentrated in vacuo. The resulting solution is acidified to pH~3 using saturated aqueous citric acid solution. The solution is evaporated and the residue is purified by preparative HPLC to give 2-[5-(4-tert-Butoxycarbonyl-piperazin-1-yl)-pyridin-2-ylamino]-7-cyclopentyl-5-methyl-7H-pyrrolo[2,3-d]pyrimidine-6-carboxylic acid as a yellow solid (105 mg, 53%). [M+H]⁺=522.3

To a solution of 12 2-[5-(4-tert-Butoxycarbonyl-piperazin-1-yl)-pyridin-2-ylamino]-7-cyclopentyl-5-methyl-7H-pyrrolo[2,3-d]pyrimidine-6-carboxylic acid (120 mg, 0.23 mmol), HBTU (130.9 mg, 0.345 mmol) and HOAt (46.97 mg, 0.345 mmol) in dry DMF (15 mL) is added a solution of acetic hydrazide (34.09 mg, 0.46 mmol) and diisopropylethylamine (121 ul, 0.693 mmol) in dry DMF (5 mL). The reaction mixture is stirred at room temperature overnight. The reaction mixture is diluted with water and extracted with ethyl acetate three times. The organic layers are combined, washed with brine and dried over anhydrous sodium sulfate. The solvent is evaporated and the crude product is purified by preparative HPLC to give 4-{6-[6-(N'-Acetyl-hydrazinocarbonyl)-7-cyclopentyl-5-methyl-7H-pyrrolo[2,3-d]pyrimidin-2-ylamino]-pyridin-3-yl}-piperazine-1-carboxylic acid tert-butyl ester as a yellow solid (120 mg, 75.4%). [M+H]⁺=578.32.

A mixture of 4-{6-[6-(N'-Acetyl-hydrazinocarbonyl)-7-cyclopentyl-5-methyl-7H-pyrrolo[2,3-d]pyrimidin-2-ylamino]-pyridin-3-yl}-piperazine-1-carboxylic acid tert-butyl ester (80 mg, 0.139 mmol) and polyphosphoric acid (20 mL) is heated to 120° C. for 1 h. The reaction mixture is diluted with cold water in an ice-water bath and neutralized to pH~8 with 6 N sodium hydroxide solution. The aqueous solution is extracted with ethyl acetate three times. The organic layers are combined, washed with brine and dried over anhydrous sodium sulfate. The solvent is evaporated and the crude product is washed with MeOH to give [7-Cyclopentyl-5-methyl-6-(5-methyl-[1,3,4]oxadiazol-2-yl)-7H-pyrrolo[2,3d]pyrimidin-2-yl]-(5-piperazin-1-yl-pyridin-2-yl)-amine as a yellow solid (28 mg). The methanolic solution is purified by preparative HPLC to give a TFA salt of [7-Cyclopentyl-5-methyl-6-(5-methyl-[1,3,4]oxadiazol-2-yl)-7H-pyrrolo[2,3d]pyrimidin-2-yl]-(5-piperazin-1-yl-pyridin-2-yl)-amine as a yellow solid (20 mg). [M+H]$^+$=460.2572.

Examples 387-408 are prepared using methods similar to those described in the syntheses of Examples 383-386 and standard synthetic methodology used in the synthesis of azole heterocycles with appropriate choice of starting materials.

| Example | Structure | MS found (M + 1) |
|---|---|---|
| 387 | | 420.25 |
| 388 | | 436 |
| 389 | 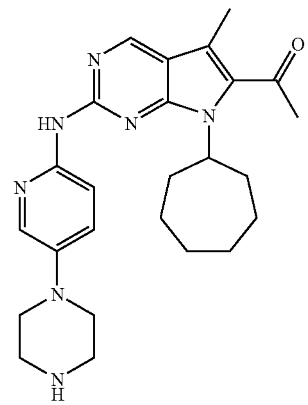 | 448.3 |
| 390 | 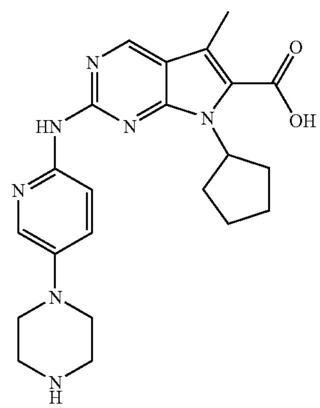 | 422.23 |
| 391 | 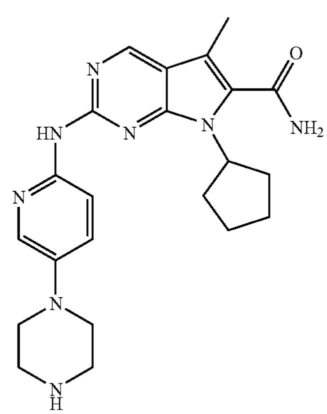 | 421.25 |

205
-continued
| Example | Structure | MS found (M + 1) |
|---|---|---|
| 392 | 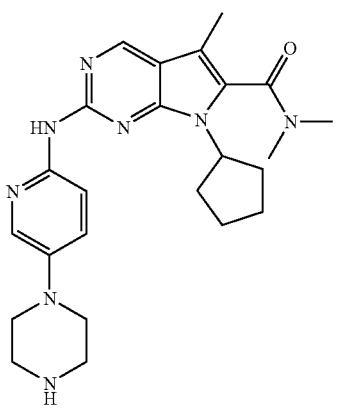 | 449.28 |
| 393 | 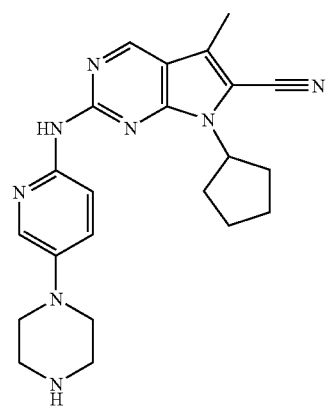 | 403.24 |
| 394 | 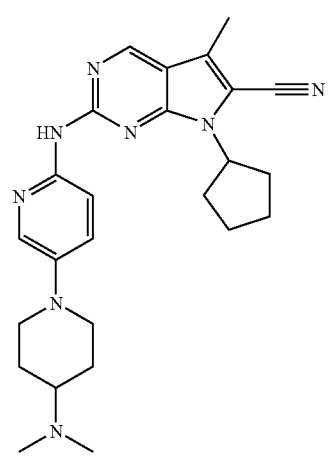 | awaited |
206
-continued
| Example | Structure | MS found (M + 1) |
|---|---|---|
| 395 | 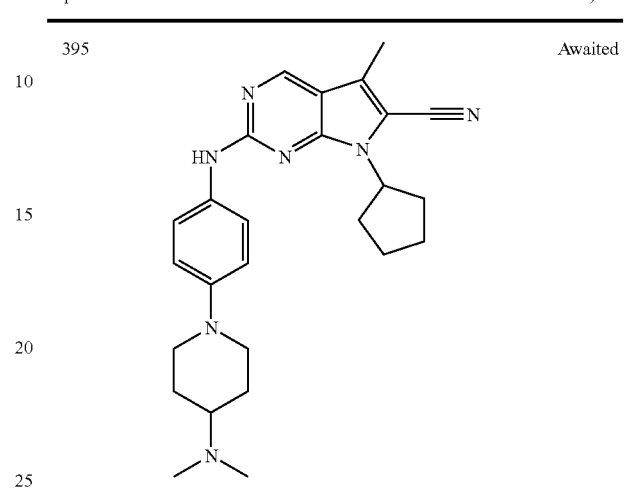 | Awaited |
| 396 | 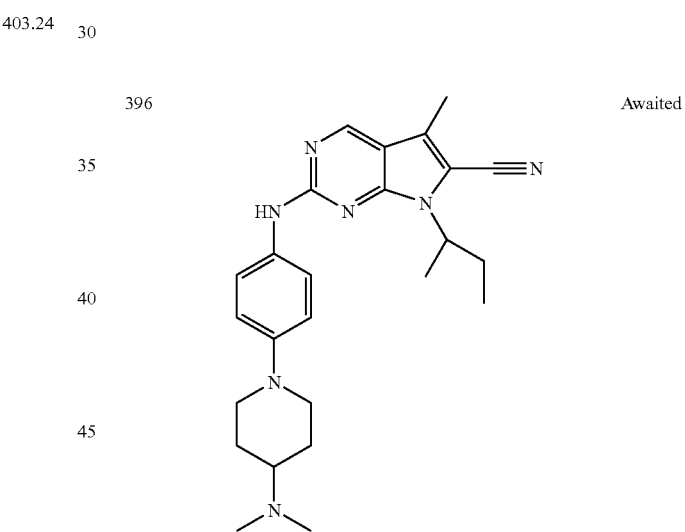 | Awaited |
| 397 | 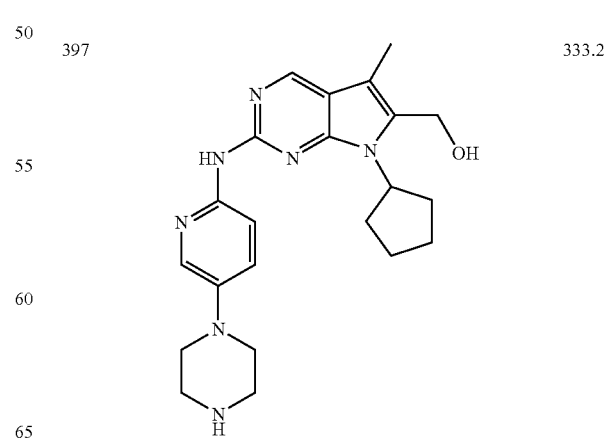 | 333.2 |

| Example | Structure | MS found (M + 1) |
|---|---|---|
| 398 | 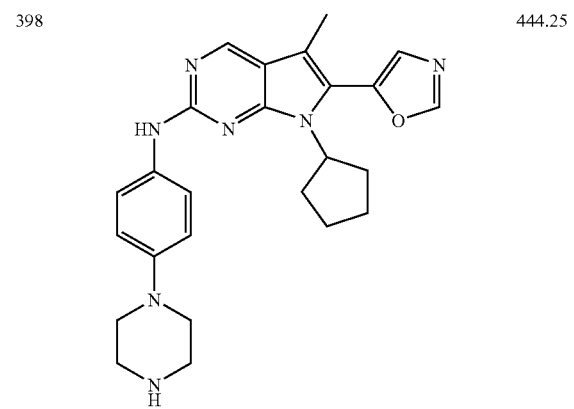 | 444.25 |
| 399 | 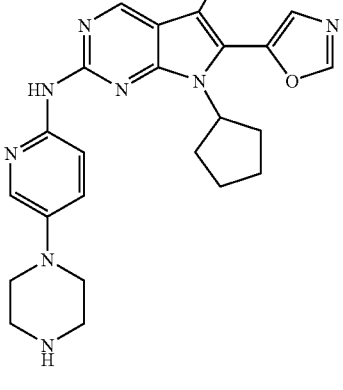 | 445.25 |
| 400 |  | 473.3 |
| Example | Structure | MS found (M + 1) |
|---|---|---|
| 401 | 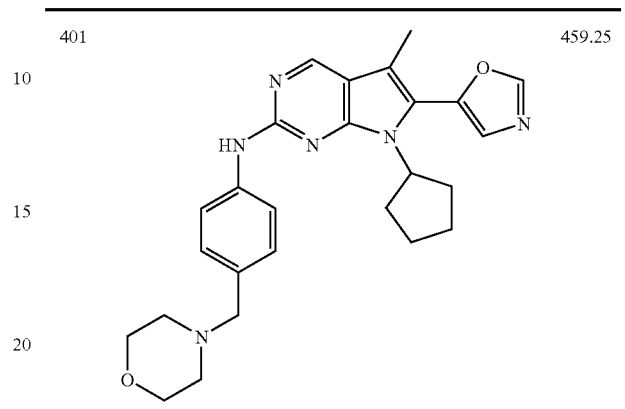 | 459.25 |
| 402 | 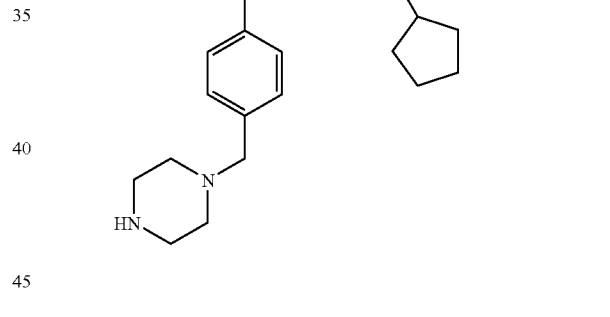 | 458.26 |
| 403 | 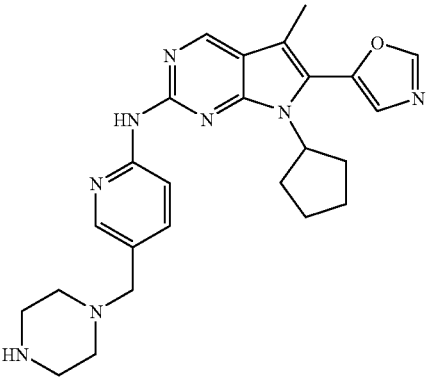 | 459.26 |

| Example | Structure | MS found (M+1) |
|---|---|---|
| 404 | 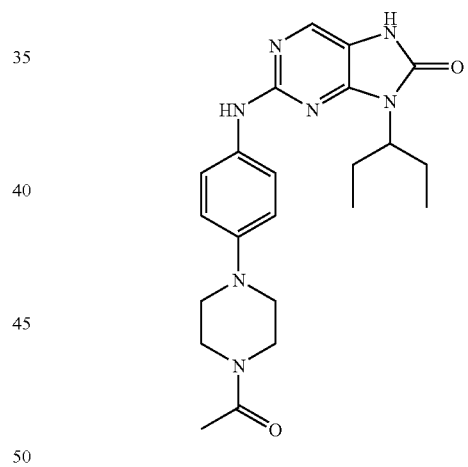 | 458.23 |
| 405 | 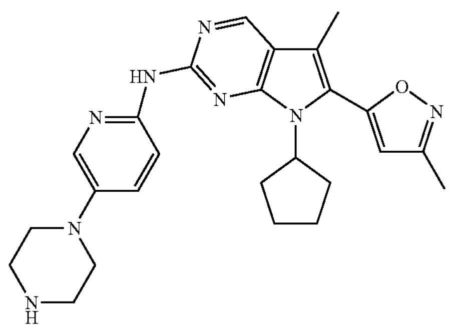 | 459.26 |
| 406 | 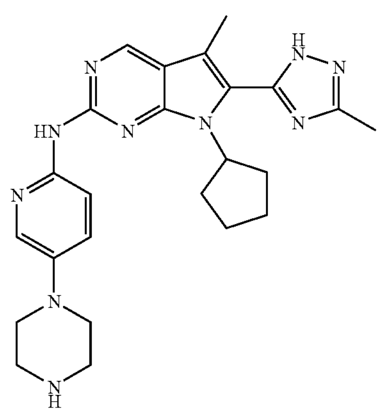 | 459.27 |
| 407 | 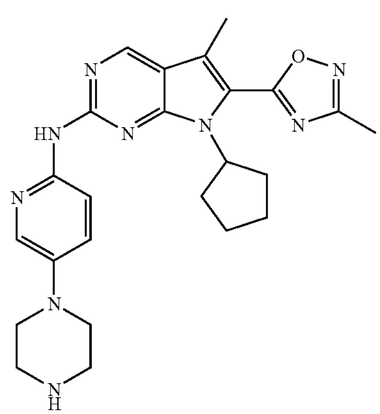 | 460.26 |
| 408 | 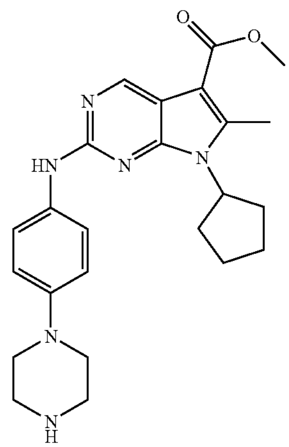 | 435.25 |

EXAMPLE 409

2-[4-(4-Acetyl-piperazin-1-yl)-phenylamino]-9-(1-ethyl-propyl)-7,9-dihydro-purin-8-one To a solution of 2,4-dichloro-5-nitro-pyrimidine (2 g, 10.3 mmol) in anhydrous EtOH (20 mL) is added 1-ethylpropylamine (1.3 mL, 11.3 mmol) and N,N-diisopropylethylamine (2.7 mL, 15.5 mmol) at 0° C. The reaction mixture is stirred for 8 h and concentrated in vacuo. The residue is dissolved with EtOAc, washed with saturated NaHCO$_3$ and brine, dried over Na$_2$SO$_4$, and concentrated in vacuo. Purification with column chromatography (SiO$_2$, EtOAC/Hexane 1:3) gives 1.5 g of (2-chloro-5-nitro-pyrimidin-4-yl)-(1-ethyl-propyl)-amine.

LCMS: 245.1 (M+H)$^+$

To a solution of (2-chloro-5-nitro-pyrimidin-4-yl)-(1-ethyl-propyl)-amine (1 g, 4.1 mmol) in anhydrous EtOH (50 mL) is added Tin(II) chloride (2.3 g, 12.3 mmol) and concentrated HCl (1 mL) at ambient temperature. The reaction is heated to 80° C. for 1 h and quenched with 1N NaOH at 0° C.

The mixture is extracted with EtOAc, washed with brine, dried over Na₂SO₄, and concentrated in vacuo to give 0.5 g of (2-chloro-5-amino-pyrimidin-4-yl)-(1-ethyl-propyl)-amine. The crude is used as is.

LCMS: 215.2 (M+H)⁺

To a microwave vial is added the crude (2-chloro-5-amino-pyrimidin-4-yl)-(1-ethyl-propyl)-amine (0.5 g, 2.3 mmol) and anhydrous DMF (15 mL) followed by 1,1'-carbonyldiimidazole (1.1 g, 7.0 mmol). Sealed vial and microwave are heated at 100° C. for 10 min. The reaction mixture is diluted with EtOAc, washed with water, dried over Na₂SO₄, and concentrated in vacuo. Purification with column chromatography (SiO₂, EtOAC/Hexane 1:1) gives 0.3 g of 2-chloro-9-(1-ethyl-propyl)-7,9-dihydro-purin-8-one. LCMS: 241.1 (M+H)⁺

To a mixture of 2-chloro-9-(1-ethyl-propyl)-7,9-dihydro-purin-8-one (95 mg, 0.4 mmol) and TsOH (1.6 mL, 0.2 M in 1,4-dioxane) in DMF (0.25 mL) is added 1-[4-(4-amino-phenyl)-piperazin-1-yl]-ethanone (105 mg, 0.5 mmol). The reaction mixture is sealed in a microwave reactor and heated at 140° C. for 30 min. The mixture is diluted with EtOAc and washed with NaHCO₃ aqueous solution and brine. The organic layer is dried over Na₂SO₄, filtered and concentrated. The crude product is purified by preparative HPLC to give 52 mg of 2-[4-(4-acetyl-piperazin-1-yl)-phenylamino]-9-(1-ethyl-propyl)-7,9-dihydro-purin-8-one as a brown solid.

LCMS: 424.2 (M+H)⁺

EXAMPLES 410-418

By repeating the procedures described in example x1, using appropriate starting materials, the following compounds are obtained.

| Example | Structure | MS found (M + 1) |
|---|---|---|
| 410 | 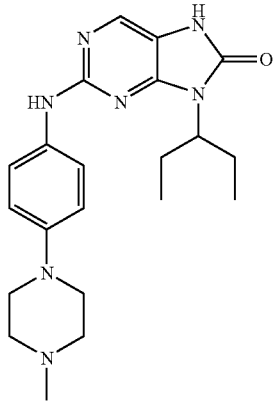 | 395.5 |
| 411 | 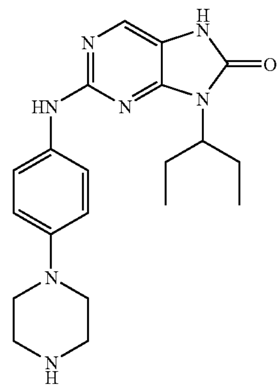 | 382.2 |
| 412 | 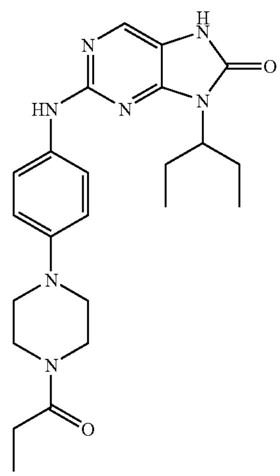 | 438.2 |
| 413 | 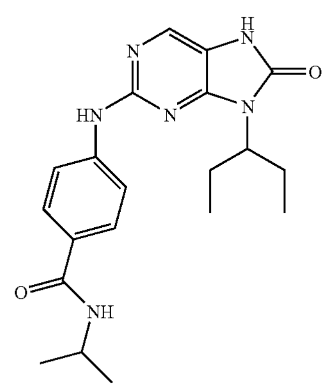 | 383.2 |

-continued

| Example | Structure | MS found (M + 1) |
|---|---|---|
| 414 | 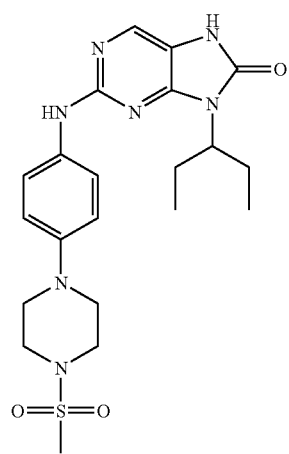 | 383.2 |
| 415 | 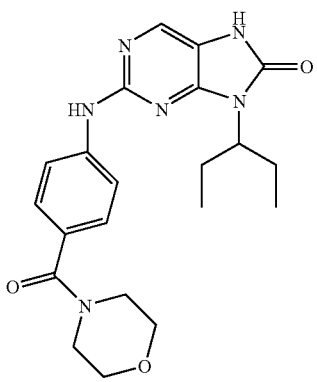 | 460.2 |
| 416 | 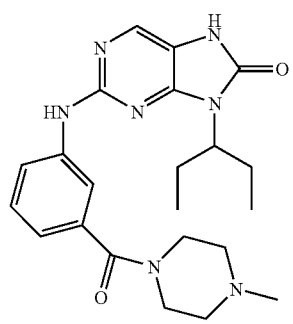 | 411.2 |
| 417 | 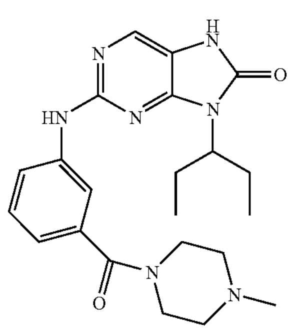 | 424.2 |

-continued

| Example | Structure | MS found (M + 1) |
|---|---|---|
| 418 | 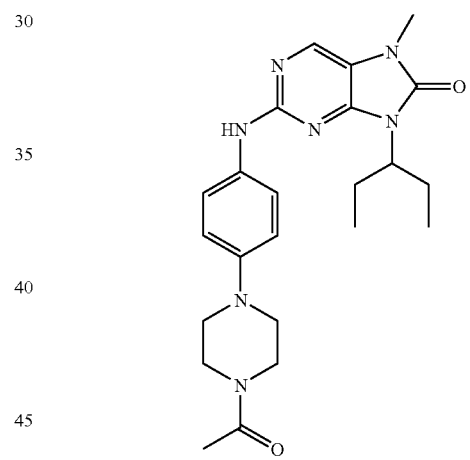 | 409.2 |

EXAMPLE 419

2-[4-(4-Acetyl-piperazin-1-yl)-phenylamino]-9-(1-ethyl-propyl)-7-methyl-7,9-dihydro-purin-8-one To a solution of 2-chloro-9-(1-ethyl-propyl)-7,9-dihydro-purin-8-one (100 mg, 0.41 mmol) in anhydrous DMF (2 mL) is added methyl iodide (21 uL, 0.41 mmol) and NaH (50% dispersion in mineral oil, 22 mg, 0.46 mmol). The reaction is stirred for 1.5 h. The reaction mixture is quenched with ice water and extracted with EtOAc. The extracts are dried over $Na_2SO_4$ and concentrated in vacuo to give 104 mg of 2-chloro-9-(1-ethyl-propyl)-7-methyl-7,9-dihydro-purin-8-one. The crude product is used as is.

LCMS: 255.1 $(M+H)^+$

To a mixture of 2-chloro-9-(1-ethyl-propyl)-7-methyl-7,9-dihydro-purin-8-one (102 mg, 0.4 mmol) and TsOH (1.6 mL, 0.2 M in 1,4-dioxane) in DMF (0.25 mL) is added 1-[4-(4-amino-phenyl)-piperazin-1-yl]-ethanone (105 mg, 0.5 mmol). The reaction mixture is sealed in a microwave reactor and heated at 140° C. for 30 min. The mixture is diluted with EtOAc and washed with $NaHCO_3$ aqueous solution and brine. The organics are dried over $Na_2SO_4$, filtered and concentrated. The crude product is purified by preparative HPLC to give 50 mg of 2-[4-(4-acetyl-piperazin-1-yl)-phenylamino]-9-(1-ethyl-propyl)-7,9-dihydro-purin-8-one.

LCMS: 437.6 (M+H)+

EXAMPLE 420

9-(1-Ethyl-propyl)-7-methyl-2-[4-(4-methyl-piperazin-1-yl)-phenylamino]-7,9-dihydro-purin-8-one

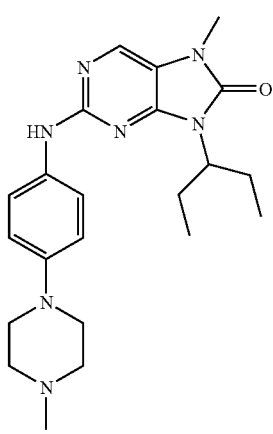

By repeating the procedures described in example x11, using appropriate starting materials, 9-(1-ethyl-propyl)-7-methyl-2-[4-(4-methyl-piperazin-1-yl)-phenylamino]-7,9-dihydro-purin-8-one is obtained.

LCMS: 409.5 (M+H)+.

EXAMPLE 421

1-(4-{4-[9-(1-Ethyl-propyl)-9H-purin-2-ylamino]-phenyl}-piperazin-1-yl)-ethanone

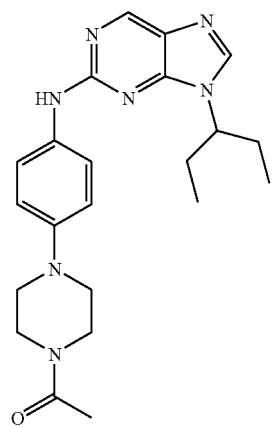

To a solution of 2-chloro-9-(1-ethyl-propyl)-7,9-dihydro-purin-8-one (0.5 g, 2.3 mmol) in DMF (5 mL) is added triethyl orthoformate (3.8 mL, 23 mmol) and TsOH (0.88 g, 2.6 mmol). The reaction is stirred overnight. The reaction mixture is quenched with ice water and extracted with EtOAc. The extracts are dried over Na2SO4 and concentrated in vacuo. Purification by flash chromatography (SiO2, EtOAC/Hexane 1:3) gives 0.39 g of 2-chloro-9-(1-ethyl-propyl)-9H-purine.

LCMS: 225.1 (M+H)+

To a mixture of 2-chloro-9-(1-ethyl-propyl)-9H-purine (90 mg, 0.4 mmol) and TsOH (1.6 mL, 0.2 M in 1,4-dioxane) in DMF (0.25 mL) is added 1-[4-(4-amino-phenyl)-piperazin-1-yl]-ethanone (105 mg, 0.5 mmol). The reaction mixture is sealed in a microwave reactor and heated at 140° C. for 30 min. The mixture is diluted with EtOAc and washed with NaHCO3 aqueous solution and brine. The organics are dried over Na2SO4, filtered and concentrated. The crude product is purified by preparative HPLC to give 40 mg of 1-(4-{4-[9-(1-ethyl-propyl)-9H-purin-2-ylamino]-phenyl}-piperazin-1-yl)-ethanone.

LCMS: 407.5 (M+H)+

EXAMPLE 422

[9-(1-Ethyl-propyl)-9H-purin-2-yl]-[4-(4-methyl-piperazin-1-yl)-phenyl]-amine

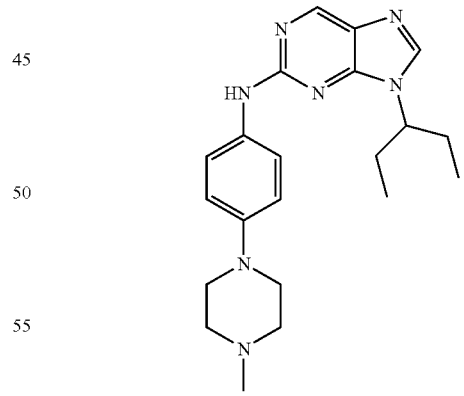

By repeating the procedures described in example x13, using appropriate starting materials, [9-(1-ethyl-propyl)-9H-purin-2-yl]-[4-(4-methyl-piperazin-1-yl)-phenyl]-amine is obtained.

LCMS: 379.5 (M+H)+

The following examples of compounds were also produced using the materials and methods as described above.
| Structure | Example Number | MS |
|---|---|---|
| 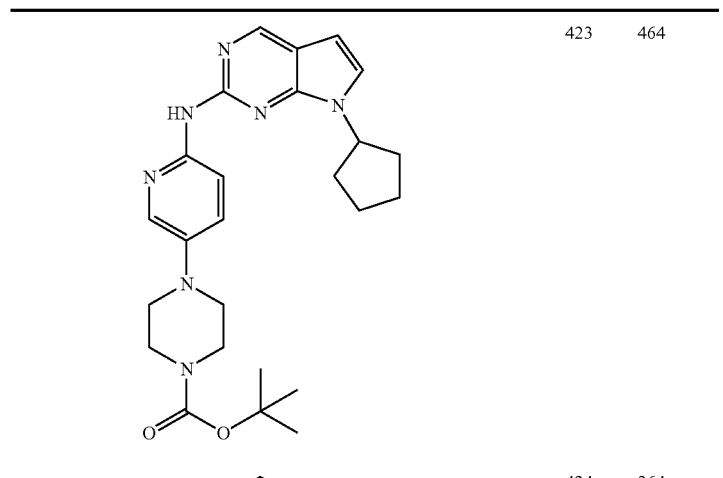 | 423 | 464 |
| 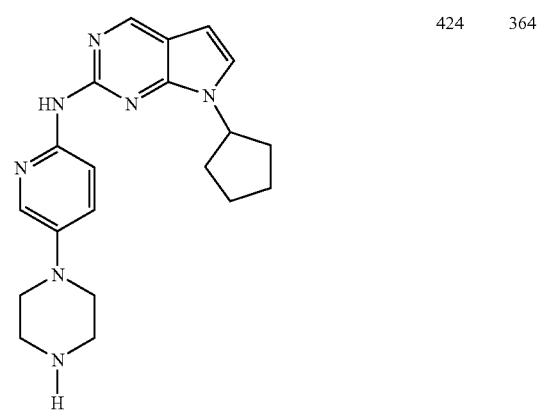 | 424 | 364 |
| 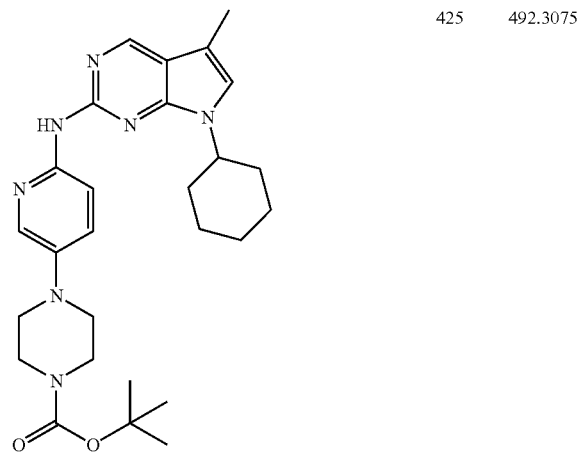 | 425 | 492.3075 |

| Structure | Example Number | MS |
| --- | --- | --- |
| 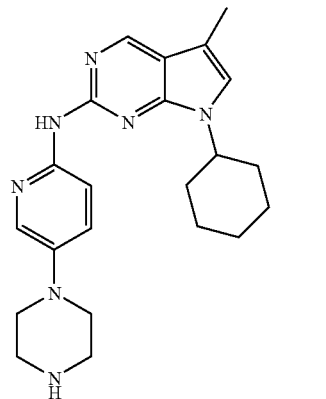 | 426 | 392.2561 |
| 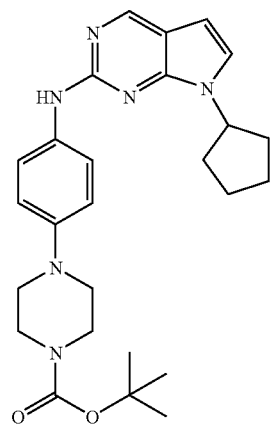 | 427 | 463.2818 |
| 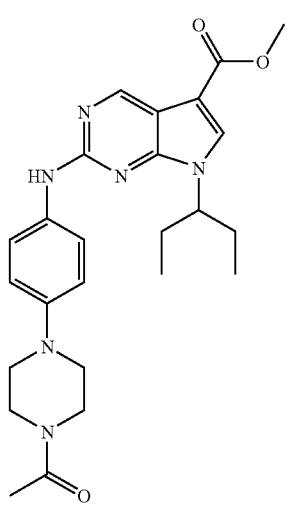 | 428 | |

-continued
| Structure | Example Number | MS |
|---|---|---|
| 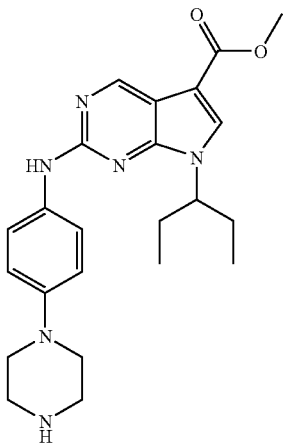 | 429 | |
| 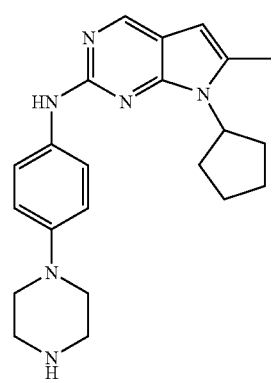 | 430 | 377.1 |
| 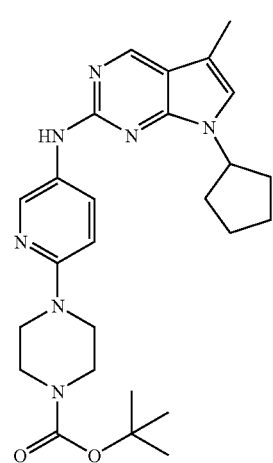 | 431 | 478.2925 |

| Structure | Example Number | MS |
|---|---|---|
| 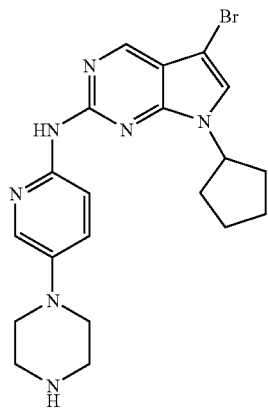 | 432 | 442.1345 |
| 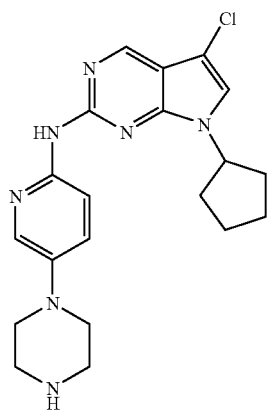 | 433 | 398.1864 |
| 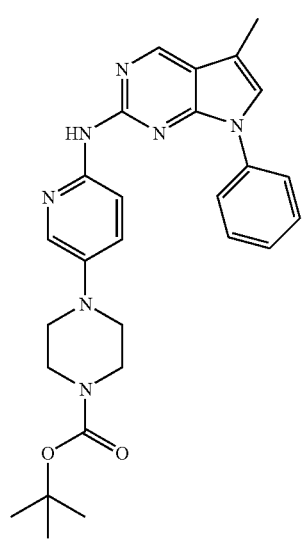 | 436 | 486.22 |

| Structure | Example Number | MS |
|---|---|---|
| 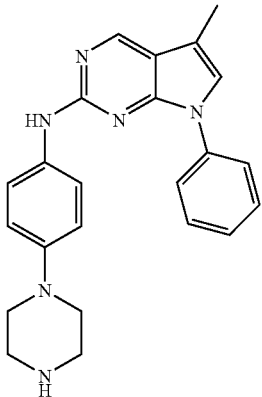 | 437 | 385.2 |
| 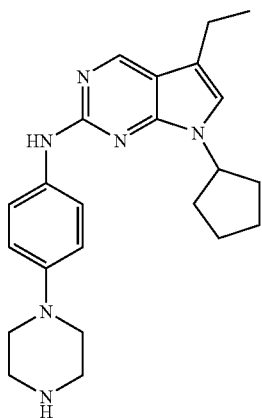 | 438 | 391.2605 |
| 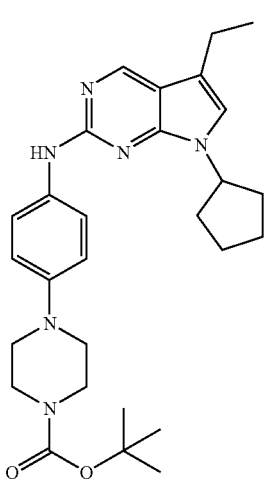 | 439 | 491.3114 |

-continued
| Structure | Example Number | MS |
|---|---|---|
| 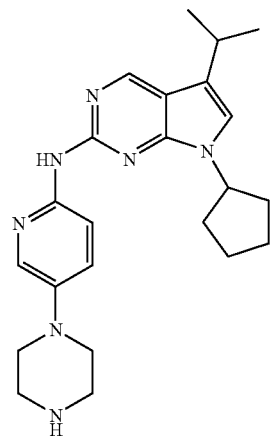 | 440 | 406.21 |
| 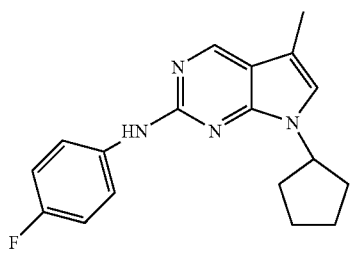 | 442 | |
| 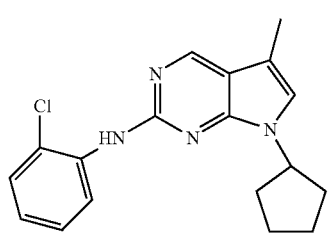 | 443 | |
| 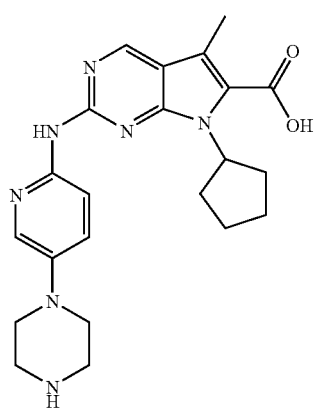 | 444 | 422.2306 |

-continued
| Structure | Example Number | MS |
|---|---|---|
| 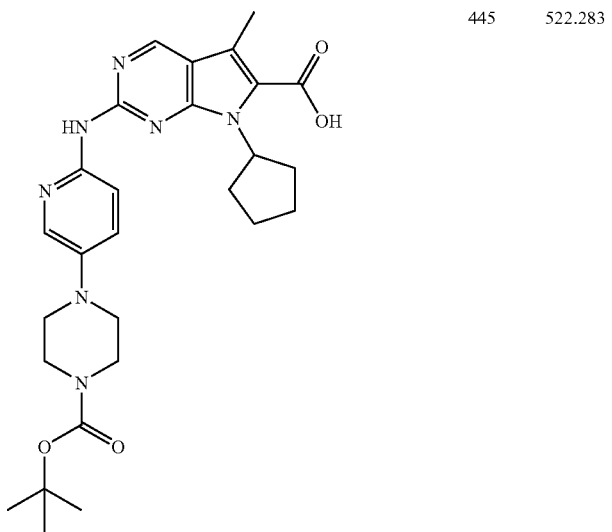 | 445 | 522.283 |
| 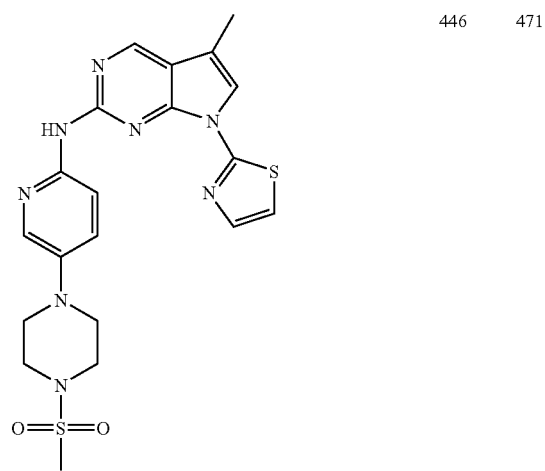 | 446 | 471 |
| 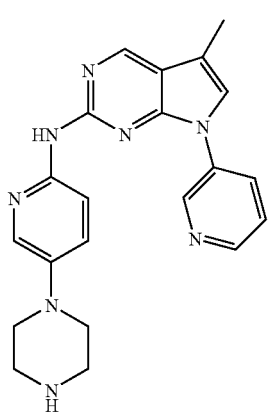 | 447 | 387.04 |

| Structure | Example Number | MS |
|---|---|---|
| 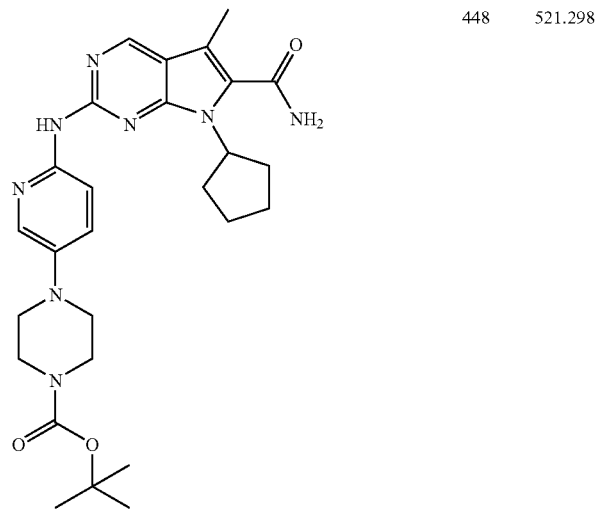 | 448 | 521.298 |
| 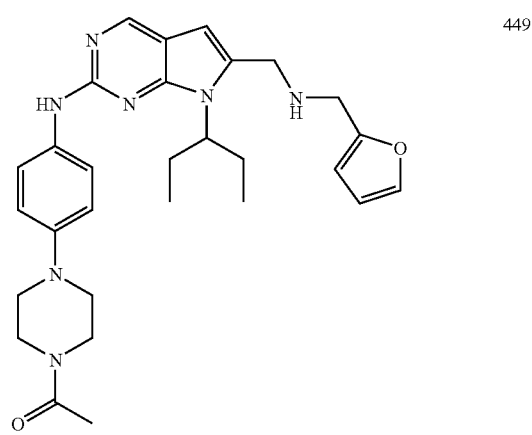 | 449 | |
| 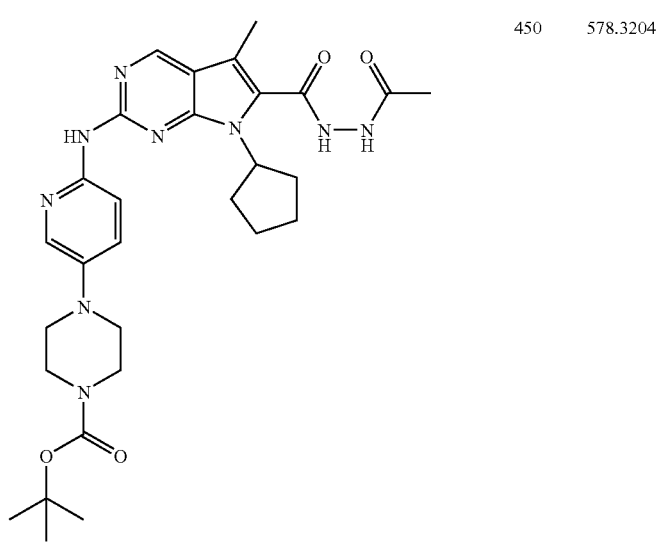 | 450 | 578.3204 |

| Structure | Example Number | MS |
|---|---|---|
| 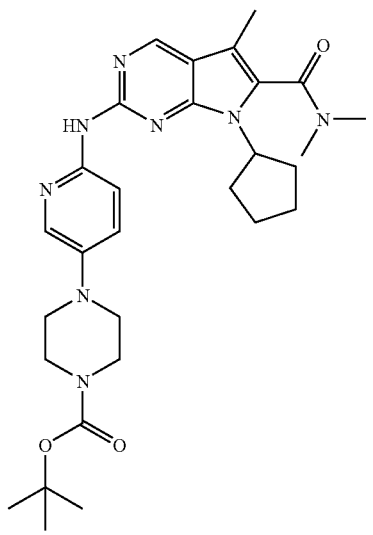 | 451 | 549.3301 |
| 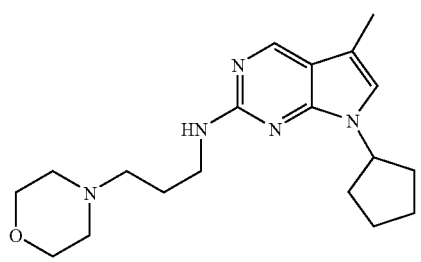 | 452 | |
| 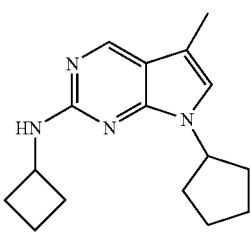 | 453 | |
| 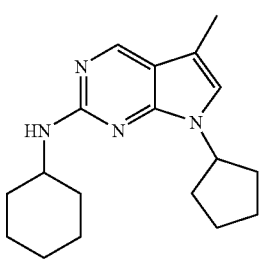 | 454 | |
| 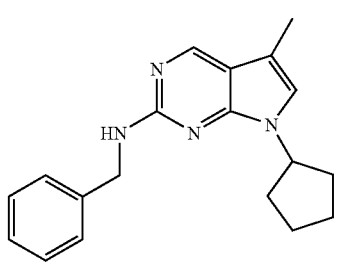 | 455 | |

-continued
| Structure | Example Number | MS |
|---|---|---|
| 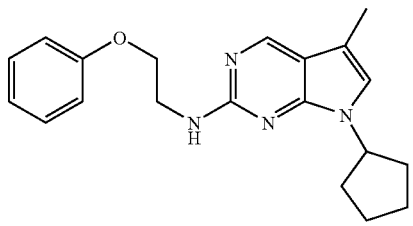 | 456 | |
| 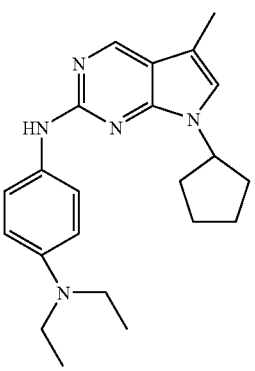 | 457 | |
| 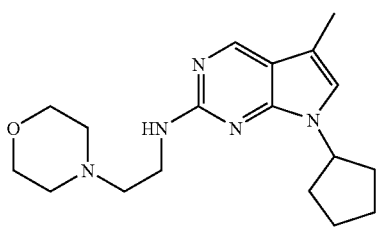 | 458 | |
| 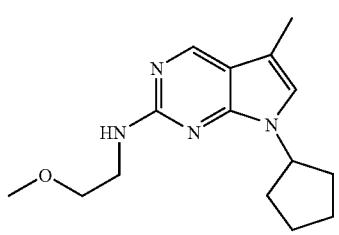 | 459 | |
| 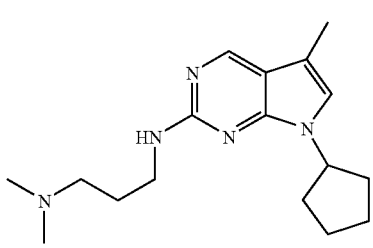 | 460 | |
| 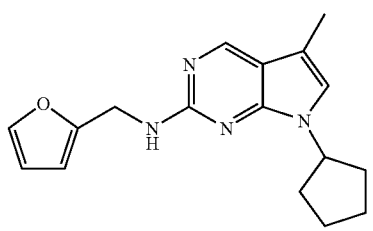 | 461 | |

237
-continued
| Structure | Example Number | MS |
|---|---|---|
| 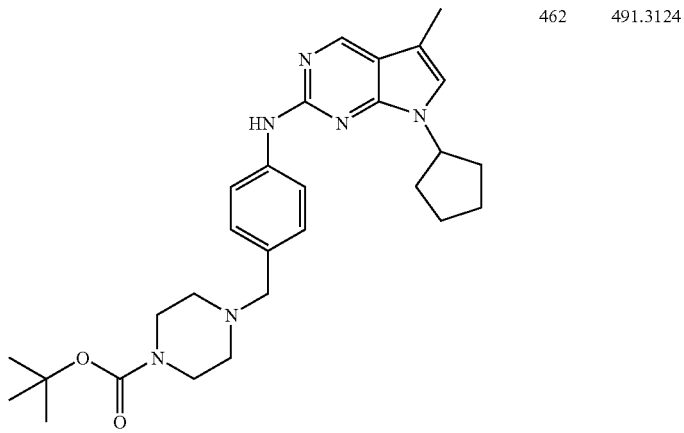 | 462 | 491.3124 |
| 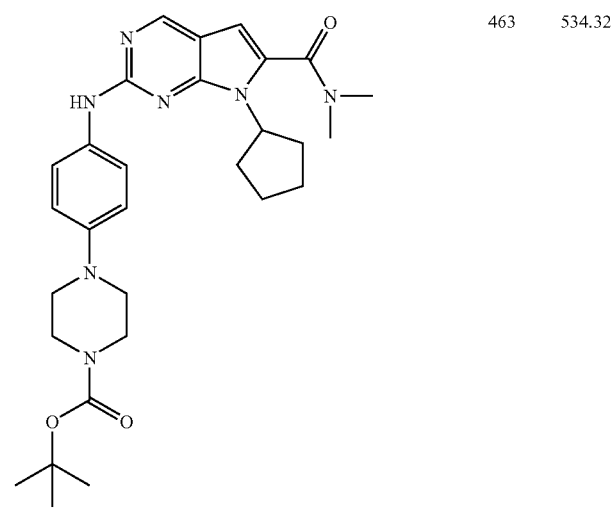 | 463 | 534.32 |
| 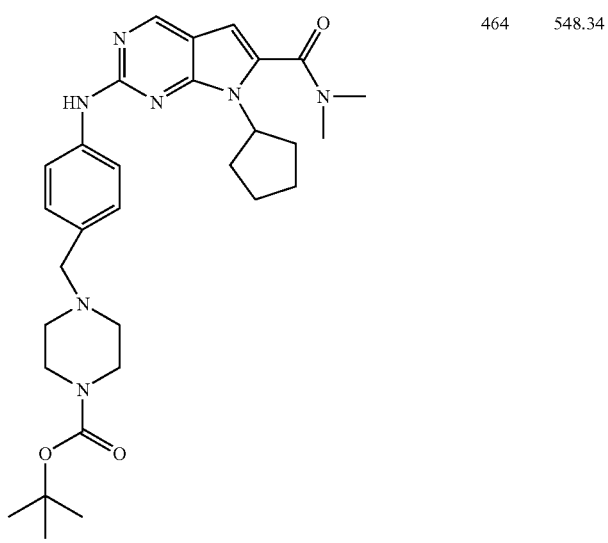 | 464 | 548.34 |
238

| Structure | Example Number | MS |
|---|---|---|
| 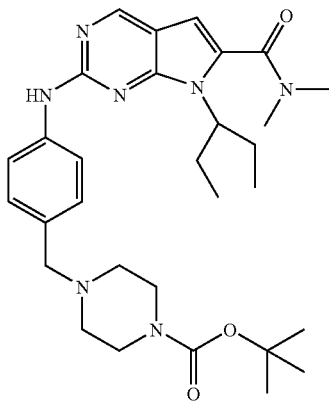 | 465 | 550.3506 |
| 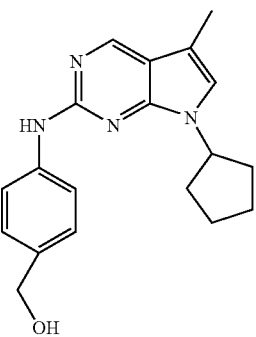 | 466 | 323.19 |
| 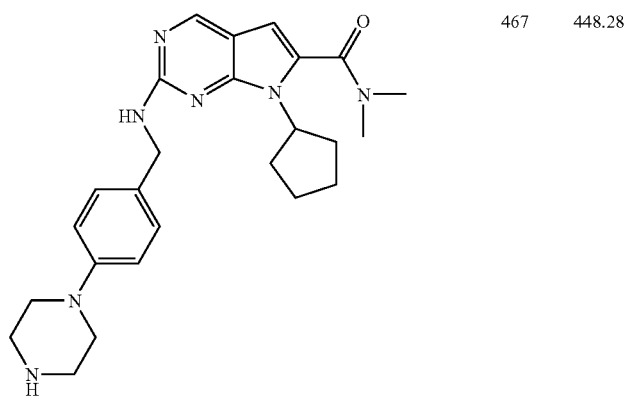 | 467 | 448.28 |

-continued
| Structure | Example Number | MS |
|---|---|---|
| 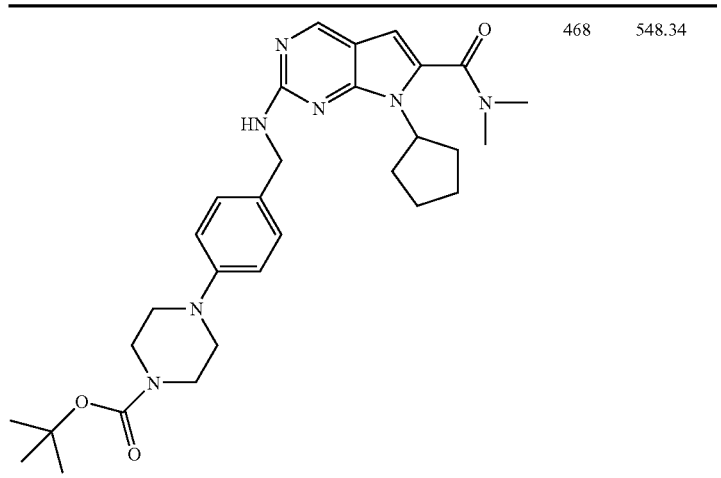 | 468 | 548.34 |
| 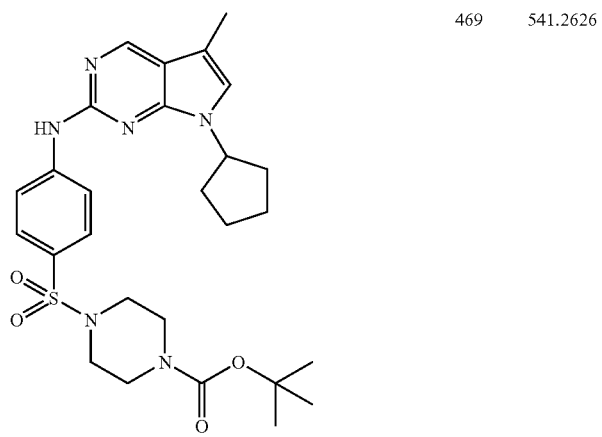 | 469 | 541.2626 |
| 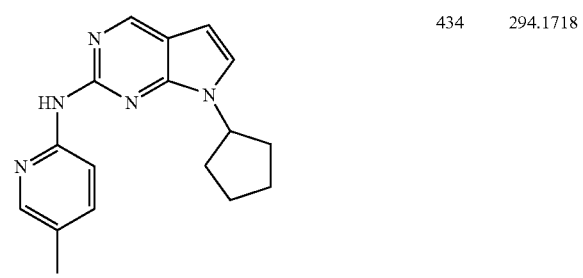 | 434 | 294.1718 |
| 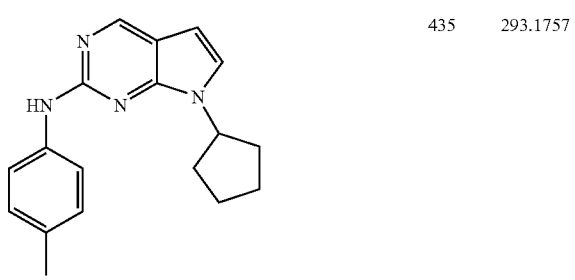 | 435 | 293.1757 |

| Structure | Example Number | MS |
|---|---|---|
| (structure: 2-(2-fluorophenylamino)-5-methyl-7-cyclopentyl-7H-pyrrolo[2,3-d]pyrimidine) | 441 | |

Biological Activity

Binding of cytokines and certain growth factors to their respective receptors trigger activation of Janus kinases, which phosphorylate members of the STAT family. Phosphorylated STAT molecules dimerize and migrate to the nucleus where they bind to DNA and initiate transcription of responsive genes. Inhibitors of pathways downstream of cytokine/growth factor receptors have therapeutic potential for several indications. An enzymatic assay for JAK-3 and JAK-2 has been developed to identify T-cell selective inhibitors. GST fusion constructs of the kinase domains of both enzymes are used and a biotinylated, tyrosine containing peptide serves as substrate. Phosphorylation of this peptide by the respective kinase is quantified with an europium-labeled anti-phosphotyrosine antibody (Eu-PT66) as energy donor and a streptavidin-allophycocyanine conjugate (SA-APC) as energy acceptor. The assay has been established in a 384 well format.

In the JAK LANCE™ assay, a biotinylated peptide is incubated together with compounds and ATP in buffer. The phosphorylation reaction starts after addition of JAK kinase. After incubation at RT the reaction is stopped with EDTA and the product detected by addition Streptavidin-Allophycocyanin and Europium-labeled antiphosphotyrosine antibody. The signal is measured using an EnVision Reader. Exc: 320 nm, Em, Donor: 615 nm and Em, Acceptor: 665 nm in time resolved fashion with a delay of 60 s and a window of 100 s.

Data acquired for the compounds of the invention using these assays are shown in Tables A and B.

In order to test the CDK4 activity of the compounds of the invention, an ELISA based assay can be utilized, where the enzyme is a purified active CDK4/Cyclin-D1 kinase complex and the substrate is a purified Retinoblastoma (Rb) protein. The active CDK4/Cyclin-D1 kinase complex phosphorylates the Rb substrate at Serine780 residue, and then the phosphorylated Rb/S780 is detected via an antibody specific to the phosphorylated site. The compounds that inhibit the CDK4 kinase activity would inhibit the signal output of the assay. Data acquired for the compounds of the invention using this assay are shown in Table C.

In order to test the CDK2 activity of the compounds of the invention, the CDK2 assay is a fluorescence polarization assay, where the enzyme is a purified active CDK2/Cyclin-A kinase complex and the substrate is a synthesized peptide derived from Histone H1. This assay utilizes the IMAP technology from Molecular Devices. The active CDK2/Cyclin-A complex phosphorylates the peptide substrate, which is conjugated with the TAMRA tag. The phosphorylated site is then recognized by a metal containing molecule that interacts with the TAMRA tag to induce a high fluorescence polarization. The compounds that inhibit the CDK2 kinase activity would inhibit the fluorescence output of the assay. Data acquired for the compounds of the invention using this assay are shown in Table C.

p-pRb/S780 ELISA Cellular Assay

Maxisorp plates (Nunc 442-404) are coated with 50 ul of 1 ug/mL total phospholated Retinoblast Protein (pRb) antibody (4H1 Cell Signaling 9309L) diluted in DPBS (Phosphate Buffered Saline) overnight at 4° C. The next day plates are blocked with Superblock in TBST (Pierce 37535) for one hour to overnight—changing block once during that time. Cells are plated at 50-60% confluency in a 96 well plate (Corning 3585) in 100 uL complete media (media containing fetal bovine serum (Gibco 1600-044), 2 mM L-Glutamine (Gibco 25030), and 1% Penicillin/Streptomycin (Gibco 15140-122) and grown overnight in a humidified chamber at 37° C. and 5% $CO_2$. Compounds (in DMSO) are diluted in media to create a 7 point dilution series of compound with concentrations ranging from 110 uM to 0.027 uM. 10 ul of the diluted compounds are added to the cells, with final concentrations on cells ranging from 10 uM to 0.002 uM. Cells are treated for 24 hrs in a humidified chamber at 37° C. and 5% $CO_2$. Following compound incubation, cells are lysed with 40 uL/well lysis buffer (50 mM Tris-HCL pH 7.5 (Invitrogen 15567-027), 120 mM NaCl (Promega V4221), 1 mM EDTA (Gibco 15575-038), 6 mM EGTA (Fisher 02783-100), 1% Nonidet P40 (Fluka R02771). Plates are placed on Titerplate shaker (Labline model 4625) for 5 minutes at 4° C. to lyse cells. After lysis, 10 ul of cell lysate and 50 ul 1×PBS/10% Superblock (Gibco 10010 and Pierce 37535) is added to each well of the precoated and blocked Maxisorp plate and allowed to bind at room temperature for 2 hours on Oribtron Rotator II (Boekel Industries Model 260250). Plates are then washed 3× with 1×TBST (Teknova T9201) using Biotek platewasher equipped with a Biostack. The final wash is not aspirated. The final wash is removed by flicking off and tapping plate on paper towels. ppRbS780 antibody (Cell Signaling 9307L) is diluted 1:1000 in 1×PBS/10% Superblock (Gibco 10010 and Pierce 37535) and 50 ul is added to each well. Plates are then incubated 1 hour on Oribtron Rotator II (Boekel Industries Model 260250). Plates are then washed as previously described. Goat anti-rabbit HRP (Promega W401B) is diluted 1:2500 1×PBS/10% Superblock (Gibco 10010 and Pierce 37535) and 50 ul is added to each well. Plates are then incubated 30 minutes on Oribtron Rotator II. Plates are then washed as previously described. 50 uL Ultra TMB ELISA (Pierce 34028) is then added to each well. Plates are incubated 5-20 minutes until blue color develops. 50 ul 2M Sulfuric acid (Mallinckrodt 2468-46) is then added to each well to stop the reaction. Absorbance at 450 nm for each plate is read on Spectramax Plus (Molecular Devices). The results of this assay are summarized in Table E.

BrdU Assay

Cell Proliferation ELISA BrdU (calorimetric) kit from Roche Diagnostic (Cat. #: 11647229001, 9115 Hague, Road, Indianapolis, Ind. 50414) is used for this assay. Briefly, cells are plated in 96 well plates at 50-60% confluency in RMPI 1640 media. The next day, cells are treated with compounds at a desired concentration range and then incubated for 24 hrs in a humidified chamber at 37° C. and 5% $CO_2$. Following the protocol provided by the kit, cells are labeled with BrdU labeling agent for 2 hrs, and then fixed with 200 uL of FixDenat for 30 min at room temperature. 100 uL of anti-BrdU antibody is added to the cells and incubated for 2 hrs at room temperature. The cells are then washed three times with 200 uL/well of PBS, and then 100 uL of color developing solution is added per well. After 5-10 min incubation, the absorbance is read at 370 nM using Spectramax Plus (Molecular Devices). The results of this assay are summarized in Table E.

TABLE E

| Example Number | CDK4 ELISA assay IC50 [umol l−] | CDK4 HTRF/IC50 [umol l − 1] | CDK2cyA IMAP/IC50 [umol l − 1] | hCDK1/B/IC50 [umol l − 1] |
|---|---|---|---|---|
| 201 | | | <10 | |
| 201A | <10 | | <1 | |
| 205 | <10 | | <10 | |
| 206 | >10 | | >10 | |
| 207 | <10 | | >10 | |
| 208 | <10 | | <10 | |
| 209 | <10 | | <10 | |
| 210 | >10 | | | |
| 211 | <10 | | <10 | |
| 212 | <10 | | <1 | |
| 213 | <10 | | <1 | |
| 214 | <10 | | >10 | |
| 215 | >10 | | | |
| 216 | <10 | | <10 | |
| 265 | <10 | | <10 | |
| 266 | | <1 | <10 | <10 |
| 266A | <1 | <1 | <10 | <10 |
| 267 | <10 | <10 | >10 | >10 |
| 217 | >10 | | | |
| 218 | >10 | | | |
| 263 | >10 | | >10 | |
| 269 | <10 | | >10 | |
| 264 | >10 | | >10 | |
| 423 | >10 | | | |
| 424 | >10 | <1 | >10 | |
| 252 | >10 | | >10 | |
| 253 | <10 | | <10 | |
| 254 | >10 | | <1 | |
| 330 | >10 | | <1 | |
| 255 | >10 | <10 | >10 | |
| 269 | | | >10 | |
| 319 | >10 | | | |
| 360 | >10 | | >10 | |
| 361 | <1 | <1 | <1 | |
| 362 | >10 | | <1 | |
| 274 | | | >10 | |
| 270 | | | >10 | |
| 271 | <10 | | >10 | |
| 331 | >10 | | <1 | |
| 329 | >10 | | <1 | |
| 426 | <10 | <1 | >10 | |
| 275 | 8 | >10 | >10 | |
| 379 | >10 | <10 | >10 | |
| 380 | >10 | <10 | | |
| 381 | >10 | >10 | | |
| 382 | >10 | <1 | <10 | |
| 427 | >10 | >10 | | |
| 364 | >10 | <1 | <10 | |
| 256 | <10 | <1 | <10 | |
| 276 | <10 | >10 | >10 | |

TABLE E-continued

| Example Number | CDK4 ELISA assay IC50 [umol l−] | CDK4 HTRF/IC50 [umol l − 1] | CDK2cyA IMAP/IC50 [umol l − 1] | hCDK1/B/IC50 [umol l − 1] |
|---|---|---|---|---|
| 373 | <10 | <10 | <10 | |
| 280 | <10 | >10 | >10 | |
| 375 | <1 | <1 | <1 | |
| 374 | <1 | <1 | <1 | |
| 428 | >10 | | | |
| 383 | <1 | <1 | <1 | |
| 429 | >10 | | | |
| 257 | <10 | | <10 | |
| 387 | <1 | <1 | 10 | |
| 430 | <1 | <1 | <1 | |
| 326 | >10 | 10 | | |
| 333 | <10 | 10 | 10 | |
| 219 | <10 | <10 | <10 | |
| 220 | >10 | >10 | | |
| 221 | <10 | <10 | <10 | |
| 222 | <10 | <10 | <10 | |
| 223 | <10 | <10 | >10 | |
| 224 | >10 | >10 | | |
| 225 | <1 | <1 | <10 | |
| 226 | <10 | <10 | >10 | |
| 227 | | <10 | <10 | |
| 228 | | <10 | <10 | |
| 229 | | <10 | | |
| 230 | <1 | | <10 | |
| 231 | <1 | | >10 | |
| 232 | <1 | | <1 | |
| 376 | <1 | | <10 | |
| 377 | <1 | | <1 | |
| 398 | <1 | | <1 | <1 |
| 234 | <10 | | >10 | |
| 235 | <10 | | >10 | |
| 399 | <1 | | <10 | |
| 399A | <1 | | <10 | <10 |
| 399C | <1 | | >15 | <10 |
| 432 | >10 | | >10 | |
| 433 | <1 | | >10 | |
| 283 | <10 | | >10 | |
| 285 | <10 | | <10 | |
| 258 | >10 | | <10 | |
| 202 | <1 | | <10 | |
| 434 | >10 | | >10 | |
| 435 | >10 | | <10 | |
| 261 | >10 | | <10 | |
| 262 | >10 | | <10 | |
| 385 | >10 | | >10 | |
| 408 | >10 | | >10 | |
| 273 | >10 | | >10 | |
| 437 | <10 | | >10 | |
| 236 | <10 | | <1 | |
| 237 | <10 | | <10 | |
| 438 | <10 | | <10 | |
| 238 | <1 | | <10 | <10 |
| 384 | <1 | | >10 | |
| 239 | <1 | | <10 | <1 |
| 440 | <10 | | >10 | |
| 320 | <10 | | >10 | |
| 240 | <1 | | <10 | |
| 241 | <10 | | <10 | |
| 242 | <1 | | <10 | |
| 388 | <10 | | >10 | |
| 246 | <1 | | <1 | |
| 321 | <10 | | >10 | |
| 287 | 10 | | >10 | |
| 404 | <1 | | >10 | |
| 405 | <10 | | >10 | |
| 243 | <1 | | <1 | |
| 244 | <1 | | <1 | |
| 245 | <1 | | <1 | |
| 378 | <1 | | <10 | |
| 441 | 10 | | >10 | |
| 336 | <10 | | <10 | |
| 337 | <10 | | >10 | |
| 442 | 10 | | <10 | |
| 443 | 10 | | >10 | |
| 363 | <1 | | <1 | |

TABLE E-continued

| Example Number | CDK4 ELISA assay IC50 [umol l−] | CDK4 HTRF/IC50 [umol l − 1] | CDK2cyA IMAP/IC50 [umol l − 1] | hCDK1/B/IC50 [umol l − 1] |
|---|---|---|---|---|
| 247 | | <1 | <1 | <1 |
| 335 | | <1 | <10 | |
| 343 | | <10 | >10 | |
| 344 | | <10 | >10 | |
| 444 | | <1 | >10 | |
| 446 | | 10 | <10 | |
| 286 | | <10 | <10 | |
| 447 | | 10 | >10 | |
| 345 | | <1 | <10 | |
| 345A | | <1 | <10 | <1 |
| 288 | | <10 | <1 | |
| 322 | | <10 | >10 | |
| 293 | | 10 | >10 | |
| 334 | | <1 | >10 | |
| 248 | | <1 | <10 | |
| 249 | | <10 | <10 | |
| 366 | | <10 | <10 | |
| 367 | | <10 | <10 | |
| 294 | | 10 | <10 | |
| 295 | | 10 | >10 | |
| 296 | | 10 | >10 | |
| 297 | | 10 | >10 | |
| 299 | | 10 | <10 | |
| 300 | | <10 | <1 | |
| 301 | | 10 | >10 | |
| 298 | | <10 | <1 | |
| 346 | | <1 | <10 | <10 |
| 250 | | <1 | <1 | <1 |
| 303 | | >10 | >10 | >10 |
| 304 | | >10 | >10 | >10 |
| 391 | | <1 | >10 | >10 |
| 305 | | >10 | <10 | <10 |
| 406 | | <1 | >10 | >10 |
| 368 | | <1 | <1 | <10 |
| 449 | | <10 | <10 | <10 |
| 369 | | <10 | <10 | <10 |
| 370 | | <10 | <10 | <10 |
| 371 | | <10 | <10 | <1 |
| 372 | | <10 | <1 | <10 |
| 232 | | >10 | >10 | >10 |
| 306 | | >10 | >10 | >10 |
| 324 | | <1 | >10 | >10 |
| 325 | | <10 | >10 | >10 |
| 389 | | <1 | <10 | >10 |
| 400 | | <1 | <1 | <1 |
| 386 | | <1 | <10 | <10 |
| 386A | | <1 | >10 | <10 |
| 277 | | >10 | >10 | >10 |
| 278 | | <10 | >10 | >10 |
| 312 | | <10 | <10 | <10 |
| 392 | | <10 | <10 | >10 |
| 279 | | <1 | <10 | <10 |
| 393 | | <1 | <10 | <10 |
| 407 | | <1 | <10 | <10 |
| 302 | | <10 | >10 | >10 |
| 457 | | >10 | >10 | >10 |
| 311 | | <10 | >10 | >10 |
| 313 | | <1 | <10 | <10 |
| 347 | | <1 | >10 | >10 |
| 348 | | <1 | >15 | >15 |
| 349 | | <10 | >15 | >15 |
| 350 | | <1 | >15 | >10 |
| 782 | | <1 | >15 | <10 |
| 351 | | <1 | <10 | <10 |
| 352 | | <1 | >10 | <10 |
| 353 | | <1 | >15 | >15 |
| 282 | | >10 | >15 | >15 |
| 284 | | >10 | >15 | >15 |
| 462 | | <10 | >15 | >15 |
| 354 | | <10 | >15 | >15 |
| 314 | | <1 | <10 | <10 |
| 356 | | <1 | <10 | <10 |
| 357 | | <1 | <10 | <10 |
| 358 | | <1 | >15 | >15 |
| 359 | | <1 | <10 | <10 |
| 397 | | <1 | >15 | >15 |
| 281 | | <10 | <10 | <10 |
| 401 | | <1 | <1 | <1 |
| 402 | | <1 | <1 | <1 |
| 315 | | <1 | <1 | <10 |
| 315A | | <1 | <10 | <10 |
| 316 | | <1 | <1 | <10 |
| 463 | | <1 | <10 | <10 |
| 338 | | <1 | <10 | <10 |
| 339 | | <1 | >10 | >10 |
| 340 | | <1 | <10 | <10 |
| 290 | | <1 | <10 | <10 |
| 465 | | <1 | <10 | <10 |
| 291 | | <1 | >10 | <10 |
| 341 | | <1 | >10 | <10 |
| 342 | | <1 | <10 | <10 |
| 292 | | <10 | <10 | <10 |
| 403 | | <1 | <10 | <10 |
| 466 | | <10 | <10 | <10 |
| 467 | | <10 | >15 | >15 |
| 468 | | >10 | >15 | >15 |
| 394 | | <1 | >10 | >15 |
| 395 | | <1 | <1 | <1 |
| 396 | | <1 | <1 | <1 |

EQUIVALENTS

Those skilled in the art will recognize, or be able to ascertain using no more than routine experimentation, many equivalents to the specific embodiments and methods described herein. Such equivalents are intended to be encompassed by the scope of the following claims.

INCORPORATION BY REFERENCE

The entire contents of all patents, published patent applications and other references cited herein are hereby expressly incorporated herein in their entireties by reference.

The invention claimed is:

1. A compound of Formula I:

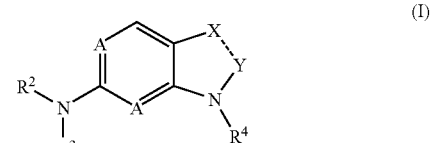

or a pharmaceutically acceptable salt thereof, wherein:
the dashed line indicates a double bond;
A is N;
$R^2$ is hydrogen and $R^3$ is selected from the group consisting of hydrogen, hydroxyl, $C_1$-$C_3$-alkyl, $C_3$-$C_8$-cycloalkyl, heterocyclyl, aryl, heteroaryl, substituted $C_1$-$C_3$-alkyl, substituted $C_3$-$C_8$-cycloalkyl, substituted heterocyclyl, substituted aryl and substituted heteroaryl;
$R^4$ is selected from the group consisting of hydrogen, branched $C_1$-$C_5$-alkyl, branched $C_1$-$C_5$-alkyl substituted by phenyl and $C_3$-$C_6$-cycloalkyl;
X is $CR^{11}$ and Y is $CR^{12}$;
$R^{11}$ is hydrogen or $C_1$-$C_3$-alkyl and
$R^{12}$ is $BC(O)NR^{13}R^{14}$; wherein B is a bond, $C_1$-$C_3$-alkyl or branched $C_1$-$C_3$-alkyl; wherein $R^{13}$ and $R^{14}$ are each, independently, selected from the group consisting of hydrogen, $C_1$-$C_3$-alkyl, $C_3$-$C_8$-cycloalkyl, heterocyclyl, aryl, heteroaryl, substituted alkyl, substituted cycloalkyl, substituted heterocyclyl, substituted aryl, and substituted heteroaryl.

2. The compound of claim 1, wherein $R^4$ is $C(H)(CH_2CH_3)_2$, $C(H)(CH_2CH_3)Ph$, $CH_2CH_3$, cyclopropyl, cyclopentyl or cyclohexyl.

3. The compound of claim 1, wherein $R^3$ is an aryl group, which is further independently substituted one or more times by halogen, $C_1$-$C_4$-alkoxy, $R^{15}$-amine, $R^{15}$-heterocycle, or $R^{15}$-heteroaryl, wherein $R^{15}$ is a bond, $C(O)$, $N(H)C(O)$, $N(H)SO_2$, $OC(O)$ or $(CH_2)_{1-4}$, wherein the $(CH_2)_{1-4}$ group may be interrupted by O, $N(CH_3)$ or $N(H)$.

4. The compound of claim 3, wherein the aryl group is phenyl.

5. The compound of claim 1, wherein the phenyl group is $R^3$ is phenyl which is further independently substituted one or more times with fluoro, methoxy, diethylamine, $R^{15}$-piperazinyl, $R^{15}$-morpholinyl, $R^{15}$-piperidinyl, $R^{15}$-triazolyl, $R^{15}$-phenyl, $R^{15}$-pyridinyl, $R^{15}$-piperazinyl, $R^{15}$-indazolyl, $R^{15}$-pyrrolidinyl or $R^{15}$-imidazolyl, wherein the piperazinyl, morpholinyl, piperidinyl, triazolyl, phenyl, pyridinyl, piperazinyl, indazolyl, pyrrolidinyl or imidazolyl groups may be further substituted with $C_1$-$C_4$-alkyl, $C(O)C_1$-$C_4$-alkyl, $S(O)_2C_1$-$C_4$-alkyl, OH, $C(O)(CH_2)_{1-3}CN$ or $N(H)C(O)C_1$-$C_4$-alkyl and wherein $R^{15}$ is a bond, $C(O)$, $N(H)C(O)$, $N(H)SO_2$, $OC(O)$ or $(CH_2)_{1-4}$, wherein the $(CH_2)_{1-4}$ group may be interrupted by O, $N(CH_3)$ or $N(H)$.

6. The compound of claim 1, wherein $R^3$ is phenyl which is further substituted by $N(H)C(O)aryl$, $C(O)N(H)C_1$-$C_4$-alkyl, $C(O)N(C_1$-$C_4$-alkyl$)_2$ or $C(O)N(H)C_3$-$C_6$-cycloalkyl.

7. The compound of claim 1, wherein the compound is selected from the group consisting of

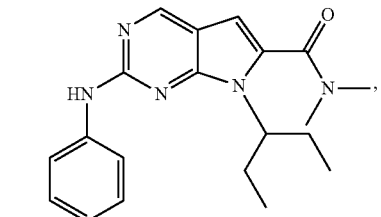

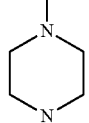

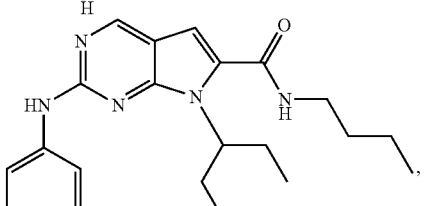

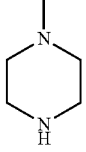

-continued

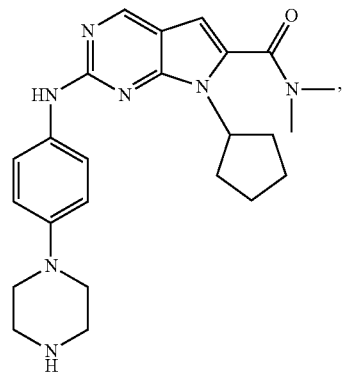

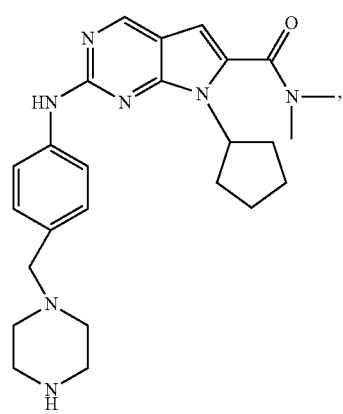

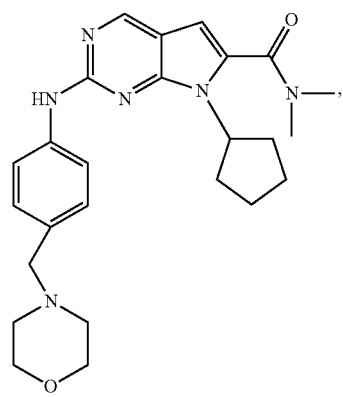

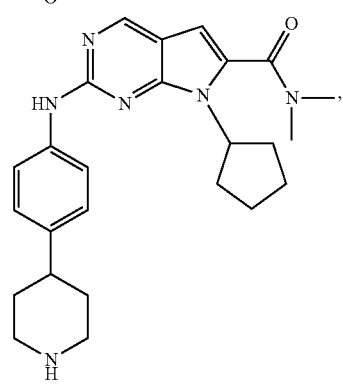

251
-continued
252
-continued
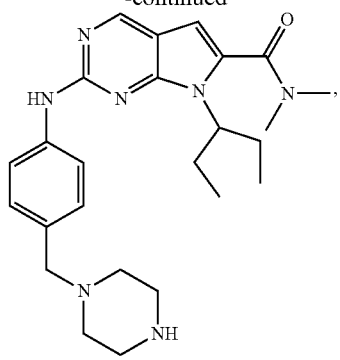
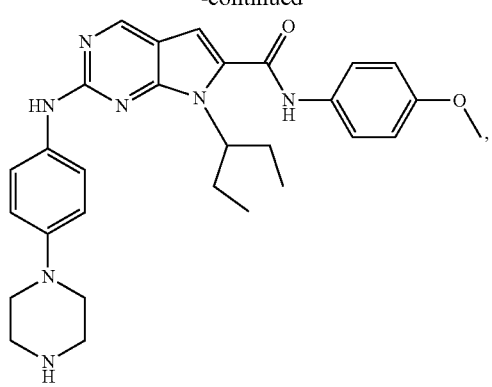

253
-continued
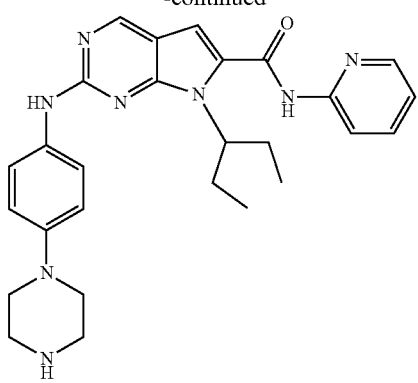
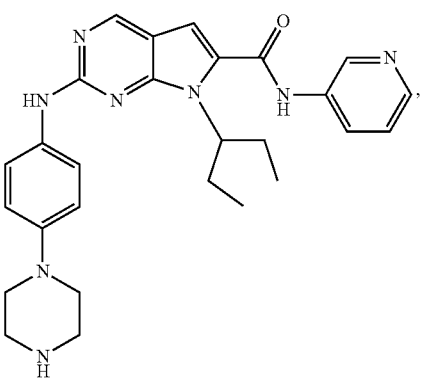
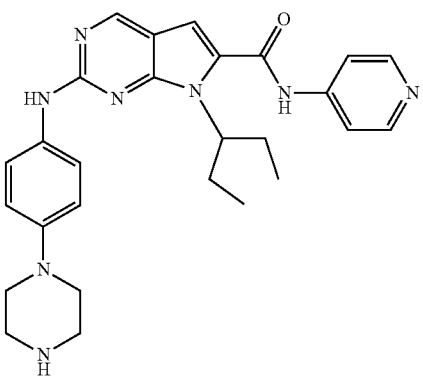
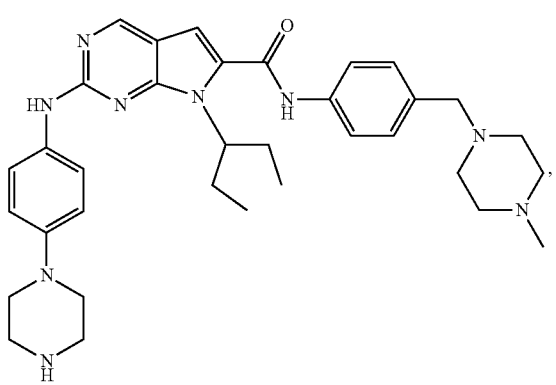
254
-continued
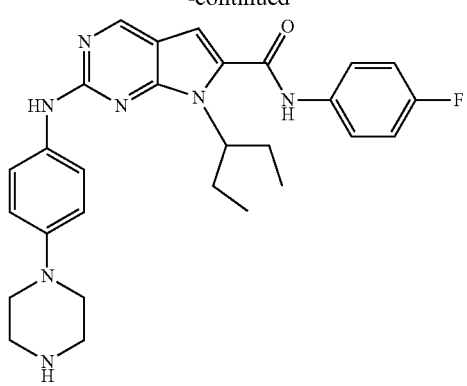
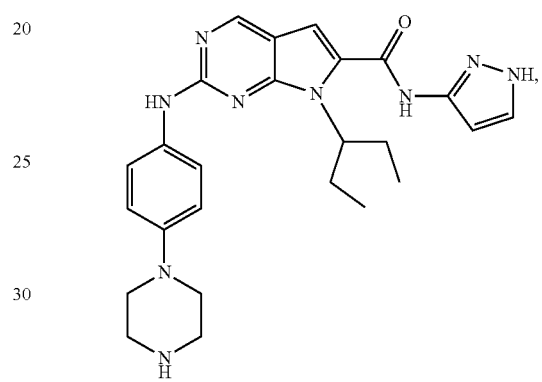
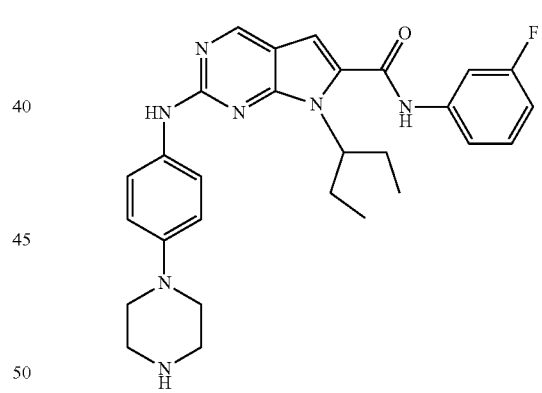
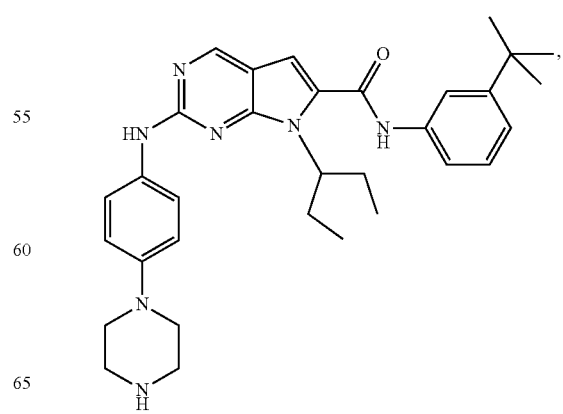

255
-continued
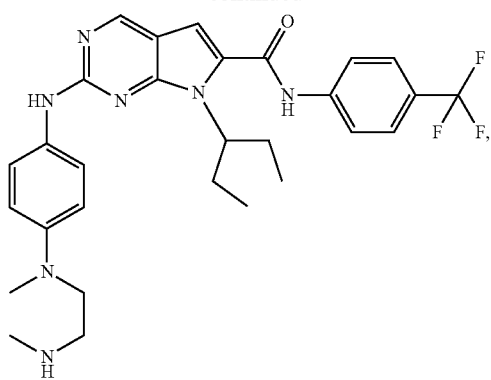
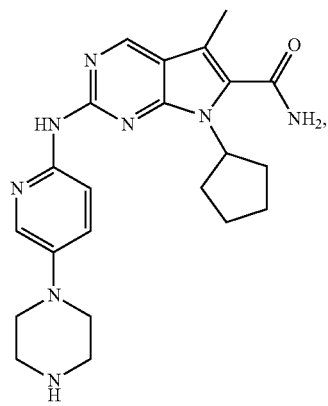
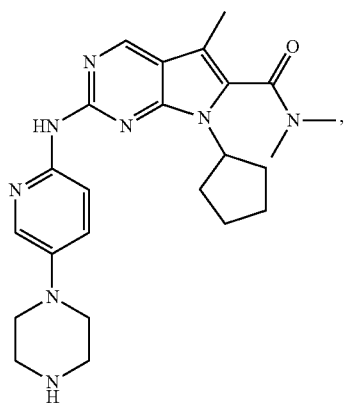
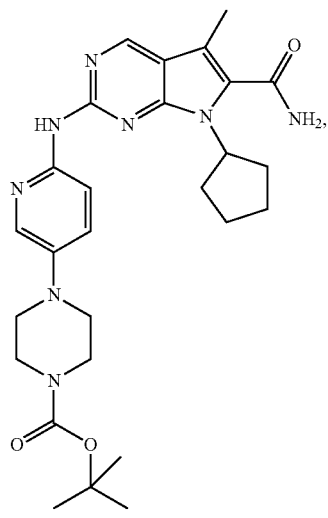
256
-continued
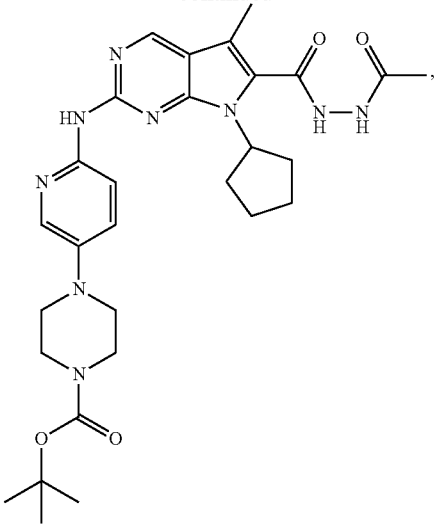
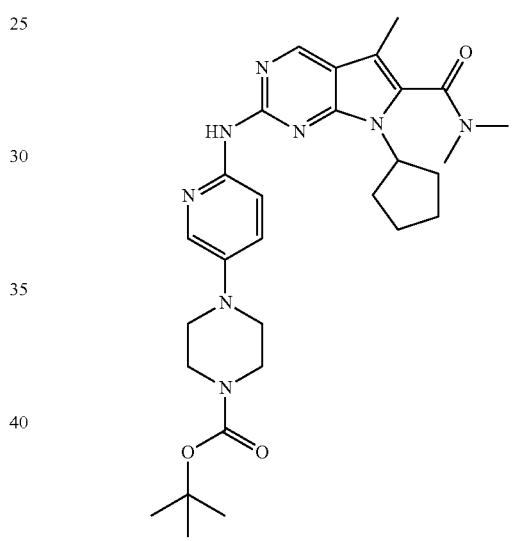
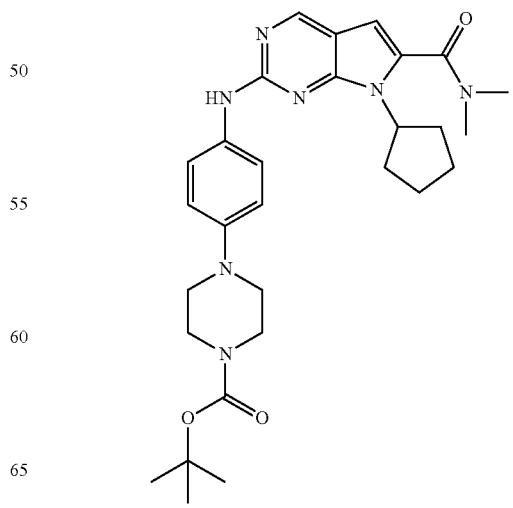

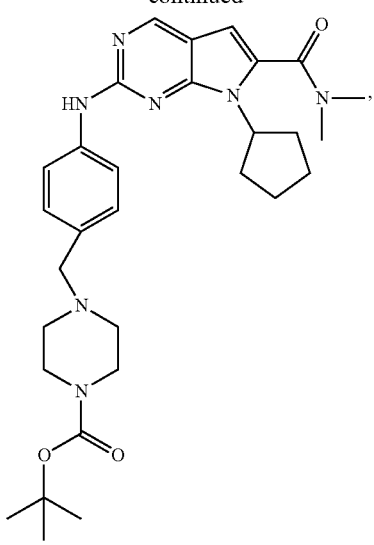

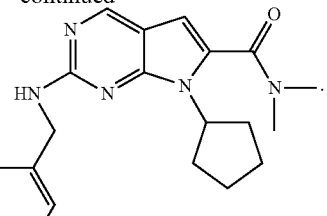

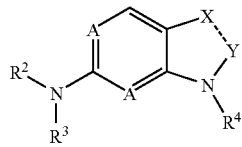

8. A compound of Formula I:

(I)

or a pharmaceutically acceptable salt thereof, wherein:
the dashed line indicates a double bond;
A is N;
$R^2$ is hydrogen and $R^3$ is selected from the group consisting of hydrogen, hydroxyl, $C_1$-$C_3$-alkyl, $C_3$-$C_8$-cycloalkyl, heterocyclyl, aryl, heteroaryl, substituted $C_1$-$C_3$-alkyl, substituted $C_3$-$C_8$-cycloalkyl, substituted heterocyclyl, substituted aryl and substituted heteroaryl;
$R^4$ is branched or linear $C_1$-$C_5$-alkyl, wherein the branched $C_1$-$C_5$-alkyl group may be interrupted by one or more heteroatoms, and/or substituted with one or more heteroatoms, halogens, $C_3$-$C_8$ cycloalkyl groups, substituted $C_3$-$C_8$ cycloalkyl groups, $C_3$-$C_8$ hetrocyclyl groups, aryl groups, heteroaryl groups, substituted aryl groups, or substituted heteroaryl groups;
X is $CR^{11}$ and Y is $CR^{12}$;
$R^{11}$ is hydrogen or $C_1$-$C_3$-alkyl and
$R^{12}$ is $BC(O)NR^{13}R^{14}$; wherein B is a bond, $C_1$-$C_3$-alkyl or branched $C_1$-$C_3$-alkyl; wherein $R^{13}$ and $R^{14}$ are each, independently, selected from the group consisting of hydrogen, $C_1$-$C_3$-alkyl, $C_3$-$C_8$-cycloalkyl, heterocyclyl, aryl, heteroaryl, substituted alkyl, substituted cycloalkyl, substituted heterocyclyl, substituted aryl, and substituted heteroaryl.

9. A pharmaceutical composition comprising a compound according to claim 1 or a pharmaceutically acceptable salt thereof and a pharmaceutically acceptable carrier or excipient.

* * * * *

UNITED STATES PATENT AND TRADEMARK OFFICE
CERTIFICATE OF CORRECTION

PATENT NO. : 8,324,225 B2
APPLICATION NO. : 12/302223
DATED : December 4, 2012
INVENTOR(S) : Brain et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 390 days.

Signed and Sealed this
Twenty-eighth Day of May, 2013

Teresa Stanek Rea
*Acting Director of the United States Patent and Trademark Office*